(12) United States Patent
Cheo et al.

(10) Patent No.: US 7,393,632 B2
(45) Date of Patent: Jul. 1, 2008

(54) USE OF MULTIPLE RECOMBINATION SITES WITH UNIQUE SPECIFICITY IN RECOMBINATIONAL CLONING

(75) Inventors: David Cheo, Kensington, MD (US); Michael A. Brasch, Gaithersburg, MD (US); Gary F. Temple, Washington Grove, MD (US); James L. Hartley, Frederick, MD (US); Devon R. N. Byrd, Montgomery Village, MD (US)

(73) Assignee: Invitrogen Corp., Carlsbad, CA (US)

( * ) Notice: Subject to any disclaimer, the term of this patent is extended or adjusted under 35 U.S.C. 154(b) by 273 days.

(21) Appl. No.: 09/732,914

(22) Filed: Dec. 11, 2000

(65) Prior Publication Data

US 2002/0007051 A1   Jan. 17, 2002

Related U.S. Application Data

(60) Provisional application No. 60/169,983, filed on Dec. 10, 1999, provisional application No. 60/188,020, filed on Mar. 9, 2000.

(51) Int. Cl.
C12Q 1/68 (2006.01)

(52) U.S. Cl. .................. 435/6; 435/91.41; 435/489; 435/194

(58) Field of Classification Search .............. 435/91.41, 435/6, 462
See application file for complete search history.

(56) References Cited

U.S. PATENT DOCUMENTS

| | | | |
|---|---|---|---|
| 4,626,505 A | 12/1986 | Falco | 435/172.3 |
| 4,673,640 A | 6/1987 | Backman | 435/68 |
| 4,683,195 A | 7/1987 | Mullis et al. | |
| 4,683,202 A | 7/1987 | Mullis | |
| 4,743,546 A | 5/1988 | Backman et al. | 435/108 |
| 4,808,537 A | 2/1989 | Stroman et al. | |
| 4,855,231 A | 8/1989 | Stroman et al. | |
| 4,959,217 A | 9/1990 | Sanders et al. | |
| 4,959,317 A | 9/1990 | Sauer | 435/172.3 |
| 4,965,188 A | 10/1990 | Mullis et al. | |
| 5,093,257 A | 3/1992 | Gray | |
| 5,102,797 A | 4/1992 | Tucker et al. | |
| 5,159,062 A | 10/1992 | Knapp et al. | |
| 5,227,288 A | 7/1993 | Blattner | 435/6 |
| 5,286,632 A | 2/1994 | Jones | |
| 5,334,375 A | 8/1994 | Nabi et al. | |
| 5,334,575 A | 8/1994 | Noonan et al. | |
| 5,348,886 A | 9/1994 | Lee et al. | 435/320.1 |
| 5,354,668 A | 10/1994 | Auerbach | 435/91.1 |
| 5,378,618 A | 1/1995 | Sternberg et al. | |
| 5,434,066 A | 7/1995 | Bebee et al. | 435/172.3 |
| 5,451,513 A | 9/1995 | Maliga et al. | |
| 5,470,727 A | 11/1995 | Mascarenhas et al. | 435/172.3 |
| 5,527,695 A * | 6/1996 | Hodges et al. | 435/172.3 |
| 5,552,314 A | 9/1996 | Greener | |
| 5,591,609 A | 1/1997 | Auerbach | 435/91.2 |
| 5,605,793 A | 2/1997 | Stemmer | |
| 5,614,389 A | 3/1997 | Auerbach | 435/91.2 |
| 5,635,381 A | 6/1997 | Hooykaas et al. | 435/172.3 |
| 5,650,308 A | 7/1997 | Baum | |
| 5,650,557 A | 7/1997 | Hannah et al. | |
| 5,654,182 A | 8/1997 | Wahl et al. | |
| 5,658,772 A | 8/1997 | Odell et al. | 435/172.3 |
| 5,677,170 A | 10/1997 | Devine et al. | 435/20.1 |
| 5,677,177 A | 10/1997 | Wahl et al. | 435/325 |
| 5,695,971 A | 12/1997 | Kadokami et al. | |
| 5,710,248 A | 1/1998 | Grose | 530/327 |
| 5,723,765 A | 3/1998 | Oliver et al. | 800/208 |
| 5,728,551 A | 3/1998 | Devine et al. | |
| 5,733,733 A | 3/1998 | Auerbach | 435/6 |
| 5,733,743 A | 3/1998 | Johnson et al. | 435/320.1 |
| 5,744,336 A | 4/1998 | Hodges et al. | 435/172.3 |
| 5,766,891 A | 6/1998 | Shuman | 435/91.41 |
| 5,776,449 A | 7/1998 | Baum et al. | 424/93.2 |

(Continued)

FOREIGN PATENT DOCUMENTS

CA    2141412    2/1994

(Continued)

OTHER PUBLICATIONS

Abremski, K., and Gottesman, S., "Purification of the Bacteriophage λ xis Gene Product Required for λ Excisive Recombination," *J. Biol. Chem.* 257(16):9658-9662, American Society for Biochemistry and Molecular Biology, Inc., Baltimore, MD (1982).

(Continued)

*Primary Examiner*—James Ketter
(74) *Attorney, Agent, or Firm*—Peter G. Foiles

(57) ABSTRACT

The present invention provides compositions and methods for recombinational cloning. The compositions include vectors having multiple recombination sites with unique specificity. The methods permit the simultaneous cloning of two or more different nucleic acid molecules. In some embodiments the molecules are fused together while in other embodiments the molecules are inserted into distinct sites in a vector. The invention also generally provides for linking or joining through recombination a number of molecules and/or compounds (e.g., chemical compounds, drugs, proteins or peptides, lipids, nucleic acids, carbohydrates, etc.) which may be the same or different. Such molecules and/or compounds or combinations of such molecules and/or compounds can also be bound through recombination to various structures or supports according to the invention.

65 Claims, 34 Drawing Sheets

U.S. PATENT DOCUMENTS

| | | | |
|---|---|---|---|
| 5,801,030 A | 9/1998 | McVey et al. | |
| 5,814,300 A * | 9/1998 | Scott et al. | 424/9.1 |
| 5,830,707 A | 11/1998 | Bushman | 435/69.7 |
| 5,837,242 A | 11/1998 | Holliger et al. | 424/136.1 |
| 5,837,458 A | 11/1998 | Minshull et al. | 435/6 |
| 5,843,772 A | 12/1998 | Devine et al. | 435/69.1 |
| 5,851,808 A | 12/1998 | Elledge et al. | 435/172.3 |
| 5,858,657 A | 1/1999 | Winter et al. | 435/6 |
| 5,871,907 A * | 2/1999 | Winter et al. | 435/6 |
| 5,874,259 A | 2/1999 | Szybalski | 435/91.1 |
| 5,888,732 A | 3/1999 | Hartley et al. | 435/6 |
| 5,910,438 A | 6/1999 | Bernard et al. | |
| 5,916,804 A | 6/1999 | Bushman | 435/325 |
| 5,919,676 A | 7/1999 | Graham et al. | 435/172.3 |
| 5,928,914 A | 7/1999 | Leboulch et al. | 435/172.3 |
| 5,981,177 A | 11/1999 | Demirjian et al. | |
| 5,989,872 A | 11/1999 | Luo et al. | 435/91.2 |
| 5,994,136 A | 11/1999 | Naldini et al. | |
| 6,010,884 A | 1/2000 | Griffiths et al. | 435/69.7 |
| 6,025,192 A | 2/2000 | Beach et al. | |
| 6,040,138 A | 3/2000 | Lockhart et al. | |
| 6,040,430 A | 3/2000 | Stewart | 530/358 |
| 6,063,627 A | 5/2000 | McVey et al. | 435/440 |
| 6,066,778 A | 5/2000 | Ginsburg et al. | |
| 6,080,576 A | 6/2000 | Zambrowicz et al. | |
| 6,110,735 A | 8/2000 | Chartier et al. | |
| 6,120,764 A | 9/2000 | Graham et al. | |
| 6,121,043 A | 9/2000 | Cochran et al. | |
| 6,140,087 A | 10/2000 | Graham et al. | |
| 6,143,557 A | 11/2000 | Hartley et al. | |
| 6,156,497 A | 12/2000 | Kaleko | |
| 6,165,782 A | 12/2000 | Naldini et al. | |
| 6,171,861 B1 | 1/2001 | Hartley et al. | 435/455 |
| 6,225,121 B1 | 5/2001 | Savakis et al. | |
| 6,228,646 B1 | 5/2001 | Hardy | |
| 6,262,341 B1 * | 7/2001 | Baszczynski et al. | 800/278 |
| 6,270,969 B1 | 8/2001 | Hartley et al. | |
| 6,271,436 B1 * | 8/2001 | Piedrahita et al. | 800/21 |
| 6,277,608 B1 * | 8/2001 | Hartley et al. | 435/91.4 |
| 6,281,000 B1 | 8/2001 | Chartier et al. | |
| 6,303,301 B1 | 10/2001 | Mack | |
| 6,309,822 B1 | 10/2001 | Fodor et al. | |
| 6,333,155 B1 | 12/2001 | Lockhart et al. | |
| 6,361,972 B1 | 3/2002 | Harrington et al. | |
| 6,365,377 B1 | 4/2002 | Patten et al. | 435/91.1 |
| 6,410,266 B1 | 6/2002 | Harrington et al. | |
| 6,410,317 B1 | 6/2002 | Farmer | |
| 6,436,707 B1 | 8/2002 | Zambrowicz et al. | |
| 6,544,790 B1 | 4/2003 | Sabatini | |
| 6,576,463 B1 | 6/2003 | Kasahara et al. | |
| 6,720,140 B1 | 4/2004 | Hartley et al. | |
| 6,964,861 B1 | 11/2005 | Gerard et al. | |
| 2002/0007051 A1 | 1/2002 | Cheo et al. | |
| 2002/0068290 A1 | 6/2002 | Yarovinsky | |
| 2002/0094574 A1 | 7/2002 | Hartley et al. | |
| 2002/0106797 A1 | 8/2002 | Miles et al. | |
| 2002/0162126 A1 | 10/2002 | Beach et al. | |
| 2002/0172997 A1 | 11/2002 | Hartley et al. | |
| 2002/0182731 A1 | 12/2002 | Ji et al. | |
| 2002/0192819 A1 | 12/2002 | Hartley et al. | |
| 2003/0022179 A1 | 1/2003 | Chesnut et al. | |
| 2003/0027289 A1 | 2/2003 | Farmer | |
| 2003/0027337 A1 | 2/2003 | Droge et al. | |
| 2003/0054552 A1 | 3/2003 | Hartley et al. | |
| 2003/0054555 A1 | 3/2003 | Farmer et al. | |
| 2003/0059900 A1 | 3/2003 | Farmer | |
| 2003/0064515 A1 | 4/2003 | Hartley et al. | |
| 2003/0068799 A1 | 4/2003 | Hartley et al. | |
| 2003/0077804 A1 | 4/2003 | Byrd et al. | |
| 2003/0100110 A1 | 5/2003 | Hartley et al. | |
| 2003/0124555 A1 | 7/2003 | Brasch et al. | |
| 2003/0135888 A1 | 7/2003 | Zhu et al. | |
| 2003/0153055 A1 | 8/2003 | Miles et al. | |
| 2003/0157662 A1 | 8/2003 | Gerard et al. | |
| 2003/0157716 A1 | 8/2003 | Hartley et al. | |
| 2003/0175772 A1 | 9/2003 | Wang | |
| 2003/0175970 A1 | 9/2003 | Hartley et al. | |
| 2003/0176644 A1 | 9/2003 | Byrd et al. | |
| 2003/0186233 A1 | 10/2003 | Chesnut et al. | |
| 2003/0220249 A1 | 11/2003 | Hackett et al. | |
| 2004/0040053 A1 | 2/2004 | Nomura et al. | |
| 2004/0053412 A1 | 3/2004 | Hartley et al. | |
| 2004/0063207 A1 | 4/2004 | Hartley et al. | |
| 2004/0171156 A1 | 9/2004 | Hartley et al. | |
| 2004/0171157 A1 | 9/2004 | Hartley et al. | |
| 2004/0219516 A1 | 11/2004 | Bennett et al. | |
| 2004/0229229 A1 | 11/2004 | Cheo et al. | |
| 2004/0253631 A1 | 12/2004 | Hartley et al. | |
| 2004/0265863 A1 | 12/2004 | Chestnut et al. | |
| 2005/0009091 A1 | 1/2005 | Hartley et al. | |
| 2005/0069929 A1 | 3/2005 | Chestnut et al. | |
| 2005/0095615 A1 | 5/2005 | Welch et al. | |
| 2005/0176065 A1 | 8/2005 | Hanson | |

FOREIGN PATENT DOCUMENTS

| | | |
|---|---|---|
| EP | 0 160 571 A2 | 11/1985 |
| EP | 0 220 009 | 4/1987 |
| EP | 0 300 422 | 1/1989 |
| EP | 0 427 074 A2 | 5/1991 |
| EP | 1 035 208 | 9/2000 |
| FR | 2 670 502 | 6/1992 |
| WO | WO90/11375 | 10/1990 |
| WO | WO91/02801 | 3/1991 |
| WO | WO91/09957 | 7/1991 |
| WO | WO91/16427 | 10/1991 |
| WO | WO92/10577 | 6/1992 |
| WO | WO92/15694 | 9/1992 |
| WO | WO92/20791 | 11/1992 |
| WO | WO92/22650 | 12/1992 |
| WO | WO93/15191 | 8/1993 |
| WO | WO93/19172 | 9/1993 |
| WO | WO94/03624 | 2/1994 |
| WO | WO94/09127 | 4/1994 |
| WO | WO94/17176 | 8/1994 |
| WO | WO94/18333 | 8/1994 |
| WO | WO94/20604 | 9/1994 |
| WO | WO95/00555 | 1/1995 |
| WO | WO96/04393 | 2/1996 |
| WO | WO 96/19497 | 6/1996 |
| WO | WO 96/23904 | 8/1996 |
| WO | WO96/30498 | 10/1996 |
| WO | WO96/40722 | 12/1996 |
| WO | WO96/40724 | 12/1996 |
| WO | WO97/06265 | 2/1997 |
| WO | WO97/09436 | 3/1997 |
| WO | WO97/25446 | 7/1997 |
| WO | WO97/32481 | 9/1997 |
| WO | WO 97/47758 | 12/1997 |
| WO | WO98/10086 | 3/1998 |
| WO | WO 98/38326 | 9/1998 |
| WO | WO98/53056 | 11/1998 |
| WO | WO99/10488 | 3/1999 |
| WO | WO99/21977 | 5/1999 |
| WO | WO99/25851 | 5/1999 |
| WO | WO 01/11058 | 9/1999 |
| WO | WO99/55851 | 11/1999 |
| WO | WO 00/12687 | 3/2000 |
| WO | WO 00/29000 | 5/2000 |
| WO | WO 00/52027 | 9/2000 |
| WO | WO 00/52141 | 9/2000 |
| WO | WO 00/60091 | 10/2000 |
| WO | WO 01/05961 A1 | 1/2001 |
| WO | WO 01/07572 A2 | 2/2001 |

| | | |
|---|---|---|
| WO | WO 01/11058 A1 | 2/2001 |
| WO | WO 01/25466 | 4/2001 |
| WO | WO 01/31039 | 5/2001 |
| WO | WO 01/42509 | 6/2001 |
| WO | WO 01/62892 A2 | 8/2001 |
| WO | WO 01/68836 | 9/2001 |
| WO | WO 02/00875 | 1/2002 |
| WO | WO 02/05294 A1 | 1/2002 |
| WO | WO 02/08391 | 1/2002 |
| WO | WO 02/16594 | 2/2002 |
| WO | WO 02/46372 | 6/2002 |
| WO | WO 02/61034 | 8/2002 |
| WO | WO 02/62957 | 8/2002 |
| WO | WO 02/86144 | 10/2002 |
| WO | WO 02/95055 | 11/2002 |
| WO | WO 03/25161 | 3/2003 |
| WO | WO 03/044207 | 5/2003 |
| WO | WO 04/009768 | 1/2004 |
| WO | WO 04/013290 | 2/2004 |
| WO | WO 05/012487 | 2/2005 |
| WO | WO 05/014796 | 2/2005 |

OTHER PUBLICATIONS

Abremski, K., and Hoess, R., "Bacteriophage P1 Site-specific Recombination—Purification and Properties of the Cre Recombinase Protein," *J. Biol. Chem.* 259:1509-1514, American Society for Biochemistry and Molecular Biology, Inc., Baltimore, MD (1984).

Abremski, K., et al., "Bacteriophage P1 Cre-*loxP* Site-specific Recombination: Site-specific DNA Topoisomerase Activity of the Cre Recombination Protein," *J. Biol. Chem.* 261(1):391-396, American Society for Biochemistry and Molecular Biology, Inc., Baltimore, MD (1986).

Abremski, K., et al., "Studies on the Properties of P1 Site-Specific Recombination: Evidence for Topologically Unlinked Products Following Recombination," *Cell* 32:1301-1311, Cell Press, Cambridge, MA (1993).

Adams, D.E., et al., "Cre-*lox* Recombination in *Escherichia coli* Cells: Mechanistic Differences from the *in Vitro* Reaction," *J. Mol. Biol.* 226:661-673, Academic Press, Inc., New York, NY (1992).

Andrews, B.J., et al., "The FLP Recombinase of the 2μ Circle DNA of Yeast: Interaction with Its Target Sequences," *Cell* 40:795-803, Cell Press, Cambridge, MA (1985).

Andrews, B.J., et al., "Interaction of the FLP Recombinase of the *Saccharomyces cerevisiae* 2μm Plasmid with Mutated Target Sequences," *Mol. Cell. Biol.* 6:2482-2489, American Society for Microbiology, Washington, D.C. (1986).

Anton, M., and Graham, F.L., "Site-Specific Recombination Mediated by an Adenovirus Vector Expressing the Cre Recombinase Protein: a Molecular Switch for Control of Gene Expression," *J. Virol.* 69:4600-4606, American Society for Microbiology, Washington, D.C. (1995).

Araki, H., et al., "Site-specific Recombinase, R, Encoded by Yeast Plasmid pSR1," *J. Mol. Biol.* 225:25-37, Academic Press, Inc., New York, NY (1992).

Argos, P., et al., "The integrase family of site-specific recombinases: regional similarities and global diversity," *EMBO J.* 5(2):433-440, IRL Press Limited, Oxford, England (1986).

Astumian, J.H., et al., "Site-specific recombination between cloned attP and attB sites from the Haemophilus influenza bacteriophage HP1 propagated in recombination deficient *Escherichia coli*," *J. Bacteriol.* 171:1747-1750, American Society for Microbiology, Washington, D.C. (1989).

Atlung, T., et al., "A versatile method for integration of genes and gene fusions into the λ attachment site of *Escherichia coli*," *Gene* 107:11-17, Elsevier/North-Holland, Netherlands (1991).

Ausubel, F.M., et al., "Maps of Plasmids pBR322 and pUC19," in *Current Protocols in Molecular Biology*, John Wiley & Sons, Inc., Boston, MA, (1995).

Ausubel, F.M., et al., "Mutagenesis by the Polymerase Chain reaction," in: *Current Protocols in Molecular Biology*, John Wiley & Sons, Inc., Boston, MA, pp. 8.5.1-8.5.9 (1995).

Babineau, D. et al., "The FLP Protein of the 2-micron Plasmid of Yeast," *J. Biol. Chem.* 260:12313-12391, American Society for Biochemistry and Molecular Biology, Inc., Baltimore, MD (1985).

Balakrishnan, R., et al., "A gene cassette for adapting *Escherichia coli* strains as hosts for *att*-Int-mediated rearrangement and $p_L$ expression vectors," *Gene* 138:101-104, Elsevier/North-Holland, Netherlands (Jan. 1994).

Bayley, C.C., et al., "Exchange of gene activity in transgenic plants catalyzed by the Cre-*lox* site specific recombination system," *Plant Mol. Biol.* 18: 353-361, Dordrecht Kluwer Academic, Boston, MA (1992).

Bethke, B., and Sauer, B., "Segmental genomic replacement by Cre-mediated recombination: genotoxic stress activation of the p53 promoter in single-copy transformants," *Nucl. Acids Res.* 25:2828-2834, Oxford University Press, Oxford, England (1997).

Bernard, P., and Couturier, M., "Cell Killing by the F plasmid Ccdb Protein Involves Poisoning of DNA-topoisomerase II Complexes," *J. Mol. Biol.* 226:735-745, Academic Press, Inc., New York, NY (1992).

Bernard, P., et al., "Positive Selection of vectors using the F plasmid ccd B killer gene," *Gene* 148:71-74, Elsevier Science Publishers B.V., Amsterdam, Netherlands (1994).

Betz, U.A.K., et al., "Bypass of lethality with mosaic mice generated by Cre-*loxP*-mediated recombination," *Curr. Biol.* 6:1307-1316, Current Biology Ltd., London, England (Oct. 1996).

Bhandari, P. and Gowrishankar, J., "An *Escherichia coli* host strain useful for efficient overproduction of cloned gene products with NaCl as the inducer," *J. Bacteriol.* 179:4403-4406, American Society for Microbiology, Washington, D.C. (Jul. 1997).

Black, L.W., "In vitro packaging into phage T4 particles and specific recircularization of phage lambda DNAs," *Gene* 46:97-101, Elsevier/North-Holland, Netherlands (1986).

Bloch, C.A., et al., "Purification of *Escherichia coli* Chromosomal Segments without Cloning," *Biochem. Biophys. Res. Comm.* 223:104-111, Academic Press, Inc., New York, NY (1996).

Bochner, B. R., et al., "Positive Selection for Loss of Tetracycline Resistance," *J. Bacteriol.* 143:926-933, American Society for Microbiology, Washington, D.C. (1980).

Boyd, A. C., "Turbo cloning: a fast, efficient method for cloning PCR products and other blunt-ended DNA fragments into plasmids," *Nucl. Acids Res.* 21(4):817-821, Oxford University Press, Oxford, England (1993).

Broach, J. R., et al., "Recombination within the Yeast Plasmid 2μ Circle is Site-Specific," *Cell* 29:227-234, Cell Press, Cambridge, MA (1982).

Brunelli, J. P. and Pall, M. L., "A Series of Yeast/*Escherichia coli* λ Expression Vectors Designed for Directional Cloning of cDNAs and *cre/lox*-Mediated Plasmid Excision," *Yeast* 9:1309-1318, John Wiley, Chichester, NY (1993).

Brunelli, J.P., and Pall, M.L., "Lambda/Plasmid Vector Construction by *In Vivo cre/lox*-Mediated Recombination," *BioTechniques* 16(6):1061-1064, Eaton Publishing Company, Natick, MA (Jun. 1994).

Bubeck, P. et al., "Rapid cloning by homologous recombination *in vivo*," *Nucl. Acids Res.* 21:3601-3602, Oxford University Press, Oxford, England (1993).

Buchholz, F., et al., "A simple assay to determine the functionality of Cre or FLP recombination targets in genomic manipulation constructs," *Nucl. Acids Res.* 24(15):3118-3119, Oxford University Press, Oxford, England (1996).

Buchholz, F., et al., "Different thermostabilities of FLP and Cre recombinases: implications for applied site-specific recombination," *Nucl. Acids Res.* 24(21):4256-4262, Oxford University Press, Oxford, England (1996).

Bushman, W., et al., "Control of Directionality in Lambda Site Specific Recombination," *Science* 230:906-911, Association for the Advancement of Science, Washington D.C. (1985).

Campbell, A. M., "Chromosomal Insertion Sites for Phages and Plasmids," *J. Bacteriol.* 174(23):7495-7499, American Society for Microbiology, Washington, D.C. (1992).

Chapin, S.J., et al., "Differential expression of alternatively spliced forms of MAP4: a repertoire of structurally different microtubule-binding domains," *Biochem.* 34:2289-2301, American Chemical Society, Washington D.C. (1995).

Chatterjee, P.K., and Coren, J.S., "Isolating large nested deletions in bacterial and P1 artificial chromosomes by *in vivo* P1 packaging of products o Cre-catalyzed recombination between the endogenous and a transposed *loxP* site," *Nucl. Acids Res.* 25:2205-2212, Oxford University Press, Oxford, England (1997).

Cox, M.M., "The FLP protein of the yeast 2-μm plasmid: Expression of a eukaryotic genetic recombination system in *Escherichia coli*," *Proc. Natl. Acad. Sci. USA* 80:4223-4227, National Academy of Sciences of the USA, Washington, D.C. (1983).

Craig, N.L. and Nash, H.A., "The Mechanism of Phage λ Site-Specific Recombination: Site-Specific Breakage of DNA by Int Topoisomerase," *Cell* 35:795-803, Cell Press, Cambridge, MA (1983).

Dale, E.C. and Ow, D.W., "Intra- and intermolecular site-specific recombination in plant cells mediated by bacteriophage P1 recombinase," *Gene* 91:79-85, Elsevier/North-Holland, Netherlands (1990).

Dale, E.C. and Ow, D.W., "Gene transfer with subsequent removal of the selection gene from the host genome," *Proc. Natl. Acad. Sci. USA* 88:10558-10562, National Academy of Sciences of the USA, Washington, D.C. (1991).

Dang, D.T. and Perrimon, N., "Use of a Yeast Site-Specific Recombinase to Generate Embryonic Mosaics in *Drosophila*," *Develop. Genetics* 13:367-375, Wiley-Liss, Inc., New York, NY (1992).

Degryse, E., "In vivo intermolecular recombination in *Escherichia coli*: application to plasmid constructions," *Gene* 170:45-50, Elsevier/North-Holland, Netherlands (1996).

Devine, S. E., and Boeke, J.D., "Efficient integration of artificial transposons into plasmid targets *in vitro*: a useful tool for DNA mapping, sequencing and genetic analysis," *Nucl. Acids Res.* 22(18):3765-3772, Oxford University Press, Oxford, England (Sep. 1994).

Diederich, L., et al., "New Cloning Vectors for Integration into the λ Attachment Site *attB* of the *Escherichia coli* Chromosome," *Plasmid* 28:14-24, Academic Press, New York, NY (1992).

Dymecki, S. M., "A modular set of *Flp, FRT* and *lacZ* fusion vectors for manipulating genes by site-specific recombination," *Gene* 171:197-201, Elsevier/North-Holland, Netherlands (Jun. 1996).

Elledge, S. J., et al., "λYES: A Multifunctional cDNA expression vector for the isolation of genes by complementation of yeast and *Escherichia coli* mutations," *Proc. Natl. Acad. Sci. USA* 88:1731-1735, National Academy of Sciences of the USA, Washington, D.C. (1991).

Feil, R., et al., "Regulation of Cre Recombinase Activity by Mutated Estrogen Receptor Ligand-Binding Domains," *Biochem. Biophys. Res. Comm.* 237:752-757, Academic Press, Inc., New York, NY (1997).

Ferguson, J., et al., "Construction and characterization of three yeast-*Escherichia coli* shuttle vectors designed for rapid subcloning of yeast genes on small DNA fragments," *Gene* 16:191-197, Elsevier/North-Holland, Netherlands (1981).

Fiering, S., et al., "An "in-out" strategy using gene targeting and FLP recombinase for the functional dissection of complex DNA regulatory elements: Analysis of the β-globin locus control region," *Proc. Natl. Acad. Sci. USA* 90:8469-8473, National Academy of Sciences of the USA, Washington, D.C. (1993).

Filutowicz, M., et al., "Purification of the *Escherichia coli* integration host factor (IHF) in one chromatographic step," *Gene* 147:149-150, Elsevier/North-Holland, Netherlands (Sep. 1994).

Francia, M.V., and Lobo, J.M.G., "Gene Integration in the *Escherichia coli* Chromosome Mediated by Tn*21* Integrase (Int21)," *J. Bacteriol.* 178:894-898, American Society for Microbiology, Washington, D.C. (Feb. 1996).

Fukushige, S. and Sauer, B., "Genomic targeting with a positive-selection *lox* integration vector allows highly reproducible gene expression in mammalian cells," *Proc. Natl. Acad. Sci. USA* 89:7905-7909, National Academy of Sciences of the USA, Washington, D.C. (1992).

Geoffroy, F., et al., "A new phage display system to construct multicombinatorial libraries of very large antibody repertoires," *Gene* 151:109-113, Elsevier/North-Holland, Netherlands (Dec. 1994).

Glasgow, A.C., et al., "DNA-binding Properties of the Hin Recombinase," *J. Biol. Chem.* 264:10072-10082, American Society for Biochemistry and Molecular Biology, Inc., Baltimore, MD (1989).

Golic, K. G. and Lindquist, S., "The FLP Recombinase of Yeast Catalyzes Site-Specific Recombination in the Drosophila Genome," *Cell* 59:499-509, Cell Press, Cambridge, MA (1989).

Gu, H., et al., "Deletion of a DNA Polymerase β Gene Segment in T Cells Using Cell Type-Specific Gene Targeting," *Science* 265:103-106, Association for the Advancement of Science, Washington D.C. (1994).

Guo, F., et al., "Asymmetric DNA bending in the Cre-*loxP* site-specific recombination synapse," *Proc. Natl. Acad. Sci. USA* 96:7143-7148, National Academy of Sciences of the USA, Washington, D.C. (1999).

Hardy, S., et al., "Construction of Adenovirus Vectors through Cre-*lox* Recombination," *J. Virol.* 71(3):1842-1849, American Society for Microbiology, Washington, D.C. (1997).

Hasan, N., and Szybalski, W., "Control of cloned gene expression by promoter inversion in vivo: construction of improved vectors with a multiple cloning site and the $p_{tac}$ promoter," *Gene* 56:145-151, Elsevier/North-Holland, Netherlands (1987).

Hasan, N., et al., "*Escherichia coli* genome targeting, I. Cre-*lox*-mediated in vitro generation of ori⁻ plasmids and their in vivo chromosomal integration and retrieval," *Gene* 150:51-56, Elsevier/North-Holland, Netherlands (Dec. 1994).

Hashimoto-Gotoh, T., et al., "Improved vector, pHSG664, for direct streptomycin-resistance selection: cDNA cloning with G:C-tailing procedure and subcloning of double-digested DNA fragments," *Gene* 41:125-128, Elsevier/North-Holland, Netherlands (1986).

Hoekstra, M. F., et al., "Shuttle Mutagenesis: Bacterial Transposons for Genetic Manipulations in Yeast," *Meth. Enzymol.* 194:329-342, Academic Press Inc., New York, NY (1991).

Hoess, R.H., et al., "P1 site-specific recombination: Nucleotide sequence of the recombining sites," *Proc. Natl. Acad. Sci. USA* 79:3398-3402, National Academy of Sciences of the USA, Washington, D.C. (1982).

Hoess, R.H., et al., "Mechanism of Strand Cleavage and Exchange in the Cre-*lox* Site-specific Recombination System," *J. Mol. Biol.* 181:351-362, Academic Press, Inc., New York, NY (1985).

Hoess, R., et al., "Formation of small circular DNA molecules via an in vitro site-specific recombination system" *Gene* 40:325-329, Elsevier/North-Holland, Netherlands (1985).

Hoess, R. H., et al., "The role of the *loxP* spacer region in P1 site-specific recombination," *Nucl. Acids Res.* 14(5):2287-2300, Oxford University Press, Oxford, England (1986).

Hoess, R. H., and Abremski, K., "The Cre-*lox* Recombination System," in: *Nucleic Acids and Molecular Biology*, vol. 4, ed. by Eckstein, F. and D. M. J. Lilley, Springer-Verlag, Berlin, pp. 99-109 (1990).

Hoogenboom, H.R., et al., "Multi-subunit proteins on the surface of filamentous phage: methodologies for displaying antibody (Fab) heavy and light chains," *Nucl. Acids Res.* 19:4133-4137, Oxford University Press, Oxford, England (1991).

Holt, C.L., and May, G.S., "A novel phage λ replacement Cre-*lox* vector that has automatic subcloning capabilities," *Gene* 133:95-97, Elsevier/North-Holland, Netherlands (1993).

Jaffé, et al., "Effects of the *ccd* Function of the F Plasmid on Bacterial Growth," *J. Bacteriol.* 163:841-849, American Society for Microbiology, Washington, D.C. (1985).

Kanaar, R., et al., "Gin-Mediated Recombination of Catenated and Knotted DNA Substrates: Implications for the Mechanism of Interaction Between *Cis*-Acting Sites," *Cell* 58:147-159, Cell Press, Cambridge, MA (1989).

Katz, L., et al., "Site-specific Recombination in *Esherichia coli* between the *att* sites of plasmid pSE211 from *Saccharopolyspora erythraea*," *Mol. Gen. Genet.* 227:155-159, Springer-Verlag, New York, NY (1991).

Kilby, N.J., et al., "Site-specific recombinases: tools for genome engineering," *Trends Genet.* 9:413-421, Elsevier Science Publishers Ltd., Cambridge, England (1993).

Kim, S., et al., "Lambda Int Protein Bridges Between Higher Complexes at Two Distant Chromosomal Loci *att*L and *att*R," *Science* 256:198-203, Association for the Advancement of Science, Washington D.C. (1992).

Kozak, M., "Comparison of Initiation of Protein Synthesis in Prokaryotes, Eucaryotes, and Organelles," *Microbiol. Rev.* 47:1-45, American Society For Microbiology, Washington, D.C. (1983).

Kozak, M., "An analysis of 5'-noncoding sequences from 699 vertebrate messenger RNAs," *Nucl. Acids res.* 15:8125-8132, Oxford University Press, Oxford, England (1987).

Kozak, M., "Structural features in eukaryotic mRNAs that modulate the initiation of translation," *J. Biol. Chem* 266:19867-19870, American Society for Biochemistry and Molecular Biology, Inc., Baltimore, MD (1991).

Kühn, R., et al., "Inducible Gene Targeting in Mice," *Science* 269:1427-1429, Association for the Advancement of Science, Washington D.C. (Sep. 1995).

Lafontaine, D., and Tollervey, D., "One-step PCR mediated strategy for the construction of conditionally expressed and epitope tagged yeast proteins," *Nucl. Acids Res.* 24:2469-2472, Oxford University Press, Oxford, England (1996).

Lakso, M., et al., "Targeted oncogene activation by site-specific recombination in transgenic mice," *Proc. Natl. Acad. Sci. USA* 89:6232-6236, National Academy of Sciences of the USA, Washington, D.C. (1992).

Lander, E.S., "The New Genomics: Global Views of Biology," *Science* 274:536-539, Association for the Advancement of Science, Washington D.C. (Oct. 1996).

Landy, A., "Dynamic, Structural, and Regulatory Aspects of λ Site-Specific Recombination," *Annu. Rev. Biochem.* 58:913-949, American Chemical Society, Washington D.C. (1989).

Landy, A., "Mechanistic and structural complexity in the site-specific recombination pathways of Int and FLP," *Curr. Op. Genet. Develop.* 3:699-707, Current Biology Ltd., London, England (1993).

Lebreton, B., et al., "Mutations That Improve the Binding of Yeast FLP Recombinase to Its Substrate," *Genetics* 118:393-400, Genetics Society of America, Baltimore, MD (1988).

Lee, E.C., et al., "Genetic Analysis of *Escherichia coli* Integration Host Factor Interactions with Its Bacteriophage λ H' Recognition Site," *J. Bacteriol.* 173:609-617, American Society for Microbiology, Washington, D.C. (1991).

Leong, J.M., et al., "Generation of single base-pair deletions, insertions, and substitutions by a site-specific recombination system," *Proc. Natl. Acad. Sci. USA* 82:6990-6994, National Academy of Sciences of the USA, Washington, D.C. (1985).

Liu, Q., et al., "The univector plasmid-fusion system, a method for rapid construction of recombinant DNA without restriction enzymes," *Curr. Biol.* 8:1300-1309, Current Biology Ltd., London, England (1998).

Lorbach, E. et al., "Site-specific Recombination in Human Cells Catalyzed by Phage λ Integrase Mutants," *J. Mol. Biol.* 296:1175-1181, Academic Press, Inc., New York, NY (Mar. 2000).

Luckow, V. A., et al., "Efficient Generation of Infectious Recombinant Baculoviruses by Site-Specific Transposon-Mediated Insertion of Foreign Genes into a Baculovirus Genome Propagated in *Escherichia coli*," *J. Virol.* 67(8):4566-4579, American Society for Microbiology, Washington, D.C. (1993).

Maeser, S., and Kahmann, R., "The Gin recombinase of phage Mu can catalyze site-specific recombination in plant protoplasts," *Mol. Gen. Genet.* 230:170-176, Springer-Verlag, New York, NY (1991).

Matsuzaki, H., et al., "Chromosome Engineering in *Saccharomyces cerevisiae* by Using a Site-Specific Recombination System of a Yeast Plasmid," *J. Bacteriol.* 172:610-618, American Society for Microbiology, Washington, D.C. (1990).

Mahillon, J., et al., "IS*231* and other *Bacillus thuringiensis* transposable elements: a review," *Genetica* 93:13-26, Dordrecht Kluwer Academic Publishers (Nov. 1994).

McCarthy, J.E. and Brimacombe, R., "Prokaryotic translation: the interactive pathway leading to initiation," *Trends Genet.* 10:402-407, Elsevier Science Publishers Ltd., Cambridge, England (Nov. 1994).

Medberry, S.L., et al., "Intra-chromosomal rearrangements generated by Cre-*lox* site-specific recombination," *Nucl. Acids Res.* 23:485-490, Oxford University Press, Oxford, England (1995).

Miki, T. et al., "Control of Segregation of Chromosomal DNA by Sex Factor F in *Escherichia coli*. Mutants of DNA Gyrase Subunit A Suppress *letD* (*ccdB*) Product Growth Inhibition," *J. Mol. Biol.* 225:39-52, Academic Press, Inc., New York, NY (1992).

Mizuuchi, K., and Mizuuchi, M., "Integrative Recombination of Bacteriophage λ: In Vitro Study of the Intermolecular Reaction," *Cold Spring Harb. Symp. Quant. Biol.* 43:1111-1114, Cold Spring Harbor Laboratory Press, Cold Spring Harbor, NY (1979).

Mizuuchi, M. and Mizuuchi, K., "The extent of DNA sequence required for a functional bacterial attachment site of phage lambda," *Nucl. Acids Res.* 13:1193-1208, Oxford University Press, Oxford, England (1985).

Mozo, T. and Hooykaas, P. J. J., "Design of a novel system for the construction of vectors for Agrobacterium-mediated plant transformation," *Mol. Gen. Genet* 236:1-7, Springer-Verlag, New York, NY (1992).

Mullins, L.J., et al., "Efficient Cre-lox linearisation of BACs: applications to physical mapping and generation of transgenic animals," *Nucl. Acids Res.* 25(12):2539-2540, Oxford University Press, Oxford, England (1997).

Nagaraja, R. and Weisberg, R. A., "Specificity Determinants in the Attachment Sites of Bacteriophages HK022 and λ," *J. Bacteriol.* 172:6540-6550, American Society for Microbiology, Washington, D.C. (1990).

Nash, H.A., "Integrative Recombination of Bacteriophage Lambda DNA *In Vitro*," *Proc. Natl. Acad. Sci. USA* 72:1072-1076, National Academy of Sciences of the USA, Washington, D.C. (1975).

Nash, H.A., and Robertson, C.A., "Purification and properties of the *Escherichia coli* protein factor required for lambda integrative recombination," *J. Biol. Chem.* 256:9246-9253, American Society for Biochemistry and Molecular Biology, Inc., Baltimore, MD (1981).

Nash, H. A., "Purification and Properties of the Bacteriophage Lambda Int Protein," *Meth. Enzymol.* 100:210-216, Academic Press Inc., New York, NY (1983).

Nash, H. A., et al., "Role of homology in site-specific recombination of bacteriophage λ: Evidence against joining of cohesive ends," *Proc. Natl. Acad. Sci. USA* 84:4049-4053, National Academy of Sciences of the USA, Washington, D.C. (1987).

Nash, H. and C.A. Robertson, "Heteroduplex substrates for bacteriophage lambda site-specific recombination: cleavage and strand transfer products," *EMBO J.* 8:3523-3533, IRL Press Limited, Oxford, England (1989).

Nash, H.A., "Bending and supercoiling of DNA at the attachment site of bacteriophage λ," *Trends Biochem. Sci* 15:222-227, International Union of Biochemistry and Elsevier Trends Journal, Cambridge, England (1990).

Numrych, T. E., et al., "A comparison of the effects of single-base and triple-base changes in the integrase arm-type binding sites on the site-specific recombination of bacteriophage lambda," *Nucl. Acids Res.* 18:3953-3959, Oxford University Press, Oxford, England (1990).

Numrych, T.E., et al., "Characterization of the bacteriophage lambda excisionase (Xis) protein: the C-terminus is required for Xis-integrase cooperativity but not for DNA binding," *EMBO J.* 11(10):3797-3806, IRL Press Limited, Oxford, England (1992).

Nunes-Düby, S.E., et al., "Half-*att* Site Substrates Reveal that Homology Independence and Minimal Protein Requirements for Productive Synapsis in λ Excisive Recombination," *Cell* 59:197-206, Cell Press, Cambridge, MA (1989).

Nunes-Düby, et al., "Similarities and differences among 105 members of the Int family of site-specific recombinases," *Nucl. Acids Res.* 26:391-406, Oxford University Press, Oxford, England (1998).

Oberto, J., et al., "A segment of the phage HK022 chromosome is a mosaic of other lambdoid chromosomes," *Nucl. Acids Res.* 22(3):354-356, Oxford University Press, Oxford, England (Feb. 1994).

Oliner, J.D., et al., "*In vivo* cloning of PCR products in *E. coli*," *Nucl. Acids Res.* 21:5192-5197, Oxford University Press, Oxford, England (1993).

Orban, P. C., et al., "Tissue- and site-specific DNA recombination in transgenic mice," *Proc. Natl. Acad. Sci. USA* 89:6861-6865, National Academy of Sciences of the USA, Washington, D.C. (1992).

Osborne, B.I., et al., "A system for insertional mutagenesis and chromosomal rearrangement using the Ds transposon and Cre-*lox*," *Plant J.* 7:687-701, Oxford Bios Scientific Publishers And Blackwell Scientific Publications In Association With The Society For Experimental Biology, Oxford, England (1995).

Padgett, K. A. and Sorge, J. A., "Creating seamless junctions independent of restriction sites in PCR cloning," *Gene* 168:31-35, Elsevier/North-Holland, Netherlands (Feb. 1996).

Palazzolo, M. J., et al., "Phage lambda cDNA cloning vectors for subtractive hybridization, fusion-protein synthesis and Cre-*loxP* automatic plasmid subcloning," *Gene* 88:25-36, Elsevier/North-Holland, Netherlands (1990).

Pan, G., et al., "Ligation of Synthetic Activated DNA Substrates by Site-specific Recombinases and Topoisomerase I," *J. Biol. Chem.* 268(5):3683-3689, American Society for Biochemistry and Molecular Biology, Inc., Baltimore, MD (1993).

Parks, R.J., and Graham, FL., "A Helper-Dependent System for Adenovirus Vector Production Helps Define a Lower Limit for Efficient DNA Packaging," *J. Virol.* 71(4):3293-3298, American Society for Microbiology, Washington, D.C. (1997).

Peakman, T. C., et al., "Highly efficient generation of recombinant baculoviruses by enzymatically mediated site-specific *in vitro* recombination," *Nucl. Acids Res.* 20:495-500, Oxford University Press, Oxford, England (1992).

Peredelchuk, M.Y., and Bennett, G.N., "A method for construction of *E. coli* strains with multiple DNA insertions in the chromosome," *Gene* 187:231-238, Elsevier/North-Holland, Netherlands (1997).

Pichel, J. G., et al., "Timing of SV40 oncogene activation by site-specific recombination determines subsequent tumor progression during murine lens development," *Gene* 8:3333-3342, Elsevier/North-Holland, Netherlands (1993).

Pierce, J. C., et al., "A positive selection vector for cloning high molecular weight DNA by the bacteriophage P1 system: Improved cloning efficacy," *Proc. Natl. Acad. Sci. USA* 89:2056-2060, National Academy of Sciences of the USA, Washington, D.C. (1992).

Podhajska, A. J., et al., "Control of cloned gene expression by promoter inversion in vivo: construction of the heat-pulse-activated *att-nutL-p-att-N* module," *Gene* 40:163-168, Elsevier/North Holland, Netherlands (1985).

Pósfai, G., et al., "*In vivo* excision and amplification of large segments of the *Escherichia coli* genome," *Nucl. Acids Res.* 22(12):2392-2398, Oxford University Press, Oxford, England (Jun. 1994).

Prasad, P. V., et al., "Substrate Recognition by the 2 μm Circle Site-Specific Recombinase: Effect of Mutations within the Symmetry Elements of the Minimal Substrate," *Mol. Cell. Biol.* 6:4329-4334, American Society for Microbiology, Washington, D.C. (1986).

Qian, X., et al., "Reactions between Half- and Full-FLP Recombination Target Sites: A Model System for Analyzing Early Steps in FLP Protein-Mediated Site-Specific Recombination," *J. Biol. Chem* 267(11):7794-7805, American Society for Biochemistry and Molecular Biology, Inc., Baltimore, MD (1992).

Reed, R.R., "Transposon-Mediated Site-Specific Recombination: A Defined in Vitro System," *Cell* 25:713-719, Cell Press, Cambridge, MA (1981).

Reed, R.R. and N.D. Grindley, "Transposon-Mediated Site-Specific Recombination in Vitro: DNA Cleavage and Protein-DNA Linkage at the Recombination Site," *Cell.* 25:721-728, Cell Press, Cambridge, MA (1981).

Richet, E., et al., "The Interaction of Recombination Proteins with Supercoiled DNA: Defining the Role of Supercoiling in Lambda Integrative Recombination," *Cell* 46:1011-1021, Cell Press, Cambridge, MA (1986).

Richet, E., et al., "Synapsis of Attachment Sites during Lambda Integrative Recombination Involves Capture of a Naked DNA by a Protein-DNA Complex," *Cell* 52:9-17, Cell Press, Cambridge, MA (1988).

Sadowski, P., "Site-Specific Recombinases: Changing Partners and Doing the Twist," *J. Bacteriol.* 165(2):341-347, American Society for Microbiology, Washington, D.C. (1986).

Sadowski, P.D., "The Flp recombinase of the 2-microns plasmid of *Saccharomyces cerevisiae*," *Prog. Nucl. Acid Res. Mol. Biol.* 51:53-91, Academic Press, New York, NY (1995).

Sauer, B., et al., "Site-specific insertion of DNA into a pseudorabies virus vector," *Proc. Natl. Acad. Sci. USA* 84:9108-9112, National Academy of Sciences of the USA, Washington, D.C. (1987).

Sauer, B., "Functional Expression of the *cre-lox* Site-Specific Recombination System in the Yeast *Saccharomyces cerevisiae*," *Mol. Cell. Biol.* 7:2087-2096, American Society for Microbiology, Washington, D.C. (1987).

Sauer, B. and Henderson, N., "The cyclization of linear DNA in *Escherichia coli* by site-specific recombination," *Gene* 70:331-341, Elsevier/North-Holland, Netherlands (1988).

Sauer, B. and Henderson, N., "Cre-stimulated recombination at *loxP*-containing DNA sequences placed into the mammalian genome," *Nucl. Acids Res.* 17:147-161, Oxford University Press, Oxford, England (1989).

Sauer, B., "Manipulation of Transgenes by Site-Specific Recombination: Use of Cre Recombinase," *Meth. Enzymol.* 225:890-900, Academic Press Inc., New York, NY (1993).

Sauer, B., "Site-specific recombination: developments and applications," *Curr. Op. Biotechnol.* 5:521-527, Current Biology, Ltd., London, England (Oct. 1994).

Sauer, B., "Multiple Cre/*lox* recombination permits selective site-specific DNA targeting to both a natural and an engineered site in the yeast genome," *Nucl. Acids Res.* 24(23):4608-4613, Oxford University Press, Oxford, England (1996).

Sauer, B., "Inducible Gene Targeting in Mice Using the Cre/*lox* System," *Methods* 14:381-392, Academic Press, Inc., New York, NY (Apr. 1998).

Schindelhauer, D., and Cooke, H.J., "Efficient combination of large DNA *in vitro*: in gel site specific recombination (IGSSR) of PAC fragments containing α satellite DNA and the human HPRT gene locus," *Nucl. Acids Res.* 25(11):2241-2243, Oxford University Press, Oxford, England (1997).

Schlake, T., and Bode, J., "Use of Mutated FLP Recognition Target (FRT) Sites for the Exchange of Expression Cassettes at Defined Chromosomal Loci," *Biochem.* 33:12746-12751, American Chemical Society, Washington D.C. (Nov. 1994).

Segall, A. M. and Nash, H. A., "Synaptic intermediates in bacteriophage lambda site-specific recombination: integrase can align pairs of attachment sites," *EMBO J.* 12:4567-4576, IRL Press Limited, Oxford, England (1993).

Segall, A.M., and Nash, H.A., "Architectural flexibility in lambda site-specific recombination: three alternate conformations channel the *attL* site into three distinct pathways," *Genes to Cells* 1:453-463, Blackwell Science Ltd., Oxford, England (1996).

Senecoff, J.F., et al., "DNA Recognition by the FLP Recombinase of the Yeast 2μ Plasmid—A Mutational Analysis of the FLP Binding Site," *J. Mol. Biol.* 201:405-421, Academic Press, Inc., New York, NY (1988).

Sheffield, P. et al., "Overcoming Expression and Purification Problems of RhoGDI Using a Family of "Parallel" Expression Vectors," *Protein Expr. Purific.* 15:34-39, Academic Press, New York, NY (1999).

Shuman, S., "Recombination mediated by vaccinia virus DNA topoisomerase I in *Escherichia coli* is sequence specific," *Proc. Natl. Acad. Sci. USA* 88:10104-10108, National Academy of Sciences of the USA, Washington, D.C. (1991).

Sizemore, C., et al., "Quantitative analysis of Tn*10* Tet repressor binding to a complete set of *tet* operator mutants," *Nucl. Acids Res.* 18(10):2875-2880, Oxford University Press, Oxford, England (1990).

Smith, A. J. H., et al., "A site-directed chromosomal translocation induced in embryonic stem cells by Cre-*lox*P recombination," *Nat. Gen.* 9:376-385, Nature Publishing Co., New York, NY (Apr. 1995).

Snaith, M.R., et al., "Multiple cloning sites carrying *loxP* and *FRT* recognition sites for the Cre and Flp site-specific recombinases," *Gene* 166:173-174, Elsevier/North-Holland, Netherlands (Dec. 1995).

Spengler, S.J., et al., "The Stereostructure of Knots and Catenanes Produced by Phage λ Integrative Recombination: Implications for Mechanism and DNA Structure," *Cell* 42:325-334, Cell Press, Cambridge, MA (1985).

Sternberg, N., et al., "Site-specific Recombination and Its Role in the Life Cycle of Bacteriophage P1," *Cold Spring Harbor Symp. Quant. Biol. 45*:297-309, Cold Spring Harbor Laboratory Press, Cold Spring Harbor, NY (1981).

Sternberg, N., et al., "Bacteriophage P1 cre Gene and its Regulatory Region," *J. Mol. Biol. 187*:197-212, Academic Press, Inc., New York, NY (1986).

Sternberg, N., "Bacteriophage P1 cloning system for the isolation, amplification, and recovery of DNA fragments as large as 100 kilobase pairs," *Proc. Natl. Acad. Sci. USA 87*:103-107, National Academy of Sciences of the USA, Washington, D.C. (1990).

Storck, T., et al., "Rapid construction in yeast of complex targeting vectors for gene manipulation in the mouse," *Nucl. Acids Res. 24*:4594-4596, Oxford University Press, Oxford, England (1996).

Strathmann, M., et al., "Transposon-facilitated DNA sequencing," *Proc. Natl. Acad. Sci. USA 88*:1247-1250, National Academy of Sciences of the USA, Washington, D.C. (1991).

Thompson, J. F., et al., "Mutations in an Integration Host Factor-Binding Site: Effect on Lambda Site-Specific Recombination and Regulatory Implications," *J. Bacteriol. 168*:1343-1351, American Society for Microbiology, Washington, D.C. (1986).

Thompson, J.F., et al., "Helical-repeat dependence of integrative recombination of bacteriophage λ: Role of the *P1* and *H1* protein binding sites," *Proc. Natl. Acad. Sci. USA 85*:6323-6327, National Academy of Sciences of the USA, Washington, D.C. (1988).

Thorpe, H.M., and Smith, M.C.M., "*In vitro* site-specific integration of bacteriophage DNA catalyzed by a recombinase of the resolvase/invertase family," *Proc. Natl. Acad. Sci. USA 95*:5505-5510, National Academy of Sciences of the USA, Washington, D.C. (May 1998).

Tsurushita, N., et al., "Phage display vectors for in vivo recombination of immunoglobulin heavy and light chain genes to make large combinatorial libraries," *Gene 172*:59-63, Elsevier/North-Holland, Netherlands (1996).

Vanin, E.F., et al., "Development of High-Titer Retroviral Producer Cell Lines by Using Cre-Mediated Recombination," *J. Virol. 71*:7820-7826, American Society for Microbiology, Washington, D.C. (1997).

Waterhouse, P., et al., "Combinatorial infection and *in vivo* recombination: a strategy for making large phage antibody repertoires," *Nucl. Acids Res. 21*(9):2265-2266, Oxford University Press, Oxford, England (1993).

Wang, G., et al., "pDUAL: A transposon-based cosmid cloning vector for generating nested deletions and DNA sequencing templates *in vivo*," *Proc. Natl. Acad. Sci. USA 90*:7874-7878, National Academy of Sciences of the USA, Washington, D.C. (1993).

Wasserman, S.A., et al., "The helical repeat of double-stranded DNA varies as a function of catenation and supercoiling," *Nature 334*:448-450, Macmillan Publishers Ltd., London, England (1988).

Wierzbicki, A., et al., "A Mutational Analysis of the Bacteriophage P1 Recombinase Cre," *J. Mol. Biol. 195*:785-794, Academic Press, Inc., New York, NY (1987).

Weisberg, R. A., and Landy, A., "Site-specific Recombination in Phage Lambda," *in: "Lambda II,"* Hendrix, R. W. et al., eds., Cold Spring Harbor Laboratory Press, Cold Spring Harbor, N. Y. pp. 211-250 (1983).

Wild, J., et al., "A broad-host-range in vivo pop-out and amplification system for generating large quantities of 50- to 100-kb genomic fragments for direct DNA sequencing," *Gene 179*:181-188, Elsevier/North-Holland, Netherlands (1996).

Wild, J., et al., "Targeting and retrofitting pre-existing libraries of transposon insertions with *FRT* and *oriV* elements for in-vivo generation of large quantities of any genomic fragment," *Gene 223*:55-66, Elsevier/North-Holland, Netherlands (1998).

Winoto, A., et al., "Directional Control of Site-specific Recombination by Bacteriophage λ," *J. Mol. Biol. 192*:677-680, Academic Press, Inc., New York, NY (1986).

Yang, W., and Mizuuchi, K., "Site-specific recombination in plane view," *Structure 5*:1401-1406, Current Biology, London, England (1997).

Yanisch-Perron, C., et al., "Improved M13 phage cloning vectors and host strains: nucleotide sequences of the M13mp18 and pUC19 vectors," *Gene 33*:103-119, Elsevier/North-Holland, Netherlands (1985).

Yoon, Y.G., et al., "Cre/*loxP*-mediated in vivo excision of large segments from yeast genome and their amplification based on the 2 µm plasmid-derived system," *Gene 223*:67-76, Elsevier/North-Holland, Netherlands (1998).

York, D., et al., "Simple and efficient generation *in vitro* of nested deletions and inversions: Tn5 intramolecular transposition," *Nucl. Acids Res. 26*:1927-1933, Oxford University Press, Oxford, England (1998).

Zhang, Y. et al., "A new logic for DNA engineering using recombination in *Escherichia coli*," *Nat. Genet. 20*:123-128, Nature Publishing Co., New York, NY (1998).

Zhu, et al., "Homology requirements for ligation and strand exchange by the FLP recombinase," *J. Biol. Chem. 270*:11646-11653, American Society for Biochemistry and Molecular Biology, Inc., Baltimore, MD (1995).

International Search Report for International Application No. PCT/US98/22589, mailed Oct. 26, 1998.

Gage, P.J., et al., "A Cell-Free Recombination System for Site-Specific Integration of Multigenic Shuttle Plasmids into Herpes Simplex Type 1 Genome," *J. Virol. 66*:5509-5515, American Society for Microbiology, Washington, D.C. (1992).

Götz, F. et al., "*Esherichia coli* 30S mutants lacking protein S20 are defective in translation initiation," *Biochim. Biophys. Acta 1050*:93-97, Elsevier Publishing Co., Amsterdam, Netherlands (1990).

Green, R. and Noller, H.F., "Ribosomes and Translation," *Ann. Rev. Biochem. 66*:679-716, Annual Reviews, Inc., Palo Alto, CA (1997).

Jeong, J.-H., et al., "Cloning and nucleotide sequencing of the genes, *rplU* and *rpmA*, for ribosomal proteins L21 and L27 of *Escherichia coli*," *J. DNA sequencing and Mapping 4*:59-67, Harwood Academic Publishers GmbH, Switzerland (1993).

Kitts, P.A. and Nash, H.A., "Bacteriophage Lambda Site-Specific Recombination Proceeds with a Defined Order of Strand Exchanges," *J. Mol. Biol. 204*:95-107, Academic Press, Inc., New York, NY (1988).

Lake, J.A., "Evolving Ribosome Structure: Domains in Archaebacteria, Eubacteria, Eocytes and Eukaryotes," *Ann. Rev. Biochem. 54*:507-530, Annual Reviews, Inc., Palo Alto, CA (1985).

Mackie, G.A., "Nucleotide Sequence of the Gene for Ribosomal Protein S20 and Its Flanking Regions," *J. Biol. Chem. 256*:8177-8182, American Society for Biochemistry and Molecular Biology, Inc., Baltimore, MD (1981).

Nomura, M., et al., "Regulation of the Synthesis of Ribosomes and Ribosomal Components," *Ann. Rev. Biochem. 53*:75-117, Annual Reviews, Inc., Palo Alto, CA (1984).

Whittman, H.G., "Components of Bacterial Ribosomes," *Ann. Rev. Biochem. 51*:155-183, Annual Reviews, Inc., Palo Alto, CA (1982).

Wittmann, H.G., "Architecture of Prokaryotic Ribosomes," *Ann. Rev. Biochem. 52*:35-65, Annual Reviews, Inc., Palo Alto, CA (1983).

Jayaram, M., "The Int family of site-specific recombinases: Some thoughts on a general reaction mechanism," *J. Genet. 67*:29-36, Indian Academy Of Sciences Bangalore, Bangalore, India (1988).

Angelasro, J.M., et al., "Identification of diverse nerve growth factor-regulated genes by serial analysis of gene expression (SAGE) profiling," *Proc. Natl. Acad. Sci. USA 97*:10424-10429, National Academy of Sciences of the USA, Washington, D.C. (Sep. 2000).

Burioni, R., et al., "An improved phage display vector for antibody repertoire cloning by construction of combinatorial libraries," *Res. Virol. 148*:161-164, Elsevier, Paris, France (1997).

Capone, J.P., et al., "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells," *Mol. Cell. Biol. 6*:3059-3067, American Society for Microbiology, Baltimore, MD (1986).

Chanock, R.M., et al., "Human Monoclonal Antibody Fab Fragments Cloned from Combinatorial Libraries: Potential Usefulness in Prevention and/or Treatment of Major Human Viral Diseases," *Infect. Agents Dis. 2*:118-131, Raven Press, New York, NY (1993).

Chong, S., et al., "Single-column purification of free recombinant proteins using a self-cleavable affinity tag derived from a protein splicing element," *Gene 192*:271-281, Elsevier Science B.V., Amsterdam, Netherlands (1997).

Chuang, C.-F., et al., "Specific and heritable genetic interference by double-stranded RNA in *Arabidopsis thaliana*," *Proc. Natl. Acad. Sci. USA* 97:4985-4990, National Academy of Sciences of the USA, Washington, D.C. (Apr. 2000).

Datson, N.A., et al., "MicroSAGE: a modified procedure for serial analysis of gene expression in limited amounts of tissue," *Nucl. Acids Res.* 27:1300-1307, Oxford University Press, Oxford, England (Mar. 1999).

Davis, C.R., et al., "Analysis of the Mechanisms of Action of the *Saccharomyces cerevisiae* Dominant Lethal cdc42$^{G12V}$ and Dominant Negative cdc42$^{D118A}$ Mutations," *J. Biol. Chem.* 273:849-858, The American Society for Biochemistry and Molecular Biology, Inc., Baltimore, MD (1998).

Deng, M.-D., and Coleman, J.R., "Ethanol Synthesis by Genetic Engineering in Cyanobacteria," *Appl. Environ. Microbiol.* 65:523-528, American Society for Microbiology, Washington D.C. (Feb. 1999).

Derbyshire, V., and Belfort, M., "Lightning strikes twice: Intron-intein coincidence," *Proc. Natl. Acad. Sci. USA* 95:1356-1357, National Academy of Sciences of the USA, Washington, D.C. (1998).

Esposito, D., et al., "The integrase family of tyrosine recombinases: evolution of a conserved active site domain," *Nucl. Acids Res.* 25:3605-3614, Oxford University Press, Oxford, England (1997).

Flores, A., et al., "A protein-protein interaction map of yeast RNA polymerase III," *Proc. Natl. Acad. Sci. USA* 96:7815-7820, National Academy of Sciences of the USA, Washington, D.C. (Jul. 1999).

Francia, M.V., et al., "The IntI1 Integron Preferentially Binds Single-Stranded DNA of the *attC* Site," *J. Bacteriol.* 181:6844-6849, American Society for Microbiology, Baltimore, MD (1999).

Hancock, R.E.W., and Scott, M.G., "The role of antimicrobial peptides in animal defenses," *Proc. Natl. Acad. Sci. USA* 97:8856-8861, National Academy of Sciences of the USA, Washington, D.C. (Aug. 2000).

Kealy, J.T., et al., "Production of a polyketide natural product in nonpolyketide-producing prokaryotic and eukaryotic hosts," *Proc. Natl. Acad. Sci. USA* 95:505-509, National Academy of Sciences of the USA, Washington, D.C. (1998).

Kholodenko, B.N., et al., "Metabolic Design: How to Engineer a Living Cell to Desired Metabolite Concentrations and Fluxes," *Biotechnol. Bioengineer.* 59:239-247, John Wiley & Son, Chichester, NY (1998).

Kouprina, N., et al., "Rescue of Targeted Regions of Mammalian Chromosomes by in Vivo Recombination in Yeast," *Genome Res.* 8:666-672, Cold Spring Harbor Research Laboratory Press, Cold Spring Harbor, NY (1998).

Leung, L.L.K., "Application of Combinatorial Libraries and Protein Engineering to the Discovery of Novel Anti-Thrombotic Drugs," *Thromb. Haemost.* 74:373-376, F.K. Schattauer Verlagsgesellschaft mbH, Stuttgart, Germany (1995).

Madison, L.L., and Huisman, G.W., "Metabolic Engineering of Poly(3-Hydroxyalkanoates): From DNA to Plastic," *Microbiol. Mol. Biol. Reviews* 63:21-53, American Society for Microbiology, Washington D.C. (Mar. 1999).

Maemura, K., et al., "Generation of a Dominant-negative Mutant of Endothelial PAS Domain Protein 1 by Deletion of a Potent C-terminal Transactivation Domain," *J. Biol. Chem.* 274:31565-31570, The American Society for Biochemistry and Molecular Biology, Inc., Baltimore, MD (1999).

Panke, S., et al., "Engineering of Quasi-Natural *Pseudomonas putida* Strains for Toluene Metabolism through an *ortho*-Cleavage Degradation Pathway," *Appl. Environ. Microbiol.* 64:748-751, American Society for Microbiology, Washington, D.C. (1998).

Patel, P.H., and Loeb, L.A., "DNA polymerase active site is highly mutable: Evolutionary consequences," *Proc. Natl. Acad. Sci. USA* 97:5095-5100, National Academy of Sciences of the USA, Washington, D.C. (May 2000).

Perler, F.B., "InBase, the New England Biolabs Intein Database," *Nucl. Acids Res.* 27:346-347, Oxford University Press, Oxford, England (Jan. 1999).

Persson, M.A.A., "Combinatorial Libraries," *Intern. Rev. Immunol.* 10:153-63, Harwood Academic Publishers GmbH, Chur, New York (1993).

Phillips-Jones, M.K., et al., "Context Effects on Misreading and Suppression at UAG Codons in Human Cells," *Mol. Cell. Biol.* 15:6593-6600, American Society for Microbiology, Baltimore, MD (1995).

Powell, J., "Enhanced concatemer cloning—a modification to the SAGE (Serial Analysis of Gene Expression) technique," *Nucl. Acids Res.* 26:3445-3446, Oxford University Press, Oxford, England (1998).

Prieto, M.A., et al., "Molecular Characterization of the 4-Hydroxyphenylacetate Catabolic Pathway of *Escherichia coli* W: Engineering a Mobile Aromatic Degradative Cluster," *J. Bacteriol.* 178:111-120, American Society for Microbiology, Washington, D.C. (1996).

Ross, W., and Landy, A., "Patterns of λ Int Recognition in the Regions of Strand Exchange," *Cell* 33:261-272, MIT Press, Cambridge, MA (1983).

Sandhu, J.S., "Protein Engineering of Antibodies," *Crit. Rev. Biotechnol.* 12:437-62, CRC Press, Inc., Boca Raton, FL (1992).

Schnepf, E., et al., "*Bacillus thuringiensis* and Its Pesticidal Crystal Proteins," *Microbiol. Mol. Biol. Rev.* 62:775-806, American Society for Microbiology, Washington, D.C. (1998).

Shim, J., et al., "Distinct and Redundant Functions of µ1 Medium Chains of the AP-1 Clathrin-Associated Protein Complex in the Nematode *Caenorhabditis elegans*," *Mol. Biol. Cell* 11:2743-2756, American Society for Biology, Washington, D.C. (Aug. 2000).

Simpson, J.C., et al., "Systematic subcellular localization of novel proteins identified by large-scale cDNA sequencing," *EMBO Reports* 1:287-292, European Molecular Biology Organization, Oxford, England (Sep. 2000).

Skraly, F.A., et al., "Construction and Characterization of a 1,3-Propanediol Operon," *Appl. Environ. Microbiol.* 64:98-105, American Society for Microbiology, Washington, D.C. (1998).

Spinella, D.G., et al., "Tandem arrayed ligation of expressed sequence tags (TALEST): a new method for generating global gene expression profiles," *Nucl. Acids Res.* 27(e22):i-viii, Oxford University Press, Oxford, England (1999).

Stassi, D.L., et al., "Ethyl-substituted erythromycin derivatives produced by directed metabolic engineering," *Proc. Natl. Acad. Sci. USA* 95:7305-7309, National Academy of Sciences of the USA, Washington, D.C. (1998).

Stellwagen, A.E., and Craig, N.L., "Mobile DNA elements: controlling transposition with ATP-dependent molecular switches," *Trends Biochem. Sci.* 23:486-490, Elsevier Science Publishers, Amsterdam, Netherlands (1998).

van den Berg, A., et al., "Serial analysis of gene expression: rapid RT-PCR analysis of unknown SAGE tags," *Nucl. Acid Res.* 27(e17):i-iii, Oxford University Press, Oxford, England (1999).

Voziyanov, Y., et al., "A general model for site-specific recombination by the integrase family recombinases," *Nucl. Acids Res.* 27:930-941, Oxford University Press, Oxford, England (1999).

Wild, J., et al., "Targeting and retrofitting pre-existing libraries of transposon insertions with *FRT* and *oriV* elements for in-vivo generation of large quantities of any genomic fragment," *Gene* 223:55-66, Elsevier Science B.V., Amsterdam, Netherlands (1998).

"Gateway™ Cloning Technology," Version 1, GIBCO BRL, Life Technologies Instruction Manual, http://www.lifetech.com/gateway, pp. 1-60 (Nov. 1999).

"Gateway™ Cloning Technology," GIBCO BRL, Life Technologies Instruction Manual, http://www.lifetech.com/gateway, pp. 1-54 (Dec. 2000).

Simpson, J.C., et al., "Systematic subcellular localization of novel proteins identified by large-scale cDNA sequencing," *EMBO Reports* 1:287-292, IRL Press Limited, Oxford, England (Sep. 2000).

Pending U.S. Appl. No. 09/177,387, filed Oct. 23, 1998.
Pending U.S. Appl. No. 09/233,492, filed Jan. 20, 1999.
Pending U.S. Appl. No. 09/296,280, filed Apr. 22, 1999.
Pending U.S. Appl. No. 09/296,281, filed Apr. 22, 1999.
Pending U.S. Appl. No. 09/432,085, filed Nov. 2, 1999.
Pending U.S. Appl. No. 09/438,358, filed Nov. 12, 1999.
Pending U.S. Appl. No. 09/498,074, filed Feb. 4, 2000.
Pending U.S. Appl. No. 09/517,466, filed Mar. 2, 2000.
Pending U.S. Appl. No. 09/518,188, filed Mar. 2, 2000.
Pending U.S. Appl. No. 09/648,790, filed Aug. 28, 2000.

Pending U.S. Appl. No. 09/695,065, filed Oct. 25, 2000.
Albert, H., et al., "Site-specific integration of DNA into wild-type and mutant *lox* sites placed in the plant genome," *Plant J.* 7:649-659, BIOS Scientific Publishers (1995).
Backman, K., et al., "Use of Synchronous Site-Specific Recombination In Vivo to Regulate Gene Expression," *Biotechnology* (NY) 2:1045-1049, Nature Publishing Co. (1984).
Bernard, P., et al., "The F Plasmid CcdB Protein Induces Efficient ATP-dependent DNA Cleavage by Gyrase," *J. Mol. Biol.* 234:534-541, Academic Press Ltd. (1993).
Curcio, M.J., and Garfinkel, D.J., "Single-step selection for Ty1 element retrotransposition," *Proc. Natl. Acad. Sci. USA* 88:936-940, National Academy of Sciences (1991).
Dale, E.C., and Ow, D.W., "Mutations in the Cre/Lox Recombination Site Enhance the Stability of Recombination Products; Applications for Gene Targeting in Plants," *J. Cell. Biochem. 16* (*Supplement F*):206, Abstract No. Y108, Wiley-Liss (1991).
Davies, J., and Riechmann, L., "An antibody VH domain with a *lox*-Cre site integrated into its coding region: bacterial recombination within a single polypeptide chain," *FEBS Lett.* 377:92-96, Federation of European Biochemical Societies (1995).
Hall, R.M., and Collis, C.M., "Mobile gene cassettes and integrons: capture and spread of genes by site-specific recombination," *Mol. Microbiol.* 15:593-600, Blackwell Scientific Publications (1995).
Hehl, R., et al., "Structural analysis of Tam3, a transposable element from *Antirrhinum majus*, reveals homologies to the Ac element from maize," *Plant. Mol. Biol.* 16:369-371, Kluwer Academic Publishers (1991).
Henikoff, S., "Unidirectional digestion with exonuclease III creates targeted breakpoints for DNA sequencing," *Gene* 28:351-359, Elsevier Science Publishers (1984).
Iida, S., et al., "A site-specific, conservative recombination system carried by bacteriophage P1. Mapping the recombinase gene *cin* and the cross-over sites *cix* for the inversion of the C segment," *EMBO J.* 1:1445-1453, IRL Press Limited (1982).
Krafte, D.S., et al., "Stable Expression and Functional Characterization of a Human Cardiac Na$^+$ Channel Gene in Mammalian Cells," *J. Mol. Cell. Cardiol.* 27:823-830, Academic Press Limited (1995).
Lee, G., and Saito, I., "Role of nucleotide sequences of *loxP* spacer region in Cre-mediated recombination," *Gene* 216:55-65, Elsevier Science B.V. (Aug. 1998).
Mahillon, J., et al., "Subdivision of the *Escherichia coli* K-12 genome for sequencing: manipulation and DNA sequence of transposable elements introducing unique restriction sites," *Gene* 223:47-54, Elsevier Science B.V. (Nov. 1998).
Nagy, A., "Cre Recombinase: The Universal Reagent for Genome Tailoring," *Genesis* 26:99-109, Wiley-Liss, Inc. (2000).
Qin, M., et al., "Cre recombinase-mediated site-specific recombination between plant chromosomes," *Proc. Natl. Acad. Sci. USA* 91:1706-1710, National Academy of Sciences (1994).
Sauer, B., et al., "Construction of Isogenic Cell Lines Expressing Human and Rat Angiotensin II AT$_1$ Receptors by Cre-Mediated Site-Specific Recombination," *Methods* 4:143-149, Academic Press, Inc. (1992).
Segall, A.M., et al., "Architectural elements in cucleoprotein complexes: interchangeability of specific and non-specific DNA binding proteins," *EMBO J.* 13:4536-4548, Oxford University Press (1994).
Venkatesh, T.V., and Radding, C.M., "Ribosomal Protein S1 and NusA Protein Complexed to Recombination Protein β of Phage λ," *J. Bacteriol.* 175:1844-1846, American Society for Microbiology (1993).
Voziyanov, Y., et al., "A general model for site-specific recombination by the integrase family recombinases," *Nucl. Acids Res.* 27:930-941, Oxford University Press (Feb. 1999).
Zahra, D.G., et al., "Selectable in-vivo recombination to increase antibody library size—an improved phage display vector system," *Gene* 227:49-54, Elsevier Science B.V. (Feb. 1999).
Akagi, K., et al., "Cre-mediated somatic site-specific recombination in mice," *Nucl. Acids Res.* 25:1781-1788, Oxford University Press (1997).
Aladjem, M.I., et al., "Positive Selection of FLP-Mediated Unequal Sister Chromatid Exchange Products in Mammalian Cells," *Mol. Cell. Biol.* 17:857-861, American Society for Microbiology (1997).

Angrand, P.-O., et al., "Inducible expression based on regulated recombination: a single vector strategy for stable expression in cultured cells," *Nucl. Acids Res.* 26:3263-3269, Oxford University Press (Jul. 1998).
Ayres, E.K., et al., "Precise Deletions in Large Bacterial Genomes by Vector-mediated Excision (VEX). The *trfA* Gene of Promiscuous Plasmid RK2 is Essential for Replication in Several Gram-negative Hosts," *J. Mol. Biol.* 230:174-185, Academic Press Limited (1993).
Bai, C., et al., "*SKP1* Connects Cell Cycle Regulators to the Ubiquitin Proteolysis Machinery through a Novel Motif, the F-Box," *Cell* 86:263-274, Cell Press (1996).
Bernard, P., "Positive Selection of Recombinant DNA by CcdB," *BioTechniques* 21:320-323, Eaton Publishing Company (1996).
Boshart, M., et al., "A Very Strong Enhancer Is Located Upstram of an Immediate Early Gene of Human Cytomegalovirus," *Cell* 41:521-530, MIT (1985).
Bouhassira, E.E., et al., "Transcriptional Behavior of LCR Enhancer Elements Integrated at the Same Chromosomal Locus by Recombinase-Mediated Cassette Exchange," *Blood* 90:3332-3344, The American Society of Hematology (1997).
Choulika, A., et al. "Transfer of Single Gene-Containing Long Terminal Repeats into the Genome of Mammalian Cells by a Retroviral Vector Carrying the *cre* Gene and the *loxP* site." *J. Virol.* 70:1792-1798, American Society for Microbiology (1996).
Cigan, A.M., et al., "Mutational Analysis of the *HIS4* Translational Initiator Region in *Saccharomyces cerevisiae*," *Mol. Cell. Biol.* 8:2964-2975, American Society for Microbiology (1988).
Dijkema, R., et al., "Cloning and expression of the chromosomal immune interferon gene of the rat," *EMBO J.* 4:761-767, IRL Press Limited (1985).
Flanagan, P.M., and Fennewald, M.A., "Analysis of Inhibitors of the Site-specific Recombination Reaction Mediated by Tn3 Resolvase," *J. Mol. Biol.* 206:295-304, Academic Press Limited (1989).
Gay, P., et al., "Positive Selection Procedure for Entrapment of Insertion Sequence Elements in Gram-Negative Bacteria," *J. Bacteriol.* 164:918-921, American Society for Microbiology (1985).
Gay, P., et al., "Cloning Structural Gene *sacB*, Which Codes for Exoenzyme Levansucrase of *Bacillus subtilis*: Expression of the Gene in *Escherichia coli*," *J. Bacteriol.* 153:1424-1431, American Society for Microbiology (1983).
Gorman, C.M., et al., "The Rous sarcoma virus long terminal repeat is a strong promoter when introduced into a variety of eukaryotic cells by DNA-mediated transfection," *Proc. Natl. Acad. Sci. USA* 79:6777-6781, National Academy of Sciences (1982).
Grindley, N.D.F., and Kelley, W.S., "Effects of Different Alleles of the *E. coli* K12 *polA* Gene on the Replication of Non-transferring Plasmids," *Molec. Gen. Genet.* 143:311-318, Springer-Verlag (1976).
Gronostajski, R.M., and Sadowski, P.D., "The FLP Protein of the 2-micron Plasmid of Yeast. Inter- and Intramolecular Reactions," *J. Biol. Chem.* 260:12328-12335, The American Society of Biological Chemists, Inc. (1985).
Haffter, P., and Bickle, T.A., "Enhancer-independent mutants of the Cin recombinase have a relaxed topological specificity," *EMBO J.* 7:3991-3996, IRL Press Limited (1988).
Hoess, R.H., and Abremski, K., "Interaction of the bacteriophage P1 recombinase Cre with the recombining site *loxP*," *Proc. Natl. Acad. Sci. USA* 81:1026-1029, National Academy of Sciences (1984).
Kaniga, K., et al., "A wide-host-range suicide vector for improving reverse genetics in Gram-negative bacteria: inactivation of the *blaA* gene of *Yersinia enterocolitica*," *Gene* 109:137-141, Elsevier Science B.V. (1991).
Kim, D.W., "Use of the human elongation factor 1α promoter as a versatile and efficient expression system," *Gene* 91:217-223, Elsevier Science B.V. (1990).
Kolb, A.F., and Siddell, S.G., "Genomic targeting with an MBP-Cre fusion protein," *Gene* 183:53-60, Elsevier Science B.V. (1996).
Leslie, N.R., and Sherratt, D.J., "Site-specific recombination in the replication terminus region of *Eschericihia coli*: functional replacement of *dif*," *EMBO J.* 14:1561-1570, Oxford University Press (1995).
Li, Z.-W., et al. "Generation of mice with a 200-kb amyloid precursor protein gene deletion by Cre recombinase-mediated site-specific recombination in embryonic stem cells," *Proc. Natl. Acad. Sci. USA* 93:6158-6162, National Academy of Sciences (1996).

Lu, F., and Churchward, G., "Conjugative transposition: Tn*916* integrase contains two independent DNA binding domains that recognize different DNA sequences," *EMBO J.* 13:1541-1548, Oxford University Press (1994).

Malynn, B.A., et al., "The *scid* Defect Affects the Final Step of the Immunoglobulin VDJ Recombinase Mechanism," *Cell* 54:453-460, Cell Press (1988).

Maniatis, T., et al., "Regulation of Inducible and Tissue-Specific Gene Expression," *Science* 236:1237-1245, American Association for the Advancement of Science (1987).

Mendiola, M.V., and del la Cruz, F., "Specificity of insertion of IS*91*, an insertion sequence present in α-haemolysin plasmids of *Escherichia coli,*" *Mol. Microbiol.* 3:979-984, Blackwell Scientific Publications (1989).

Mercier, J., et al., "Structural and Functional Characterization of *tnpI*, a Recombinase Locus in Tn*21* and Related β-Lactamase Transposons," *J. Bacteriol.* 172:3745-3757, American Society for Microbiology (1990).

Metcalf, W.W., et al., "Conditionally Replicative and Conjugative Plasmids Carrying *lacZα* for Cloning, Mutagenesis, and Allele Replacement in Bacteria," *Plasmid* 35:1-13, Academic Press, Inc. (1996).

Meyer-Leon, L., et al., "Purification of the FLP site-specific recombinase by affinity chromatography and re-examination of basic properties of the system" *Nucl. Acids Res.* 15:6469-6488, IRL Press Limited (1987).

Mizushima, S., and Nagata, S., "pEF-BOS, a powerful mammalian expression vector," *Nucl. Acids Res.* 18:5322, Oxford University Press (1990).

Odell, J.T., et al., "Seed-Specific Gene Activation Mediated by the Cre/*lox* Site Specific Recombination System," *Plant Physiol.* 106:447-458, American Society of Plant Physiologists (1994).

Pal, S.K., et al., "P1 Plasmid Replication. Role of Initiator Titration in Copy Number Control," *J. Mol. Biol.* 192:275-285, Academic Press Inc. (1986).

Qin, M., et al., "Site-specific cleavage of chromosomes *in vitro* through Cre-*lox* recombination," *Nucl. Acids Res.* 23:1923-1927, Oxford University Press (1995).

Sato, T., et al., "The *cisA* Cistron of *Bacillus subtilis* Sporulation Gene *spoIVC* Encodes a Protein Homologous to a Site-Specific Recombinase," *J. Bacteriol.* 172:1092-1098, American Society for Microbiology (1990).

Schild, D., et al., "Cloning of three human multifunctional *de novo* purine biosynthetic genes by functional complementation of yeast mutations," *Proc. Natl. Acad. Sci. USA* 87:2916-2920, National Academy of Sciences (1990).

Stark, W.M., et al., "Site-Specific Recombination by Tn3 Resolvase: Topological Changes in the Forward and Reverse Reactions," *Cell* 58:779-790, Cell Press (1989).

Stenzel, T.T., et al., "The Integration Host Factor of *Escherichia coli* Binds to Bent DNA at the Origin of Replication of the Plasmid pSC101," *Cell* 49:709-717, Cell Press (1987).

Sugiura, S., et al., "Minimal Essential Origin of Plasmid pSC101 Replication: Requirement of a Region Downstream of Iterons," *J. Bacteriol.* 175:5993-6001, American Society for Microbiology (1993).

Uetsuki, T., et al., "Isolation and Characterization of the Human Chromosomal Gene for Polypeptide Chain Elongation Factor-1α," *J. Biol. Chem.* 264:5791-5798, The American Society for Biochemistry and Molecular Biology, Inc. (1989).

Voss, S.D., et al., "The role of enhancers in the regulation of cell-type-specific transcriptional control," *Trends Biochem. Sci.* 11:287-289, Elsevier Science (1986).

Yoon, H., et al., "SSL1, a suppressor of a *HIS4* 5'-UTR stem-loop mutation, is essential for translation initiation and affects UV resistance in yeast," *Genes Dev.* 6:2463-2477, Cold Spring Harbor Laboratory Press (1992).

Baum, J.A., "Tn*5401*, a New Class II Transposable Element From *Bacillus thuringiensis,*" *J. Bacteriol.* 176:2835-2845, American Society for Microbiology (1994).

Short, J.M. et al., "λ ZAP: a bacteriophage λ expression vector with *in vivo* excision properties," *Nucleic Acids Research* 16:7583-7600, IRL Press Limited (1988).

Barnes, G., and Rine, J., "Regulated expression of endonuclease EcoRI In *Saccharomyces cerevisiae*: Nuclear entry and biological consequences," *Proc. Natl. Acad. Sci. USA* 82: 1354-1358, National Academy of Sciences (1985).

Bauer, C.E. et al., "Extent of Sequence Homology Required for Bacteriophage Lambda Site-specific Recombination," *J. Mol. Biol.* 181: 187-197, Academic Press Inc. (1985).

Brent, R., and Ptashne, M., "A bacterial repressor protein or a yeast transcriptional terminator can block upstream activation of a yeast gene," *Nature* 312: 612-615, Macmillan Journals Ltd. (1984).

Cherapanov, P.P., and Wackernagel, W., "Gene disruption in *Escherichia coli*: $Tc^R$ and $Km^R$ cassettes with the option of Flp-catalyzed excision of the antibiotic-resistance determinant," *Gene* 158: 9-14, Elsevier Science B.V. (1995).

Collis, C.M, and Hall, R.M., "Expression of Antibiotic Resistance Genes in the Integrated Cassettes of Integrons," *Antimicrobial Agents and Chemotherapy* 39: 155-162 (1995).

CLONTECH, "Creator™ Acceptor Vector Construction Kit" *CLONTECHniques* 16:2 pages, CLONTECH (Oct. 2001).

CLONTECH, "Creator™ Gene Cloning & Expression System," *CLONTECHniques* 15:7-11, CLONTECH (Apr. 2000).

CLONTECH, "Creator™ pDNR-Dual Cloning Kit," *CLONTECHniques* 16:3 pages, CLONTECH (Oct. 2001).

CLONTECH, "Creator™ SMART™ Library Construction Kit," *CLONTECHniques* 16:2 pages, CLONTECH (Oct. 2001).

CLONTECH, "Creator™: The Universal Platform for Analysis of Gene Function," *Powerpoint Presentation*, pp. 1-9, CLONTECH (Jul. 24, 2001), available at http://www.clontech.com/products/families/creator/popups/s1page1.html.

CLONTECH, "New Additions to the Creator™ Platform," *CLONTECHniques* 16:1-4, CLONTECH (Jan. 2001).

CLONTECH, "New Creator™-Compatible Expression Systems," *CLONTECHniques* 15:2 pages, CLONTECH (Oct. 2000).

Enquist, L.W., and Weisberg, R.A., "The Red Plaque Test: A Rapid Method for Identification of Excision Defective Variants of Bacteriophage Lambda," *Virology* 72: 147-153, Academic Press, Inc. (1976).

Iino, T., and Kutsukake, K., "*Trans*-acting Genes of Bacteriophages P1 and Mu Mediate Inversion of a Specific DNA Segment Involved in Flagellar Phase Variation of *Salmonella,*" *Cold Spring Harbor Symposia on Quantitative Biology* 45: 11-16, Cold Spring Harbor Laboratory (1981).

Klippel, A. et al., "Isolation and characterization of unusual *gin* mutants," *The EMBO Journal* 7: 3983-3989, IRL Press Inc. (1988).

Langeveld, S.A. et al., "Expression of an *Escherichia coli phr* gene in the yeast *Saccharomyces cerevisiae,*" *Mol. Gen. Genet.* 199: 396-400, Springer-Verlag (1985).

Miller, H.I. et al., "*int*-h: an *int* Mutation of Phage λ That Enhances Site-Specific Recombination," *Cell* 20: 721-729, MIT (1980).

Okayama, H., and Berg, P., "Bacteriophage Lambda Vector for Transducing a cDNA Clone Library into Mammalian Cells," *Molecular and Cellular Biology* 5: 1136-1142, American Society for Microbiology (1985).

Sauer, B., "Expression and Functioning in Yeast of a Bacterial Site Specific Recombination System," *J. Cell. Biol. Chem. Supp.* 10(b): 242 (1340), Alan R. Liss, Inc. (1986).

Sauer, B., and Henderson, N., "Site-specific DNA recombination in mammalian cells by the Cre recombinase of bacteriophage P1," *Proc. Natl. Acad. Sci. USA* 85: 5166-5170, National Academy of Sciences (1988).

Scott, S.D., and Marples, B., "Comment on the use of the cre/loxp recombinase system for gene therapy vectors," *Gene Therapy* 7: 1706, Macmillan Publishers Ltd. (2000).

Vetter, D. et al., "Site-specific recombination of yeast 2-μm DNA *in vitro,*" *Proc. Natl. Acad. Sci. USA* 80: 7284-7288, National Academy of Sciences (1983).

Cormack, B., "Directed Mutagenesis Using the Polymerase Chain Reaction," in *Current Protocols in Molecular Biology* 1:8.5.1-8.5.10, Ausubel, F.M., et al., eds., John Wiley & Sons, Inc. (1997).

Feinbaum, R., "Vectors Derived from Plasmids," in *Current Protocols in Molecular Biology* 1:1.5.1-1.5.17, Ausubel, F.M., et al., eds., John Wiley & Sons, Inc. (1998).

Johnson, R.C., et al., "Isolation of the gene encoding the Hin recombinational enhancer binding protein," *Proc. Natl. Acad. Sci. USA* 85:3484-3488, National Academy of Sciences (1988).

Koch, C., et al., "*Escherichia coli* host factor for site-specific DNA inversion: Cloning and characterization of the *fis* gene," *Proc. Natl. Acad. Sci. USA* 85: 4237-4241, National Academy of Sciences (1988).

Osuna, R., et al., "Identification of two functional regions in Fis: the N-terminus is required to promote Hin-mediated DNA inversion but not λ excision," *The EMBO Journal* 10: 1593-1603, Oxford University Press (1991).

Sambrook, J., et al., "Expression of Cloned Genes in Cultured Mammalian Cells," in *Molecular Cloning A Laboratory Manual*, Second Edition, Cold Spring Harbor Laboratory Press, Cold Spring Harbor, NY, pp. 16.6-16.8 (1989).

Stryer, L., *Biochemistry*, Second Edition, W.H. Freeman and Company, New York, pp. 610 (1981).

Kuempel, P., et al., "Use of a transposon (Tn*dif*) to obtain suppressing and nonsuppressing insertions of the *dif* resolvase site of *Escherichia coli*," *Genes Dev.* 10:1162-1171, Cold Spring Harbor Laboratory Press (Jul. 1, 1996).

Lee, M.H., et al., "Site-Specific integration of mycobacteriophage L5: Integration-proficient vectors for *Mycobacterium smegmatis, Mycobacterium tuberculosis* and bacille Calmette-Guérin," *Proc. Natl. Acad. Sci. USA* 88:3111-3115, National Academy of Sciences (1991).

Manning, P.A., et al., "Gene Capture in *Vibrio cholera*," *Trends in Microbiology* 7:93-95, Elsevier Science (1999).

Murayama, N. et al. "Evidence for Involvement of *Escherichia coli* Genes *pmbA, csrA* and a Previously Unrecognized Gene *tldD*, in the Control of DNA Gyrase by *letD* (*ccdB*) of Sex Factor F," *J. Mol. Biol.* 256:483-502 Academic Press Limited (1996).

Shuman, S., "Novel Approach to Molecular Cloning and Polynucleotide Synthesis Using Vaccina DNA Topoisomerase," *J. Biol. Chem.* 269:32678-32684, The American Society for Biochemistry and Molecular Biology, Inc. (1994).

Zechiedrich, E.L., et al., "Topoisomerase IV, not gyrase, decatenates products of site-specific recombination in *Escherichia coli*," *Genes Dev.* 11:2580-2592, Cold Spring Harbor Laboratory Press (1997).

Institut Pasteur Website, Introduction: http://www.pasteur.fr/recherche/unites/pmtg/integ/intro.html (accessed Jun. 19, 2003).

Institut Pasteur Website, Figure 1: http://www.pasteur.fr/recherche/unites/pmtg/integ/fig1.html (accessed Jun. 19, 2003).

Institut Pasteur Website, Figure 2: http://www.pasteur.fr/recherche/unites/pmtg/integ/fig2.html (accessed Jun. 19, 2003).

Institut Pasteur Website, Figure 3: http://www.pasteur.fr/recherche/unites/pmtg/integ/fig3.html (accessed Jun. 19, 2003).

Institut Pasteur Website, Main page: http://www.pasteur.fr/recherche/unites/pmtg (accessed Jun. 19, 2003).

Stuurman, J., et al., "Single-site manipulation of tomato chromosomes *in vitro* and *in vivo* using Cre-*lox* site-specific recombination," *Plant Molec. Biol.* 32:901-913, Kluwer Academic Publishers (1996).

Ball, C.A. and Johnson, R.C., "Efficient Excision of Phage λ from the *Escherichia coli* Chromosome Requires the Fis Protein," *J. Bacteriol.* 173: 4027-4031, American Society for Microbiology (Jul. 1991).

Bruckner, R.C. and Cox, M.M., "The Histone-like H Protein of *Escherichia coli* is ribosomal protein S3," *Nucl. Acids Res.* 17:3145-3161, Oxford University Press (1989).

Hartley, J.L., et al., "DNA Cloning Using In Vitro Site-Specific Recombination," *Genome Res.* 10:1788-1795, Cold Spring Harbor Laboratory Press (Nov. 2000).

Heyman, J.A., et al., "Genome-Scale Cloning and Expression of Individual Open Reading Frames Using Topoisomerase I-Mediated Ligation," *Genome Res.* 9:383-392, Cold Spring Harbor Laboratory Press (Apr. 1999).

Lenski, R.E., et al., "Genetic Analysis of a Plasmid-Encoded, Host Genotype-Specific Enhancement of Bacterial Fitness," *J. Bacteriol.* 176:3140-3147, American Society For Microbiology (1994).

Ohara, O. and Temple, G., "Directional cDNA library construction assisted by the *in vitro* recombination reaction," *Nucl. Acids Research* 29:e22(1-8), Oxford University Press (2001).

Russell, M., "A recombination-based cloning system that decreases time to protein analysis," *Am. Biotechnol. Lab.* 18:8,10, International Scientific Communications, Inc. (Jun. 2000).

Sinclair, B., "Honing Your Cloning," *The Scientist* 14:29-32, The Scientist Inc. (Aug. 21, 2000).

Invitrogen Online Catalog, "The Echo™ Cloning System: The Future of Cloning is Here," available at: http://web.archive.org/web/20010112191100/www.invitrogen.com/catalog_project/cat_echo.html (accessed Jul. 7, 2004).

Invitrogen Online Catalog, "The Echo™ Cloning System: The Future of Cloning is Here," available at: http://invitrogen.com/content.cfm?pageid=3371&cfid=16767784&cftoken=62396683 (accessed Jul. 7, 2004).

Agah, R., et al., "Gene Recombination in Postmitotic Cells. Targeted Expression of Cre Recombinase Provokes Cardiac-restricted, Site-specific Rearrangement in Adult Ventricular Muscle In Vivo," *J. Clin. Invest.* 100:169-179, The American Society for Clinical Investigation, Inc. (Jul. 1997).

Benoist, C. and Chambon, P., "*In vivo* sequence requirements of the SV40 early promoter region," *Nature* 290:304-310, Macmillan Journals, Ltd. (1981).

Botstein, D., et al., "Making Mutations *In Vitro* and Putting Them Back Into Yeast," in *From Gene to Protein: Translation into Biotechnology*, Ahmad, F., et al., eds., Academic Press, New York, NY, pp. 265-274 (1982).

Broach, J.R., "The Yeast Plasmid 2μ Circle," *Cell* 28:203-204, MIT (1982).

Cenatiempo, Y., "Prokaryotic gene expression *in vitro*: transcription-translation coupled systems," *Biochimie* 68:505-515, Elsevier (1986).

Christiansen, B., et al., "A Resolvase-Like Protein Is Required for the Site-Specific Integration of the Temperate Lactococcal Bacteriophage TP901-1," *J. Bacteriol.* 178:5164-5173, American Society for Microbiology (Sep. 1996).

Crellin, P.K. and Rood, J.I., "The Resolvase/Invertase Domain of the Site-Specific Recombinase TnpX Is Functional and Recognizes a Target Sequence That Resembles the Junction of the Circular Form of the *Clostridium perfringens* Transposon Tn*4451*," *J. Bacteriol.* 179:5148-5156, American Society for Microbiology (Aug. 1997).

Ferrin, L.J. and Camerini-Otero, R.D., "Sequence-specific ligation of DNA using RecA protein," *Proc. Natl. Acad. Sci. USA* 95:2152-2157, National Academy of Sciences (Mar. 1998).

Golic, K.G. and Golic, M.M., "Engineering the Drosophilia Genome: Chromosome Rearrangements by Design," *Genetics* 144:1693-1711, The Genetics Society of America (1996).

Gottesman, S., "Bacterial Regulation: Global Regulatory Networks," *Ann. Rev. Genet.* 18:415-441, Annual Reviews, Inc. (1984).

Guo, F., et al., "Structure of Cre recombinase complexed with DNA in a site-specific recombination synapse," *Nature* 389:40-46, Nature Publishing Group (Sep. 1997).

Hallet, B. and Sherratt, D.J., "Transposition and site-specific recombination: adapting DNA cut-and-paste mechanisms to a variety of genetic rearrangements," *FEMS Microbiol. Rev.* 21:157-178, Elsevier Science B.V. (Sep. 1997).

Hamer, D.H. and Walling, M., "Regulation *In Vivo* of a Cloned Mammalian Gene: Cadmium Induces the Transcription of a Mouse Metallothionein Gene in SV40 Vectors," *J. Mol. Appl. Genet.* 1:273-288, Raven Press (1982).

Hanks, S.K. and Hunter, T., "The eukaryotic protein kinase superfamily: kinase (catalytic) domain structure and classification," *FASEB J.* 9:576-596, The Federation of American Societies for Experimental Biology (May 1995).

Huang, L.-C., et al., "Convenient and Reversible Site-Specific Targeting of Exogenous DNA into a Bacterial Chromosome by Use of the FLP Recombinase: the FLIRT System," *J. Bacteriol.* 179:6076-6083, American Society for Microbiology (Oct. 1997).

John, Jr., J.F. and Twitty, J.A., "Plasmids as Epidemiologic Markers in Nosocomial Gram-Negative Bacilli: Experience at a University and Review of the Literature," *Rev. Infect. Dis.* 8:693-704, University of Chicago (1986).

Johnston, S.A. and Hopper, J.E., "Isolation of the yeast regulatory gene *GAL4* and analysis of its dosage effects on the galactose/melibiose regulon," *Proc. Natl. Acad. Sci. USA* 79:6971-6975, National Academy of Sciences (1982).

Kendall, K.J. and Cohen, S.N., "Plasmid Transfer in *Streptomyces lividans*: Identification of a *kil-kor* System Associated with the Transfer Region of pIJ101," *J. Bacteriol.* 169:4177-4183, American Society for Microbiology (1987).

Lyznik, L.A., et al., "Activity of yeast FLP recombinase in maize and rice protoplasts," *Nucleic Acids Res.* 21:969-975, Oxford University Press (1993).

Maniatis, T., "Recombinant DNA Procedures in the Study of Eukaryotic Genes," in *Cell Biology: A Comprehensive Treatise, vol. 3, Gene Expression: The Production of RNA's*, Goldstein, L., and Prescott, D.M., eds., Academic Press, Inc., New York, NY, pp. 563-608 (1980).

Mayer, B.J. and Baltimore, D., "Signalling through SH2 and SH3 domains," *Trends Cell Biol.* 3:8-13, Elsevier Science (1993).

McKnight, S.L., "Functional Relationships between Transcriptional Control Signals of the Thymidine Kinase Gene of Herpes Simplex Virus," *Cell* 31:355-365, MIT (1982).

Nunes-Düby, S.E., et al., "λ Integrase cleaves DNA *in cis*," *EMBO J.* 13:4421-4430, Oxford University Press (1994).

Odell, J., et al., "Site-directed recombination in the genome of transgenic tobacco," *Mol. Gen. Genet.* 223:369-378, Springer-Verlag (1990).

Peterson, B.Ø. and Shuman, S., "Hisitidine 265 Is Important for Covalent Catalysis by Vaccinia Topoisomerase and Is Conserved in All Eukaryotic Type I Enzymes," *J. Biol. Chem.* 272:3891-3896, The American Society for Biochemistry and Molecular Biology, Inc. (Feb. 1997).

Rausch, H. and Lehmann, M., "Structural analysis of the actinophage ΦC31 attachment site," *Nucleic Acids Res.* 19:5187-5189, IRL Press (1991).

Sadowski, I., et al., "A Noncatalytic Domain Conserved among Cytoplasmic Protein-Tyrosine Kinases Modifies the Kinase Function and Transforming Activity of Fujinami Sarcoma Virus P130$^{gag-fps}$," *Mol. Cell. Biol.* 6:4396-4408, American Society for Microbiology (1986).

Sauer, B. and Henderson, N., "Targeted Insertion of Exogenous DNA into the Eukaryotic Genome by the Cre Recombinase," *New Biol.* 2:441-449, Saunders Scientific Publications/W.B. Saunders Company (1990).

Senecoff, J.F., et al., "The FLP recombinase of the yeast 2-μm plasmid: Characterization of its recombination site," *Proc. Natl. Acad. Sci. USA* 82:7270-7274, National Academy of Sciences (1985).

Shaikh, A.C. and Sadowski, P.D., "The Cre Recombinase Cleaves the *lox* Site *in trans*," *J. Biol. Chem.* 272:5695-5702, The American Society for Biochemistry and Molecular Biology, Inc. (Feb. 1997).

Shirai, M., et al., "Site-Specific Integration of the Actinophage R4 Genome into the Chromosome of *Streptomyces parvulus* upon Lysogenization," *J. Bacteriol.* 173:4237-4239, American Society for Microbiology (1991).

Shuman, S., et al., "Characterization of Vaccinia Virus DNA Topoisomerase I Expressed in *Escherichia coli*," *J. Biol. Chem.* 263:16401-16407, The American Society for Biochemistry and Molecular Biology, Inc. (1988).

Shuman, S., "Site-specific Interaction of Vaccinia Virus Topoisomerase I with Duplex DNA. Minimal DNA Substrate for Strand Cleavage *In Vitro*," *J. Biol. Chem.* 266:11372-11379, The American Society for Biochemistry and Molecular Biology, Inc. (1991).

Shuman, S., "Erratum: Site-specific Interaction of Vaccinia Virus Topoisomerase I with Duplex DNA. Minimas DNA Substrate for Strand Cleavage *In Vitro*," *J. Biol. Chem.* 266:20576-20577, The American Society for Biochemistry and Molecular Biology, Inc. (1991).

Silver, P.A., et al., "Amino terminus of the yeast *GAL4* gene product is sufficient for nuclear localization," *Proc. Natl. Acad. Sci. USA* 81:5951-5955, National Academy of Sciences (1984).

Stark, W.M., et al., "Catalysis by site-specific recombinases," *Trends Genet.* 8:432-439, Elsevier Science (1992).

Ulmanen, I., et al., "Transcription and Translation of Foreign Genes in *Bacillus subtilis* by the Aid of a Secretion Vector," *J. Bacteriol.* 162:176-182, American Society for Microbiology (1985).

van Deursen, J., et al., "Cre-mediated site-specific translocation between nonhomologous mouse chromosomes," *Proc. Natl. Acad. Sci. USA* 92:7376-7380, National Academy of Sciences (1995).

Ward, J.M., et al., "Construction and characterisation of a series of multi-copy promoter-probe plasmid vectors for *Streptomyces* using the aminoglycoside phosphotransferase gene from Tn5 as indicator," *Mol. Gen. Genet.* 203:468-478, Springer-Verlag (1986).

Invitrogen Life Technologies online catalog, "Directional TOPO Entry Vectors," 4 pages, accessed Sep. 27, 2002, available at: http://www.invitrogen.com/content.cfm?pageid=3799&cfid=2897960&cftoken=88086554.

Dialog File 351, Derwent World Patent Index, unverified English Language Abstract for French Patent No. FR 2 670 502 (Document AL20) and PCT Patent No. WO 92/10577 (Document AM20), WPI Accession No. 9107201.

Mahillon, J., et al., "Subdivision of the *Escherichia coli* K-12 genome for sequencing: manipulation and DNA sequence of transposable elements introducing unique restriction sites," *Gene* 223:47-54, Elsevier Science B.V., Amsterdam, Netherlands (1998).

Mette, M.F., et al., "Transcriptional silencing and promoter methylation triggered by double-stranded RNA," *EMBO J.* 19:5194-5201, European Molecular Biology Organization, Oxford, England (Oct. 2000).

O'Gara, J.P., et al., "Identification and Molecular Genetic Analysis of Multiple Loci Contributing to High-Level Tellurite Resistance in *Rhodobacter sphaeroides* 2.4.1," *Appl. Environ. Microbiol.* 63:4713-4720, American Society for Microbiology, Washington D.C. (1997).

Bliska, J.B., and Cozzarelli, N.R., "Use of Site-specific Recombination as a Probe of DNA Structure and Metabolism in Vivo," *J. Mol. Biol.* 194:205-218, Academic Press (1987).

Carninci, P., and Hayashizaki, Y., "High-Efficiency Full-Length cDNA Cloning," *Methods Enzymol.* 303:19-44, Academic Press (1999).

Chatterjee, P.K., and Sternberg, N.L., "Retrofitting high molecular weight DNA cloned in P1: introduction of reporter genes, markers selectable in mammalian cells and generation of nested deletions," *Genet. Anal.* 13:33-42, Elsevier (1996).

Liu, X., and Gorovsky, M.A., "Mapping the 5' and 3' ends of *Tetrahymena thermophila* mRNAs using RNA ligase mediated amplification of cDNA ends (RLM-RACE)," *Nucleic Acids Res.* 21:4954-4960, Oxford University Press (1993).

Alonso, J.C., "Site-specific recombination in Gram-positive theta-replicating plasmids," *FEMS Microbiol. Lett.* 142:1-10 Elsevier Science B.V. (1996).

Amin, A.A., et al., "Synthesis of an Enzymatically Active FLP Recombinase In Vitro: Search for a DNA-Binding Domain," *Molec. and Cell Biol.* 9: 1987-1995, American Society for Microbiology (1989).

Aoki, K., et al., "Efficient Generation of Recombinant Adenoviral Vectors by Cre-lox Recombination In Vitro," *Mol. Med.* 5:224-231, Picower Institute Press (Apr. 1999).

Huang, L.-C., et al., "A bacterial model system for chromosomal targeting," *Nucl. Acids Res.* 19:443-448, Oxford University Press (1991).

Kanegae, Y., et al., "Efficient gene activation in mammalian cells by using recombinant adenovirus expressing site-specific Cre recombinase," *Nucl. Acids Res.* 23:3816-3821, Oxford University Press (1995).

Kijima, T., et al., "Application of the Cre Recombinase/loxP System Further Enhances Antitumor Effects in Cell Type-specific Gene Therapy Against Carcinoembryonic Antigen-producing Cancer," *Cancer Res.* 59:4906-4911, American Association for Cancer Research (Oct. 1999).

Lieber, A., et al., "Recombinant Adenoviruses with Large Deletions Generated by Cre-Mediated Excision Exhibit Different Biological Properties Compared with First-Generation Vectors In Vitro and In Vivo," *J. Virol.* 70:8944-8960, American Society for Microbiology (1996).

Ng, P., et al., "A High-Efficiency Cre/loxP-Based System for Construction of Adenoviral Vectors," *Human Gene Ther*. 10:2667-2672, Mary Ann Liebert, Inc. (Nov. 1999).

Walhout, A.J.M., "Protein Interaction Mapping in C. elegans Using Proteins Involved in Vulval Development," *Science* 287:116-122, American Association for the Advancement of Science (Jan. 2000).

Walhout, A.J.M., "GATEWAY Recombinational Cloning: Application to the Cloning of Large Numbers of Open Reading Frames or ORFeomes," *Meth. in Enzymol*. 328:575-592, Academic Press (Oct. 2000).

Wang, Y., et al., "Targeted DNA recombination in vivo using an adenovirus carrying the cre recombinase gene," *Proc. Natl. Acad. Sci*. 93:3932-3936, The National Academy of Sciences (1996).

Gotou, N., et al., "Gateway™ Cloning Technology," *Experimental Medicine* 18:2716-2717 (Dec. 2000) (in Japanese Language).

Unverified English Language Translation of Document AS219.

* cited by examiner

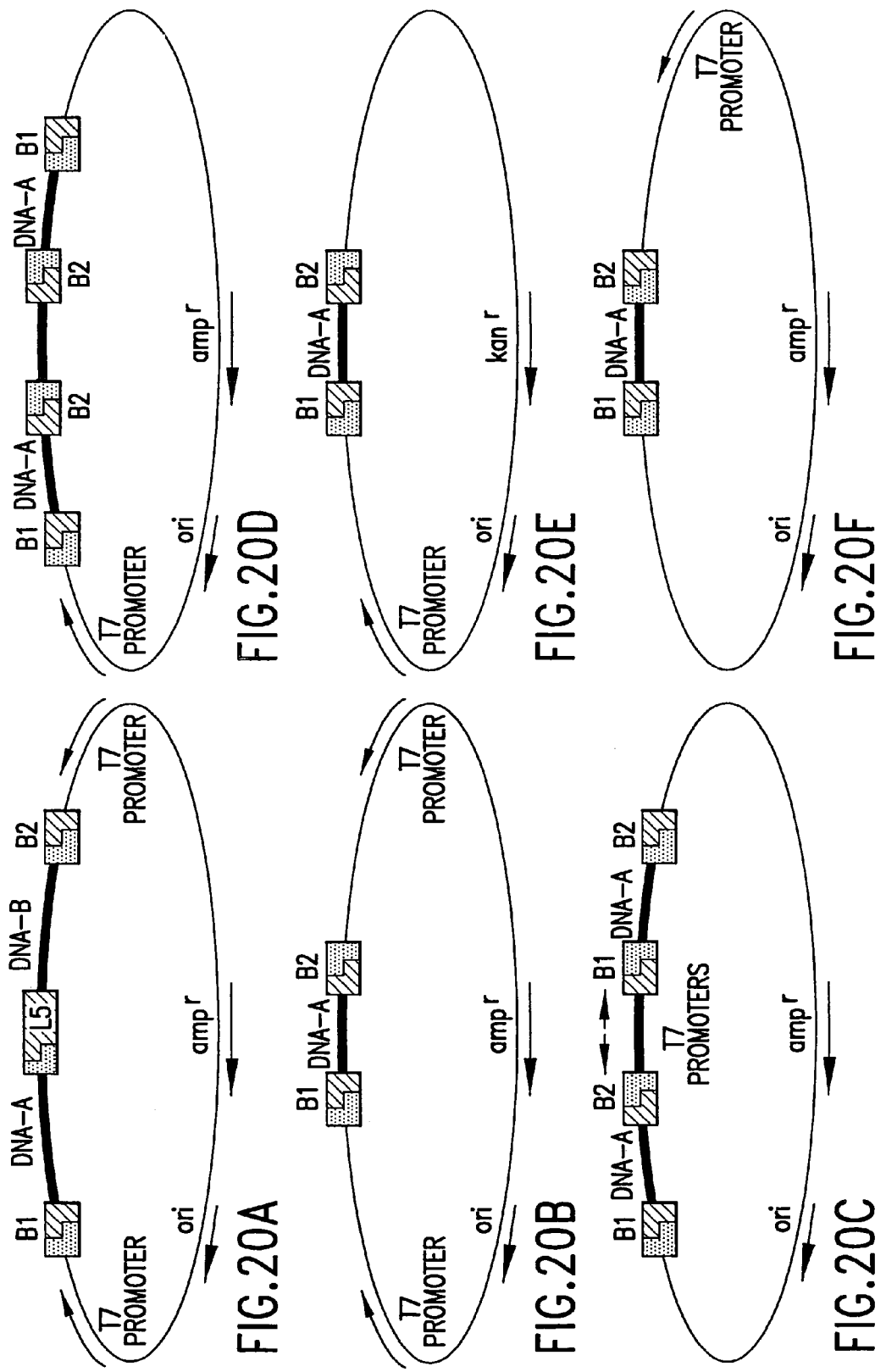

| | | |
|---|---|---|
| *attB0* | AGCCTGCTTT<u>TTTATAC</u>TAACTTGAGC<br>TCGGACGAAAAAATATGATTGAACTCG | (SEQ ID NO:1) |
| *attP0* | GTTCAGCTTT<u>TTTATAC</u>TAAGTTGGCA<br>CAAGTCGAAAAAATATGATTCAACCGT | (SEQ ID NO:2) |
| *attL0* | AGCCTGCTTT<u>TTTATAC</u>TAAGTTGGCA<br>TCGGACGAAAAAATATGATTCAACCGT | (SEQ ID NO:3) |
| *attR0* | GTTCAGCTTT<u>TTTATAC</u>TAACTTGAGC<br>CAAGTCGAAAAAATATGATTGAACTCG | (SEQ ID NO:4) |
| *attB1* | AGCCTGCTTT<u>TTTGTAC</u>AAACTTGT<br>TCGGACGAAAAAATATGTTTGAACA | (SEQ ID NO:5) |
| *attP1* | GTTCAGCTTT<u>TTTGTAC</u>AAAGTTGGCA<br>CAAGTCGAAAAAACATGTTTCAACCGT | (SEQ ID NO:6) |
| *attL1* | AGCCTGCTTT<u>TTTGTAC</u>AAAGTTGGCA<br>TCGGACGAAAAAACATGTTTCAACCGT | (SEQ ID NO:7) |
| *attR1* | GTTCAGCTTT<u>TTTGTAC</u>AAACTTGT<br>CAAGTCGAAAAAACATGTTTGAACA | (SEQ ID NO:8) |
| *attB2* | ACCCAGCTTT<u>CTTGTAC</u>AAAGTGGT<br>TGGGTCGAAAGAATATGTTTCACCA | (SEQ ID NO:9) |
| *attP2* | GTTCAGCTTT<u>CTTGTAC</u>AAAGTTGGCA<br>CAAGTCGAAAGAACATGTTTCAACCGT | (SEQ ID NO:10) |
| *attL2* | ACCCAGCTTT<u>CTTGTAC</u>AAAGTTGGCA<br>TGGGTCGAAAGAACATGTTTCAACCGT | (SEQ ID NO:11) |
| *attR2* | GTTCAGCTTT<u>CTTGTAC</u>AAAGTGGT<br>CAAGTCGAAAGAACATGTTTGACCA | (SEQ ID NO:12) |
| *attB5* | CAACTTT<u>ATTATAC</u>AAAGTTGT<br>GTTGAAATAATATGTTTCAACA | (SEQ ID NO:13) |
| *attP5* | GTTCAACTTT<u>ATTATAC</u>AAAGTTGGCA<br>CAAGTTGAAATAATATGTTTCAACCGT | (SEQ ID NO:14) |

FIG.24A

| | | |
|---|---|---|
| attL5 | CAACTTTATTATACAAAGTTGGCA<br>GTTGAAATAATATGTTTCAACCGT | (SEQ ID NO:15) |
| attR5 | GTTCAACTTTATTATACAAAGTTGT<br>CAAGTTGAAATAATATGTTTCAACA | (SEQ ID NO:16) |
| attB11 | CAACTTTTCTATACAAAGTTGT<br>GTTGAAAAGATATGTTTCAACA | (SEQ ID NO:17) |
| attP11 | GTTCAACTTTTCTATACAAAGTTGGCA<br>CAAGTTGAAAAGATATGTTTCAACCGT | (SEQ ID NO:18) |
| attL11 | CAACTTTTCTATACAAAGTTGGCA<br>GTTGAAAAGATATGTTTCAACCGT | (SEQ ID NO:19) |
| attR11 | GTTCAACTTTTCTATACAAAGTTGT<br>CAAGTTGAAAAGATATGTTTCAACA | (SEQ ID NO:20) |
| attB17 | CAACTTTTTGTATACAAAGTTGT<br>GTTGAAAACATATGTTTCAACA | (SEQ ID NO:21) |
| attP17 | GTTCAACTTTTTGTATACAAAGTTGGCA<br>CAAGTTGAAAACATATGTTTCAACCGT | (SEQ ID NO:22) |
| attL17 | CAACTTTTTGTATACAAAGTTGGCA<br>GTTGAAAACATATGTTTCAACCGT | (SEQ ID NO:23) |
| attR17 | GTTCAACTTTTTGTATACAAAGTTGT<br>CAAGTTGAAAACATATGTTTCAACA | (SEQ ID NO:24) |
| attB19 | CAACTTTTTTCGTACAAAGTTGT<br>GTTGAAAAAGCATGTTTCAACA | (SEQ ID NO:25) |
| attP19 | GTTCAACTTTTTTCGTACAAAGTTGGCA<br>CAAGTTGAAAAAGCATGTTTCAACCGT | (SEQ ID NO:26) |
| attL19 | CAACTTTTTTCGTACAAAGTTGGCA<br>GTTGAAAAAGCATGTTTCAACCGT | (SEQ ID NO:27) |
| attR19 | GTTCAACTTTTTTCGTACAAAGTTGT<br>CAAGTTGAAAAAGCATGTTTCAACA | (SEQ ID NO:28) |

FIG. 24B

| | | |
|---|---|---|
| attB20 | CAACTTTTTTGGTACAAAGTTGT<br>GTTGAAAAACCATGTTTCAACA | (SEQ ID NO:29) |
| attP20 | GTTCAACTTTTTGGTACAAAGTTGGCA<br>CAAGTTGAAAAACCATGTTTCAACCGT | (SEQ ID NO:30) |
| attL20 | CAACTTTTTTGGTACAAAGTTGGCA<br>GTTGAAAAACCATGTTTCAACCGT | (SEQ ID NO:31) |
| attR20 | GTTCAACTTTTTGGTACAAAGTTGT<br>CAAGTTGAAAAACCATGTTTCAACA | (SEQ ID NO:32) |
| attB21 | CAACTTTTTTAATACAAAGTTGT<br>GTTGAAAAATTATGTTTCAACA | (SEQ ID NO:33) |
| attP21 | GTTCAACTTTTTAATACAAAGTTGGCA<br>CAAGTTGAAAAATTATGTTTCAACCGT | (SEQ ID NO:34) |
| attL21 | CAACTTTTTTAATACAAAGTTGGCA<br>GTTGAAAAATTATGTTTCAACCGT | (SEQ ID NO:35) |
| attR21 | GTTCAACTTTTTAATACAAAGTTGT<br>CAAGTTGAAAAATTATGTTTCAACA | (SEQ ID NO:36) |

FIG.24C

VECTOR ASSEMBLY USING
MODULAR VECTOR ELEMENT ENTRY CLONES

VECTOR ASSEMBLY USING
MODULAR VECTOR ELEMENT ENTRY CLONES

USE OF MULTIPLE RECOMBINATION SITES WITH UNIQUE SPECIFICITY IN RECOMBINATIONAL CLONING

CROSS-REFERENCE TO RELATED APPLICATIONS

The present application claims the benefit of the filing dates of U.S. Appl. Ser. No. 60/169,983, filed Dec. 10, 1999, and U.S. Appl. Ser. No. 60/188,020, filed Mar. 9, 2000, both of which are incorporated herein by reference.

BACKGROUND OF THE INVENTION

1. Field of the Invention

The present invention relates to the fields of biotechnology and molecular biology. In particular, the present invention relates to joining multiple nucleic acid molecules containing recombination sites, preferably using recombination sites having a unique specificity. The present invention also relates to cloning such joined nucleic acid molecules using recombinational cloning methods. The invention also relates to joining multiple peptides, and combinations of peptides and nucleic acid molecules through the use of recombination sites. Other molecules and compounds or combinations of molecules and compounds may also be joined through recombination sites according to the invention. Such peptides, nucleic acids and other molecules and/or compounds (or combinations thereof) may also be joined or bound through recombination to one or a number of supports or structures in accordance with the invention.

2. Related Art

Site-specific Recombinases

Site-specific recombinases are proteins that are present in many organisms (e.g., viruses and bacteria) and have been characterized as having both endonuclease and ligase properties. These recombinases (along with associated proteins in some cases) recognize specific sequences of bases in a nucleic acid molecule and exchange the nucleic acid segments flanking those sequences. The recombinases and associated proteins are collectively referred to as "recombination proteins" (see, e.g., Landy, A., *Current Opinion in Biotechnology* 3:699–707 (1993)).

Numerous recombination systems from various organisms have been described. See, e.g., Hoess, et al., *Nucleic Acids Research* 14(6):2287 (1986); Abremski, et al., *J Biol. Chem.* 261(1):391 (1986); Campbell, *J. Bacteriol.* 174(23):7495 (1992); Qian, et al., *J Biol. Chem.* 267(11):7794 (1992); Araki, et al., *J Mol. Biol.* 225(1):25 (1992); Maeser and Kahnmann, *Mol. Gen. Genet.* 230:170–176) (1991); Esposito, et al., *Nucl. Acids Res.* 25(18):3605 (1997). Many of these belong to the integrase family of recombinases (Argos, et al., *EMBO J.* 5:433–440 (1986); Voziyanov, et al., *Nucl. Acids Res.* 27:930 (1999)). Perhaps the best studied of these are the Integrase/att system from bacteriophage λ(Landy, A. *Current Opinions in Genetics and Devel.* 3:699–707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp.90–109), and the FLP/FRT system from the *Saccharoinyces cerevisiae* 2 μ circle plasmid (Broach, et al., *Cell* 29:227–234 (1982)).

Transposons

Transposons are mobile genetic elements. Transposons are structurally variable, being described as simple or compound, but typically encode a transposition catalyzing enzyme, termed a transposase, flanked by DNA sequences organized in inverted orientations. For a more thorough discussion of the characteristics of transposons, one may consult *Mobile Genetic Elements*, D. J. Sherratt, Ed., Oxford University Press (1995) and *Mobile DNA*, D. E. Berg and M. M. Howe, Eds., American Society for Microbiology (1989), Washington, D.C. both of which are specifically incorporated herein by reference.

Transposons have been used to insert DNA into target DNA. As a general rule, the insertion of transposons into target DNA is a random event. One exception to this rule is the insertion of transposon Tn7. Transposon Tn7 can integrate itself into a specific site in the *E. coli* genome as one part of its life cycle (Stellwagen, A. E., and Craig, N. L. *Trends in Biochemical Sciences* 23, 486–490, 1998 specifically incorporated herein by reference). This site specific insertion has been used in vivo to manipulate the baculovirus genome (Lucklow et al., *J Virol.* 67:4566–4579 (1993) specifically incorporated herein by reference). The site specificity of Tn7 is atypical of transposable elements whose hallmark is movement to random positions in acceptor DNA molecules. For the purposes of this application, transposition will be used to refer to random or quasi-random movement, unless otherwise specified, whereas recombination will be used to refer to site specific recombination events. Thus, the site specific insertion of Tn7 into the attTn7 site would be referred to as a recombination event while the random insertion of Tn7 would be referred to as a transposition event.

York, et al. (*Nucleic Acids Research,* 26(8):1927–1933, (1998)) disclose an in vitro method for the generation of nested deletions based upon an intramolecular transposition within a plasmid using Tn5. A vector containing a kanamycin resistance gene flanked by two 19 base pair Tn5 transposase recognition sequences and a target DNA sequence was incubated in vitro in the presence of purified transposase protein. Under the conditions of low DNA concentration employed, the intramolecular transposition reaction was favored and was successfully used to generate a set of nested deletions in the target DNA. The authors suggested that this system might be used to generate C-terminal truncations in a protein encoded by the target DNA by the inclusion of stop signals in all three reading frames adjacent to the recognition sequences. In addition, the authors suggested that the inclusion of a His tag and kinase region might be used to generate N-terminal deletion proteins for further analysis.

Devine, et al., (*Nucleic Acids Research,* 22:3765–3772 (1994) and U.S. Pat. Nos. 5,677,170 and 5,843,772, all of which are specifically incorporated herein by reference) disclose the construction of artificial transposons for the insertion of DNA segments into recipient DNA molecules in vitro. The system makes use of the insertion-catalyzing enzyme of yeast TY1 virus-like particles as a source of transposase activity. The DNA segment of interest is cloned, using standard methods, between the ends of the transposon-like element TY1. In the presence of the TY1 insertion-catalyzing enzyme, the resulting element integrates randomly into a second target DNA molecule.

Another class of mobile genetic elements are integrons. Integrons generally consist of a 5'- and a 3'-conserved sequence flanking a variable sequence. Typically, the 5'-conserved sequence contains the coding information for an integrase protein. The integrase protein may catalyze site-specific recombination at a variety of recombination sites including attI, attC as well as other types of sites (see Francia et al., *J Bacteriology* 181(21):6844–6849, 1999, and references cited therein).

Recombination Sites

Whether the reactions discussed above are termed recombination, transposition or integration and are catalyzed by a recombinase or integrase, they share the key feature of specific recognition sequences, often termed "recombination sites," on the nucleic acid molecules participating in the reactions. These recombination sites are sections or segments of nucleic acid on the participating nucleic acid molecules that are recognized and bound by the recombination proteins during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. (See FIG. 1 of Sauer, B., *Curr. Opin. Biotech.* 5:521–527 (1994).) Other examples of recognition sequences include the attB, attP, attL, and attR sequences which are recognized by the recombination protein λ Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). (See Landy, *Curr. Opin. Biotech.* 3:699–707 (1993).)

Stop Codons and Suppressor tRNAs

Three codons are used by both eukaryotes and prokaryotes to signal the end of gene. When transcribed into mRNA, the codons have the following sequences: UAG (amber), UGA (opal) and UAA (ochre). Under most circumstances, the cell does not contain any tRNA molecules that recognize these codons. Thus, when a ribosome translating an mRNA reaches one of these codons, the ribosome stalls and falls of the RNA, terminating translation of the mRNA. The release of the ribosome from the mRNA is mediated by specific factors (see S. Mottagui-Tabar, *NAR* 26(11), 2789, 1998). A gene with an in-frame stop codon (TAA, TAG, or TGA) will ordinarily encode a protein with a native carboxy terminus. However, suppressor tRNAs, can result in the insertion of amino acids and continuation of translation past stop codons.

Mutant tRNA molecules that recognize what are ordinarily stop codons suppress the termination of translation of an mRNA molecule and are termed suppressor tRNAs. A number of such suppressor tRNAs have been found. Examples include, but are not limited to, the supE, supP, supD, supF and supZ suppressors which suppress the termination of translation of the amber stop codon, supB, glT, supL, supN, supC and supM suppressors which suppress the function of the ochre stop codon and glyT, trpT and Su-9 which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. For a more detailed discussion of suppressor tRNAs, the reader may consult Eggertsson, et al., (1988) *Microbiological Review* 52(3):354–374, and Engleerg-Kukla, et al. (1996) in *Escherichia coli* and *Salmonella* Cellular and Molecular Biology, Chapter 60, pps 909–921, Neidhardt, et al. eds., ASM Press, Washington, D.C.

Mutations which enhance the efficiency of termination suppressors, i.e., increase the read through of the stop codon, have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Under ordinary circumstances, host cells would not be expected to be healthy if suppression of stop codons is too efficient. This is because of the thousands or tens of thousands of genes in a genome, a significant fraction will naturally have one of the three stop codons; complete read-through of these would result in a large number of aberrant proteins containing additional amino acids at their carboxy termini. If some level of suppressing tRNA is present, there is a race between the incorporation of the amino acid and the release of the ribosome. Higher levels of tRNA may lead to more read-through although other factors, such as the codon context, can influence the efficiency of suppression.

Organisms ordinarily have multiple genes for tRNAs. Combined with the redundancy of the genetic code (multiple codons for many of the amino acids), mutation of one tRNA gene to a suppressor tRNA status does not lead to high levels of suppression. The TAA stop codon is the strongest, and most difficult to suppress. The TGA is the weakest, and naturally (in *E. coli*) leaks to the extent of 3%. The TAG (amber) codon is relatively tight, with a read-through of ~1% without suppression. In addition, the amber codon can be suppressed with efficiencies on the order of 50% with naturally occurring suppressor mutants.

Suppression has been studied for decades in bacteria and bacteriophages. In addition, suppression is known in yeast, flies, plants and other eukaryotic cells including mammalian cells. For example, Capone, et al. (*Molecular and Cellular Biology* 6(9):3059–3067, 1986) demonstrated that suppressor tRNAs derived from mammalian tRNAs could be used to suppress a stop codon in mammalian cells. A copy of the *E. coli* chloramphenicol acetyltransferase (cat) gene having a stop codon in place of the codon for serine 27 was transfected into mammalian cells along with a gene encoding a human serine tRNA which had been mutated to form an amber, ochre, or opal suppressor derivative of the gene. Successful expression of the cat gene was observed. An inducible mammalian amber suppressor has been used to suppress a mutation in the replicase gene of polio virus and cell lines expressing the suppressor were successfully used to propagate the mutated virus (Sedivy, et al., (1987) *Cell* 50: 379–389). The context effects on the efficiency of suppression of stop codons by suppressor tRNAs has been shown to be different in mammalian cells as compared to *E. coli* (Phillips-Jones, et al., (1995) *Molecular and Cellular Biology* 15(12): 6593–6600, Martin, et al.,(1993) *Biochemical Society Transactions* 21:) Since some human diseases are caused by nonsense mutations in essential genes, the potential of suppression for gene therapy has long been recognized (see Temple, et al. (1982) *Nature* 296(5857):537–40). The suppression of single and double nonsense mutations introduced into the diphtheria toxin A-gene has been used as the basis of a binary system for toxin gene therapy (Robinson, et al., (1995) *Human Gene Therapy* 6:137–143).

Conventional Nucleic Acid Cloning

The cloning of nucleic acid segments currently occurs as a daily routine in many research labs and as a prerequisite step in many genetic analyses. The purpose of these clonings is various, however, two general purposes can be considered: (1) the initial cloning of nucleic acid from large DNA or RNA segments (chromosomes, YACs, PCR fragments, mRNA, etc.), done in a relative handful of known vectors such as pUC, pGem, pBlueScript, and (2) the subcloning of these nucleic acid segments into specialized vectors for functional analysis. A great deal of time and effort is expended both in the transfer of nucleic acid segments from the initial cloning vectors to the more specialized vectors. This transfer is called subcloning.

The basic methods for cloning have been known for many years and have changed little during that time. A typical cloning protocol is as follows:

(1) digest the nucleic acid of interest with one or two restriction enzymes;

(2) gel purify the nucleic acid segment of interest when known;

(3) prepare the vector by cutting with appropriate restriction enzymes, treating with alkaline phosphatase, gel purify etc., as appropriate;

(4) ligate the nucleic acid segment to the vector, with appropriate controls to eliminate background of uncut and self-ligated vector;

(5) introduce the resulting vector into an *E. coli* host cell;

(6) pick selected colonies and grow small cultures overnight;

(7) make nucleic acid minipreps; and (8) analyze the isolated plasmid on agarose gels (often after diagnostic restriction enzyme digestion) or by PCR.

The specialized vectors used for subcloning nucleic acid segments are functionally diverse. These include but are not limited to: vectors for expressing nucleic acid molecules in various organisms; for regulating nucleic acid molecule expression; for providing tags to aid in protein purification or to allow tracking of proteins in cells; for modifying the cloned nucleic acid segment (e.g., generating deletions); for the synthesis of probes (e.g., riboprobes); for the preparation of templates for nucleic acid sequencing; for the identification of protein coding regions; for the fusion of various protein-coding regions; to provide large amounts of the nucleic acid of interest, etc. It is common that a particular investigation will involve subcloning the nucleic acid segment of interest into several different specialized vectors.

As known in the art, simple subclonings can be done in one day (e.g., the nucleic acid segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. One of the most tedious and time consuming type of subcloning involves the sequential addition of several nucleic acid segments to a vector in order to construct a desired clone. One example of this type of cloning is in the construction of gene targeting vectors. Gene targeting vectors typically include two nucleic acid segments, each identical to a portion of the target gene, flanking a selectable marker. In order to construct such a vector, it may be necessary to clone each segment sequentially, i.e., first one gene fragment is inserted into the vector, then the selectable marker and then the second fragment of the target gene. This may require a number of digestion, purification, ligation and isolation steps for each fragment cloned. Subcloning nucleic acid fragments is thus often viewed as a chore to be done as few times as possible.

Several methods for facilitating the cloning of nucleic acid segments have been described, e.g., as in the following references.

Ferguson, J., et al., *Gene* 16:191 (1981), disclose a family of vectors for subcloning fragments of yeast nucleic acids. The vectors encode kanamycin resistance. Clones of longer yeast nucleic acid segments can be partially digested and ligated into the subcloning vectors. If the original cloning vector conveys resistance to ampicillin, no purification is necessary prior to transformation, since the selection will be for kanamycin.

Hashimoto-Gotoh, T., et al., *Gene* 41:125 (1986), disclose a subcloning vector with unique cloning sites within a streptomycin sensitivity gene; in a streptomycin-resistant host, only plasmids with inserts or deletions in the dominant sensitivity gene will survive streptomycin selection.

Notwithstanding the improvements provided by these methods, traditional subclonings using restriction and ligase enzymes are time consuming and relatively unreliable. Considerable labor is expended, and if two or more days later the desired subclone can not be found among the candidate plasmids, the entire process must then be repeated with alternative conditions attempted.

Recombinational Cloning

Cloning systems that utilize recombination at defined recombination sites have been previously described in the related applications listed above, and in U.S. application Ser. No. 09/177,387, filed Oct. 23, 1998; U.S. application Ser. No. 09/517,466, filed Mar. 2, 2000; and U.S. Pat. Nos. 5,888,732 and 6,143,557, all of which are specifically incorporated herein by reference. In brief, the GATEWAY™ Cloning System, described in this application and the applications referred to in the related applications section, utilizes vectors that contain at least one recombination site to clone desired nucleic acid molecules in vivo or in vitro. More specifically, the system utilizes vectors that contain at least two different site-specific recombination sites based on the bacteriophage lambda system (e.g., att1 and att2) that are mutated from the wild-type (att0) sites. Each mutated site has a unique specificity for its cognate partner att site (i.e., its binding partner recombination site) of the same type (for example attB1 with attP 1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the GATEWAY™ system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

Mutating specific residues in the core region of the att site can generate a large number of different att sites. As with the att1 and att2 sites utilized in GATEWAY™, each additional mutation potentially creates a novel att site with unique specificity that will recombine only with its cognate partner att site bearing the same mutation and will not cross-react with any other mutant or wild-type att site. Novel mutated att sites (e.g., attB1-10, attP 1-10, attR 1-10 and attL1-10) are described in previous patent application Ser. No. 09/517,466, filed Mar. 2, 2000, which is specifically incorporated herein by reference. Other recombination sites having unique specificity (i.e., a first site will recombine with its corresponding site and will not recombine or not substantially recombine with a second site having a different specificity) may be used to practice the present invention. Examples of suitable recombination sites include, but are not limited to, loxP sites; loxP site mutants, variants or derivatives such as loxP511 (see U.S. Pat. No. 5,851,808);frt sites; frt site mutants, variants or derivatives; difsites; difsite mutants, variants or derivatives;

psi sites; psi site mutants, variants or derivatives; cer sites; and cer site mutants, variants or derivatives. The present invention provides novel methods using such recombination sites to join or link multiple nucleic acid molecules or segments and more specifically to clone such multiple segments (e.g., two, three, four, five, seven, ten, twelve, fifteen, twenty, thirty, fifty, seventy-five, one hundred, two hundred, etc.) into one or more vectors (e.g., two, three, four, five, seven, ten, twelve, etc.) containing one or more recombination sites (e.g., two, three, four, five, seven, ten, twelve, fifteen, twenty, thirty, fifty, seventy-five, one hundred, two hundred, etc.), such as any GATEWAY™ Vector including Destination Vectors.

BRIEF SUMMARY OF THE INVENTION

The present invention generally provides materials and methods for joining or combining two or more (e.g., two, three, four, five, seven, ten, twelve, fifteen, twenty, thirty, fifty, seventy-five, one hundred, two hundred, etc.) segments or molecules of nucleic acid by the recombination reaction between recombination sites, at least one of which is present on each molecule or segment. Such recombination reactions to join multiple nucleic acid molecules according to the invention may be conducted in vivo (e.g., within a cell, tissue, organ or organism) or in vitro (e.g., cell-free systems). Accordingly, the invention relates to methods for creating novel or unique combinations of nucleic acid molecules and to the nucleic acid molecules created by such methods. The invention also relates to host and host cells comprising the nucleic acid molecules of the invention. The invention also relates to kits for carrying out the methods of the invention, and to compositions for carrying out the methods of the invention as well as compositions made while carrying out the methods of the invention.

The nucleic acid molecules created by the methods of the invention may be used for any purpose known to those skilled in the art. For example, the nucleic acid molecules of the invention may be used to express proteins or peptides encoded by the nucleic acid molecules and may be used to create novel fusion proteins by expressing different sequences linked by the methods of the invention. Such expression can be accomplished in a cell or by using well known in vitro expression/transcription systems. In one aspect, at least one (and preferably two or more) of the nucleic acid molecules or segments to be joined by the methods of the invention comprise at least two recombination sites, although each molecule may comprise multiple recombination sites (e.g., two, three, four, five, seven, ten, twelve, fifteen, twenty, thirty, fifty, etc.). Such recombination sites (which may be the same or different) may be located at various positions in each nucleic acid molecule or segment and the nucleic acid used in the invention may have various sizes and be in different forms including circular, supercoiled, linear, and the like. The nucleic acid molecules used in the invention may also comprise one or more vectors or one or more sequences allowing the molecule to function as a vector in a host cell (such as an origin of replication). The nucleic acid molecules of the invention may also comprise non-coding segments (e.g., intronic, untranslated, or other segments) that serve a structural or other non-expressive functions.

In a preferred aspect, the nucleic acid molecules or segments for use in the invention are linear molecules having at least one recombination site at or near at least one termini of the molecule and preferably comprise at least one recombination site at or near both termini of the molecule. In another preferred aspect, when multiple recombination sites are located on a nucleic acid molecule of interest, such sites do not substantially recombine or do not recombine with each other on that molecule. In this embodiment, the corresponding binding partner recombination sites preferably are located on one or more other nucleic acid molecules to be linked or joined by the methods of the invention. For instance, a first nucleic acid molecule used in the invention may comprise at least a first and second recombination site and a second nucleic acid molecule may comprise at least a third and fourth recombination site, wherein the first and second sites do not recombine with each other and the third and fourth sites do not recombine with each other, although the first and third and/or the second and fourth sites may recombine.

The nucleic acid molecules to be joined by the methods of the invention (i.e., the "starting molecules") are used to produce one or more (e.g., two, three, four, five, seven, ten, twelve, fifteen, twenty, thirty, fifty, seventy-five, one hundred, two hundred, etc.) hybrid molecules (e.g., the "product nucleic acid molecules") containing all or a portion of the starting molecules. The starting molecules can be any nucleic acid molecule derived from any source or produced by any method. Such molecules may be derived from natural sources (such as cells (e.g., prokaryotic cells such as bacterial cells, eukaryotic cells such as fungal cells (e.g., yeast cells), plant cells, animals cells (e.g., mammalian cells such as human cells), etc.), viruses, tissues, organs from any animal or non-animal source, and organisms) or may be non-natural (e.g., derivative nucleic acids) or synthetically derived. Such molecules may also include prokaryotic and eukaryotic vectors, plasmids, integration sequences (e.g., transposons), phage or viral vectors, phagemids, cosmids, and the like. The segments or molecules for use in the invention may be produced by any means known to those skilled in the art including, but not limited to, amplification such as by PCR, isolation from natural sources, chemical synthesis, shearing or restriction digest of larger nucleic acid molecules (such as genomic or cDNA), transcription, reverse transcription and the like, and recombination sites may be added to such molecules by any means known to those skilled in the art including ligation of adapters containing recombination sites, attachment with topoisomerases of adapters containing recombination sites, attachment with topoisomerases of adapter primers containing recombination sites, amplification or nucleic acid synthesis using primers containing recombination sites, insertion or integration of nucleic acid molecules (e.g., transponsons or integration sequences) containing recombination sites etc. In a preferred aspect, the nucleic acid molecules used in the invention are populations of molecules such as nucleic acid libraries or cDNA libraries.

Recombination sites for use in the invention may be any recognition sequence on a nucleic acid molecule which participates in a recombination reaction mediated or catalyzed by one or more recombination proteins. In those embodiments of the present invention utilizing more than one (e.g., two, three, four, five, seven, ten, twelve, fifteen, twenty, thirty, fifty, etc.) recombination sites, such recombination sites may be the same or different and may recombine with each other or may not recombine or not substantially recombine with each other. Recombination sites contemplated by the invention also include mutants, derivatives or variants of wild-type or naturally occurring recombination sites. Preferred recombination site modifications include those that enhance recombination, such enhancements being selected from the group consisting of substantially (i) favoring integrative recombination; (ii) favoring excisive recombination; (iii) relieving the requirement for host factors; (iv) increasing the efficiency of co-integrate or product formation; and (v) increasing the specificity of co-integrate or product formation.

Preferred modifications to the recombination sites include those that enhance recombination specificity, remove one or more stop codons, and/or avoid hair-pin formation. Desired modifications can also be made to the recombination sites to include desired amino acid changes to the transcription or translation product (e.g., mRNA or protein) when translation or transcription occurs across the modified recombination site. Preferred recombination sites used in accordance with the invention include att sites, frt sites, dif sites, psi sites, cer sites, and lox sites or mutants, derivatives and variants thereof (or combinations thereof). Recombination sites contemplated by the invention also include portions of such recombination sites. Depending on the recombination site specificity used, the invention allows directional linking of nucleic acid molecules to provide desired orientations of the linked molecules or non-directional linking to produce random orientations of the linked molecules.

In specific embodiments, the recombination sites which recombine with each other in compositions and used in methods of the invention comprise att sites having identical seven base pair overlap regions. In specific embodiments of the invention, the first three nucleotides of these seven base pair overlap regions comprise nucleotide sequences selected from the group consisting of AAA, AAC, AAG, AAT, ACA, ACC, ACG, ACT, AGA, AGC, AGG, AGT, ATA, ATC, ATG; ATT, CAA, CAC, CAG, CAT, CCA, CCC, CCG, CCT, CGA, CGC, CGG, CGT, CTA, CTC, CTG CTT, GAA, GAC, GAG, GAT, GCA, GCC, GCG, GCT, GGA, GGC, GGG, GGT, GTA, GTC, GTG, GTT, TAA, TAC, TAG, TAT, TCA, TCC, TCG, TCT, TGA, TGC, TGG, TGT, TTA, TTC, TTG, and TTT.

Each starting nucleic acid molecule may comprise, in addition to one or more recombination sites (e.g., two, three, four, five, seven, ten, twelve, fifteen, twenty, thirty, fifty, etc.), a variety of sequences (or combinations thereof) including, but not limited to sequences suitable for use as primer sites (e.g., sequences which a primer such as a sequencing primer or amplification primer may hybridize to initiate nucleic acid synthesis, amplification or sequencing), transcription or translation signals or regulatory sequences such as promoters or enhancers, ribosomal binding sites, Kozak sequences, start codons, transcription and/or translation termination signals such as stop codons (which may be optimally suppressed by one or more suppressor tRNA molecules), origins of replication, selectable markers, and genes or portions of genes which may be used to create protein fusion (e.g., N-terminal or carboxy terminal) such as glutathione S-transferase (GST), β-glucuronidase (GUS), histidine tags (HIS6), green fluorescent protein (GFP), yellow fluorescent protein (YFP), cyan fluorescent protein (CFP), open reading frame (ORF) sequences, and any other sequence of interest which may be desired or used in various molecular biology techniques including sequences for use in homologous recombination (e.g., for use in gene targeting).

In one aspect, the invention provides methods for producing populations of hybrid nucleic acid molecules comprising (a) mixing at least a first population of nucleic acid molecules comprising one or more recombination sites with at least one target nucleic acid molecule comprising one or more recombination sites; and (b) causing some or all of the nucleic acid molecules of the at least first population to recombine with all or some of the target nucleic acid molecules, thereby forming the populations of hybrid nucleic acid molecules. In certain specific embodiments of the above methods, the recombination is caused by mixing the first population of nucleic acid molecules and the target nucleic acid molecule with one or more recombination proteins under conditions which favor the recombination to produce hybrid nucleic acid molecules. In other specific embodiments, methods of the invention further comprise mixing the hybrid nucleic acid molecules with at least a second population of nucleic acid molecules comprising one or more recombination sites to produce a second population of product nucleic acid molecules. Alternatively, the first population, second population and target nucleic acid molecules may be mixed together to form a hybrid population through recombination. In additional specific embodiments, methods of the invention further comprise selecting for the populations of hybrid nucleic acid molecules generated by the methods described above. In yet additional specific embodiments, methods of the invention further comprise selecting for the population of hybrid nucleic acid molecules, against the first population of nucleic acid molecules, against the target nucleic acid molecules, and/or against the second population of nucleic acid molecules.

In related embodiments, the invention provides methods for recombining a first nucleic acid segment containing a first recombination site, a second nucleic acid segment containing a second and third recombination site, and a third nucleic acid segment containing a fourth recombination site, wherein the first, second, or third nucleic acid segments may be identical nucleic acid segments or populations of nucleic acid molecules, such that recombination generates a linear or closed, circle product comprising the first, second and third nucleic acid segments. Further, members of the recombination products may be amplified using oligonucleotides which either contain or do not contain recombination sites and are homologous or degenerate to the first or third nucleic acid segments. Thus, for example, by performing amplification with primers specific for the first and third nucleic acid segments, a product comprising the first-second-third hybrid molecules can be amplified, where other undesired molecules (e.g., products comprising the first-second hybrid molecules) are not amplified. In this way, amplification can be used to select for desired products and against undesired products. Such amplification can be designed to select for any desired products or intermediates of a recombination reaction. For example, four different molecules (e.g., A, B, C, and D) can be joined and various intermediate products can be selected for (e.g., A-B-C, or A-B) using primers designed to amplify the desired products (e.g., primers corresponding to molecules A and C, when A-B-C is amplified and A and B when A-B is amplified). The resulting amplified products may then be cloned. In related embodiments, the process described above can be performed using two or more (e.g., two, three, four, five, six, seven, eight, nine, ten, eleven, twelve, thirteen, fifteen, etc.) nucleic acid segments.

In another aspect, the invention provides methods of producing populations of hybrid nucleic acid molecules comprising (a) mixing at least a first population of nucleic acid molecules comprising one or more recombination sites with at least a second population of nucleic acid molecules comprising one or more recombination sites; and (b) causing some or all of the nucleic acid molecules of the at least first population to recombine with all or some nucleic acid molecules of the at least second population, thereby forming one or more populations of hybrid nucleic acid molecules. In certain specific embodiments of the above methods, recombination is caused by mixing the first population of nucleic acid molecules and the second population of nucleic acid molecules with one or more recombination proteins under conditions which favor their recombination. In other specific embodiments, methods of the invention further comprise mixing the first and second populations of nucleic acid molecules with at least a third population of nucleic acid molecules comprising one or more recombination sites. In additional other specific embodiments, methods of the invention further comprise selecting for the population of hybrid nucleic acid molecules. In yet other specific embodiments, methods of the invention further comprise selecting for the population of hybrid nucleic acid molecules and against the first, second, and/or third populations of nucleic acid molecules. In further specific embodiments, methods of the invention further comprise selecting for or against cointegrate molecules and/or byproduct molecules.

The invention further includes populations of hybrid nucleic acid molecules produced by the above methods and populations of recombinant host cells comprising the above populations of hybrid nucleic acid molecules.

In certain embodiments, the recombination proteins used in the practice of the invention comprise one or more proteins selected from the group consisting of Cre, Int, IHF, Xis, Flp, Fis, Hin, Gin, Cin, Tn3 resolvase, TndX, XerC, XerD, and ΦC31. In specific embodiments, the recombination sites comprise one or more recombination sites selected from the group consisting of lox sites; psi sites; dif sites; cer sites; frt sites; att sites; and mutants, variants, and derivatives of these recombination sites which retain the ability to undergo recombination.

In a specific aspect, the invention allows controlled expression of fusion proteins by suppression of one or more stop codons. According to the invention, one or more starting molecules (e.g., one, two, three, four, five, seven, ten, twelve, etc.) joined by the invention may comprise one or more stop codons which may be suppressed to allow expression from a first starting molecule through the next joined starting molecule. For example, a first-second-third starting molecule joined by the invention (when each of such first and second molecules contains a stop codon) can express a tripartite fusion protein encoded by the joined molecules by suppressing each of the stop codons. Moreover, the invention allows selective or controlled fusion protein expression by varying the suppression of selected stop codons. Thus, by suppressing the stop codon between the first and second molecules but not between the second and third molecules of the first-second-third molecule, a fusion protein encoded by the first and second molecule may be produced rather than the tripartite fusion. Thus, use of different stop codons and variable control of suppression allows production of various fusion proteins or portions thereof encoded by all or different portions of the joined starting nucleic acid molecules of interest. In one aspect, the stop codons may be included anywhere within the starting nucleic acid molecule or within a recombination site contained by the starting molecule. Preferably, such stop codons are located at or near the termini of the starting molecule of interest, although such stop codons may be included internally within the molecule. In another aspect, one or more of the starting nucleic acid molecules may comprise the coding sequence of all or a portion of the target gene or open reading frame of interest wherein the coding sequence is followed by a stop codon. The stop codon may then be followed by a recombination site allowing joining of a second starting molecule. In some embodiments of this type, the stop codon may be optionally suppressed by a suppressor tRNA molecule. The genes coding for the suppressor tRNA molecule may be provided on the same vector comprising the target gene of interest, on a different vector, or in the chromosome of the host cell into which the vector comprising the coding sequence is inserted. In some embodiments, more than one copy (e.g., two, three, four, five, seven, ten, twelve, fifteen, twenty, thirty, fifty, etc. copies) of the suppressor tRNA may be provided. In some embodiments, the transcription of the suppressor tRNA may be under the control of a regulatable (e.g., inducible or repressible) promoter.

Thus, in one aspect, the invention relates to a method of expressing one or more fusion proteins (e.g., one, two, three, four, five, seven, ten, twelve, fifteen, twenty, thirty, fifty, etc.) comprising:

(a) obtaining at least a first nucleic acid molecule comprising at least one recombination site and at least one stop codon (preferably the recombination site and/or stop codon are located at or near a terminus or termini of said first nucleic acid molecule), and a second nucleic acid molecule comprising at least one recombination site (which is preferably located at or near a terminus or termini of said second nucleic acid molecule);

(b) causing said first and second nucleic acid molecules to recombine through recombination of said recombination sites, thereby producing a third nucleic acid molecule comprising said at least one stop codon and all or a portion of said first and second molecules; and (c) expressing one or more peptides or proteins (e.g., two, three, four, five, seven, ten, twelve, fifteen, twenty, thirty, fifty, etc.) encoded by said third molecule while suppressing said at least one stop codon.

Further, recombination sites described herein (e.g., recombination sites having various recombination specificities) may contain stop codons in one, two or all three forward or reverse reading frames. Such termination codons may be suppressed as described above. Further, in appropriate instances, such recombination sites may be designed so as to eliminate stop codons in one, two and/or all three forward and/or reverse reading frames.

In another aspect, the invention provides methods of synthesizing proteins comprising (a) providing at least a first nucleic acid molecule comprising a coding sequence followed by a stop codon; (b) providing at least a second nucleic acid molecule comprising a coding sequence, optionally, followed by a stop codon; (c) causing recombination such that the nucleic acid molecules are joined; (d) inserting said joined nucleic acid molecules into a vector to produce modified vectors with the two coding sequences connected in frame; (e) transforming host cells which express suppressor tRNAs with the modified vectors; and (f) causing expression of the two coding sequences such that fusion proteins encoded by at least a portion of both of the coding sequences are produced, wherein the nucleic acid molecules of (a) and (b) are each flanked by at least one recombination site. Further, the fused nucleic acid molecules or the vector may comprise at least one suppressible stop codon (e.g., amber, opal and/or ochre codons). In addition, either the first or second nucleic acid molecule may already be present in the vector prior to application of the methods described above. In specific embodiments of the invention, the vectors and/or host cells comprise genes which encode at least one suppressor tRNA molecule. In other specific embodiments, methods of the invention further comprise transforming the host cell with a nucleic acid molecule comprising genes which encode at least one suppressor tRNA molecule. In yet other specific embodiments, the fusion proteins may comprise N- or C-terminal tags (e.g., glutathione S-transferase, P-glucuronidase, green fluorescent protein, yellow fluorescent protein, red fluorescent protein, cyan fluorescent protein, maltose binding protein, a six histidine tag, an epitope tag, etc.) encoded by at least a portion of the vector.

The invention also relates to a method of expressing one or more fusion proteins (e.g., one, two, three, four, five, seven, ten, twelve, fifteen, twenty, thirty, fifty, etc.) comprising:

(a) obtaining at least a first nucleic acid molecule comprising at least one recombination site (preferably the recombination site is located at or near a terminus or termini of said first nucleic acid molecule) and a second nucleic acid molecule comprising at least one recombination site (which is preferably located at or near a terminus or termini of said second nucleic acid molecule);

(b) causing said at least first and second nucleic acid molecules to recombine through recombination of said recombination sites, thereby producing a third nucleic acid molecule comprising all or a portion of said at least first and second molecules; and (c) expressing one or more peptides or proteins (e.g., one, two, three, four, five, seven, ten, twelve, fifteen, twenty, thirty, fifty, etc.) encoded by said third nucleic acid molecule. In certain such embodiments, at least part of the expressed fusion protein will be encoded by the third nucleic acid molecule and at least another part will be encoded by at least part of the first and/or second nucleic acid molecules. Such a fusion protein may be produced by translation of nucleic acid which corresponds to recombination sites located between the first and second nucleic acid molecules. Thus, fusion proteins may be expressed by "reading through" mRNA corresponding to recombination sites used to connect two or more nucleic acid segments. The invention further includes fusion proteins produced by methods of the invention and mRNA which encodes such fusion proteins.

As discussed below in more detail, the methods discussed above can be used to prepare fusion proteins which are encoded by different nucleic acid segments, as well as nucleic acid molecules which encode such fusion proteins. Thus, in one general aspect, the invention provides methods for producing fusion proteins prepared by the expression of nucleic acid molecules generated by connecting two or more nucleic acid segments. In related embodiments, the invention provides methods for producing fusion RNAs prepared by the expression of nucleic acid molecules generated by connecting two or more nucleic acid segments. These RNAs may be mRNA or may be untranslated RNAs which have activities other than protein coding functions. Examples of such RNAs include ribozymes and tRNAs. The invention further provides nucleic acid molecules produced by methods of the invention, expression products of these nucleic acid molecules, methods for producing these expression products, recombinant host cells which contain these nucleic acid molecules, and methods for making these host cells. As discussed below in more detail, the invention further provides combinatorial libraries which may be screened to identify nucleic acid molecules and expression products having particular functions or activities.

In one specific aspect, the present invention provides materials and methods for joining two nucleic acid molecules or portions thereof, each of which contains at least one recombination site, into one or more product nucleic acid molecules by incubating the molecules under conditions causing the recombination of a recombination site present on one nucleic acid molecule with a recombination site present on the other nucleic acid molecule. The recombination sites are preferably located at or near the ends of the starting nucleic acid molecules. Depending on the location of the recombination sites within the starting molecules, the product molecule thus created will contain all or a portion of the first and second starting molecules joined by a recombination site (which is preferably a new recombination site). For example, recombination between an attB1 recombination site and an attP1 recombination site results in generation of an attL1 and/or attR1 recombination sites.

In another specific aspect, the present invention provides materials and methods for joining two or more nucleic acid molecules (e.g., two, three, four, five seven, ten, twelve, fifteen, twenty, thirty, fifty, etc.) into one or more product nucleic acid molecules (e.g., one, two, three, four, five seven, ten, twelve, etc.) wherein each starting nucleic acid molecule has at least one recombination site and at least one of the starting nucleic acid molecules has at least two recombination sites. The recombination sites preferably are located at or near one or both termini of the starting nucleic acid molecules. Thus, the invention provides a method of joining at least two nucleic acid molecules wherein at least a first nucleic acid molecule contains at least one recombination site and at least a second nucleic acid molecule contains two or more recombination sites. The molecules are incubated in the presence of at least one recombination protein under conditions sufficient to combine all or a portion of the starting molecules to create one or more product molecules. The product molecules thus created will contain all or a portion of each of the starting molecules joined by a recombination site (which is preferably a new recombination site).

In another specific aspect, the present invention provides a method to join at least three nucleic acid molecules (e.g., two, three, four, five seven, ten, twelve, fifteen, twenty, thirty, fifty, etc.) wherein the molecules have at least one recombination site and at least one of the starting nucleic acid molecules contains at least two recombination sites. Incubating such molecules in the presence of at least one recombination protein provides one or more product molecules (e.g., one, two, three, four, five seven, ten, twelve, fifteen, twenty, thirty, fifty, etc.) containing all or a portion of the starting molecules, wherein each molecule is joined by a recombination site (which is preferably a new recombination site).

In another specific embodiment, the present invention provides compositions and methods for joining two or more nucleic acid molecules (e.g., two, three, four, five seven, ten, twelve, fifteen, twenty, thirty, fifty, etc.), at least two of which (and preferably all of which) have two or more recombination sites. The recombination sites located on each molecule are preferably located at or near the ends of the starting nucleic acid molecules. According to the method of the invention, the two or more nucleic acid molecules or portions thereof are joined by a recombination reaction (e.g., incubate the molecules in the presence of at least one recombination protein) to form one or more product molecules comprising all or a portion of each starting molecule joined by a recombination site (which is preferably a new recombination site).

In another specific aspect, the present invention provides compositions and methods for joining at least three nucleic acid molecules comprising providing at least a first, a second and a third nucleic acid molecule, wherein the first nucleic acid molecule comprises at least a first recombination site, the second nucleic acid molecule comprises at least a second and a third recombination site and the third nucleic acid molecule comprises at least a fourth recombination site, wherein the first recombination site is capable of recombining with the second recombination site and the third recombination site is capable of recombining with the fourth recombination site and conducting at least one recombination reaction such that the first and the second recombination sites recombine and the third and the fourth recombination sites recombine, thereby combining all or a portion of the molecules to make one or more product molecules.

Thus, the present invention generally relates to a method of combining n nucleic acid molecules or segments, wherein n is an integer greater than 1 (e.g., 2, 3, 4, 5, 6, 7, 8, 9, 10, 12, 15, 18, 20, 30, 40, 50, etc.), comprising the steps of providing a $1^{st}$ through an $n^{th}$ nucleic acid molecule or segment, each molecule from 2 through n−1 having at least two recombination sites and molecules 1 and n having at least one recombination site (and preferably having at least two recombination sites), and contacting the molecules or segments with one or more recombination proteins (e.g., two, three, four, etc.) under conditions sufficient to cause all or a portion of the segments or molecules to recombine to form one or more product nucleic acid molecules comprising all or a portion of each $1^{st}$ through $n^{th}$ molecule or segment. Joining of molecules through recombination sites (e.g., interacting a first recombination site on first molecule with a second recombination site on a second molecule) preferably creates a new recombination site at the junction of the two molecules and may create a new recombination site at each junction where each molecule is joined to the next. For example, when joining a number of molecules (e.g., a first or "x" molecule, a second or "y" molecule, and a third or "z" molecule) when each molecule has at least two recombination sites, the first recombination site on the x molecule interacts with a second recombination site on the y molecule and the second recombination site on the x molecule interacts with a first recombination site on the z molecule to create a hybrid nucleic acid molecule comprising y:x:z joined by recombination sites. Of course, other recombination events may produce hybrid molecules comprising, for example, x:y:z, x:z:y, y:z:x, z:x:y, and/or z:y:x or fragments thereof, joined by recombination sites. Additional molecules can be added to product molecules by recombination between at least one recombination site located another molecules with one or more recombination sites located on the product molecule (e.g., interacting a second recombination site on the z molecule with a first recombination site on an e molecule, etc. and/or interacting a first recombination site on the y molecule with a second recombination site on an f molecule, etc.). Further, the hybrid nucleic acid molecule comprising y:x:z (or other sequences as noted above) can be circularized by the interaction of recombination sites on the free ends of y and z. Addition of all or a portion of the starting molecules may be done sequentially or simultaneously.

In instances where nucleic acid segments joined by methods of the invention contain a terminus, or termini, which do not contain recombination sites, this terminus or termini may be connected to the same nucleic acid segment or another nucleic acid molecule using a ligase or a topoisomerase (e.g., a Vaccinia virus topoisomerase; see U.S. Pat. No. 5,766,891, the entire disclosure of which is incorporated herein by reference).

In addition to joining multiple molecules, the invention also provides a means to replace one or more molecules (or combinations thereof) contained in a product molecule. For instance, any one or more n molecules comprising the product molecule may be replaced or substituted by recombination with all or a portion of a different molecule (m) which comprises one or more recombination sites. Thus, in one example, m may replace x in the y:x:z molecule described above by recombining a first recombination site on m with the first recombination site flanking x (e.g., the recombination site between y and x) and recombining a second recombination site on m with the second recombination site flanking x (e.g., the recombination site between x and z), to produce y:m:z. Multiple substitutions or replacements may be made within or on any nucleic acid molecule of the invention by recombining one or more recombination sites on such molecule with one or more recombination sites within or on the molecule to be substituted. Moreover, one or more deletions (e.g., two, three, four, five seven, ten, twelve, etc.) of various sizes on the product molecules of the invention may be accomplished by recombining two or more recombination sites within the molecule of interest for creating the deletion. For example, to create a deletion within the y:x:z (or other arrangement thereof) molecule described above, recombination of the recombination sites flanking the x molecule will create a new molecule from which x is deleted; that is, the new molecule will comprise y:z. Thus, multiple deletions, multiple replacements and combinations of deletions and replacements of various portions of a molecule of interest may be accomplished by directed recombination within the molecule of interest.

Further, the invention also provides a means to insert one or more molecules (or combinations thereof) into a product molecule. For instance, using the molecule y:x:z described above for illustration, molecule w, which comprises one or more recombination sites may be inserted between y and x to form a new molecule: y:w:x:z. In one specific embodiment, molecule w is flanked by loxP sites and insertion of molecule w is mediated by Cre recombinase between the loxP sites on the w molecule and corresponding loxP sites on the y and x molecules. As one skilled in the art would recognize, numerous variations of the above are possible and are included within the scope of the invention. For example, molecule o, which comprises one or more recombination sites may be inserted between y and x to form a new molecule comprising either y:o:x:z or y:o:w:x:z, depending on the starting molecule. The methods described herein can be used to insert virtually any number of molecules into other molecules. Further, these methods can be used sequentially, for example, to prepare molecules having diverse structures.

The product molecules produced by the methods of the invention may comprise any combination of starting molecules (or portions thereof) and can be any size and be in any form (e.g., circular, linear, supercoiled, etc.), depending on the starting nucleic acid molecule or segment, the location of the recombination sites on the molecule, and the order of recombination of the sites.

Importantly, the present invention provides a means by which populations of nucleic acid molecules (known or unknown) can be combined with one or more known or unknown target sequences of interest (e.g., two, three, four, five seven, ten, twelve, fifteen, twenty, thirty, fifty, etc.) or with other populations of nucleic acid molecules (known or unknown), thereby creating populations of combinatorial molecules (e.g., combinatorial libraries) from which unique and/or novel molecules (e.g., hybrid molecules) and proteins or peptides encoded by these molecules may be obtained and further analyzed.

In a preferred aspect, the population of nucleic acid molecules used to create combinatorial libraries according to the invention may comprise a population of segments or molecules having at least one (and preferably two or more) recombination sites (e.g., two, three, four, five seven, ten, twelve, etc.). Such populations of molecules are preferably obtained from genomic or cDNA libraries (or portions thereof) or random nucleic acids, amplification products (e.g., PCR products generated with various primers) and domains (e.g., nucleic acids encoding different protein domains from the same or different proteins) constructed to contain such recombination sites. Thus, in accordance with the invention, a first population of molecules comprising recombination sites can be randomly joined or combined through recombination (by directed and/or random orientation) with at least one target sequence of interest or with a second population of molecules comprising recombination sites to produce a third population of molecules or hybrid molecules.

In accordance with the invention, multiple populations of molecules from various sources may be combined multiple times to create a new population which comprises molecules having multiple combinations of sequences. For instance, a first population, a second population and a third population can be recombined to create a fourth population comprising a random population of tripartite molecules (e.g., some or all of the molecules of the fourth population contain all or a portion of the segments from the first, second and third population).

In a preferred aspect, the newly created population of molecules (e.g., the third population) created by the combinatorial methods may be preferentially selected and thus separated or isolated from the original molecules (e.g., target molecules, and first and second population molecules) and from undesired product molecules (e.g., cointegrates and/or byproduct molecules). Such selection may be accomplished by assaying or selecting for the presence of a desired nucleic acid fusion (PCR with diagnostic primers) and/or the presence of a desired activity of a protein encoded by the desired nucleic acid fusion. Such selective may also be accomplished by positive and/or negative selection. One or more toxic genes (e.g., two, three, four, five seven, ten, etc.) are preferably used according to the invention in such negative selection scheme.

Combinations of selection of the desired fusion product (nucleic acid and/or protein) and positive and/or negative selection may also be used in the invention. Thus, the invention provides a means for selecting a population of Product molecules (or even a specific class of product molecules or specific product molecule) created by recombinational cloning and selecting against a population of Insert Donors, Vector Donors and Cointegrates or, in similar fashion, selecting for a population of Insert Donors, Vector Donors, Byproducts and/or Cointegrates and selecting against a population of Product molecules (see FIG. 1).

Referring to FIG. 2, in the recombinatorial library methods of the invention, a first population of molecules of the invention, represented by segment A, may be provided as one population of Insert Donor molecules while a second population of molecules, represented by segment B, may be provided as a second population of Insert Donor molecules. While these segments are depicted as linear fragments, they may be provided as segments within a larger molecule, for example, as segments in a plasmid.

Those skilled in the art will appreciated that in this situation, cointegrate molecules, other than the one shown in FIG. 1, may be produced. For example, cointegrates comprising a segment A and a segment B Insert Donor molecule may be formed. In addition, cointegrates comprising segment A and/or segment B Insert Donor molecules and a Vector Donor molecule may be formed. The selection methods of the present invention permit selection against the Insert Donor molecules and against the various cointegrate molecules and for the newly created population of hybrid molecules which may be referred to as a population of Product molecules. Conversely, the selection methods may permit selection against Products and for Insert/Vector Donors, Byproducts, and/or Cointegrates.

Thus, the invention relates to a method to create a population of hybrid nucleic acid molecules comprising:

(a) mixing at least a first population of nucleic acid molecules comprising one or more recombination sites (e.g., two, three, four, five seven, ten, twelve, etc.) with at least one target nucleic acid molecule of interest comprising one or more recombination sites (e.g., two, three, four, five seven, ten, twelve, etc.);

(b) causing (preferably randomly) some or all of the molecules of said at least first population to recombine with all or some molecules of said target molecule of interest, thereby forming a third population of hybrid molecules; and (c) optionally selecting specifically for said third population of hybrid molecules.

In accordance with the invention, the hybrid molecules contained by the third population preferably comprise all or a portion of a molecule obtained from the first population and all or a portion of the target molecule. The orientation in which the molecules are joined may be done in a directed or random manner, depending on the need.

In one aspect, the target molecule used to produce said third population described above can be a DNA binding domain or a transcription activation domain, such that the third population of hybrid molecules can be used in 2-hybrid screening methods well known in the art.

The invention more specifically relates to a method of creating a population of combinatorial molecules comprising:

(a) obtaining at least a first population of nucleic acid molecules comprising one or more recombination sites (e.g. two, three, four, five seven, ten, twelve, etc.) and at least a second population of nucleic acid molecules comprising one or more recombination sites (e.g., two, three, four, five seven, ten, twelve, etc.);

(b) causing (preferably randomly) some or all of the molecules of at least said first population to recombine with some or all of the molecules of at least said second population, thereby creating a third population of hybrid molecules; and (c) optionally selecting specifically for said third population of hybrid molecules.

In accordance with the invention, each or many of the hybrid molecules contained by the third population preferably comprises all or a portion of a molecule obtained from the first population and all or a portion of a molecule obtained from the second population. The orientation which the molecules are joined may be done in a directed or random manner, depending on the need.

Populations of nucleic acid molecules used in accordance with the combinatorial methods of the invention can comprise synthetic, genomic, or cDNA libraries (or portions thereof), random synthetic sequences or degenerate oligonucleotides, domains and the like. Preferably, the population of nucleic acid molecules used comprises a random population of molecules, each having at least two recombination sites which preferably do not recombine with each other and which are preferably located at or near both termini of each molecule. Random recombination of populations of molecules by the methods of the invention provides a powerful technique for generating populations of molecules having significant sequence diversity. For example, recombination of a first library having about $10^6$ sequences with a second population having about $10^6$ sequences results in a third population having about $10^{12}$ sequences.

The invention further provides methods for preparing and screening combinatorial libraries in which segments of the nucleic acid molecules of the library members have been altered. Such alterations include mutation, shuffling, insertion, and/or deletion of nucleic acid segments. In particular, the invention provides methods for preparing nucleic acid libraries which contain members having such alterations and methods for introducing such alterations in existing libraries. In a related aspect, the invention includes combinatorial libraries produced by methods of the invention, methods for screening such libraries to identify members which encode expression products having particular functions or activities, and expression products of these libraries (e.g., RNA, proteins, etc.).

Further, in aspects related to those described above, the invention provides methods for generating populations of nucleic acid molecule containing one or more (e.g., one, two, three, four, five, ten, fifteen) nucleic acid segments which are the same and one or more nucleic acid segments which are derived from members of one or more populations of nucleic acid molecules. One method for producing such nucleic acid molecules involves the use of a vector which contains two recombination sites. A first nucleic acid segment, which encodes a protein having a particular function or activity (e.g., signal peptide activity, DNA binding activity, affinity for a particular ligand, etc.), is inserted in the first recombination site and a second nucleic acid segment, which is derived from a population of nucleic acid molecules, is inserted into the second recombination site. Further, these nucleic acid segments are operably linked to a sequence which regulates transcription, thereby producing a fusion peptide and an RNA molecule produced by the fusion sequence. The resulting combinatorial library may then be screened to identify nucleic acid molecules which encode expression products having particular functions or activities (e.g., transcriptional activation activity; DNA binding activity; the ability to form multimers; localization to a sub-cellular compartments, such as the endoplasmic reticulum, the nucleus, mitochondria, chloroplasts, the cell membrane, etc.; etc.). When three or more (e.g., three, four, five, six, eight, ten, etc.) nucleic acid segments are used in methods such as those described above, one or more of the nucleic acid segments may be kept constant and one or more of the nucleic acid segments may be derived from members of one or more populations of nucleic acid molecules. For example, in constructing a four part molecule, represented by A-B-C-D, A and D may be known molecules having known functions (e.g., tags such as HIS6, promoters, transcription or translation signals, selectable markers, etc.) while molecules B and C may be derived from one or more populations of nucleic acid molecules.

Any of the product molecules of the invention may be further manipulated, analyzed or used in any number of standard molecular biology techniques or combinations of such techniques (in vitro or in vivo). These techniques include sequencing, amplification, nucleic acid synthesis, making RNA transcripts (e.g., through transcription of product molecules using RNA promoters such as T7 or SP6 promoters), protein or peptide expression (for example, fusion protein expression, antibody expression, hormone expression etc.), protein-protein interactions (2-hybrid or reverse 2-hybrid analysis), homologous recombination or gene targeting, and combinatorial library analysis and manipulation. The invention also relates to cloning the nucleic acid molecules of the invention (preferably by recombination) into one or more vectors (e.g., two, three, four, five seven, ten, twelve, fifteen, twenty, thirty, fifty, etc.) or converting the nucleic acid molecules of the invention into a vector by the addition of certain functional vector sequences (e.g., origins of replication). In a preferred aspect, recombination is accomplished in vitro (e.g., in cell-free systems) and further manipulation or analysis is performed directly in vitro. Thus, further analysis and manipulation will not be constrained by the ability to introduce the molecules of the invention into a host cell and/or maintained in a host cell. Thus, less time and higher throughput may be accomplished by further manipulating or analyzing the molecules of the invention directly in vitro. Alternatively, in vitro analysis or manipulation can be done after passage through host cells or can be done directly in vivo (e.g., while in the host cells, tissues, organs, or organisms).

Nucleic acid synthesis steps, according to the invention, may comprise:

(a) mixing a nucleic acid molecule of interest or template with one or more primers (e.g., one, two, three, four, five seven, ten, twelve, fifteen, twenty, thirty, fifty, etc.) and one or more nucleotides (e.g., one, two, three, or four) to form a mixture; and (b) incubating said mixture under conditions sufficient to synthesize a nucleic acid molecule complementary to all or a portion of said molecule or template.

The synthesized molecule may then be used as a template for further synthesis of a nucleic acid molecule complementary to all or a portion of the first synthesized molecule. Accordingly, a double stranded nucleic acid molecule (e.g., DNA) may be prepared. Preferably, such second synthesis step is preformed in the presence of one or more primers and one or more nucleotides under conditions sufficient to synthesize the second nucleic acid molecule complementary to all or a portion of the first nucleic acid molecule. Typically, synthesis of one or more nucleic acid molecules (e.g., one, two, three, four, five seven, ten, twelve, fifteen, twenty, thirty, fifty, etc.) is performed in the presence of one or more polymerases (preferably DNA polymerases which may be thermostable or mesophilic), although reverse transcriptases may also be used in such synthesis reactions. Accordingly, the nucleic acid molecules used as templates for the synthesis of additional nucleic acid molecules may be RNA, mRNA, DNA or non-natural or derivative nucleic acid molecules. Nucleic acid synthesis, according to the invention, may be facilitated by incorporating one or more primer sites (e.g., two, three, four, five, seven, ten, twelve, fifteen, twenty, thirty, fifty, etc.) into the product molecules through the use of starting nucleic acid molecules containing such primer sites. Thus, by the methods of the invention, primer sites may be added at one or a number of desired locations in the product molecules, depending on the location of the primer site within the starting molecule and the order of addition of the starting molecule in the product molecule.

Sequencing steps, according to the invention, may comprise:

(a) mixing a nucleic acid molecule to be sequenced with one or more primers (e.g., one, two, three, four, five seven, ten, twelve, fifteen, twenty, thirty, fifty, etc.), one or more nucleotides (e.g., one, two, three, or four) and one or more termination agents (e.g., one, two, three, four, or five) to form a mixture;

(b) incubating said mixture under conditions sufficient to synthesize a population of molecules complementary to all or a portion of said molecules to be sequenced; and (c) separating said population to determine the nucleotide sequence of all or a portion of said molecule to be sequenced.

Such sequencing steps are preferably performed in the presence of one or more polymerases (e.g., DNA polymerases and/or reverse transcriptases) and one or more primers. Preferred terminating agents for sequencing include derivative nucleotides such as dideoxynucleotides (ddATP, ddTTP, ddGTP, ddCTP and derivatives thereof). Nucleic acid sequencing, according to the invention, may be facilitated by incorporating one or more sequencing primer sites (e.g., one, two, three, four, five, seven, ten, twelve, fifteen, twenty, thirty, fifty, etc.) into the product molecules through the use of starting nucleic acid molecules containing such primer sites. Thus, by the methods of the invention, sequencing primer sites may be added at one or a number of desired locations in the product molecules, depending on the location of the primer site within the starting molecule and the order of addition of the starting molecule in the product molecule.

Protein expression steps, according to the invention, may comprise:

(a) obtaining a nucleic acid molecule to be expressed which comprises one or more expression signals (e.g., one, two, three, or four); and (b) expressing all or a portion of the nucleic acid molecule under control of said expression signal thereby producing a peptide or protein encoded by said molecule or portion thereof.

In this context, the expression signal may be said to be operably linked to the sequence to be expressed. The protein or peptide expressed can be expressed in a host cell (in vivo), although expression may be conducted in vitro (e.g., in cell-free expression systems) using techniques well known in the art. Upon expression of the protein or peptide, the protein or peptide product may optionally be isolated or purified. Moreover, the expressed protein or peptide may be used in various protein analysis techniques including 2-hybrid interaction, protein functional analysis, and agonist/antagonist-protein interactions (e.g., stimulation or inhibition of protein function through drugs, compounds or other peptides). Further, expressed proteins or peptides may be screened to identify those which have particular biological activities. Examples of such activities include binding affinity for nucleic acid molecules (e.g., DNA or RNA) or proteins or peptides. In particular, expressed proteins or peptides may be screened to identify those with binding affinity for other proteins or themselves. Proteins or peptides which have binding affinities for themselves will generally be capable of forming multimers or aggregates. Proteins or peptides which have binding affinities for themselves and/or other proteins will often be capable of forming or participating in the formation of multi-protein complexes such as antibodies, splicesomes, multi-subunit enzymes, multi-subunit enzymes, ribosomes, etc. Further included within the scope of the invention are the expressed proteins or peptides described above, nucleic acid molecules which encodes these proteins, methods for making these nucleic acid molecules, methods for producing recombinant host cells which contain these nucleic acid molecules, recombinant host cells produced by these methods, and methods for producing the expressed proteins or peptides.

The novel and unique hybrid proteins or peptides (e.g., fusion proteins) produced by the invention and particularly from expression of the combinatorial molecules of the invention may generally be useful for any number of applications. More specifically, as one skilled in the art would recognize, hybrid proteins or peptides of the invention may be designed and selected to identify those which to perform virtually any function. Examples of applications for which these proteins may be used include therapeutics, industrial manufacturing (e.g., microbial synthesis of amino acids or carbohydrates), small molecule identification and purification (e.g., by affinity chromatography), etc.

Protein expression, according to the invention, may be facilitated by incorporating one or more transcription or translation signals (e.g., one, two, three, four, five, seven, ten, twelve, fifteen, etc.) or regulatory sequences, start codons, termination signals, splice donor/acceptor sequences (e.g., intronic sequences) and the like into the product molecules through the use of starting nucleic acid molecules containing such sequences. Thus, by the methods of the invention, expression sequences may be added at one or a number of desired locations in the product molecules, depending on the location of such sequences within the starting molecule and the order of addition of the starting molecule in the product molecule.

In another aspect, the invention provides methods for performing homologous recombination between nucleic acid molecules comprising (a) mixing at least a first nucleic acid molecule which comprises one or more recombination sites with at least one target nucleic acid molecule, wherein the first and target nucleic acid molecules have one or more homologous sequences; and (b) causing the first and target nucleic acid molecules to recombine by homologous recombination. In specific embodiments of the invention, the homologous recombination methods of the invention result in transfer of all or a portion of the first nucleic acid molecule into the target nucleic acid molecule. In certain specific embodiments of the invention, the first nucleic acid molecule comprises two or more sequences which are homologous to sequences of the target nucleic acid molecule. In other specific embodiments, the homologous sequences of the first nucleic acid molecule flank at least one selectable marker and/or one or more recombination sites. In yet other specific embodiments, the homologous sequences of the first nucleic acid molecule flank at least one selectable marker flanked by recombination sites. In additional specific embodiments, the homologous sequences of the first nucleic acid molecule flank a nucleic acid segment which regulates transcription.

Further, homologous recombination, according to the invention, may comprise:

(a) mixing at least a first nucleic acid molecule of the invention (which is preferably a product molecule) comprising one or more recombination sites (e.g., one, two, three, four, five, seven, ten, twelve, fifteen, twenty, thirty, fifty, etc.) with at least one target nucleic acid molecule (e.g., one, two, three, four, five, seven, ten, twelve, etc.), wherein said first and target molecules have one or more homologous sequences (e.g., one, two, three, four, five, seven, etc.); and (b) causing said first and target nucleic acid molecules to recombine by homologous recombination.

Such homologous recombination may occur in vitro (e.g., in cell-free systems), but preferably is accomplished in vivo (e.g., in a host cell). Preferably, homologous recombination causes transfer of all or a portion of a nucleic acid molecule of the invention containing recombination sites (the first nucleic acid molecule) into one or more positions of the target nucleic acid molecule containing homologous sequences (e.g., one, two, three, four, five, seven, etc.). Selection of such homologous recombination may be facilitated by positive or negative selection (e.g., using selectable markers) to select for a desired product and/or against an undesired product. In a preferred aspect, the nucleic acid molecule of the invention comprises at least one selectable marker and at least two sequences which are homologous to the target molecule. Preferably, the first molecule comprises at least two homologous sequences flanking at least one selectable marker.

The present invention thus facilitates construction of gene targeting nucleic acid molecules or vectors which may be used to knock-out or mutate a sequence or gene of interest (or alter existing sequences, for example to convert a mutant sequence to a wild-type sequence), particularly genes or sequences within a host or host cells such as animals (including animals, such as humans), plants, insects, bacteria, yeast, and the like or sequences of adventitious agents such as viruses within such host or host cells. Such gene targeting may preferably comprise targeting a sequence on the genome of such host cells. Such gene targeting may be conducted in vitro (e.g., in a cell-free system) or in vivo (e.g., in a host cell).

Thus, in a preferred aspect, the invention relates to a method of targeting or mutating a nucleotide sequence or a gene comprising:

(a) obtaining at least one nucleic acid molecule of the invention comprising one or more recombination sites (and preferably one or more selectable markers) wherein said molecule comprises one or more nucleotide sequences homologous to the target gene or nucleotide sequence of interest (said one or more homologous sequences preferably flank one or more selectable markers e.g., one, two, three, four, five, seven, ten, etc.) on the molecule of the invention); and (b) contacting said molecule with one or more target genes or nucleotide sequences of interest (e.g., one, two, three, four, five, seven, ten, twelve, fifteen, twenty, thirty, fifty, etc.) under conditions sufficient to cause homologous recombination at one or more sites e.g., one, two, three, four, five, seven, ten, etc.) between said target nucleotide sequence or gene of interest and said molecule of the invention, thereby causing insertion of all or a portion of the molecule of the invention within the target nucleotide sequence or gene.

Such targeting method may cause deletion, activation, inactivation, partial inactivation, or partial activation of the target nucleic acid or gene such that an expression product (typically a protein or peptide) normally expressed by the target nucleic acid or gene is not produced or produced at a higher or lower level or to the extent produced is has an altered protein sequence which may result in more or less activity or in an inactive or partially inactive expression product. The selectable marker preferably present on the molecule of the invention facilitates selection of candidates (for example host cells) in which the homologous recombination event was successful. Thus, the present invention provides a method to produce host cells, tissues, organs, and animals (e.g., transgenic animals) containing the modified nucleic acid or gene produced by the targeting methods of the invention. The modified nucleic acid or gene preferably comprises at least one recombination site and/or at least one selectable marker provided by the nucleic acid molecule of the invention.

Thus, the present invention more specifically relates to a method of targeting or mutating a nucleic acid or a gene comprising:

(a) obtaining at least one nucleic acid molecule of the invention comprising one or more recombination sites (e.g., one, two, three, four, five, seven, ten, twelve, fifteen, twenty, thirty, fifty, etc.) and at least one selectable marker (e.g., one, two, three, four, five, seven, ten, etc.) flanked by one or more sequences homologous to the target nucleic acid or gene of interest (e.g., one, two, three, four, five, seven, ten, etc.);

(b) contacting said molecule with one or more target nucleic acids or genes of interest (e.g., one, two, three, four, five, seven, ten, twelve, fifteen, twenty, thirty, fifty, etc.) under conditions sufficient to cause homologous recombination at one or more sites between the target nucleic acid or gene of interest and the nucleic acid molecule, thereby causing insertion of all or a portion of the nucleic acid molecule of the invention (and preferably causing insertion of at least one selectable marker and/or at least one recombination site) within the target nucleic acid or gene of interest; and (c) optionally selecting for the target nucleic acid or gene of interest comprising all or a portion of the nucleic acid molecule of the invention or for a host cell containing the target nucleic acid or gene containing all or a portion of the nucleic acid molecule of the invention.

Preferably, selectable markers used in the methods described above are positive selection markers (e.g., antibiotic resistance markers such as ampicillin, tetracycline, kanamycin, neomycin. and G-418 resistance markers).

In one general aspect, the invention provides methods for targeting or mutating a target gene or nucleotide sequence comprising, (a) obtaining at least one first nucleic acid molecule comprising one or more recombination sites and one or more selectable markers, wherein the first nucleic acid molecule comprises one or more nucleotide sequences homologous to the target gene or nucleotide sequence; and (b) contacting the first nucleic acid molecule with one or more target genes or nucleotide sequences under conditions sufficient to cause homologous recombination at one or more sites between the target gene or nucleotide sequence and the first nucleic acid molecule, thereby causing insertion of all or a portion of the first nucleic acid molecule within the target gene or nucleotide sequence. In certain specific embodiments of the invention, the first nucleic acid molecule comprises at least one selectable marker flanked by the homologous sequences. In other specific embodiments, the selectable marker is flanked by the homologous sequences. In additional specific embodiments, the target gene or nucleotide sequence is inactivated as a result of the homologous recombination. In yet additional specific embodiments, methods of the invention further comprise selecting for a host cell containing the target gene or nucleotide sequence.

In some specific embodiments, one or more of the one or more nucleotide sequences of the first nucleic acid molecule which are homologous to the target gene or nucleotide sequence will not be 100% identical to the target gene or nucleotide sequence. In other words, the nucleic acid segments which facilitate homologous recombination need not necessarily share 100% sequence identity. However, in general, these nucleic acid segments will share at least 70% identity (e.g., at least 70%, at least 75%, at least 80%, at least 85%, at least 90%, at least 95%, at least 97%, at least 98%, or at least 99%) in their regions of homology.

The use of nucleic acid segments to facilitate homologous recombination which do not share 100% sequence identity to the nucleic acid with which they are to recombine (i.e., the target gene or nucleotide sequence) can be advantageous under a number of instances. One example of such an instance is where the homologous nucleic acids correspond to part of a target nucleotide sequence which is a gene and homologous recombination results in the introduction one or more sequence alterations in the target nucleotide sequence. In a related example, the homologous nucleic acids may correspond to a target nucleotide sequence which represents an entire gene. Thus, homologous recombination results in replacement of the target gene. Another example of such an instance is where one seeks to perform homologous recombination on an organism which has different nucleotide sequences at the site where homologous recombination is to occur as compared to the one or more homologous nucleotide sequences of the first nucleic acid molecule. The differences in these sequences may result, for example, when an organism in which homologous recombination is intended to occur is of a different strain or species than the organism from which the homologous nucleotide sequences of the first nucleic acid molecule are obtained or where the organism has a different genotype at the recombination locus.

Further, the length of the homologous regions which facilitate recombination can vary in size, but, will generally be at least 15 nucleotides in length (e.g., at least 20 nucleotides, at least 50 nucleotides, at least 100 nucleotides, at least 200 nucleotides, at least 400 nucleotides, at least 600 nucleotides, at least 800 nucleotides, at least 1000 nucleotides, at least 1500 nucleotides, at least 2000 nucleotides, at least 2500 nucleotides, at least 3000 nucleotides, at least 3500 nucleotides, at least 4000 nucleotides at least 4500 nucleotides, at least 5000 nucleotides, at least 5500 nucleotides, at least 6000 nucleotides, at least 6000 nucleotides, etc.).

The invention further provides recombinant host cells produced by the methods described herein, which may be prokaryotic (e.g., bacteria), or eukaryotic (e.g., fungal (e.g., yeasts), plant, or animal (e.g., insect, mammalian including human, etc.) hosts).

In another aspect of the invention, recombination sites introduced into targeted nucleic acids or genes according to the invention may be used to excise, replace, or remove all or a portion of the nucleic acid molecule inserted into the target nucleic acid or gene of interest. Thus, the invention allows for in vitro or in vivo removal of such nucleic acid molecules and thus may allow for reactivation of the target nucleic acid or gene. In some embodiments, after identification and isolation of a nucleic acid or gene containing the alterations introduced as above, a selectable marker present on the molecule of the present invention may be removed.

The present invention also provides methods for cloning the starting or product nucleic acid molecules of the invention into one or more vectors or converting the product molecules of the invention into one or more vectors. In one aspect, the starting molecules are recombined to make one or more product molecules and such product molecules are cloned (preferably by recombination) into one or more vectors. In another aspect, the starting molecules are cloned directly into one or more vectors such that a number of starting molecules are joined within the vector, thus creating a vector containing the product molecules of the invention. In another aspect, the starting molecules are cloned directly into one or more vectors such that the starting molecules are not joined within the vector (i.e., the starting molecules are separated by vector sequences). In yet another aspect, a combination of product molecules and starting molecules may be cloned in any order into one or more vectors, thus creating a vector comprising a new product molecule resulting from a combination of the original starting and product molecules.

Thus, the invention relates to a method of cloning comprising:

(a) obtaining at least one nucleic acid molecule of the invention (e.g., one, two, three, four, five, seven, ten, twelve, etc.) comprising recombination sites; and (b) transferring all or a portion of said molecule into one or more vectors (e.g., one, two, three, four, five, seven, ten, twelve, fifteen, etc.).

Preferably, such vectors comprise one or more recombination sites (e.g., one, two, three, four, five, seven, ten, twelve, fifteen, twenty, thirty, fifty, etc.) and the transfer of the molecules into such vectors is preferably accomplished by recombination between one or more sites on the vectors (e.g., one, two, three, four, five, seven, ten, etc.) and one or more sites on the molecules of the invention (e.g., one, two, three, four, five, seven, ten, etc.). In another aspect, the product molecules of the invention may be converted to molecules which function as vectors by including the necessary vector sequences (e.g., origins of replication). Thus, according to the invention, such vectors sequences may be incorporated into the product molecules through the use of starting molecules containing such sequences. Such vector sequences may be added at one or a number of desired locations in the product molecules, depending on the location of the sequence within the starting molecule and the order of addition of the starting molecules in the product molecule. Thus, the invention allows custom construction of a desired vector by combining (preferably through recombination) any number of functional elements that may be desired into the vector. The product molecule containing the vector sequences may be in linear form or may be converted to a circular or supercoiled form by causing recombination of recombination sites within the product molecule or by ligation techniques well known in the art. Preferably, circularization of such product molecule is accomplished by recombining recombination sites at or near both termini of the product molecule or by ligating the termini of the product molecule to circularize the molecule. As will be recognized, linear or circular product molecules can be introduced into one or more hosts or host cells for further manipulation.

Vector sequences useful in the invention, when employed, may comprise one or a number of elements and/or functional sequences and/or sites (or combinations thereof) including one or more sequencing or amplification primers sites (e.g., one, two, three, four, five, seven, ten, etc.), one or more sequences which confer translation termination suppressor activities (e.g., one, two, three, four, five, seven, ten, etc.) such as sequences which encode suppressor tRNA molecules, one or more selectable markers (e.g., one, two, three, four, five, seven, or ten toxic genes, antibiotic resistance genes, etc.), one or more transcription or translation sites or signals (e.g., one, two, three, four, five, seven, ten, etc.), one or more transcription or translation termination sites (e.g., one, two, three, four, five, seven, ten, twelve, etc.), one or more splice sites (e.g., one, two, three, four, five, seven, ten, etc.) which allows for the excision, for example, of RNA corresponding to recombination sites or protein translated from such sites, one or more tag sequences (e.g., HIS6, GST, GUS, GFP, YFP, CFP, epitope tags, etc.), one or more restriction enzyme sites (e.g., multiple cloning sites), one or more origins of replication (e.g., one, two, three, four, five, seven, ten, etc.), one or more recombination sites (or portions thereof) (e.g., one, two, three, four, five, seven, ten, twelve, fifteen, twenty, thirty, fifty, etc.), etc. The vector sequences used in the invention may also comprise stop codons which may be suppressed to allow expression of desired fusion proteins as described herein. Thus, according to the invention, vector sequences may be used to introduce one or more of such elements, functional sequences and/or sites into any of the nucleic acid molecule of the invention, and such sequences may be used to further manipulate or analyze such nucleic acid molecule. For example, primer sites provided by a vector (preferably located on both sides of the insert cloned in such vector) allow sequencing or amplification of all or a portion of a product molecule cloned into the vector.

Additionally, transcriptional or regulatory sequences contained by the vector allows expression of peptides, polypeptides or proteins encoded by all or a portion of the product molecules cloned to the vector. Likewise, genes, portions of genes or sequence tags (such as GUS, GST, GFP, YFP, CFP, His tags, epitope tags and the like) provided by the vectors allow creation of populations of gene fusions with the product molecules cloned in the vector or allows production of a number of peptide, polypeptide or protein fusions encoded by the sequence tags provided by the vector in combination with the product sequences cloned in such vector. Such genes, portions of genes or sequence tags may be used in combination with optionally suppressed stop codons to allow controlled expression of fusion proteins encoded by the sequence of interest being cloned into the vector and the vector supplied gene or tag sequence.

In a construct, the vector may comprise one or more recombination sites, one or more stop codons and one or more tag sequences. In some embodiments, the tag sequences may be adjacent to a recombination site. Optionally, a suppressible stop codon may be incorporated into the sequence of the tag or in the sequence of the recombination site in order to allow controlled addition of the tag sequence to the gene of interest. In embodiments of this type, the gene of interest may be inserted into the vector by recombinational cloning such that the tag and the coding sequence of the gene of interest are in the same reading frame.

The gene of interest may be provided with translation initiation signals (e.g., Shine-Delgarno sequences, Kozak sequences and/or IRES sequences) in order to permit the expression of the gene with a native N-terminal when the stop codon is not suppressed. Further, recombination sites which reside between nucleic acid segments which encode components of fusion proteins may be designed either to not encode stop codons or to not encode stop codons in the fusion protein reading frame. The gene of interest may also be provided with a stop codon (e.g., a suppressible stop codon) at the 3'-end of the coding sequence. Similarly, when a fusion protein is produced from multiple nucleic acid segments (e.g., three, four, five, six, eight, ten, etc. segments), nucleic acid which encodes stop codons can be omitted between each nucleic acid segment and, if desired, nucleic acid which encodes a stop codon can be positioned at the 3' end of the fusion protein coding region.

In some embodiments, a tag sequence may be provided at both the N- and C-terminals of the gene of interest. Optionally, the tag sequence at the N-terminal may be provided with a stop codon and the gene of interest may be provided with a stop codon and the tag at the C-terminal may be provided with a stop codon. The stop codons may be the same or different.

In some embodiments, the stop codon of the N-terminal tag is different from the stop codon of the gene of interest. In embodiments of this type, suppressor tRNAs corresponding to one or both of the stop codons may be provided. When both are provided, each of the suppressor tRNAs may be independently provided on the same vector, on a different vector, or in the host cell genome. The suppressor tRNAs need not both be provided in the same way, for example, one may be provided on the vector contain the gene of interest while the other may be provided in the host cell genome.

Depending on the location of the expression signals (e.g., promoters), suppression of the stop codon(s) during expression allows production of a fusion peptide having the tag sequence at the N- and/or C-terminus of the expressed protein. By not suppressing the stop codon(s), expression of the sequence of interest without the N- and/or C-terminal tag sequence may be accomplished. Thus, the invention allows through recombination efficient construction of vectors containing a gene or sequence of interest (e.g., one, two, three, four, five, six, ten, or more ORF's) for controlled expression of fusion proteins depending on the need.

Preferably, the starting nucleic acid molecules or product molecules of the invention which are cloned or constructed according to the invention comprise at least one open reading frame (ORF) (e.g., one, two, three, four, five, seven, ten, twelve, or fifteen ORFS). Such starting or product molecules may also comprise functional sequences (e.g., primer sites, transcriptional or translation sites or signals, termination sites (e.g., stop codons which may be optionally suppressed), origins of replication, and the like, and preferably comprises sequences that regulate gene expression including transcriptional regulatory sequences and sequences that function as internal ribosome entry sites (IRES). Preferably, at least one of the starting or product molecules and/or vectors comprise sequences that function as a promoter. Such starting or product molecules and/or vectors may also comprise transcription termination sequences, selectable markers, restriction enzyme recognition sites, and the like.

In some embodiments, the starting or product and/or vectors comprise two copies of the same selectable marker, each copy flanked by two recombination sites. In other embodiments, the starting or product and/or vectors comprise two different selectable markers each flanked by two recombination sites. In some embodiments, one or more of the selectable markers may be a negative selectable marker (e.g., ccdb, kicB, Herpes simplex thymidine kinase, cytosine deaminase, etc.).

In one aspect, the invention provides methods of cloning nucleic acid molecules comprising (a) providing a first nucleic acid segment flanked by a first and a second recombination site; (b) providing a second nucleic acid segment flanked by a third and a fourth recombination site, wherein either the first or the second recombination site is capable of recombining with either the third or the fourth recombination site; (c) conducting a recombination reaction such that the two nucleic acid segments are recombined into a single nucleic acid molecule; and (d) cloning the single nucleic acid molecule. In certain specific embodiments of these methods, the first recombination site is not capable of recombining with the second and fourth recombination sites and the second recombination site is not capable of recombining with the first and third recombination sites.

In a specific aspect, the invention provides a method of cloning comprising providing at least a first nucleic acid molecule comprising at least a first and a second recombination site and at least a second nucleic acid molecule comprising at least a third and a fourth recombination site, wherein either the first or the second recombination site is capable of recombining with either the third or the fourth recombination site and conducting a recombination reaction such that the two nucleic acid molecules are recombined into one or more product nucleic acid molecules and cloning the product nucleic acid molecules into one or more vectors. Preferably, the recombination sites flank the first and/or second nucleic acid molecules. Moreover, the cloning step is preferably accomplished by the recombination reaction of the product molecule into a vector comprising one or more recombination sites, although such cloning steps may be accomplished by standard ligation reactions well known in the art. In one aspect, the cloning step comprises conducting a recombination reaction between the sites in the product nucleic acid molecule that did not react in the first recombination reaction with a vector having recombination sites capable of recombining with the unreacted sites.

In another aspect, the invention provides methods of cloning nucleic acid molecules comprising (a) providing a first nucleic acid segment flanked by at least a first and a second recombination sites and a second nucleic acid segment flanked by at least a third and a fourth recombination sites, wherein none of the recombination sites flanking the first and second nucleic acid segments are capable of recombining with any of the other sites flanking the first and second nucleic acid segments; (b) providing a vector comprising at least a fifth, sixth, seventh and eighth recombination sites, wherein each of the at least fifth, sixth, seventh and eighth recombination sites is capable of recombining with one of the at least first, second, third and/or fourth recombination sites; and (c) conducting a recombination reaction such that the two nucleic acid segments are recombined into the vector thereby cloning the first and the second nucleic acid segments.

In another specific aspect, the invention provides a method of cloning comprising providing at least a first nucleic acid molecule comprising at least a first and a second recombination site and at least a second nucleic acid molecule comprising at least a third and a fourth recombination site, wherein none of the first, second, third or fourth recombination sites is capable of recombining with any of the other sites, providing one or more vectors (e.g., two, three, four, five, seven, ten, twelve, etc.), comprising at least a fifth, sixth, seventh and eighth recombination site, wherein each of the fifth, sixth, seventh and eighth recombination sites are capable of recombining with one of the first, second, third or fourth recombination site, and conducting a recombination reaction such that at least said first and second molecules are recombined into said vectors. In a further aspect, the method may allow cloning of at least one additional nucleic acid molecule (e.g., at least a third nucleic acid molecule), wherein said molecule is flanked by a ninth and a tenth recombination site and wherein the vector comprises an eleventh and a twelfth recombination site each of which is capable of recombining with either the ninth or the tenth recombination site.

The invention also specifically relates to a method of cloning comprising providing a first, a second and a third nucleic acid molecule, wherein the first nucleic acid molecule is flanked by at least a first and a second recombination sites, the second nucleic acid molecule is flanked by at least a third and a fourth recombination sites and the third nucleic acid molecule is flanked by at least a fifth and a sixth recombination sites, wherein the second recombination site is capable of recombining with the third recombination site and the fourth recombination site is capable of recombining with the fifth recombination site, providing a vector having at least a seventh and an eighth recombination sites, wherein the seventh recombination site is capable of reacting with the first recombination site and the eighth recombination site is capable of reacting with the sixth recombination site, and conducting at least one recombination reaction such that the second and the third recombination sites recombine, the fourth and the fifth recombination sites recombine, the first and the seventh recombination sites recombine and the sixth and the eighth recombination sites recombine thereby cloning the first, second and third nucleic acid segments in said vector.

In another specific aspect, the invention provides a method of cloning comprising providing at least a first, a second and a third nucleic acid molecule, wherein the first nucleic acid molecule is flanked by a first and a second recombination site, the second nucleic acid molecule is flanked by a third and a fourth recombination site and the third nucleic acid molecule is flanked by a fifth and a sixth recombination site, wherein the second recombination site is capable of recombining with the third recombination site and none of the first, fourth, fifth or sixth recombination sites is capable of recombining with any of the first through sixth recombination sites, providing one or more vectors comprising a seventh and an eighth recombination site flanking at least a first selectable marker and comprising a ninth and a tenth recombination site flanking at least a second selectable marker wherein none of the seventh through tenth recombination sites can recombine with any of the seventh through tenth recombination sites, conducting at least one recombination reaction such that the second and the third recombination sites recombine, the first and the fourth recombination sites recombine with the seventh and the eighth recombination sites and the fifth and the sixth recombination sites recombine with the ninth and the tenth recombination sites thereby cloning the first, second and third nucleic acid segments. In some embodiments, the selectable markers may be the same or may be different. Moreover, the one or more selectable markers (e.g., two, three, four, five, seven, etc.) may be negative selectable markers.

The invention also provides methods of cloning n nucleic acid segments, wherein n is an integer greater than 1, comprising (a) providing n nucleic acid segments, each segment flanked by two recombination sites which do not recombine with each other; (b) providing a vector comprising 2n recombination sites, wherein each of the 2n recombination sites is capable of recombining with one of the recombination sites flanking one of the nucleic acid segments; and (c) conducting a recombination reaction such that the n nucleic acid segments are recombined into the vector thereby cloning the n nucleic acid segments. In specific embodiments, the recombination reaction between the n nucleic acid segments and the vector is conducted in the presence of one or more recombination proteins under conditions which favor the recombination. In other specific embodiments, n is 2, 3, 4, or 5.

Thus, the invention generally provides a method of cloning n nucleic acid molecules, wherein n is an integer greater than 1, comprising the steps of providing n nucleic acid molecules, each molecule comprising at least one and preferably two recombination sites (the two recombination sites preferably flank the n nucleic acid molecule), providing at least one vector comprising one or more recombination sites (and preferably 2n recombination sites) wherein the vector containing recombination sites is capable of recombining with the recombination sites of the n molecules, and conducting a recombination reaction such that the n nucleic acid molecules are inserted into said vectors thereby cloning the n nucleic acid segments. The n molecules may be inserted next to or adjoining each other in the vector and/or may be inserted at different positions within the vector. The vectors used for cloning according to the invention preferably comprise n copies of the same or different selectable marker, each copy of which is flanked by at least two recombination sites. Preferably, one or more of the selectable markers are negative selectable markers.

The invention also generally relates to a method of cloning n nucleic acid molecules, wherein n is an integer greater than 1, comprising the steps of providing a $1^{st}$ through an $n^{th}$ nucleic acid molecules, each molecule flanked by at least two recombination sites, wherein the recombination sites are selected such that one of the two recombination sites flanking the $i^{th}$ segment, $n_i$ reacts with one of the recombination sites flanking the $n_{i-1}$th segment and the other recombination site flanking the $i^{th}$ segment, $n_i$ reacts with one of the recombination sites flanking the $n_{i+1}$th segment, providing a vector comprising at least two recombination sites wherein one of the two recombination sites on the vector react with one of the sites on the $1^{st}$ nucleic acid segment and another site on the vector reacts with a recombination site on the $n^{th}$ nucleic acid segment.

The nucleic acid molecules/segments cloned by the methods of the invention can be different types and can have different functions depending on the need and depending on the functional elements present. In one aspect, at least one of the nucleic acid segments cloned according to the invention is operably linked to a sequence which is capable of regulating transcription (e.g., a promoter, an enhancer, a repressor, etc.). For example, at least one of the nucleic acid segments may be operably linked to a promoter which is either an inducible promoter or a constitutive promoter. In yet other specific embodiments, translation of an RNA produced from the cloned nucleic acid segments results in the production of either a fusion protein or all or part of a single protein. In additional specific embodiments, at least one of the nucleic acid segments encodes all of part of an open reading frame and at least one of the nucleic acid segments contains a sequence which is capable of regulating transcription (e.g., a promoter, an enhancer, a repressor, etc.). In further specific embodiments, at least one of the nucleic acid segments produces a sense RNA strand upon transcription and at least one of the nucleic acid segments produces an antisense RNA strand upon transcription. In related embodiments, the sense RNA and antisense RNA have at least one complementary region and are capable of hybridizing to each other. In other specific embodiments, transcription of at least two of the nucleic acid segments results in the production of a single RNA or two separate RNAs. In various specific embodiments, these nucleic acid segments may be connected to each other or may be spatially separated within the same nucleic acid molecule. In specific embodiments, the nucleic acid segments comprise nucleic acid molecules of one or more libraries. Further, these libraries may comprise cDNA, synthetic DNA, or genomic DNA. In addition, the nucleic acid molecules of these libraries may encode variable domains of antibody molecules (e.g., variable domains of antibody light and heavy chains). In specific embodiments, the invention provides screening methods for identifying nucleic acid molecules which encode proteins having binding specificity for one or more antigens and/or proteins having one or more activities (e.g., secretion from a cell, sub-cellular localization (e.g., localization to the endoplasmic reticulum, the nucleus, mitochondria, chloroplasts, the cell membrane, etc.), ligand binding activity (e.g., small molecules, binding activities for nucleic acids, cell surface receptors, soluble proteins, metal ions, structural elements, protein interaction domains, etc.), enzymatic activity, etc.). Further, nucleic acid molecules/segments cloned using methods of the invention may have one or more of the activities referred to above.

In another aspect, the invention provides methods of cloning at least one nucleic acid molecule comprising (a) providing at least a first, a second and a third nucleic acid segments, wherein the first nucleic acid segment is flanked by at least a first and a second recombination sites, the second nucleic acid segment is flanked by at least a third and a fourth recombination sites and the third nucleic acid segment is flanked by at least a fifth and a sixth recombination sites, wherein the second recombination site is capable of recombining with the third recombination site and none of the first, fourth, fifth or sixth recombination sites is capable of recombining with any of the first through sixth recombination sites; (b) providing a vector comprising at least a seventh and an eighth recombination sites flanking at least a first negative selectable marker and comprising at least a ninth and a tenth recombination sites flanking at least a second negative selectable marker, wherein none of the seventh through tenth recombination sites can recombine with any of the seventh through tenth recombination sites; (c) conducting a first recombination reaction such that the second and the third recombination sites recombine; and (d) conducting a second recombination reaction such that the first and the fourth recombination sites recombine with the seventh and the eighth recombination sites and the fifth and the sixth recombination sites recombine with the ninth and the tenth recombination sites thereby cloning the first, second and third nucleic acid segments. In related embodiments, the first and second recombination reactions are conducted in the presence of one or more recombination proteins under conditions which favor the recombination. Such first and second recombination reactions may be carried out simultaneously or sequentially.

In another aspect, the invention provides methods of cloning at least one nucleic acid molecule comprising (a) providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and the fourth recombination site is capable of recombining with the fifth recombination site; (b) providing a vector comprising a seventh and an eighth recombination site; and (c) conducting at least one recombination reaction such that the second and the third recombination sites recombine and the fourth and the fifth recombination sites recombine and the first and the sixth recombination sites recombine with the seventh and the eighth recombination sites respectively, thereby cloning the first, second and third nucleic acid segments. In related embodiments, the recombination reaction is conducted in the presence of one or more recombination proteins under conditions which favor the recombination. In specific embodiments, the recombination sites which recombine with each other comprise att sites having identical seven base pair overlap regions.

In another aspect, the invention provides methods of cloning n nucleic acid fragments, wherein n is an integer greater than 2, comprising (a) providing a $1^{st}$ through an $n^{th}$ nucleic acid segment, each segment flanked by two recombination sites, wherein the recombination sites are selected such that one of the two recombination sites flanking the $i^{th}$ segment, $n_i$, reacts with one of the recombination sites flanking the $n_{i-1}$th segment and the other recombination site flanking the $i^{th}$ segment reacts with one of the recombination sites flanking the $n^{i+1th}$ segment; (b) providing a vector comprising at least two recombination sites, wherein one of the two recombination sites on the vector reacts with one of the sites on the $1^{st}$ nucleic acid segment and another site on the vector reacts with a recombination site on the nth nucleic acid segment; and (c) conducting at least one recombination reaction such that all of the nucleic acid fragments are recombined into the vector. In specific embodiments, the recombination reaction is conducted in the presence of one or more recombination proteins under conditions which favor the recombination.

In specific embodiments of the methods described above, multiple nucleic acid segments are inserted into another nucleic acid molecules. While numerous variations of such methods are possible, in specific embodiments, nucleic acid segments which contain recombination sites having different specificities (e.g., attL1 and attL2) are inserted into a vector which contains more than one set of cognate recombination sites (e.g., attR1 and attR2), each set of which flanks negative selection markers. Thus, recombination at cognate sites results can be used to select for nucleic acid molecules which have undergone recombination at one or more of the recombination sites. The nucleic acid segments which are inserted into the vector may be the same or different. Further, these nucleic acid segments may encode expression products or may be transcriptional control sequences. When the nucleic acid segments encode expression products, vectors of the invention may be used to amplify the copy number or increase expression of encoded products. Further, when nucleic acid segments are inserted in both direct and inverted orientations, vectors of the invention may be used, for example, to express RNAi, as described elsewhere herein. When the nucleic acid segments encode sequence which regulate transcription (e.g., promoters, enhancers, etc.), vectors of the invention may be used to place multiple regulatory elements in operable linkage with nucleic acid that encodes expression products. Vectors of this nature may be used to increased expression of expression products, for example, by providing multiple binding sites for proteins which activate transcription. Similarly, vectors of this nature may be used to decrease expression of expression products, for example, by providing multiple binding sites for proteins which inhibit transcription.

Vectors of this nature may be used to increased or decrease the expression of expression products, for example, by the expression of multiple copies of nucleic acid molecules which encode factors involved in the regulation of transcription. Other embodiments related to the above would be apparent to one skilled in the art.

In another aspect, the invention provides methods of cloning at least one nucleic acid molecule comprising (a) providing a first population of nucleic acid molecules wherein all or a portion of such molecules are flanked by at least a first and a second recombination sites; (b) providing at least one nucleic acid segment flanked by at least a third and a fourth recombination sites, wherein either the first or the second recombination site is capable of recombining with either the third or the fourth recombination site; (c) conducting a recombination reaction such that all or a portion of the nucleic acid molecules in the population are recombined with the segment to form a second population of nucleic acid molecules; and (d) cloning the second population of nucleic acid molecules. In related embodiments, the recombination reaction is conducted in the presence of one or more recombination proteins under conditions which favor the recombination. In specific embodiments, the second population of nucleic acid molecules encodes a fusion protein. In related embodiments, the nucleic acid segment encodes a polypeptide which comprises a sequence (preferably an N-terminal and/or a C-terminal tag sequence) encoding all or a portion of the following: the Fc portion of an immunoglobin, an antibody, a β-glucuronidase, a fluorescent protein (e.g., green fluorescent protein, yellow fluorescent protein, red fluorescent protein, cyan fluorescent protein, etc.), a transcription activation domain, a protein or domain involved in translation, protein localization tag, a protein stabilization or destabalization sequence, a protein interaction domains, a binding domain for DNA, a protein substrate, a purification tag (e.g., an epitope tag, maltose binding protein, a six histidine tag, glutathione S-transferase, etc.), and an epitope tag.

In another aspect, the invention provides methods of cloning at least one nucleic acid molecule comprising (a) providing a first population of nucleic acid molecules wherein all or a portion of such molecules are flanked by at least a first and a second recombination site; (b) providing a second population of nucleic acid molecules wherein all or a portion of such molecules are flanked by a third and a fourth recombination site, wherein either the first or the second recombination site is capable of recombining with either the third or the fourth recombination site; (c) conducting a recombination reaction such that all or a portion of the molecules in the first population is recombined with one or more molecules from the second population to form a third population of nucleic acid molecules; and (d) cloning the third population of nucleic acid molecules. In related embodiments, the recombination reaction is conducted in the presence of one or more recombination proteins under conditions which favor the recombination.

Thus, the invention generally provides methods of joining at least two segments of nucleic acid (including joining populations of nucleic acid molecules), comprising (a) providing at least two segments of nucleic acid (one or both of which may be derived from a population or library of molecules), each segment comprising at least one recombination site capable of recombining with a recombination site present on another (or second) segment; and (b) contacting the segments with one or more recombination proteins under conditions causing recombination between the recombination sites, thereby joining the segments. The invention further provides composition comprising the joined nucleic acid segments (or population of segments) prepared by such methods, hosts or host cells comprising such joined nucleic acid segments (which may be populations of host cells or recombinant host cells), and methods of making such hosts or host cells (such as by transforming or transfecting such cells with product molecules of the invention). In specific embodiments, the methods of the invention further comprises inserting the joined nucleic acid segments into one or more vectors. The invention also relates to hosts or host cells containing such vectors. In additional specific embodiments, at least one of the two segments of nucleic acid encodes an expression product (e.g. a selectable marker, an enzyme, a ribozyme, etc.) having one or more identifiable activities. In yet other specific embodiments, at least one of the two segments of nucleic acid contains all or part of an open reading frame (ORF). In another aspect, at least one of the two segments of nucleic acid contains a sequence which is capable of regulating transcription (e.g., a promoter, an enhancer, a repressor, etc.). In a specific aspect, one segment encodes an ORF and the other encodes a sequence capable of regulating transcription and/or translation and the recombination reaction allows such sequences to be operably linked. In yet other additional specific embodiments, one or more of the nucleic acid segments encode a selectable marker or contains an origin of replication. In further specific embodiments, some or all of the nucleic acid segments comprise nucleic acid molecules of one or more libraries. In certain specific embodiments, the one or more libraries comprise polynucleotides which encode variable domains of antibody molecules. In related embodiments, at least one of the nucleic acid segments encodes a polypeptide linker for connecting variable domains of antibody molecules and/or one or more libraries comprise polynucleotides which encode variable domains of antibody light and heavy chains. In specific embodiments, methods of the invention further comprises at least one screening step to identify nucleic acid molecules which encode proteins having one or more identifiable activities (e.g., binding specificities for one or more antigens, enzymatic activities, activities associated with selectable markers, etc.). Thus, the invention can be used to produce modified expression products (by variably linking different segments and/or replacing and/or deleting segments) and analyzing the expression products for desired activities. According to the invention, portions of genes and/or a number of genes can be linked to express novel proteins or novel compounds and to select for activities of interest. As described herein, substitution and/or deletions of such linked molecules can also be used to produce altered or modified proteins or compounds for testing. In one aspect, biological pathways can be modified by the methods of the invention to, for example, use different enzymes or mutant enzymes in a particular pathway (e.g., link different enzymes or mutant enzymes which participate in reactions in the same biological pathway). Such modification to biological pathways according to the invention leads to (1) the production of potentially novel compounds such as antibiotics or carbohydrates or (2) unique post-translational modification of proteins (e.g., glycosylation, sialation, etc.). The invention also allows for production of novel enzymes by manipulating or changing subunits of multimeric enzyme complexes. In other specific embodiments, the invention also provides methods of altering properties of a cell comprising introducing into the cell nucleic acid segments produced by the methods described herein. In certain specific embodiments, cells altered or produced by methods of the invention are either fungal cells or bacterial cells (e.g., *Escherichia coli*).

The invention further provides methods for altering biological pathways and generating new biological pathways.

For example, genes encoding products involved in the production of a particular pathway (e.g., a pathway which leads to the production of an antibiotic) may be altered using methods of the invention. These alterations include the deletion, replacement, and/or mutation of one or more genes which encode products that participate in the pathway. In addition, regions of genes may be deleted or exchanged following by screening to identify, for example, pathway products having particular features (e.g., a particular methylation pattern). Further, genes of different organisms which perform similar but different functions may be combined to produce novel products. Further, these products may be identified by screening for specific functional properties (e.g., the ability to inhibit an enzymatic reaction, binding affinity for a particular ligand, antimicrobial activity, antiviral activity, etc.). Thus, the invention provides, in one aspect, screening methods for identifying compounds which are produced by expression products of nucleic acid molecules of the invention.

Further, when the nucleic acid segments which encode one or more expression products involved in a particular biological pathway or process have been assembled into one or more nucleic acid molecules, regions of these molecules (e.g., regions which encode expression products) may be deleted or replaced to generate nucleic acid molecules which, for example, express additional expression products, altered expression products, or which do not express one or more expression product involved in the biological pathway or process. Further, nucleic acid segments which encode one or more expression products involved in a particular biological pathway or process may be deleted or inserted as a single unit. These methods find application in the production and screening of novel products. In particular, the invention also includes novel products produced by the expression products of nucleic acid molecules described herein.

In another aspect, the invention provides methods for preparing and identifying nucleic acid molecules containing two or more nucleic acid segments which encode gene products involved in the same biological process or biological pathway, as well as unrelated biological processes or biological pathways, comprising (a) providing a first population of nucleic acid molecules comprising at least one recombination site capable of recombining with other nucleic acid molecules in the first population; (b) contacting the nucleic acid molecules of the first population with one or more recombination proteins under conditions which cause the nucleic acid molecules to recombine and create a second population of nucleic acid molecules; and (c) screening the second population of nucleic acid molecules to identify a nucleic acid molecule which encodes two or more products involved in the same process or pathway. In specific embodiments of the invention, the nucleic acid molecules which encodes two or more products involved in the same process or pathway encode two different domains of a protein or protein complex. In other specific embodiments, the protein is a single-chain antigen-binding protein. In yet other specific embodiments, the protein complex comprises an antibody molecule or multivalent antigen-binding protein comprising at least two single-chain antigen-binding protein. The invention further provides methods similar to those described above for preparing and identifying nucleic acid molecules containing two or more nucleic acid segments which encode gene products involved in different or unrelated biological processes or biological pathways.

Methods of the invention may also be employed to determine the expression profile of genes in cells and/or tissues. In one embodiment, RNA may be obtained from cells and/or tissues and used to generate cDNA molecules. These cDNA molecules may then be linked to each other and sequenced to identify genes which are expressed in cells and/or tissues, as well as the prevalence of RNA species in these cells and/or tissues. Thus, in one aspect, the invention provides methods for identifying genes expressed in particular cells and/or tissues and the relative quantity of particular RNA species present in these cells and/or tissues as compared to the quantity of other RNA species. As discussed below, such methods may be used for a variety of applications including diagnostics, gene discovery, the identification of genes expressed in specific cell and/or tissue types, the identification of genes which are over- or under-expressed in particular cells (e.g., cells associated with a pathological condition), the screening of agents to identify agents (e.g., therapeutic agents) which alter gene expression, etc. Further, it will often be possible to identify the gene from which a particular RNA species or segment is transcribed by comparison of the sequence data obtained by methods of the invention to nucleic acid sequences cataloged in public databases. Generally, about 10 nucleotides or so of sequence data will be required to identify the gene from which RNA has been transcribed.

Thus, in a specific aspect, the invention provides methods for determining gene expression profiles in cells or tissues comprising (a) generating at least one population of cDNA molecules from RNA obtained from the cells or tissues, wherein the individual cDNA molecules of the population comprise at least two recombination sites capable of recombining with at least one recombination site present on the individual members of the same or a different population of cDNA molecules; (b) contacting the nucleic acid molecules of (a) with one or more recombination proteins under conditions which cause the nucleic acid molecules to join; and (c) determining the sequence of the joined nucleic acid molecules. In specific embodiments of the invention, the joined cDNA molecules are inserted into vectors which contain sequencing primer binding sites flanking the insertion sites. In yet other specific embodiments, the joined cDNA molecules are separated by attB recombination sites. In additional specific embodiments, the joined cDNA molecules contain between about 10 and about 30 nucleotides which corresponds to the RNA obtained from the cell or tissue.

Once the sequences of cDNA corresponding to RNA expression products have been determined, these sequences can be compared to databases which contain the sequences of known genes to determine which genes are expressed in the particular cells and/or tissues and the expression levels of individual genes. Further, the expression levels of genes can be determined using methods of the invention under particular conditions to determine if these conditions result in the alteration of the expression of one or more genes. Examples of such conditions include decreased activity of cellular gene expression products, nutrient limitation and/or deprivation, heat shock, low temperatures, contact with solutions having low or high ionic strengths, exposure to chemical agents (e.g., antibiotics, chemotherapeutic agents, metal ions, mutagens, etc.), ionizing radiation, etc. Thus, the invention provides methods for identifying genes which exhibit alterations in expression as a result of specific stimuli.

The invention further provides methods for identifying genes involved in cellular metabolism (e.g., pathological conditions). For example, methods of the invention can be used to determine the expression profile of cells of a particular strain or cells which exhibit an aberrant phenotype. The expression profile of cells of the particular strain or cells which exhibit the aberrant phenotype is compared to the expression profile of cells of another strain or cells which do not exhibit the aberrant phenotype, referred to herein as "reference cells." By comparison of expression profiles of genes of cells of the particular strain or cells which exhibit the aberrant phenotype to appropriate reference cells, expression characteristics of associated with the strain or aberrant phenotype can be determined. Thus, in one specific aspect, the invention provides diagnostic methods, wherein the gene expression profiles of cells of a patient which exhibit an aberrant phenotype (e.g., cancerous) is compared to the gene expression profiles of cells which do not exhibit the aberrant phenotype (i.e., reference cells).

In another specific aspect, the invention provides methods for screening therapeutic agents (e.g., immunostimulatory agent) comprising (a) exposing cells (e.g., human cells) to a candidate therapeutic agent, (b) determining the gene expression profile of the exposed cells, (c) comparing the gene expression profile to the gene expression profile of cells which have not been exposed to the candidate therapeutic agent (i.e., reference cells). The invention further includes therapeutic agents identified by the methods described above.

In another aspect, the invention provides a means for attaching or binding through recombination molecules and/or compounds or population of molecules and/or compounds to other molecules, compounds and/or supports (preferably solid or semisolid). Suitable molecules and compounds for use in the present invention include, but are not limited to, proteins, polypeptides, or peptides, chemical compounds, drugs, lipids, lipoproteins, carbohydrates, hormones, steroids, antibodies (or portions thereof), antigens, enzymes (e.g., nucleases, polymerases, etc.), polysaccharides, nucleosides and derivatives thereof, nucleotides and derivatives thereof, amino acids and derivatives thereof, fatty acids, receptors, ligands, haptens, small molecules (e.g., activation groups such as —COOH), binding molecules (e.g., biotin, avidin, strepavidin, Protein A, Protein B, etc.), growth factors, metal ions, cytokines, ribozymes, or nucleic acid molecules (e.g., RNA, DNA, DNA/RNA hybrids, cDNA or cDNA libraries, double stranded nucleic acids, single stranded nucleic acids, linear nucleic acids, circular nucleic acids, supercoiled nucleic acids and the like) and combinations of two or more of the foregoing. In specific embodiments, molecules may be linked to supports either directly or indirectly. Further, molecules may be linked to supports by either covalently or non-covalently. For purposes of illustration, one example of the indirect non-covalent linkage of a nucleic acid molecule to a support is where a protein which exhibits high binding affinity for nucleic acid molecules is directly linked to a support. The support containing this protein is then contacted with the nucleic acid molecules under appropriate conditions resulting in the non-covalent attachment of the nucleic acid molecules to the support through the protein. This association between nucleic acid molecule/protein interaction can be either sequence specific or non-sequence specific.

In another aspect, the invention provides supports comprising (either bound or unbound to the support) at least one first nucleic acid molecule, wherein the first nucleic acid molecule comprises one or more recombination sites or portions thereof. In specific embodiments, supports of the invention further comprise at least one second nucleic acid molecule or at least one peptide or protein molecule or other compound bound to the supports through the recombination site on the first nucleic acid molecule.

The invention also relates to supports of the invention which comprise (either bound or unbound to the support) one or more components selected from the group consisting of one or more nucleic acid molecules comprising at least one recombination site, one or more recombination proteins, and one or more peptides or compounds comprising at least one recombination site.

In another aspect, the invention provides methods for attaching or binding one or more nucleic acid molecules, protein or peptide molecules, or other compounds to supports comprising (a) obtaining at least one nucleic acid molecule, protein or peptide molecule, other compounds, or population of such molecules or compounds comprising at least one recombination site and obtaining supports comprising at least one recombination site; and (b) causing some or all of the recombination sites on the at least one nucleic acid molecule, protein or peptide molecule, other compounds, or population of such molecules or compounds to recombine with all or a portion of the recombination sites comprising the supports. In specific embodiments of the invention, the methods further comprise attaching or binding one or more nucleic acid molecules to the supports. In other specific embodiments, only one nucleic acid molecule is directly linked to the support. In yet other specific embodiments, the nucleic acid molecules form microarrays. In even more specific embodiments, the microarrays form a DNA chip. The invention further provides supports prepared by the methods described above. In specific embodiments, the support of the invention are either solid or semisolid. Further, as discussed above, nucleic acid molecules may be linked to supports either directly or indirectly. As also discussed above, nucleic acid molecules may be linked to supports either covalently or non-covalently. In addition, nucleic acid molecules may be linked to supports through linkage to a protein or small molecule (e.g., a molecule having an activation group such as —COOH). Further, nucleic acid molecules may be linked to supports through linkages which are either labile or non-labile.

In another aspect, the invention provides methods for linking or connecting two or more molecules or compounds of interest, comprising (a) providing at least a first and a second molecule or compound of interest, each of the first and second molecules or compounds of interest comprising at least one recombination site; (b) causing some or all of the recombination sites on the first molecule or compound of interest to recombine with some or all of the recombination sites on the second molecule or compound of interest. In specific embodiments of the invention, the methods further comprising attaching nucleic acids comprising recombination sites to the first and the second molecules or compounds of interest. In other specific embodiments, at least one of the molecules or compounds of interest comprises a protein or peptide, a nucleic acid, a carbohydrate, a steroid, or a lipid.

In some embodiments, one or more of the compounds and/or molecules of the invention (e.g., two, three, four, five, seven, ten, twelve, fifteen, twenty, thirty, fifty, etc.) may comprise one or more recombination sites (e.g., two, three, four, five, seven, ten, twelve, fifteen, twenty, thirty, fifty, etc.) or portions thereof. Such molecules and/or compounds may be unlabeled or detectably labeled by methods well known in the art. Detectable labels include, but are not limited to, radioactive labels, mass labels, fluorescent labels, chemiluminescent labels, bioluminescent labels, and enzyme labels. Use of such labels may allow for the detection of the presence or absence of labeled molecules and/or compounds on a support. Thus, the invention generally relates to attaching to a support any number of molecules and/or compounds or populations of molecules and/or compounds by recombination and the supports made by this method. Such compounds and/or molecules can thus be attached to a support or structure via a nucleic acid linker containing a recombination site or portion thereof. Such linkers are preferably small (e.g., 5, 20, 30, 50, 100, 200, 300, 400, or 500 base pairs in length).

Accordingly, the present invention encompasses a support comprising one or a number of recombination sites (or portions thereof) which can be used according to this aspect of the invention. Thus, one or a number of nucleic acid molecules, or proteins, peptides and/or other molecules and/or compounds having one or more recombination sites or portions thereof which are to be added or attached or bound to the support are recombined by a recombination reaction with the recombination-site-containing support, thereby creating a support containing one or more nucleic acid molecules, or protein, peptides and/or other molecules and/or compounds of interest. The recombination reaction in binding the molecule and/or compound of interest to the support is preferably accomplished in vitro by contacting the support and the molecule and/or compound of interest with at least one recombination protein under conditions sufficient to cause recombination of at least one recombination site on the molecule and/or compound of interest with at least one recombination site present on the support. This aspect of the invention is particularly useful in creating arrays of nucleic acids, or proteins and/or other molecules and/or compounds on one or more supports (e.g., two, three, four, five, seven, ten, twelve, etc.) in that it facilitates binding of a number of the same or different nucleic acids, or proteins and/or other molecules and/or compounds of interest through recombination to the support or various parts of the support. Thus, the invention relates to a method of attaching or binding one or more (e.g., two, three, four, five, seven, ten, twelve, fifteen, twenty, thirty, fifty, etc.) nucleic acid, or protein molecules and/or other molecules and/or compounds to a support comprising:

(a) obtaining at least a first molecule and/or compound or population of molecules and/or compounds comprising at least one recombination site (e.g., the starting nucleic acid molecules of the invention) and obtaining a support comprising at least one recombination site (which may also be the starting molecules of the invention); and (b) causing some or all of the recombination sites on said at least first molecule and/or compound or population of molecules and/or compounds to recombine with all or a portion of the recombination sites on the support.

Once the molecules and/or compounds are added to the support, the presence or absence or position of such molecules and/or compounds on the support can be determined (for example by using detectable labels). Additionally, the molecules and/or compounds bound to the support may be further manipulated by well known techniques.

In addition to joining one or multiple molecules and/or compounds to a support in accordance with the invention, the invention also allows replacement, insertion, or deletion of one or more molecules and/or compounds contained by the support. As discussed herein, causing recombination of specific sites within a molecule and/or compound of interest, all or a portion of molecule and/or compound may be removed or replaced with another molecule or compound of interest. This process may also be applied to molecules and/or compounds having recombination site which are attached to the support. Thus, recombination may be used to remove or replace all or a portion of the molecule and/or compound of the interest from the support, in addition to adding all or part of molecules to supports.

The molecules and/or compounds added to the support or removed from the support may be further manipulated or analyzed in accordance with the invention and as described herein. For example, further analysis or manipulation of molecules and/or compounds bound to or removed from the support include sequencing, hybridization (DNA, RNA etc.), amplification, nucleic acid synthesis, protein or peptide expression, protein-DNA interactions (2-hybrid or reverse 2-hybrid analysis), interaction or binding studies with other molecules and/or compounds, homologous recombination or gene targeting, and combinatorial library analysis and manipulation. Such manipulation may be accomplished while the molecules and/or compounds are bound to the support or after the molecules and/or compounds are removed from the support.

In accordance with the invention, any solid or semi-solid supports may be used and sequences containing recombination sites (or portions thereof) may be added by well known techniques for attaching nucleic acids to supports. Furthermore, recombination sites may be added to nucleic acid, protein molecules and/or other molecules and/or compounds of interest by techniques well known in the art. Moreover, any wild-type or mutant recombination sites or combinations of the same or different recombination sites may be used for adding and removing molecules and/or compounds of interest to or from a support.

The invention also relates to any support comprising one or more recombination sites (e.g. two, three, four, five, seven, ten, twelve, fifteen, twenty, thirty, fifty, etc.) or portions thereof and to supports comprising nucleic acid, protein molecules and/or other molecules and/or compounds having one or more recombination sites (or portions thereof) bound to said support.

The invention also relates to compositions comprising such supports of the invention. Such compositions may further comprise one or more recombination proteins (preferably site specific recombination proteins), suitable buffers (e.g., for causing recombination), nucleic acid, protein molecules and/or other molecules and/or compounds, preferably comprising recombination sites which may be unbound to the support, and any other reagents used for recombining recombination sites according to the invention (and combinations thereof). The invention also relates to compositions for use in further manipulating or analyzing the supports of the invention or the nucleic acid or protein molecules or other molecules and/or compounds attached thereto. Further manipulation and analysis may be preformed on the nucleic acids, proteins, and/or other molecules and/or compounds while bound to the support or after removal from the support. Such compositions may comprise suitable buffers and enzymes such as restriction enzymes, polymerases, ligases, recombination proteins, and the like.

In another aspect, the present invention provides a means for attaching or binding one or more (e.g., two, three, four, five, seven, ten, twelve, fifteen, twenty, thirty, fifty, etc.) molecules and/or compounds or populations of molecules and/or compounds to one or more of the same or different molecules and/or compounds or populations of molecules and/or compounds. Thus, the invention generally relates to connecting any number of molecules and/or compounds or population of molecules and/or compounds by recombination. As described herein, such linked molecules and/or compounds may be unlabeled or detectably labeled. Further, such linked molecules and/or compounds may be linked to either covalently or non-covalently. Suitable molecules and/or compounds include, but are not limited to, those described herein such as nucleic acids, proteins or peptides, chemical compounds, drugs, lipids, lipoproteins, hormones, etc. In one aspect, the same molecules and/or compounds, or the same type of molecules and/or compounds (e.g., protein-protein, nucleic acid-nucleic acid, etc.) may be linked through recombination. Thus, in one aspect, small molecules and/or proteins may be linked to recombination sites and then linked to each other in various combinations.

In another aspect, different molecules and/or compounds or different types of molecules and/or compounds (e.g., protein-nucleic acid, nucleic acid-ligand, protein-ligand, etc.) may be linked through recombination. Additionally, the molecules and/or compounds linked through recombination (e.g., protein-protein, protein-ligand, etc.) may be attached to a support or structure through recombination as described herein. Thus, the molecules and/or compounds (optionally linked to a support) produced are linked by one or more recombination sites (or portions thereof). Such recombination sites (or portions thereof) may be attached to molecules such as proteins, peptides, carbohydrates, steroids and/or lipids or combinations thereof using conventional technologies and the resulting recombination-site-containing molecules and/or compounds may be linked using the methods of the present invention. Further, the resultant linked molecules and/or compounds may be attached via one or more of the recombination sites to other molecules and/or compounds comprising recombination sites. For example, a nucleic acid comprising a recombination site may be attached to a molecule of interest and a second nucleic acid comprising a compatible recombination site may be attached to a second molecule of interest. Recombination between the sites results in the attachment of the two molecules via a small nucleic acid linker. The nucleic acid linker may be any length depending on the need but preferably is small (e.g., from about 5 to about 500 bps in length). Using this methodology, proteins, peptides, nucleic acids, carbohydrates, steroids and/or lipids or combinations thereof may be attached to proteins, peptides, nucleic acids, carbohydrates, steroids and/or lipids or combinations thereof. Thus, the present invention provides a method of connecting two or more molecules and/or compounds, comprising the steps of:

(a) obtaining at least a first and a second molecule and/or compound, each of said molecules and/or compounds comprising at least one recombination site (or portion thereof); and (b) causing some or all of the recombination sites (or portions thereof) on said first molecule and/or compound to recombine with all or a portion of the recombination sites (or portions thereof) on said second molecule and/or compound.

In some preferred embodiments, a recombination site may be attached to a molecule of interest using conventional conjugation technology. For example, oligonucleotides comprising the recombination site can be synthesized so as to include one or more reactive functional moieties (e.g., two, three, four, five, seven, ten, etc.) which may be the same or different. Suitable reactive functional moieties include, but are not limited to, amine groups, epoxy groups, vinyl groups, thiol groups and the like. The synthesis of oligonucleotides comprising one or more reactive functional moieties is routine in the art. Once synthesized, oligonucleotides comprising one or more reactive functional moieties may be attached to one or more reactive groups (e.g., two, three, four, five, seven, ten, etc.) present on the molecule or compound of interest. The oligonucleotides may be attached directly by reacting one or more of the reactive functional moieties with one or more of the reactive functional groups. In some embodiments, the attachment may be effected using a suitable linking group capable of reacting with one or more of the reactive functional moieties present on the oligonucleotide and with one or more of the reactive groups present on the molecule of interest. In other embodiments, both direct attachment and attachment through a linking group may be used. Those skilled in the art will appreciate that the reactive functional moieties on the oligonucleotide may be the same or different as the reactive functional moieties on the molecules and/or compounds of interest. Suitable reagents and techniques for conjugation of the oligonucleotide to the molecule of interest may be found in Hermanson, *Bioconjugate Techniques*, Academic Press Inc., San Diego, Calif., 1996.

The present invention also relates to kits for carrying out the methods of the invention, and particularly for use in creating the product nucleic acid molecules of the invention or other linked molecules and/or compounds of the invention (e.g., protein-protein, nucleic acid-protein, etc.), or supports comprising such product nucleic acid molecules or linked molecules and/or compounds. The invention also relates to kits for adding and/or removing and/or replacing nucleic acids, proteins and/or other molecules and/or compounds to or from one or more supports, for creating and using combinatorial libraries of the invention, and for carrying out homologous recombination (particularly gene targeting) according to the methods of the invention. The kits of the invention may also comprise further components for further manipulating the recombination site-containing molecules and/or compounds produced by the methods of the invention. The kits of the invention may comprise one or more nucleic acid molecules of the invention (particularly starting molecules comprising one or more recombination sites and optionally comprising one or more reactive functional moieties), one or more molecules and/or compounds of the invention, one or more supports of the invention and/or one or more vectors of the invention. Such kits may optionally comprise one or more additional components selected from the group consisting of one or more host cells (e.g., two, three, four, five etc.), one or more reagents for introducing (e.g., by transfection or transformation) molecules or compounds into one or more host cells, one or more nucleotides, one or more polymerases and/or reverse transcriptases (e.g., two, three, four, five, etc.), one or more suitable buffers (e.g., two, three, four, five, etc.), one or more primers (e.g., two, three, four, five, seven, ten, twelve, fifteen, twenty, thirty, fifty, etc.), one or more terminating agents (e.g., two, three, four, five, seven, ten, etc.), one or more populations of molecules for creating combinatorial libraries (e.g., two, three, four, five, seven, ten, twelve, fifteen, twenty, thirty, fifty, etc.) and one or more combinatorial libraries (e.g., two, three, four, five, seven, ten, twelve, fifteen, twenty, thirty, fifty, etc.). The kits of the invention may also contain directions or protocols for carrying out the methods of the invention.

In another aspect the invention provides kits for joining, deleting, or replacing nucleic acid segments, these kits comprising at least one component selected from the group consisting of (1) one or more recombination proteins or compositions comprising one or more recombination proteins, and (2) at least one nucleic acid molecule comprising one or more recombination sites (preferably a vector having at least two different recombination specificities). The kits of the invention may also comprise one or more components selected from the group consisting of (a) additional nucleic acid molecules comprising additional recombination sites; (b) one or more enzymes having ligase activity; (c) one or more enzymes having polymerase activity; (d) one or more enzymes having reverse transcriptase activity; (e) one or more enzymes having restriction endonuclease activity; (f) one or more primers; (g) one or more nucleic acid libraries; (h) one or more supports; (i) one or more buffers; (j) one or more detergents or solutions containing detergents; (k) one or more nucleotides; (l) one or more terminating agents; (m) one or more transfection reagents; (n) one or more host cells; and (o) instructions for using the kit components.

Further, kits of the invention may contain one or more recombination proteins selected from the goup consisting of Cre, Int, IHF, Xis, Flp, Fis, Hin, Gin, Cin, Tn3 resolvase, ΦC31, TndX, XerC, and XerD.

In addition, recombination sites of kits of the invention will generally have different recombination specificities each comprising att sites with different seven base pair overlap regions. In specific embodiments of the invention, the first three nucleotides of these seven base pair overlap regions comprise nucleotide sequences selected from the group consisting of AAA, AAC, AAG, AAT, ACA, ACC, ACG, ACT, AGA, AGC, AGG, AGT, ATA, ATC, ATG; ATT, CAA, CAC, CAG, CAT, CCA, CCC, CCG, CCT, CGA, CGC, CGG, CGT, CTA, CTC, CTG CTT, GAA, GAC, GAG, GAT, GCA, GCC, GCG, GCT, GGA, GGC, GGG, GGT, GTA, GTC, GTG, GTT, TAA, TAC, TAG, TAT, TCA, TCC, TCG, TCT, TGA, TGC, TGG, TGT, TTA, TTC, TTG, and TTT.

In specific embodiments, kits of the invention contain compositions comprising one or more recombination proteins capable of catalyzing recombination between att sites. In related embodiments, these compositions comprise one or more recombination proteins capable of catalyzing attB×attP (BP) reactions, attL×attR (LR) reactions, or both BP and LR reactions.

Nucleic acid libraries supplied with kits of the invention may comprise cDNA or genomic DNA. Further, these libraries may comprise polynucleotides which encode variable domains of antibody light and heavy chains.

The invention also relates to compositions for carrying out the methods of the invention and to compositions created while carrying out the methods of the invention. In particular, the invention includes nucleic acid molecules prepared by methods of the invention, methods for preparing host cells which contain these nucleic acid molecules, host cells prepared by these methods, and methods employing these host cells for producing products (e.g., RNA, protein, etc.) encoded by these nucleic acid molecules, products encoded by these nucleic acid molecules (e.g., RNA, protein, etc.).

The compositions, methods and kits of the invention are preferably prepared and carried out using a phage-lambda site-specific recombination system and more preferably with the GATEWAY™ Recombinational Cloning System available from Invitrogen Corp., Life Technologies Division (Rockville, Md.). The GATEWAY™ Cloning Technology Instruction Manual (Invitrogen Corp., Life Technologies Division) describes in more detail the systems and is incorporated herein by reference in its entirety.

Other preferred embodiments of the invention will be apparent to one or ordinary skill in the art in light of what is known in the art, in light of the following drawings and description of the invention, and in light of the claims.

After construction of the two plasmids as described, each of which contains three inserted DNA segments, these plasmids are reacted with LR CLONASE™ to generate another plasmid which contains the six DNA segments flanked by attB sites (i.e., B 1-DNA-A-B3-DNA-B-B4-DNA-C-B 5-DNA-D-B 3-B1-DNA-E-B4-DNA-F-B2).

FIG. 20A is a schematic representation of an exemplary vector of the invention which contains two different DNA inserts, the transcription of which is driven in different directions by T7 promoters. Depending on the type of transcripts which are to be produced, either of DNA-A and/or DNA-B may be in an orientation which results in the production of either sense or anti-sense RNA.

FIG. 20B is a schematic representation of an exemplary vector of the invention which contains one DNA insert, the transcription of which is driven in two different directions by T7 promoters. Thus, RNA produced by transcription driven by one promoter will be sense RNA and RNA produced by transcription driven by the other promoter will be anti-sense RNA.

FIG. 20C is a schematic representation of an exemplary vector of the invention which contains two different DNA inserts having the same nucleotide sequence (i.e., DNA-A), the transcription of which are driven in different directions by two separate T7 promoters. In this example, RNA produced by transcription driven by one promoter will be sense RNA and RNA produced by transcription driven by the other promoter will be anti-sense RNA.

FIG. 20D is a schematic representation of an exemplary vector of the invention which contains two DNA inserts having the same nucleotide sequence (i.e., DNA-A) in opposite orientations, the transcription of which is driven by one T7 promoter. A transcription termination signal is not present between the two copies of DNA-A and the DNA-A inserts. Transcription of one segment produces a sense RNA and of the other produces an anti-sense RNA. The RNA produced from this vector will undergo intramolecular hybridization and, thus, will form a double-stranded molecule with a hairpin turn.

FIG. 20E is a schematic representation of an exemplary vector of the invention, each of which contains a DNA insert having the same nucleotide sequence (i.e., DNA-A) and a KAN resistance marker. Transcription of these inserts results in the production of sense and anti-sense RNA which may then hybridize to form double stranded RNA molecules.

FIG. 20F is a schematic representation of an exemplary vector of the invention, which contains a DNA insert having a nucleotide sequence (i.e., DNA-A) and an AMP resistance marker. Transcription of these inserts results in the production of sense and anti-sense RNA which may then hybridize to form double stranded RNA molecules.

Figure 21A:
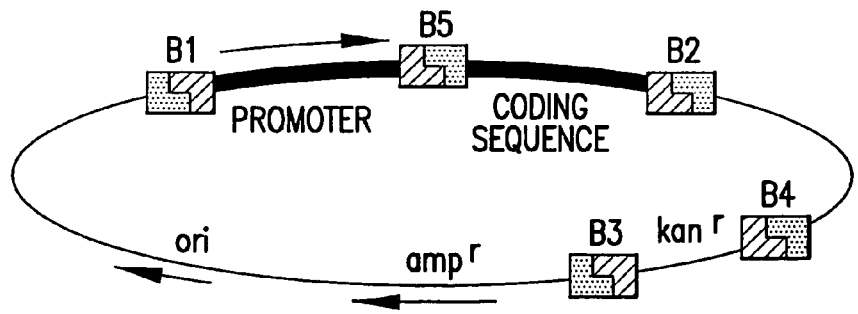

FIG. 21A is a schematic representation of an exemplary vector of the invention which contains three inserts, labeled "promoter," "coding sequence," and "Kan$^r$." In this example, the inserted promoter drives expression of the coding sequence. Further, an inserted DNA segment confers resistance to kanamycin upon host cells which contain the vector. As discussed below in more detail, a considerable number of vector components (e.g., a selectable marker (for example a kanamycin resistance gene) cassette, an ori cassette, a promoter cassette, a tag sequence cassette, and the like) can be inserted into or used to construct vectors of the invention.

Figure 21B:
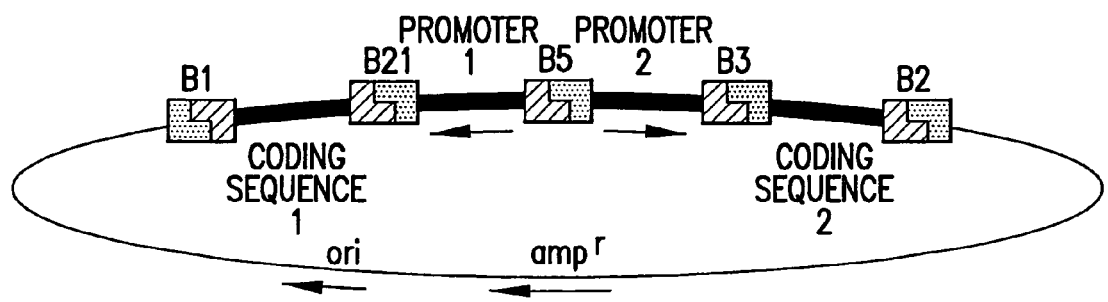

FIG. 21B is a schematic representation of an exemplary vector of the invention which contains four inserts, labeled "promoter 1," "coding sequence 1," "promoter 2," and "coding sequence 2." In this example, promoter 1 drives expression of coding sequence 1 and promoter 2 drives expression of coding sequence 2.

Figure 21C:
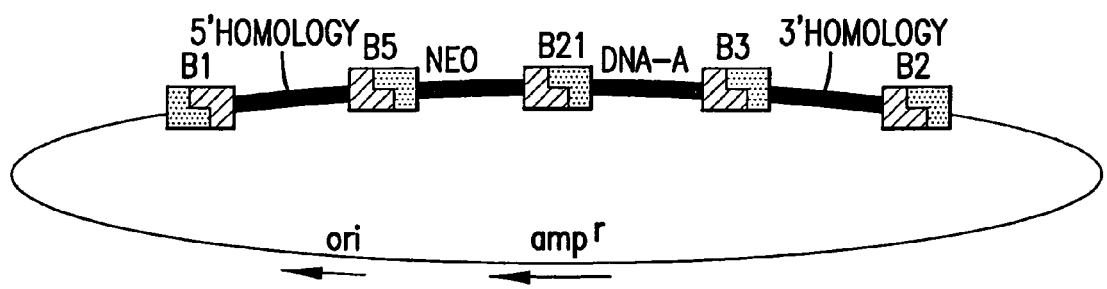

FIG. 21C is a schematic representation of an exemplary vector of the invention for homologous recombination. This vector which contains four inserts, labeled "5' homology," "NEO," "DNA-A," and "3' homology." The 5' and 3' homology regions, in this example, are homologous to a chromosomal region selected for insertion of a neomycin resistance marker ("NEO") and a DNA segment ("DNA-A"). Targeting vectors of this type can be designed to insert, delete and/or replace nucleic acid present in targeted nucleic acid molecules.

Figure 22A:
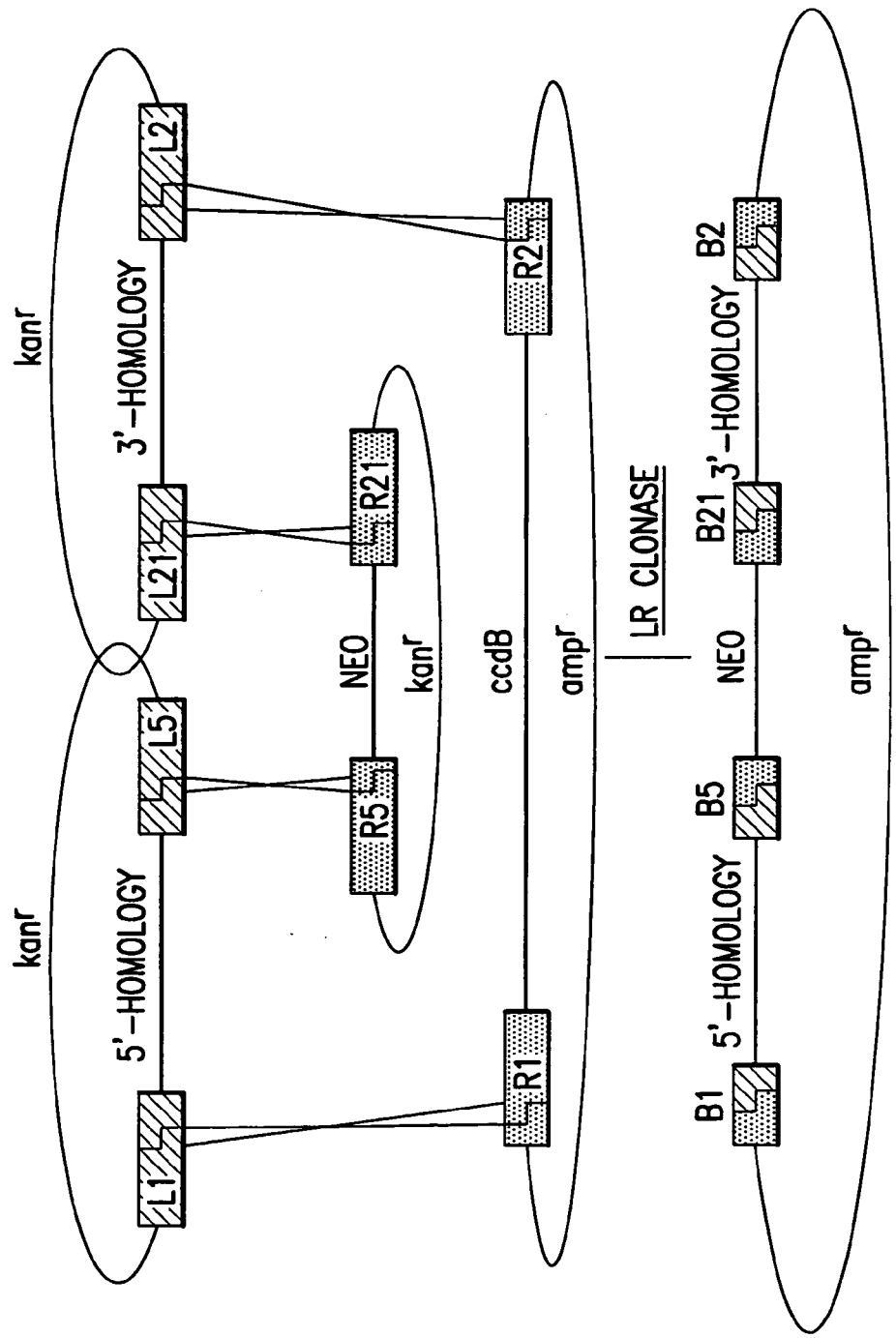
Figure 22B:
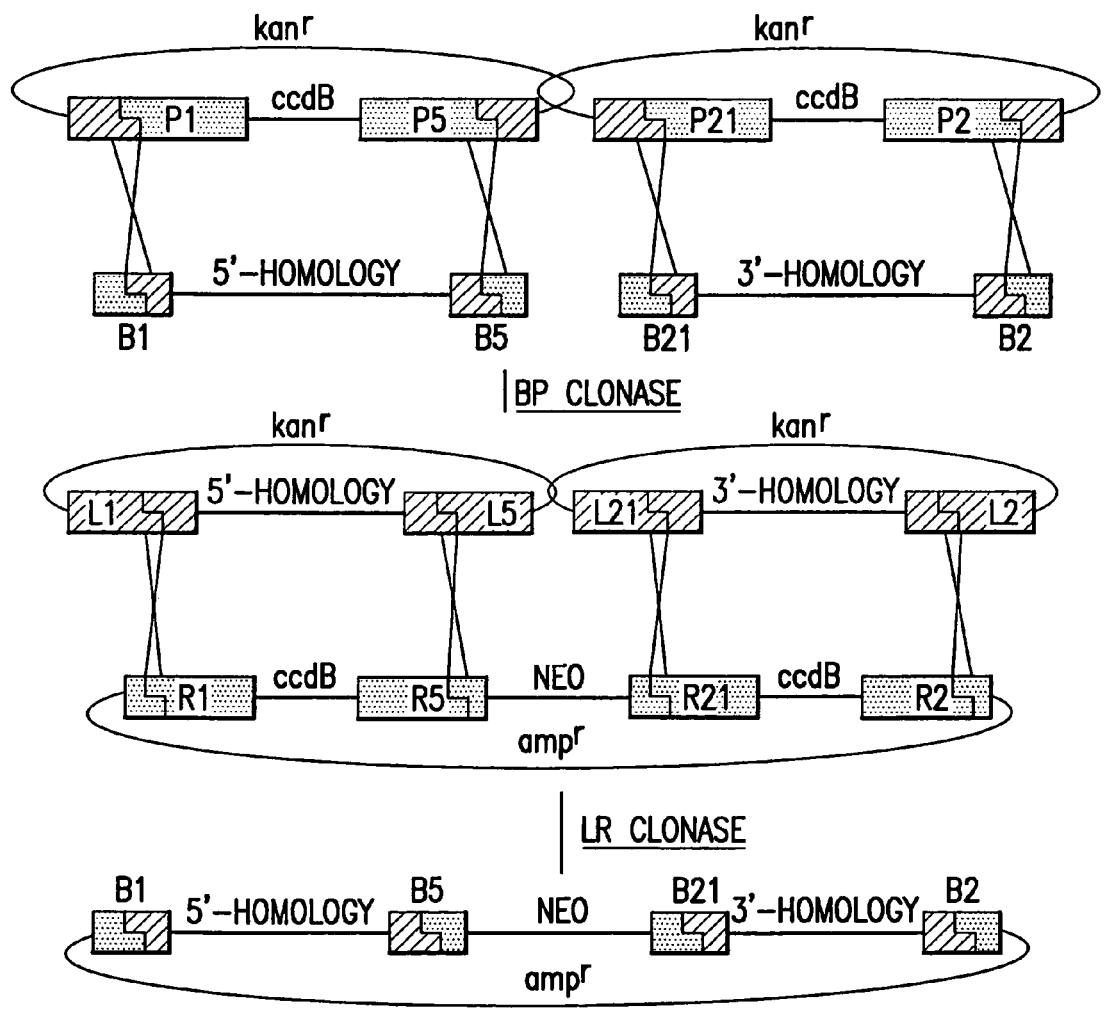

FIGS. 22A and 22B show a schematic representation of processes for preparing targeting vectors of the invention.

Figure 23:
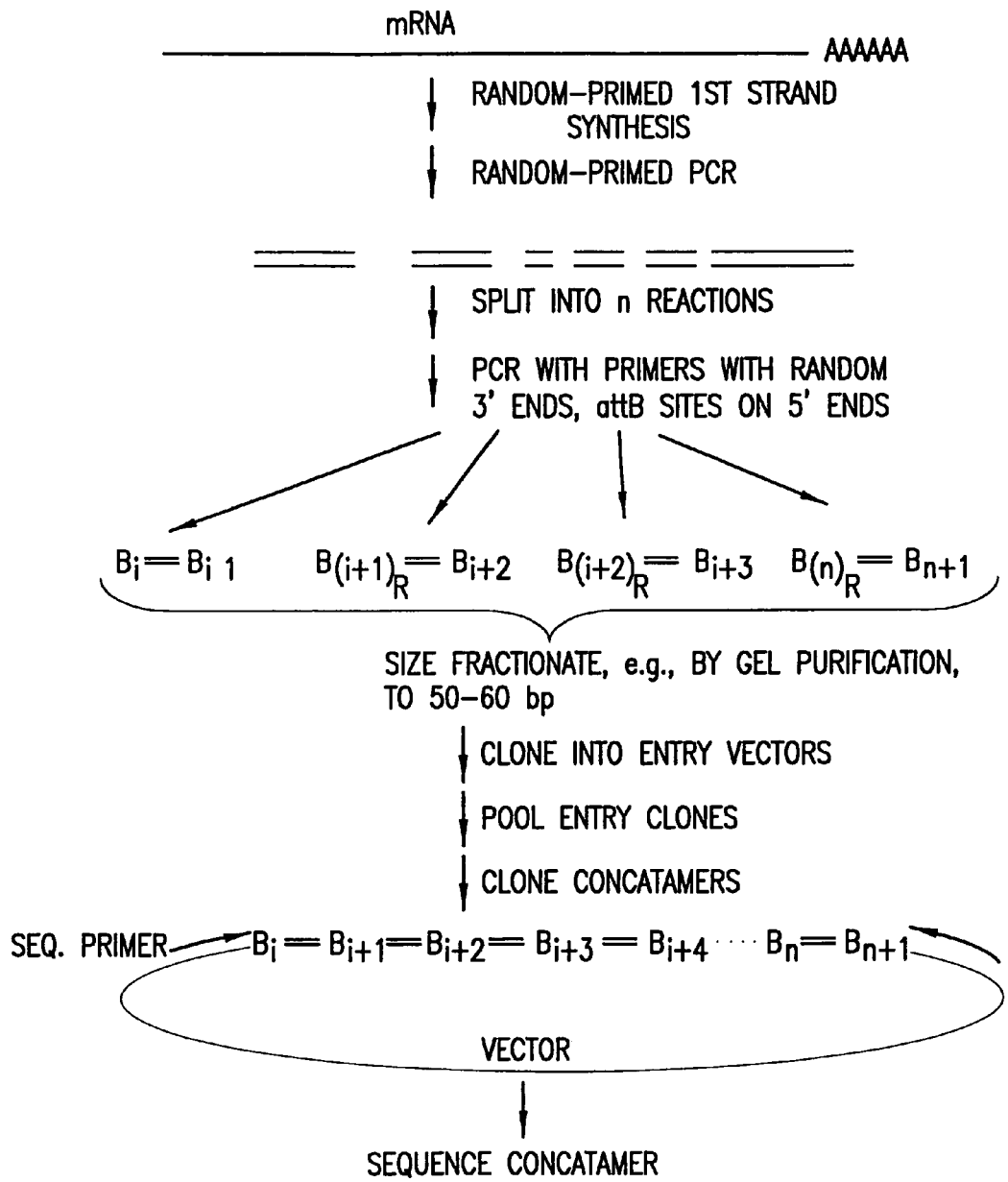

FIG. 23 shows mRNA amplified with random-primed first strand reverse transcription, then random-primed with PCR. These amplification products are split into n pools, and each pool is amplified with random primers with a different pair of attB sites. The "R" suffix shows that some of the attB sites can be in inverted orientation attB sites with either the standard or reverse orientations are used in separate pools to generate amplification products where the attB sites are linked in either standard or inverted orientation. When these sites react with inverted attP sites, attR sites are formed in the Entry Clones instead of attL sites. Hence, reacting pools with standard or inverted attRs will generate mixtures of molecules flanked by attR and attL sites. The amplification products are sized by gel purification, then cloned with the GATEWAY™ BP reaction to make Entry Clones, each containing small inserts planked by attL sites, attR sites, or attL and attR, depending on the orientation of the attB sites and attP sites used. When Entry Clones are mixed together, the inserts clone form a concatamer that can be cloned into a suitable Destination Vector, to give n inserts, each separated by an attB site. Sequencing a number of concatamers generates a profile of mRNA molecules present in the original sample.

FIGS. 24A–24C show the sequences of a number of att sites (SEQ ID NOs:1–36) suitable for use in methods and compositions of the invention.

Figure 25A:
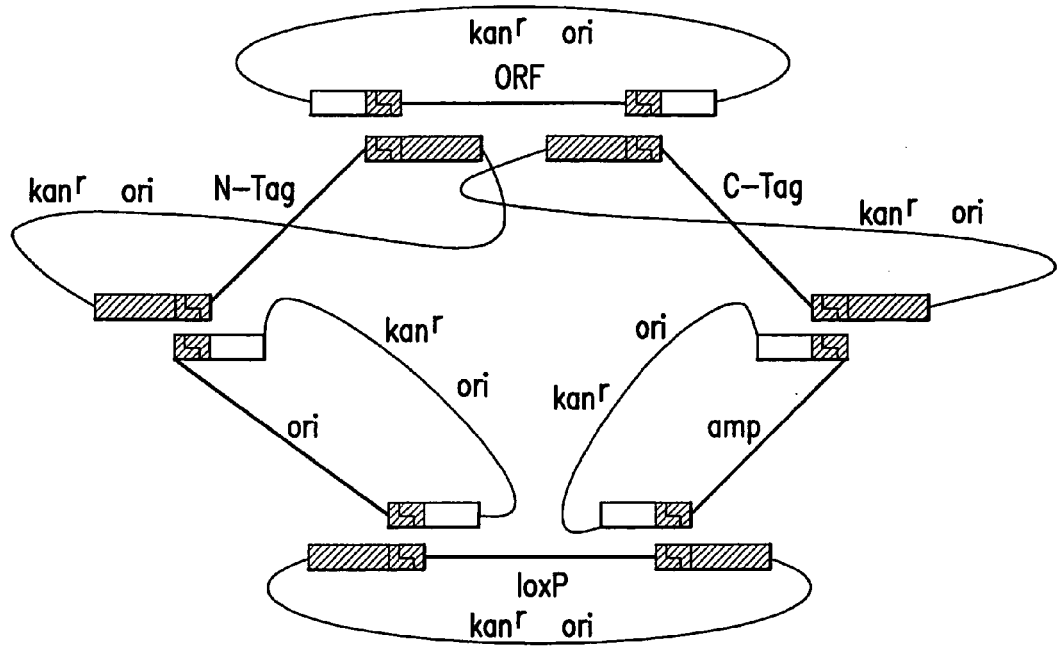
Figure 25B:
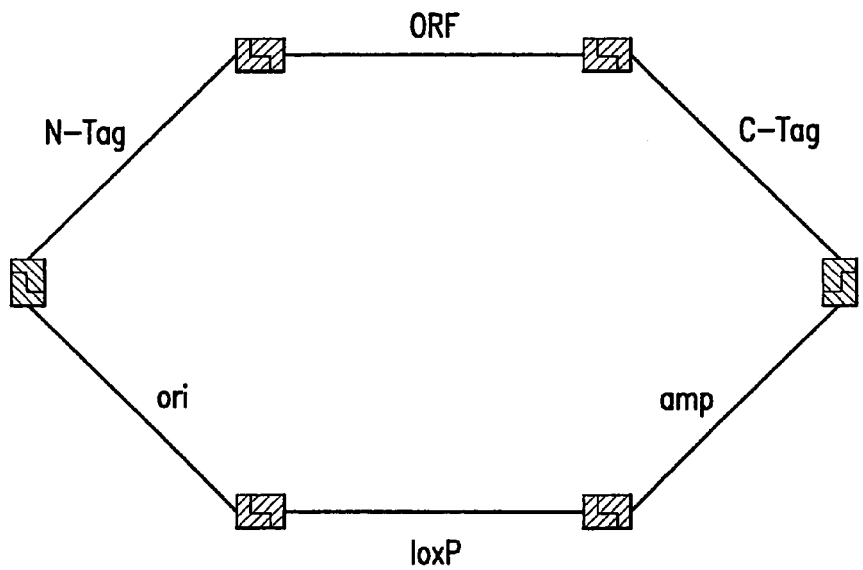

FIGS. 25A–25B show a collection of Entry Clones which contain inserts including, N-terminal tags or sequences (N-tag), open reading frames (ORF), C-terminal tags or sequences (C-tag), selectable markers (amp), origins of plasmid replication (ori) and other vector elements (for example a loxP site). Each Entry Clone vector element insert is flanked by attL or attR sites such that the vector elements can be linked together and form a new vector construct in an LR Clonase reaction (shown in FIG. 25B).

Figure 26A:
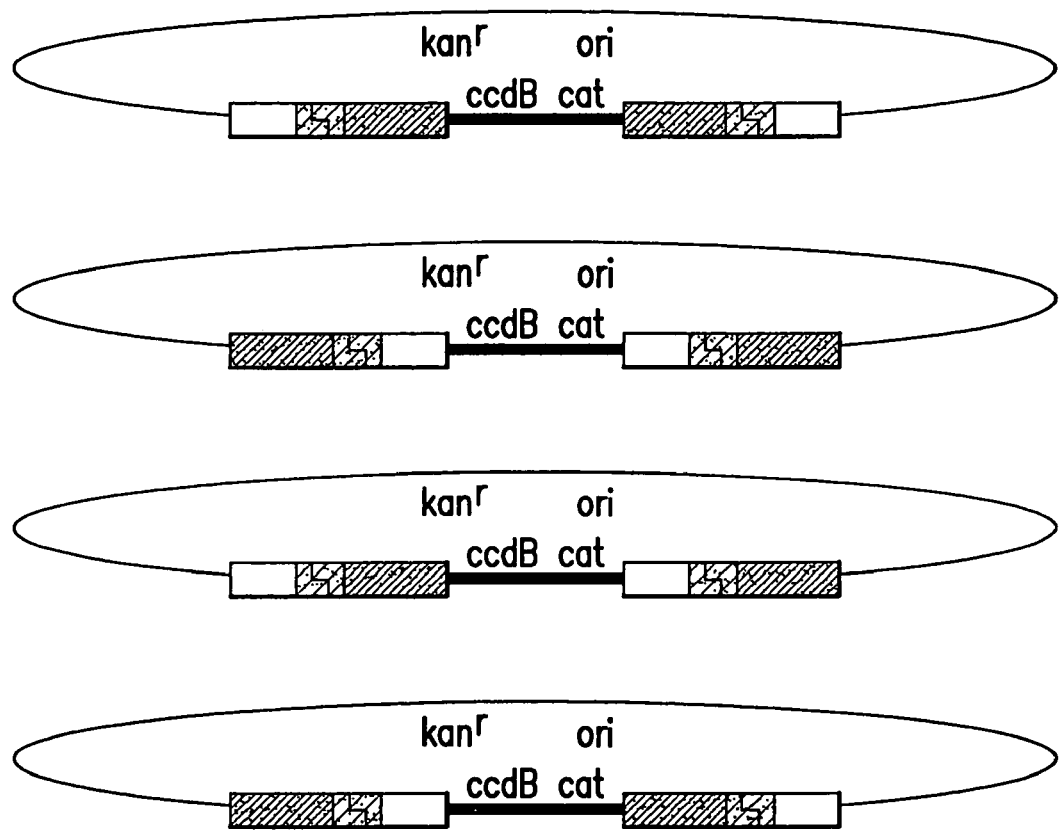
Figure 26B:
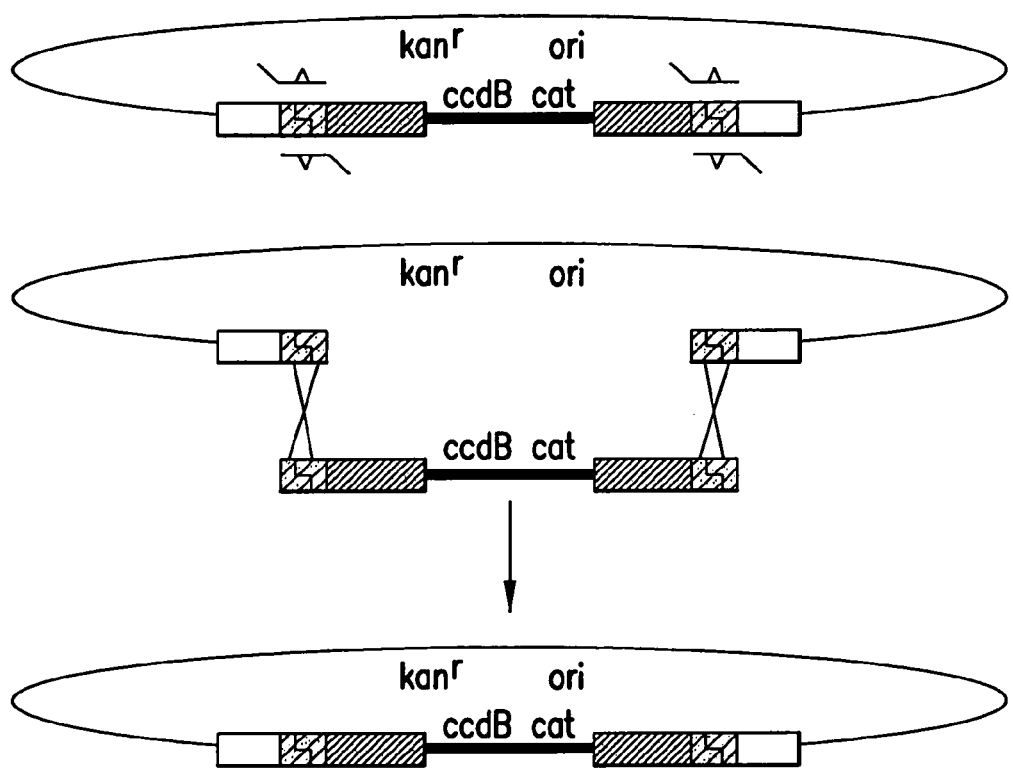

FIG. 26A–26B show a process for constructing attP DONOR plasmids containing attP sites of any orientation and specificity. FIG. 26A shows four arrangements of attP sites in attP DONOR plasmids consisting of two orientations of direct repeat and two orientations of inverted repeat attP sites. The four attP DONOR plasmids shown in FIG. 26A can be used as templates for PCR reactions with PCR primers that would anneal specifically to the core of an attP site and thus create an attL or attR site of any desired specificity at the ends of the PCR products. For each new attP DONOR vector to be constructed, two such PCR products are generated, one consisting of the plasmid backbone (ori-kan) and a second consisting of the ccdB and cat genes. The PCR products are reacted together in LR Clonase reactions to generate new plasmids with attP sites of any orientation with any att site specificity.

Figure 27A:
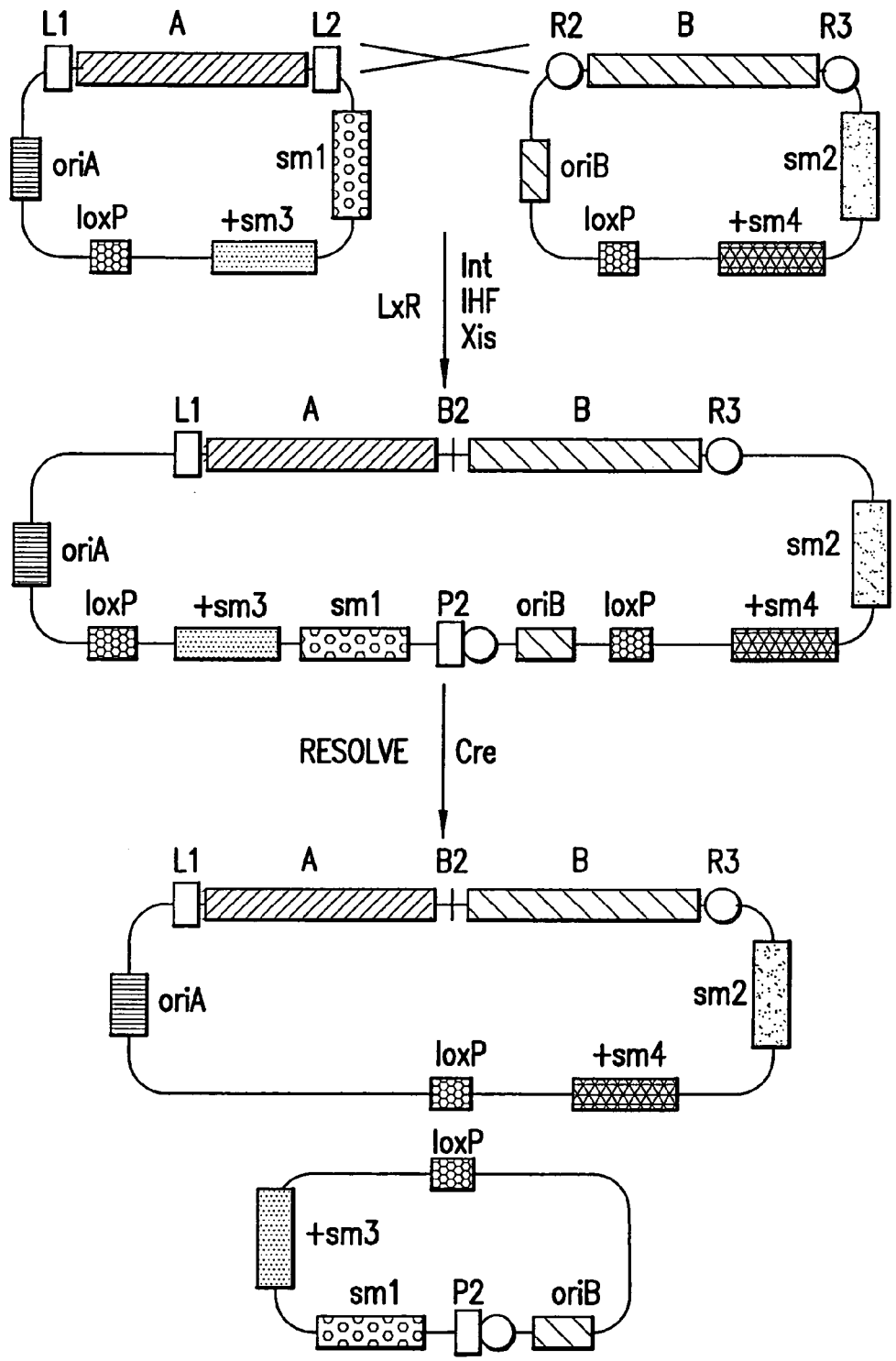

FIG. 27A shows a process for linking two nucleic acid segments, A and B. The segments are cloned in two similarly configured plasmids. Each segment is flanked by two recombination sites. One of the recombination sites on each plasmid is capable of reacting with its cognate partner on the other plasmid, whereas the other two recombination sites do not react with any other site present. Each plasmid carries a unique origin of replication which may or may not be conditional. Each plasmid also carries both positive and negative selectable markers (+smX and smY, respectively) to enable selection against, and for elements linked to a particular marker. Lastly, each plasmid carries a third recombination site (loxP in this example), suitably positioned to enable deletion of undesired elements and retention of desired elements. In this example, the two plasmids are initially fused at L2 and R2 via a Gateway L×R reaction. This results in the juxtaposition of segments A and B via a B2 recombination site, and the juxtapostion of sm1 and oriB via a P2 recombination site. The two loxP sites in the backbone that flank a series of plasmid elements are depicted in the second panel. Addition of the Cre protein will resolve the single large plasmid into two smaller ones. One of these will be the desired plasmid which carries the linked A and B segments with oriA now linked to sm2 and +sm4. The other carries a set of dispensable and/or undesirable elements. Transformation of an appropriate host and subsequent imposition of appropriate genetic selections will result in loss of the undesired plasmid, while the desired plasmid is maintained.

Figure 27B:
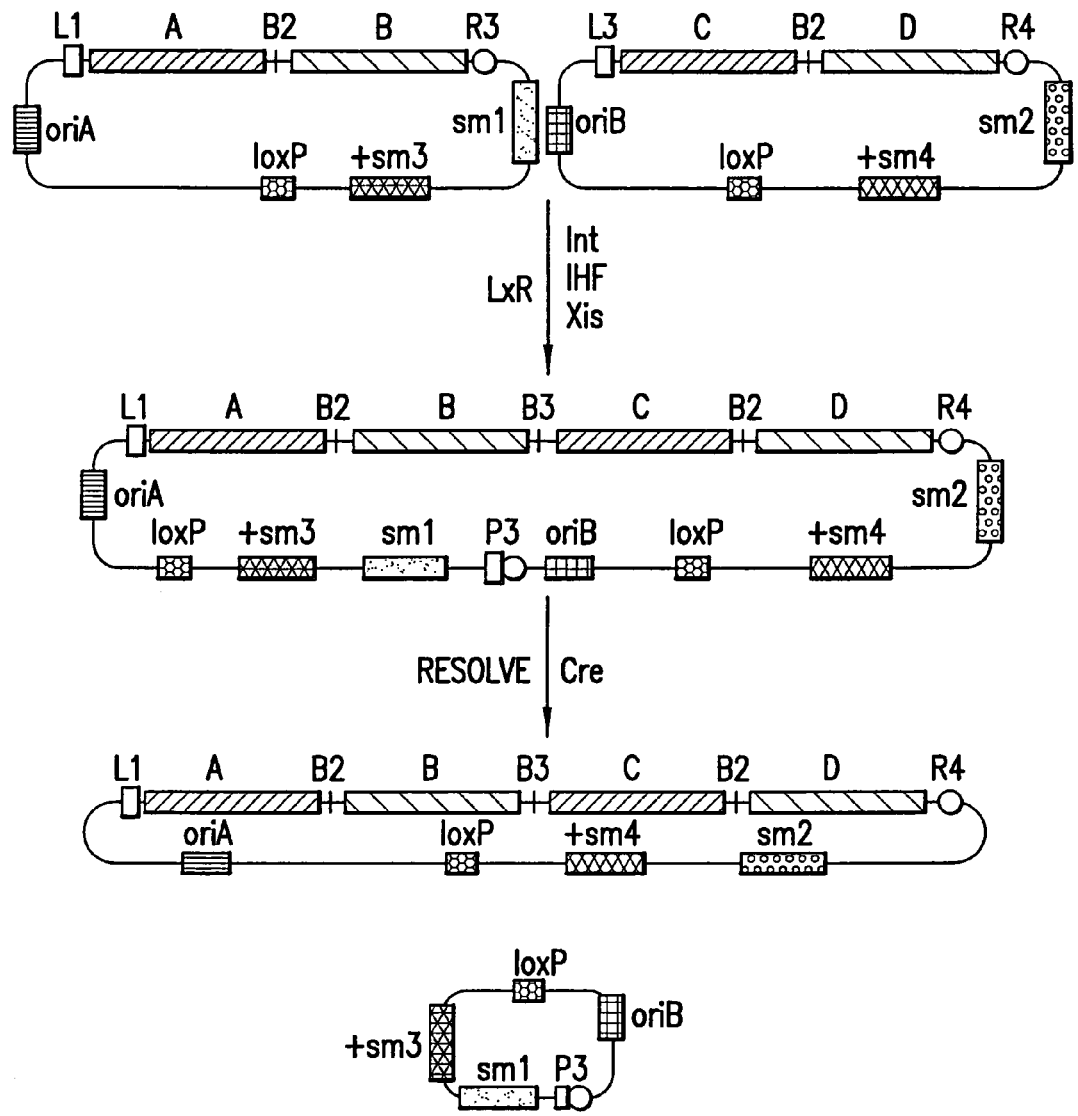

FIG. 27B shows a process for linking two chimeric nucleic acid segments, A-B and C-D, constructed as shown above in FIG. 27A. The segments are cloned in two similarly configured plasmids. Each segment is flanked by two recombination sites. One of these on each plasmid is capable of reacting with its cognate partner on the other plasmid, whereas the other two recombination sites do not react with any other site present. In this example, the two plasmids are initially fused at L2 and R2 via a Gateway L×R reaction. This results in the juxtaposition of segments A and B via a B2 recombination site, and the juxtapostion of sm1 and oriB via a P2 recombination site. The two loxP sites in the backbone that flank a series of plasmid elements are depicted in the second panel. Addition of the Cre protein will resolve the single large plasmid into two smaller ones. One of these will be the desired plasmid which carries the linked A-B and C-D segments with oriA now linked to sm2 and +sm4. The other carries a set of dispensable and/or undesirable elements. Transformation of an appropriate host and subsequent imposition of appropriate genetic selections will result in loss of the undesired plasmid, whilst the desired plasmid is maintained.

DETAILED DESCRIPTION OF THE INVENTION

Definitions

In the description that follows, a number of terms used in recombinant nucleic acid technology are utilized extensively. In order to provide a clear and more consistent understanding of the specification and claims, including the scope to be given such terms, the following definitions are provided.

Gene: As used herein, the term "gene" refers to a nucleic acid which contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. Of course, as would be clearly apparent to one skilled in the art, the transcriptional and translational machinery required for production of the gene product is not included within the definition of a gene. When the gene encodes an untranslated RNA, it includes the promoter and the nucleic acid which encodes the untranslated RNA.

Structural Gene: As used herein, the phrase "structural gene" refers to refers to a nucleic acid which is transcribed into messenger RNA that is then translated into a sequence of amino acids characteristic of a specific polypeptide.

Host: As used herein, the term "host" refers to any prokaryotic or eukaryotic organism that is a recipient of a replicable expression vector, cloning vector or any nucleic acid molecule. The nucleic acid molecule may contain, but is not limited to, a structural gene, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Maniatis et al., Molecular Cloning: A Laboratory Manual, Cold Spring Harbor Laboratory, Cold Spring Harbor, N.Y. (1982).

Transcriptional Regulatory Sequence: As used herein, the phrase "transcriptional regulatory sequence" refers to a functional stretch of nucleotides contained on a nucleic acid molecule, in any configuration or geometry, that act to regulate the transcription of (1) one or more structural genes (e.g., two, three, four, five, seven, ten, etc.) into messenger RNA or (2) one or more genes into untranslated RNA. Examples of transcriptional regulatory sequences include, but are not limited to, promoters, enhancers, repressors, and the like.

Promoter: As used herein, a promoter is an example of a transcriptional regulatory sequence, and is specifically a nucleic acid generally described as the 5'-region of a gene located proximal to the start codon or nucleic acid which encodes untranslated RNA. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Figure 2:
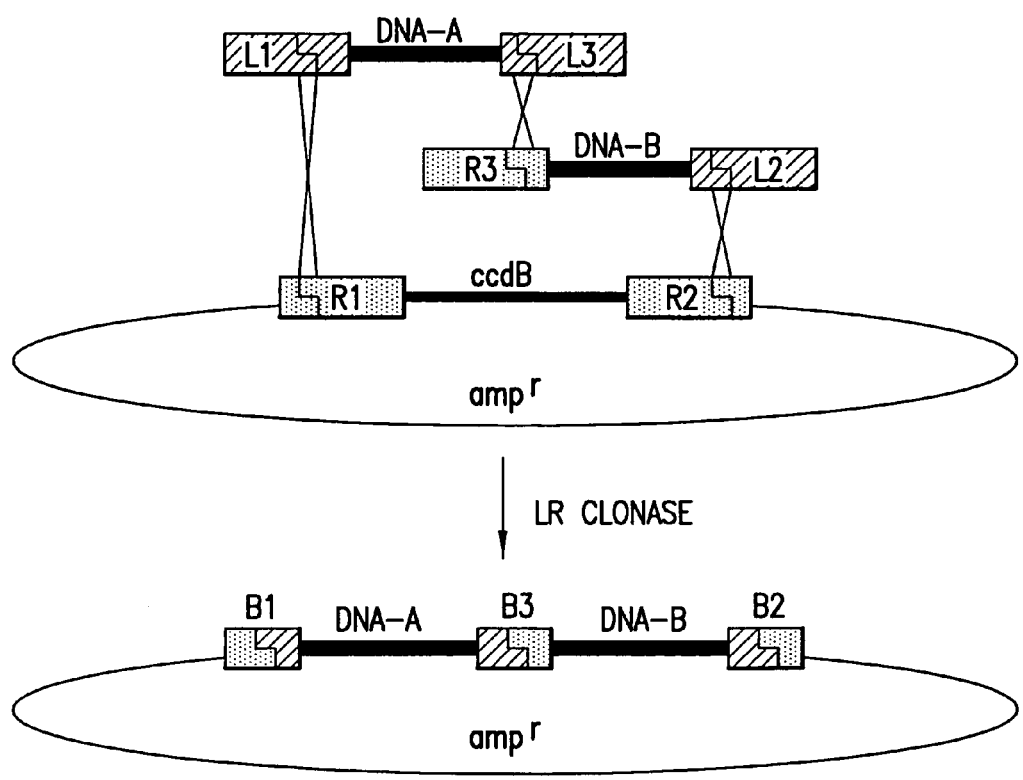
FIG. 2 is a schematic representation of the use of the present invention to clone two nucleic acid segments by performing an LR recombination reaction.

Insert: As used herein, the term "insert" refers to a desired nucleic acid segment that is a part of a larger nucleic acid molecule. In many instances, the insert will be introduced into the larger nucleic acid molecule. For example, the nucleic acid segments labeled ccdB and DNA-A in FIG. 2, are nucleic acid inserts with respect to the larger nucleic acid molecule shown therein. In most instances, the insert will be flanked by recombination sites (e.g., at least one recombination site at each end). In certain embodiments, however, the insert will only contain a recombination site on one end.

Target Nucleic Acid Molecule: As used herein, the phrase "target nucleic acid molecule" refers to a nucleic acid segment of interest, preferably nucleic acid which is to be acted upon using the compounds and methods of the present invention. Such target nucleic acid molecules preferably contain one or more genes (e.g., two, three, four, five, seven, ten, twelve, fifteen, twenty, thirty, fifty, etc.) or portions of genes.

Insert Donor: As used herein, the phrase "Insert Donor" refers to one of the two parental nucleic acid molecules (e.g., RNA or DNA) of the present invention which carries the Insert (see FIG. 1). The Insert Donor molecule comprises the Insert flanked on both sides with recombination sites. The Insert Donor can be linear or circular. In one embodiment of the invention, the Insert Donor is a circular nucleic acid molecule, optionally supercoiled, and further comprises a cloning vector sequence outside of the recombination signals. When a population of Inserts or population of nucleic acid segments are used to make the Insert Donor, a population of Insert Donors result and may be used in accordance with the invention.

Product: As used herein, the term "Product" refers to one the desired daughter molecules comprising the A and D sequences which is produced after the second recombination event during the recombinational cloning process (see FIG. 1). The Product contains the nucleic acid which was to be cloned or subcloned. In accordance with the invention, when a population of Insert Donors are used, the resulting population of Product molecules will contain all or a portion of the population of Inserts of the Insert Donors and preferably will contain a representative population of the original molecules of the Insert Donors.

Byproduct: As used herein, the term "Byproduct" refers to a daughter molecule (a new clone produced after the second recombination event during the recombinational cloning process) lacking the segment which is desired to be cloned or subcloned.

Cointegrate: As used herein, the term "Cointegrate" refers to at least one recombination intermediate nucleic acid molecule of the present invention that contains both parental (starting) molecules. Cointegrates may be linear or circular. RNA and polypeptides may be expressed from cointegrates using an appropriate host cell strain, for example E. coli DB3.1 (particularly E. coli LIBRARY EFFICIENCY® DB3.1™ Competent Cells), and selecting for both selection markers found on the cointegrate molecule.

Recognition Sequence: As used herein, the phrase "recognition sequence" refers to a particular sequence to which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprising two 13 base pair inverted repeats (serving as the recombinase binding sites) flanking an 8 base pair core sequence. (See FIG. 1 of Sauer, B., Current Opinion in Biotechnology 5:521–527 (1994).) Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). (See Landy, Current Opinion in Biotechnology 3:699–707 (1993).) Such sites may also be engineered according to the present invention to enhance production of products in the methods of the invention. For example, when such engineered sites lack the P1 or H1 domains to make the recombination reactions irreversible (e.g., attR or attP), such sites may be designated attR' or attP' to show that the domains of these sites have been modified in some way.

Recombination Proteins: As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699–707 (1993)), or mutants, derivatives (e.g., fusion proteins containing the recombination protein sequences or fragments thereof), fragments, and variants thereof. Examples of recombination proteins include Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

Recombination Site: A used herein, the phrase "recombination site" refers to a recognition sequence on a nucleic acid molecule which participates in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. (See FIG. 1 of Sauer, B., *Curr. Opin. Biotech.* 5:521–527 (1994).) Other examples of recognition sequences include the attB, attP, attL, and attR sequences described herein, and mutants, fragments, variants and derivatives thereof, which are recognized by the recombination protein λ Int and by the auxiliary proteins integration host factor (IHF), FIS and excisionase (Xis). (See Landy, *Curr. Opin. Biotech.* 3:699–707 (1993).)

Recombination sites may be added to molecules by any number of known methods. For example, recombination sites can be added to nucleic acid molecules by blunt end ligation, PCR performed with fully or partially random primers, or inserting the nucleic acid molecules into an vector using a restriction site which flanked by recombination sites.

Recombinational Cloning: As used herein, the phrase "recombinational cloning" refers to a method, such as that described in U.S. Pat. Nos. 5,888,732 and 6,143,557 (the contents of which are fully incorporated herein by reference), whereby segments of nucleic acid molecules or populations of such molecules are exchanged, inserted, replaced, substituted or modified, in vitro or in vivo. Preferably, such cloning method is an in vitro method.

Repression Cassette: As used herein, the phrase "repression cassette" refers to a nucleic acid segment that contains a repressor or a selectable marker present in the subcloning vector.

Selectable Marker: As used herein, the phrase "selectable marker" refers to a nucleic acid segment that allows one to select for or against a molecule (e.g., a replicon) or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) nucleic acid segments that encode products which provide resistance against otherwise toxic compounds (e.g., antibiotics); (2) nucleic acid segments that encode products which are otherwise lacking in the recipient cell (e.g., tRNA genes, auxotrophic markers); (3) nucleic acid segments that encode products which suppress the activity of a gene product; (4) nucleic acid segments that encode products which can be readily identified (e.g., phenotypic markers such as (β-galactosidase, green fluorescent protein (GFP), yellow flourescent protein (YFP), red fluorescent protein (RFP), cyan fluorescent protein (CFP), and cell surface proteins); (5) nucleic acid segments that bind products which are otherwise detrimental to cell survival and/or function; (6) nucleic acid segments that otherwise inhibit the activity of any of the nucleic acid segments described in Nos. 1–5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence which can be otherwise nonfunctional (e.g., for PCR amplification of subpopulations of molecules); (10) nucleic acid segments, which when absent, directly or indirectly confer resistance or sensitivity to particular compounds; and/or (11) nucleic acid segments that encode products which either are toxic (e.g., *Diphtheria toxin*) or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, etc.).

Selection Scheme: As used herein, the phrase "selection scheme" refers to any method which allows selection, enrichment, or identification of a desired nucleic acid molecules or host cells contacting them (in particular Product or Product(s) from a mixture containing an Entry Clone or Vector, a Destination Vector, a Donor Vector, an Expression Clone or Vector, any intermediates (e.g., a Cointegrate or a replicon), and/or Byproducts). In one aspect, selection schemes of the invention rely on one or more selectable markers. The selection schemes of one embodiment have at least two components that are either linked or unlinked during recombinational cloning. One component is a selectable marker. The other component controls the expression in vitro or in vivo of the selectable marker, or survival of the cell (or the nucleic acid molecule, e.g., a replicon) harboring the plasmid carrying the selectable marker. Generally, this controlling element will be a repressor or inducer of the selectable marker, but other means for controlling expression or activity of the selectable marker can be used. Whether a repressor or activator is used will depend on whether the marker is for a positive or negative selection, and the exact arrangement of the various nucleic acid segments, as will be readily apparent to those skilled in the art. In some preferred embodiments, the selection scheme results in selection of or enrichment for only one or more desired nucleic acid molecules (such as Products). As defined herein, selecting for a nucleic acid molecule includes (a) selecting or enriching for the presence of the desired nucleic acid molecule (referred to as a "positive selection scheme"), and (b) selecting or enriching against the presence of nucleic acid molecules that are not the desired nucleic acid molecule (referred to as a "negative selection scheme").

Figure 1:
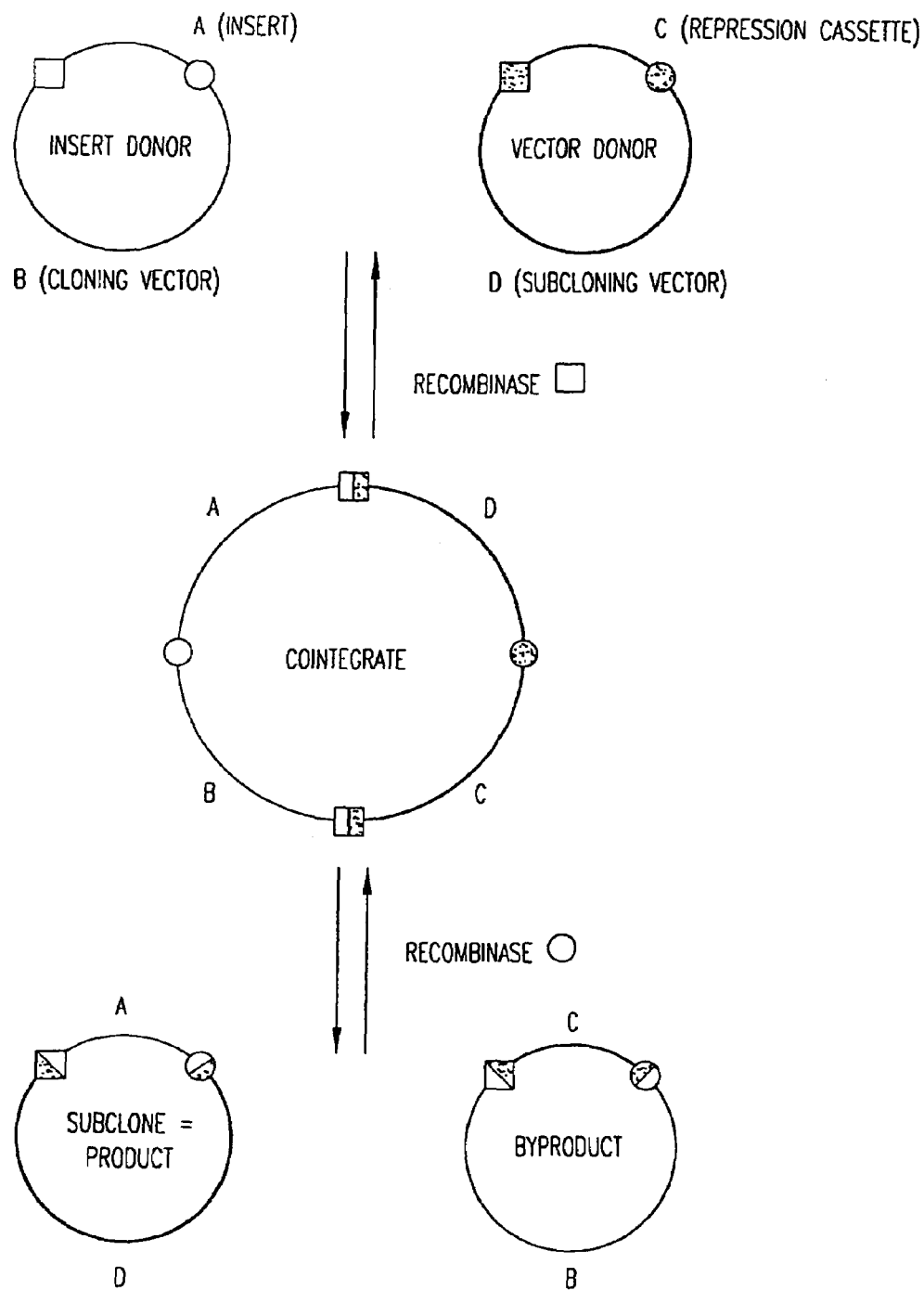
FIG. 1 is a schematic representation of the basic recombinational cloning reaction.

In one embodiment, the selection schemes (which can be carried out in reverse) will take one of three forms, which will be discussed in terms of FIG. 1. The first, exemplified herein with a selectable marker and a repressor therefore, selects for molecules having segment D and lacking segment C. The second selects against molecules having segment C and for molecules having segment D. Possible embodiments of the second form would have a nucleic acid segment carrying a gene toxic to cells into which the in vitro reaction products are to be introduced. A toxic gene can be a nucleic acid that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI, Nla3, etc.); apoptosis-related genes (e.g., ASK1 or members of the bcl-2/ced-9 family); retroviral genes; including those of the human immunodeficiency virus (HIV); defensins such as NP-1; inverted repeats or paired palindromic nucleic acid sequences; bacteriophage lytic genes such as those from ΦX174 or bacteriophage T4; antibiotic sensitivity genes such as rpsL; antimicrobial sensitivity genes such as pheS; plasmid killer genes' eukaryotic transcriptional vector genes that produce a gene product toxic to bacteria, such as GATA-1; genes that kill hosts in the absence of a suppressing function, e.g., kicB, ccdb, ΦX174 E (Liu, Q. et al., *Curr. Biol.* 8:1300–1309 (1998)); and other genes that negatively affect replicon stability and/or replication. A toxic gene can alternatively be selectable in vitro, e.g., a restriction site.

Many genes coding for restriction endonucleases operably linked to inducible promoters are known, and may be used in the present invention. (See, e.g., U.S. Pat. No. 4,960,707 (DpnI and DpnII); U.S. Pat. Nos. 5,000,333, 5,082,784 and 5,192,675 (KpnI); U.S. Pat. No. 5,147,800 (NgoAII and NgoAI); U.S. Pat. No. 5,179,015 (FspI and HaeIII); U.S. Pat. No. 5,200,333 (HaeII and TaqI); U.S. Pat. No. 5,248,605 (HpaII); U.S. Pat. No. 5,312,746(ClaI); U.S. Pat. Nos. 5,231,021 and 5,304,480 (XhoI and XhoII); U.S. Pat. No. 5,334,526 (AluI); U.S. Pat. No. 5,470,740 (NsiI); U.S. Pat. No. 5,534,428 (SstI/SacI); U.S. Pat. No. 5,202,248 (NcoI); U.S. Pat. No. 5,139,942 (NdeI); and U.S. Pat. No. 5,098,839 (PacI). (See also Wilson, G. G., *Nucl. Acids Res.* 19:2539–2566 (1991); and Lunnen, K. D., et al., *Gene* 74:25–32 (1988).)

In the second form, segment D carries a selectable marker. The toxic gene would eliminate transformants harboring the Vector Donor, Cointegrate, and Byproduct molecules, while the selectable marker can be used to select for cells containing the Product and against cells harboring only the Insert Donor.

The third form selects for cells that have both segments A and D in cis on the same molecule, but not for cells that have both segments in trans on different molecules. This could be embodied by a selectable marker that is split into two inactive fragments, one each on segments A and D.

The fragments are so arranged relative to the recombination sites that when the segments are brought together by the recombination event, they reconstitute a functional selectable marker. For example, the recombinational event can link a promoter with a structural nucleic acid molecule (e.g., a gene), can link two fragments of a structural nucleic acid molecule, or can link nucleic acid molecules that encode a heterodimeric gene product needed for survival, or can link portions of a replicon.

Site-Specific Recombinase: As used herein, the phrase "site-specific recombinase" refers to a type of recombinase which typically has at least the following four activities (or combinations thereof): (1) recognition of specific nucleic acid sequences; (2) cleavage of said sequence or sequences; (3) topoisomerase activity involved in strand exchange; and (4) ligase activity to reseal the cleaved strands of nucleic acid. (See Sauer, B., *Current Opinions in Biotechnology* 5:521–527 (1994).) Conservative site-specific recombination is distinguished from homologous recombination and transposition by a high degree of sequence specificity for both partners. The strand exchange mechanism involves the cleavage and rejoining of specific nucleic acid sequences in the absence of DNA synthesis (Landy, A. (1989) *Ann. Rev. Biochem.* 58:913–949).

Homologous Recombination: As used herein, the phrase "homologous recombination" refers to the process in which nucleic acid molecules with similar nucleotide sequences associate and exchange nucleotide strands. A nucleotide sequence of a first nucleic acid molecule which is effective for engaging in homologous recombination at a predefined position of a second nucleic acid molecule will therefore have a nucleotide sequence which facilitates the exchange of nucleotide strands between the first nucleic acid molecule and a defined position of the second nucleic acid molecule. Thus, the first nucleic acid will generally have a nucleotide sequence which is sufficiently complementary to a portion of the second nucleic acid molecule to promote nucleotide base pairing.

Homologous recombination requires homologous sequences in the two recombining partner nucleic acids but does not require any specific sequences. As indicated above, site-specific recombination which occurs, for example, at recombination sites such as att sites, is not considered to be "homologous recombination," as the phrase is used herein.

Vector: As used herein, the terms "vector" refers to a nucleic acid molecule (preferably DNA) that provides a useful biological or biochemical property to an insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment which do not require the use of recombination, transpositions or restriction enzymes (such as, but not limited to, uracil N-glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present invention. The cloning vector can further contain one or more selectable markers (e.g., two, three, four, five, seven, ten, etc.) suitable for use in the identification of cells transformed with the cloning vector.

Subcloning Vector: As used herein, the phrase "subcloning vector" refers to a cloning vector comprising a circular or linear nucleic acid molecule which includes, preferably, an appropriate replicon. In the present invention, the subcloning vector (segment D in FIG. 1) can also contain functional and/or regulatory elements that are desired to be incorporated into the final product to act upon or with the cloned nucleic acid insert (segment A in FIG. 1). The subcloning vector can also contain a selectable marker (preferably DNA).

Vector Donor: As used herein, the phrase "Vector Donor" refers to one of the two parental nucleic acid molecules (e.g., RNA or DNA) of the present invention which carries the nucleic acid segments comprising the nucleic acid vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Primer: As used herein, the term "primer" refers to a single stranded or double stranded oligonucleotide that is extended by covalent bonding of nucleotide monomers during amplification or polymerization of a nucleic acid molecule (e.g., a DNA molecule). In one aspect, the primer may be a sequencing primer (for example, a universal sequencing primer). In another aspect, the primer may comprise a recombination site or portion thereof.

Adapter: As used herein, the term "adapter" refers to an oligonucleotide or nucleic acid fragment or segment (preferably DNA) which comprises one or more recombination sites (or portions of such recombination sites) which in accordance with the invention can be added to a circular or linear Insert Donor molecule as well as other nucleic acid molecules described herein. When using portions of recombination sites, the missing portion may be provided by the Insert Donor molecule. Such adapters may be added at any location within a circular or linear molecule, although the adapters are preferably added at or near one or both termini of a linear molecule. Preferably, adapters are positioned to be located on both sides (flanking) a particular nucleic acid molecule of interest. In accordance with the invention, adapters may be added to nucleic acid molecules of interest by standard recombinant techniques (e.g., restriction digest and ligation). For example, adapters may be added to a circular molecule by first digesting the molecule with an appropriate restriction enzyme, adding the adapter at the cleavage site and reforming the circular molecule which contains the adapter(s) at the site of cleavage. In other aspects, adapters may be added by homologous recombination, by integration of RNA molecules, and the like. Alternatively, adapters may be ligated directly to one or more and preferably both termini of a linear molecule thereby resulting in linear molecule(s) having adapters at one or both termini. In one aspect of the invention, adapters may be added to a population of linear molecules, (e.g., a cDNA library or genomic DNA which has been cleaved or digested) to form a population of linear molecules containing adapters at one and preferably both termini of all or substantial portion of said population.

Adapter-Primer: As used herein, the phrase "adapter-primer" refers to a primer molecule which comprises one or more recombination sites (or portions of such recombination sites) which in accordance with the invention can be added to a circular or linear nucleic acid molecule described herein. When using portions of recombination sites, the missing portion may be provided by a nucleic acid molecule (e.g., an adapter) of the invention. Such adapter-primers may be added at any location within a circular or linear molecule, although the adapter-primers are preferably added at or near one or both termini of a linear molecule. Examples of such adapter-primers and the use thereof in accordance with the methods of the invention are shown in Example 8 herein. Such adapter-primers may be used to add one or more recombination sites or portions thereof to circular or linear nucleic acid molecules in a variety of contexts and by a variety of techniques, including but not limited to amplification (e.g., PCR), ligation (e.g., enzymatic or chemical/synthetic ligation), recombination (e.g., homologous or non-homologous (illegitimate) recombination) and the like.

Template: As used herein, the term "template" refers to a double stranded or single stranded nucleic acid molecule which is to be amplified, synthesized or sequenced. In the case of a double-stranded DNA molecule, denaturation of its strands to form a first and a second strand is preferably performed before these molecules may be amplified, synthesized or sequenced, or the double stranded molecule may be used directly as a template. For single stranded templates, a primer complementary to at least a portion of the template hybridizes under appropriate conditions and one or more polypeptides having polymerase activity (e.g., two, three, four, five, or seven DNA polymerases and/or reverse transcriptases) may then synthesize a molecule complementary to all or a portion of the template. Alternatively, for double stranded templates, one or more transcriptional regulatory sequences (e.g., two, three, four, five, seven or more promoters) may be used in combination with one or more polymerases to make nucleic acid molecules complementary to all or a portion of the template. The newly synthesized molecule, according to the invention, may be of equal or shorter length compared to the original template. Mismatch incorporation or strand slippage during the synthesis or extension of the newly synthesized molecule may result in one or a number of mismatched base pairs. Thus, the synthesized molecule need not be exactly complementary to the template. Additionally, a population of nucleic acid templates may be used during synthesis or amplification to produce a population of nucleic acid molecules typically representative of the original template population.

Incorporating: As used herein, the term "incorporating" means becoming a part of a nucleic acid (e.g., DNA) molecule or primer.

Library: As used herein, the term "library" refers to a collection of nucleic acid molecules (circular or linear). In one embodiment, a library may comprise a plurality of nucleic acid molecules (e.g., two, three, four, five, seven, ten, twelve, fifteen, twenty, thirty, fifty, one hundred, two hundred, five hundred one thousand, five thousand, or more), which may or may not be from a common source organism, organ, tissue, or cell. In another embodiment, a library is representative of all or a portion or a significant portion of the nucleic acid content of an organism (a "genomic" library), or a set of nucleic acid molecules representative of all or a portion or a significant portion of the expressed nucleic acid molecules (a cDNA library or segments derived therefrom) in a cell, tissue, organ or organism. A library may also comprise nucleic acid molecules having random sequences made by de novo synthesis, mutagenesis of one or more nucleic acid molecules, and the like. Such libraries may or may not be contained in one or more vectors (e.g., two, three, four, five, seven, ten, twelve, fifteen, twenty, thirty, fifty, etc.).

Amplification: As used herein, the term "amplification" refers to any in vitro method for increasing the number of copies of a nucleic acid molecule with the use of one or more polypeptides having polymerase activity (e.g., one, two, three, four or more nucleic acid polymerases or reverse transcriptases). Nucleic acid amplification results in the incorporation of nucleotides into a DNA and/or RNA molecule or primer thereby forming a new nucleic acid molecule complementary to a template. The formed nucleic acid molecule and its template can be used as templates to synthesize additional nucleic acid molecules. As used herein, one amplification reaction may consist of many rounds of nucleic acid replication. DNA amplification reactions include, for example, polymerase chain reaction (PCR). One PCR reaction may consist of 5 to 100 cycles of denaturation and synthesis of a DNA molecule.

Nucleotide: As used herein, the term "nucleotide" refers to a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triplhosphates such as dATP, dCTP, dITP, dUTP, dGTP, dTTP, or derivatives thereof. Such derivatives include, for example, [$\alpha$S]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Nucleic Acid Molecule: As used herein, the phrase "nucleic acid molecule" refers to a sequence of contiguous nucleotides (riboNTPs, dNTPs or ddNTPs, or combinations thereof) of any length which may encode a full-length polypeptide or a fragment of any length thereof, or which may be non-coding. As used herein, the terms "nucleic acid molecule" and "polynucleotide" may be used interchangeably and include both RNA and DNA.

Oligonucleotide: As used herein, the term "oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Polypeptide: As used herein, the term "polypeptide" refers to a sequence of contiguous amino acids, of any length. The terms "peptide," "oligopeptide," or "protein" may be used interchangeably herein with the term "polypeptide."

Hybridization: As used herein, the terms "hybridization" and "hybridizing" refer to base pairing of two complementary single-stranded nucleic acid molecules (RNA and/or DNA) to give a double stranded molecule. As used herein, two nucleic acid molecules may hybridize, although the base pairing is not completely complementary. Accordingly, mismatched bases do not prevent hybridization of two nucleic acid molecules provided that appropriate conditions, well known in the art, are used. In some aspects, hybridization is said to be under "stringent conditions." By "stringent conditions," as the phrase is used herein, is meant overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1 ×SSC at about 65° C.

Other terms used in the fields of recombinant nucleic acid technology and molecular and cell biology as used herein will be generally understood by one of ordinary skill in the applicable arts.

Overview

The present invention relates to methods, compositions and kits for the recombinational joining of two or more segments or nucleic acid molecules or other molecules and/or compounds (or combinations thereof). The invention also relates to attaching such linked nucleic acid molecules or other molecules and/or compounds to one or more supports or structures preferably through recombination sites or portions thereof. Thus, the invention generally relates to linking any number of nucleic acids or other molecules and/or compounds via nucleic acid linkers comprising one or more recombination sites (e.g., two, three, four, five, seven, ten, twelve, fifteen, twenty, thirty, fifty, etc.) or portions thereof.

The linked products produced by the invention may comprise any number of the same or different nucleic acids or other molecules and/or compounds, depending on the starting materials. Such starting materials include, but are not limited to, any nucleic acids (or derivatives thereof such as peptide nucleic acids (PNAs)), chemical compounds, detectably labeled molecules (such as fluorescent molecules and chemiluminescent molecules), drugs, peptides or proteins, lipids, carbohydrates and other molecules and/or compounds comprising one or more recombination sites or portions thereof. Through recombination of such recombination sites according to the invention, any number or combination of such starting molecules and/or compounds can be linked to make linked products of the invention. In addition, deletion or replacement of certain portions or components of the linked products of the invention can be accomplished by recombination.

In some embodiments, the joined segments may be inserted into a different nucleic acid molecule such as a vector, preferably by recombinational cloning methods but also by homologous recombination. Thus, in some embodiments, the present invention relates to the construction of nucleic acid molecules (RNA or DNA) by combining two or more segments of nucleic acid (e.g., two, three, four, five, seven, ten, twelve, fifteen, twenty, thirty, fifty, etc.) by a recombination reaction and inserting the joined two or more segments into a vector by recombinational cloning.

In embodiments where the joined nucleic acid molecules are to be further combined with an additional nucleic acid molecule by a recombination reaction, the timing of the two recombination events, i.e., the joining of the segments and the insertion of the segments into a vector, is not critical. That is to say, it is not critical to the present invention, for example, whether the two or more nucleic acid segments are joined together before insertion into the vector or whether one recombination site on each segment first reacts with a recombination site on the vector and subsequently the recombination sites on the nucleic acid segments react with each other to join the segments. Moreover, the nucleic acid segments can be cloned in any one or a number of positions within the vector and do not need to be inserted adjacent to each other, although, in some embodiments, joining of two or more of such segments within the vector is preferred.

In accordance with the invention, recombinational cloning allows efficient selection and identification of molecules (particularly vectors) containing the combined nucleic acid segments. Thus, two or more nucleic acid segments of interest can be combined and, optionally, inserted into a single vector suitable for further manipulation of the combined nucleic acid molecule.

In a fundamental embodiment, at least two nucleic acid segments, each comprising at least one recombination site, are contacted with suitable recombination proteins to effect the joining of all or a portion of the two molecules, depending on the position of the recombination sites in the molecules. Each individual nucleic acid segment may comprise a variety of sequences including, but not limited to sequences suitable for use as primer sites (e.g., sequences for which a primer such as a sequencing primer or amplification primer may hybridize to initiate nucleic acid synthesis, amplification or sequencing), transcription or translation signals or regulatory sequences such as promoters and/or enhancers, ribosomal binding sites, Kozak sequences, start codons, termination signals such as stop codons, origins of replication, recombination sites (or portions thereof), selectable markers, and genes or portions of genes to create protein fusions (e.g., N-terminal or C-terminal) such as GST, GUS, GFP, YFP, CFP, maltose binding protein, 6 histidines (HIS6), epitopes, haptens and the like and combinations thereof. The vectors used for cloning such segments may also comprise these functional sequences (e.g., promoters, primer sites, etc.). After combination of the segments comprising such sequences and optimally the cloning of the sequences into one or more vectors (e.g., two, three, four, five, seven, ten, twelve, fifteen, etc.), the molecules may be manipulated in a variety of ways, including sequencing or amplification of the target nucleic acid molecule (i.e., by using at least one of the primer sites introduced by the integration sequence), mutation of the target nucleic acid molecule (i.e., by insertion, deletion or substitution in or on the target nucleic acid molecule), insertion into another molecule by homologous recombination, transcription of the target nucleic acid molecule, and protein expression from the target nucleic acid molecule or portions thereof (i.e., by expression of translation and/or transcription signals contained by the segments and/or vectors).

The present invention also relates to the generation of combinatorial libraries using the recombinational cloning methods disclosed. Thus, one or more of the nucleic acid segments joined may comprise a nucleic acid library. Such a library may comprise, for example, nucleic acid molecules corresponding to permutations of a sequence coding for a peptide, polypeptide or protein sequence. The permutations can be joined to another nucleic acid segment consisting of a single sequence or, alternatively, the second nucleic acid segment may also be a library corresponding to permutation of another peptide, polypeptide or protein sequence such that joining of the two segments may produce a library representing all possible combinations of all the permutations of the two peptide, polypeptide or proteins sequences. These nucleic acid segments may be contiguous or non-contiguous. Numerous examples of the use of combinatorial libraries are known in the art. (See, e.g., Waterhouse, et al., *Nucleic Acids Res.*, 1993, Vol. 21, No. 9, 2265–2266, Tsurushita, et al., *Gene*, 1996, Vol.172 No. 1, 59–63, Persson, *Int. Rev. Immunol.* 1993 10:2–3 153–63, Chanock, et al., *Infect Agents Dis* 1993 Jun. 2:3 118–31, Burioni, et al., *Res Virol* 1997 Mar–Apr 148:2 161–4, Leung, *Thromb. Haemost.* 1995 Jul. 74:1 373–6, Sandhu, *Crit. Rev. Biotechnol.* 1992, 12:5–6 437–62 and U.S. Pat. Nos. 5,733,743, 5,871,907 and 5,858,657, all of which are specifically incorporated herein by reference.)

When one or more nucleic acid segments used in methods and compositions of the invention are mutated, these segments may contain either (1) a specified number of mutations or (2) an average specified number of mutations. Further, these mutations may be scored with reference to the nucleic acid segments themselves or the expression products (e.g., polypeptides of such nucleic acid segments. For example, nucleic acid molecules of a library may be mutated to produce nucleic acid molecules which are, on average, at least 50%, at least 55%, at least 60%, at least 65%, at least 70%, at least 75%, at least 80%, at least 85%, at least 90%, at least 95%, at least 96%, at least 97%, at least 98%, or at least 99% identical to corresponding nucleic acid molecules of the original library. Similarly, nucleic acid molecules of a library may be mutated to produce nucleic acid molecules which, encode polypeptides that are, on average, at least 50%, at least 55%, at least 60%, at least 65%, at least 70%, at least 75%, at least 80%, at least 85%, at least 90%, at least 95%, at least 96%, at least 97%, at least 98%, or at least 99% identical to polypeptides encoded by corresponding nucleic acid molecules of the original library.

Recombination Sites

Recombination sites for use in the invention may be any nucleic acid that can serve as a substrate in a recombination reaction. Such recombination sites may be wild-type or naturally occurring recombination sites, or modified, variant, derivative, or mutant recombination sites. Examples of recombination sites for use in the invention include, but are not limited to, phage-lambda recombination sites (such as attP, attB, attL, and attR and mutants or derivatives thereof) and recombination sites from other bacteriophage such as phi80, P22, P2, 186, P4 and P1 (including lox sites such as loxP and loxP511). Mutated att sites (e.g., attB 1-10, attP 1-10, attR 1-10 and attL1-10) are described in Example 9 below and in previous patent U.S. Appl. Ser. No. 60/136,744, filed May 28,1999, and U.S. application Ser. No. 09/517,466, filed Mar. 2, 2000, which are specifically incorporated herein by reference. Other recombination sites having unique specificity (i.e., a first site will recombine with its corresponding site and will not recombine with a second site having a different specificity) are known to those skilled in the art and may be used to practice the present invention. Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., γδ, TndX, TnpX, Tn3 resolvase, Hin, Hjc, Gin, SpCCE1, ParA, and Cin), and IS231 and other *Bacillus thuringiensis* transposable elements. Other suitable recombination systems for use in the present invention include the XerC and XerD recombinases and the psi, dif and cer recombination sites in *E. coli*. Other suitable recombination sites may be found in U.S. Pat. No. 5,851,808 issued to Elledge and Liu which is specifically incorporated herein by reference. Preferred recombination proteins and mutant, modified, variant, or derivative recombination sites for use in the invention include those described in U.S. Pat. Nos. 5,888, 732 and 6,143,557, and in U.S. application Ser. No. 09/438, 358 (filed Nov. 12, 1999), based upon U.S. provisional Appl. Ser. No. 60/108,324 (filed Nov. 13, 1998), and U.S. application Ser. No. 09/517,466 (filed Mar. 2, 2000), based upon U.S. provisional Appl. No. 60/136,744 (filed May 28, 1999), as well as those associated with the GATEWAY™ Cloning Technology available from Invitrogen Corp., Life Technologies Division (Rockville, Md.), the entire disclosures of all of which are specifically incorporated herein by reference in their entireties.

Representative examples of recombination sites which can be used in the practice of the invention include att sites referred to above. The inventors have determined that att sites which specifically recombine with other att sites can be constructed by altering nucleotides in and near the 7 base pair overlap region. Thus, recombination sites suitable for use in the methods, compositions, and vectors of the invention include, but are not limited to, those with insertions, deletions or substitutions of one, two, three, four, or more nucleotide bases within the 15 base pair core region (GCTTTTTTATAC-TAA (SEQ ID NO:37)), which is identical in all four wild-type lambda att sites, attB, attP, attL and attR (see U.S. application Ser. No. 08/663,002, filed Jun. 7, 1996 (now U.S. Pat. No. 5,888,732) and Ser. No. 09/177,387, filed Oct. 23, 1998, which describes the core region in further detail, and the disclosures of which are incorporated herein by reference in their entireties). Recombination sites suitable for use in the methods, compositions, and vectors of the invention also include those with insertions, deletions or substitutions of one, two, three, four, or more nucleotide bases within the 15 base pair core region (GCTTTTTTATACTAA (SEQ ID NO:37)) which are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

Analogously, the core regions in attB1, attP1, attL1 and attR1 are identical to one another, as are the core regions in attB2, attP2, attL2 and attR2. Nucleic acid molecules suitable for use with the invention also include those which comprising insertions, deletions or substitutions of one, two, three, four, or more nucleotides within the seven base pair overlap region (TTTATAC, which is defined by the cut sites for the integrase protein and is the region where strand exchange takes place) that occurs within this 15 base pair core region (GCTTTTTTATACTAA (SEQ ID NO:37)). Examples of such mutants, fragments, variants and derivatives include, but are not limited to, nucleic acid molecules in which (1) the thymine at position 1 of the seven bp overlap region has been deleted or substituted with a guanine, cytosine, or adenine; (2)

the thymine at position 2 of the seven bp overlap region has been deleted or substituted with a guanine, cytosine, or adenine; (3) the thymine at position 3 of the seven bp overlap region has been deleted or substituted with a guanine, cytosine, or adenine; (4) the adenine at position 4 of the seven bp overlap region has been deleted or substituted with a guanine, cytosine, or thymine; (5) the thymine at position 5 of the seven bp overlap region has been deleted or substituted with a guanine, cytosine, or adenine; (6) the adenine at position 6 of the seven bp overlap region has been deleted or substituted with a guanine, cytosine, or thymine; and (7) the cytosine at position 7 of the seven bp overlap region has been deleted or substituted with a guanine, thymine, or adenine; or any combination of one or more such deletions and/or substitutions within this seven bp overlap region. The nucleotide sequences of the above described seven base pair core region are set out below in Table 1.

As described below in Examples 9–12, altered att sites have been constructed which demonstrate that (1) substitutions made within the first three positions of the seven base pair overlap (TTTATAC) strongly affect the specificity of recombination, (2) substitutions made in the last four positions (TTTATAC) only partially alter recombination specificity, and (3) nucleotide substitutions outside of the seven bp overlap, but elsewhere within the 15 base pair core region, do not affect specificity of recombination but do influence the efficiency of recombination. Thus, nucleic acid molecules and methods of the invention include those which comprising or employ one, two, three, four, five, six, eight, ten, or more recombination sites which affect recombination specificity, particularly one or more (e.g., one, two, three, four, five, six, eight, ten, twenty, thirty, forty, fifty, etc.) different recombination sites that may correspond substantially to the seven base pair overlap within the 15 base pair core region, having one or more mutations that affect recombination specificity. Particularly preferred such molecules may comprise a consensus sequence such as NNNATAC, wherein "N" refers to any nucleotide (i.e., may be A, G, T/U or C). Preferably, if one of the first three nucleotides in the consensus sequence is a T/U, then at least one of the other two of the first three nucleotides is not a T/U.

The core sequence of each att site (attB, attP, attL and attR) can be divided into functional units consisting of integrase binding sites, integrase cleavage sites and sequences that determine specificity. As discussed below in Example 12, specificity determinants are defined by the first three positions following the integrase top strand cleavage site. These three positions are shown with underlining in the following reference sequence: CAACTTTTTTATAC AAAGTTG (SEQ ID NO:38). Modification of these three positions (64 possible combinations) which can be used to generate att sites which recombine with high specificity with other att sites having the same sequence for the first three nucleotides of the seven base pair overlap region are shown in Table 1.

TABLE 1

Modifications of the First Three Nucleotides of the att Site Seven Base Pair Overlap Region which Alter Recombination Specificity.

| AAA | CAA | GAA | TAA |
| AAC | CAC | GAC | TAC |
| AAG | CAG | GAG | TAG |
| AAT | CAT | GAT | TAT |
| ACA | CCA | GCA | TCA |
| ACC | CCC | GCC | TCC |
| ACG | CCG | GCG | TCG |

TABLE 1-continued

Modifications of the First Three Nucleotides of the att Site Seven Base Pair Overlap Region which Alter Recombination Specificity.

| ACT | CCT | GCT | TCT |
| AGA | CGA | GGA | TGA |
| AGC | CGC | GGC | TGC |
| AGG | CGG | GGG | TGG |
| AGT | CGT | GGT | TGT |
| ATA | CTA | GTA | TTA |
| ATC | CTC | GTC | TTC |
| ATG | CTG | GTG | TTG |
| ATT | CTT | GTT | TTT |

Representative examples of seven base pair att site overlap regions suitable for in methods, compositions and vectors of the invention are shown in Table 2. The invention further includes nucleic acid molecules comprising one or more (e.g., one, two, three, four, five, six, eight, ten, twenty, thirty, forty, fifty, etc.) nucleotides sequences set out in Table 2. Thus, for example, in one aspect, the invention provides nucleic acid molecules comprising the nucleotide sequence GAAATAC, GATATAC, ACAATAC, or TGCATAC. However, in certain embodiments, the invention will not include nucleic acid molecules which comprise att site core regions set out herein in FIGS. 24A–24C or in Example 9.

TABLE 2

Representative Examples of Seven Base Pair att Site Overlap Regions Suitable for with the Invention.

| AAAATAC | CAAATAC | GAAATAC | TAAATAC |
| AACATAC | CACATAC | GACATAC | TACATAC |
| AAGATAC | CAGATAC | GAGATAC | TAGATAC |
| AATATAC | CATATAC | GATATAC | TATATAC |
| ACAATAC | CCAATAC | GCAATAC | TCAATAC |
| ACCATAC | CCCATAC | GCCATAC | TCCATAC |
| ACGATAC | CCGATAC | GCGATAC | TCGATAC |
| ACTATAC | CCTATAC | GCTATAC | TCTATAC |
| AGAATAC | CGAATAC | GGAATAC | TGAATAC |
| AGCATAC | CGCATAC | GGCATAC | TGCATAC |
| AGGATAC | CGGATAC | GGGATAC | TGGATAC |
| AGTATAC | CGTATAC | GGTATAC | TGTATAC |
| ATAATAC | CTAATAC | GTAATAC | TTAATAC |
| ATCATAC | CTCATAC | GTCATAC | TTCATAC |
| ATGATAC | CTGATAC | GTGATAC | TTGATAC |
| ATTATAC | CTTATAC | GTTATAC | TTTATAC |

As noted above, alterations of nucleotides located 3' to the three base pair region discussed above can also affect recombination specificity. For example, alterations within the last four positions of the seven base pair overlap can also affect recombination specificity.

The invention thus provides recombination sites which recombine with a cognate partner, as well as molecules which contain these recombination sites and methods for generating, identifying, and using these sites. Methods which can be used to identify such sites are set out below in Example 12. Examples of such recombinations sites include att sites which contain 7 base pairs overlap regions which associate and recombine with cognate partners. The nucleotide sequences of specific examples of such 7 base pair overlap regions are set out above in Table 2.

Further embodiments of the invention include isolated nucleic acid molecules comprising a nucleotide sequence at least 50% identical, at least 60% identical, at least 70% identical, at least 75% identical, at least 80% identical, at least 85% identical, at least 90% identical, or at least 95% identical to the nucleotide sequences of the seven bp overlap regions set out above in Table 2 or the 15 base pair core region shown in SEQ ID NO:37, as well as a nucleotide sequence complementary to any of these nucleotide sequences or fragments, variants, mutants, and derivatives thereof. Additional embodiments of the invention include compositions and vectors which contain these nucleic acid molecules, as well as methods for using these nucleic acid molecules.

By a polynucleotide having a nucleotide sequence at least, for example, 95% "identical" to a reference nucleotide sequence encoding a particular recombination site or portion thereof is intended that the nucleotide sequence of the polynucleotide is identical to the reference sequence except that the polynucleotide sequence may include up to five point mutations (e.g., insertions, substitutions, or deletions) per each 100 nucleotides of the reference nucleotide sequence encoding the recombination site. For example, to obtain a polynucleotide having a nucleotide sequence at least 95% identical to a reference attB1 nucleotide sequence (SEQ ID NO:5), up to 5% of the nucleotides in the attB1 reference sequence may be deleted or substituted with another nucleotide, or a number of nucleotides up to 5% of the total nucleotides in the attB1 reference sequence may be inserted into the attB1 reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 50%, 60%, 70%, 75%, 80%, 85%, 90%, 95%, 96%, 97%, 98% or 99% identical to, for instance, a given recombination site nucleotide sequence or portion thereof can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments. Alternatively, such determinations may be accomplished using the BESTFIT program (Wisconsin Sequence Analysis Package, Genetics Computer Group, University Research Park, 575 Science Drive, Madison, Wis. 53711), which employs a local homology algorithm (Smith and Waterman, *Advances in Applied Mathematics* 2: 482–489 (1981)) to find the best segment of homology between two sequences. When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

As noted above, the invention further provides, in one aspect, methods for constructing and/or identifying recombination sites suitable for use with nucleic acid molecules of the invention, as well as recombination sites constructed and/or identified by these methods. In brief, the invention provides methods for constructing and/or identifying recombination sites which are capable of recombining with other recombination sites. For example, the invention provides methods for constructing recombination sites and identifying whether these recombination sites recombine with other recombination sites. Recombination sites which are screened for recombination activity and specificity can be constructed by any number of means, including site-directed mutagenesis and random nucleic acid synthesis.

The invention further provides "single use" recombination sites which undergo recombination one time and then either undergo recombination with low frequency (e.g., have at least five fold, at least ten fold, at least fifty fold, at least one hundred fold, or at least one thousand fold lower recombination activity in subsequent recombination reactions) or are essentially incapable of undergo recombination. The invention also provides methods for making and using nucleic acid molecules which contain such single use recombination sites and molecules which contain these sites. Examples of methods which can be used to generate and identify such single use recombination sites are set out below.

The att system core integrase binding site comprises an interrupted seven base pair inverted repeat having the following nucleotide sequence:

```
------>......<------
caactttnnnnnnnaaagttg  (SEQ ID NO:39),
``` as well as variations thereof which can comprise either perfect or imperfect repeats.

The repeat elements can be subdivided into two distal and/or proximal "domains" composed of caac/gttg segments (underlined), which are distal to the central undefined sequence (the nucleotides of which are represented by the letter "n"), and ttt/aaa segments, which are proximal to the central undefined sequence.

Alterations in the sequence composition of the distal and/or proximal domains on one or both sides of the central undefined region can affect the outcome of a recombination reaction. The scope and scale of the effect is a function of the specific alterations made, as well as the particular recombinational event (e.g., LR vs. BP reactions).

For example, it is believed that an attB site altered to have the following nucleotide sequence:

```
------>......<------
caactttnnnnnnnaaacaag  (SEQ ID NO:40),
``` will functionally interact with a cognate attP and generate attL and attR. However, whichever of the latter two recombination sites acquires the segment containing "caag" (located on the left side of the sequence shown above) will be rendered non-functional to subsequent recombination events. The above is only one of many possible alterations in the core integrase binding sequence which can render att sites non-functional after engaging in a single recombination event. Thus, single use recombination sites may be prepared by altering nucleotides in the seven base pair inverted repeat regions which abut seven base pair overlap regions of att sites. This region is represented schematically as:

CAAC TTT [Seven Base Pair Overlap Region] AAA GTTG.

In generating single use recombination sites, one, two, three, four or more of nucleotides of the sequences CAACTTT or AAAGTTG (i.e., the seven base pair inverted repeat regions) may be substituted with other nucleotides or deleted altogether. These seven base pair inverted repeat regions represent complementary sequences with respect to each other. Thus, alterations may be made in either seven base pair inverted repeat region in order to generate single use recombination sites. Further, when DNA is double stranded and one seven base pair inverted repeat region is present, the other seven base pair inverted repeat region will also be present on the other strand.

Using the sequence CAACTTT for illustration, examples of seven base pair inverted repeat regions which can form single use recombination sites include, but are not limited to, nucleic acid molecules in which (1) the cytosine at position 1 of the seven base pair inverted repeat region has been deleted or substituted with a guanine, adenine, or thymine; (2) the adenine at position 2 of the seven base pair inverted repeat region has been deleted or substituted with a guanine, cytosine, or thymine; (3) the adenine at position 3 of the seven base pair inverted repeat region has been deleted or substituted with a guanine, cytosine, or thymine; (4) the cytosine at position 4 of the seven base pair inverted repeat region has been deleted or substituted with a guanine, adenine, or thymine; (5) the thymine at position 5 of the seven base pair inverted repeat region has been deleted or substituted with a guanine, cytosine, or adenine; (6) the thymine at position 6 of the seven base pair inverted repeat region has been deleted or substituted with a guanine, cytosine, or adenine; and (7) the thymine at position 7 of the seven base pair inverted repeat region has been deleted or substituted with a guanine, cytosine, or adenine; or any combination of one, two, three, four, or more such deletions and/or substitutions within this seven base pair region. Representative examples of nucleotide sequences of the above described seven base pair inverted repeat regions are set out below in Table 3.

TABLE 3

| | | | |
|---|---|---|---|
| aagaaaa | aagagcg | aagagaa | aagatat |
| ccgccac | ccgcctc | ccgcaca | ccgcttt |
| ggtggga | ggtgctc | ggtgata | ggtgtat |
| ttcttg | ttctctc | ttctgaa | ttctttt |
| aatacac | aatagcg | aataaca | aatatat |
| cctcgga | cctccg | cctcaca | cctcttt |
| ggcgaaa | ggcgccg | ggcggaa | ggcgtat |
| ttgtcac | ttgtgcg | ttgtaca | ttgtttt |
| acaagga | acaaccg | acaaata | acaattt |
| caccttg | caccaga | caccgaa | cacctat |
| gaggcac | gagggcg | gaggaca | gaggttt |
| tattgga | tattaga | tattaca | tatttat |
| agaaaaa | agaaaga | agaagaa | agaattt |
| cgcccac | cgccctc | cgccaca | cgccttt |
| gcgggga | gcgggcg | gcggata | gcggtat |
| tcttttg | tcttccg | tcttgaa | tcttttt |
| ataacac | ataactc | ataaaca | ataattt |
| ctccaaa | ctccgcg | ctccata | ctcctat |
| gtgggga | gtggccg | gtgggaa | gtggtat |
| tgttttg | tgttctc | tgttaca | tgttttt |

Representative examples of nucleotide sequences which form single use recombination sites may also be prepared by combining a nucleotide sequence set out in Table 4, Section 1, with a nucleotide sequence set out in Table 4, Section 2. Single use recombination sites may also be prepared by the insertion of one or more (e.g., one, two, three, four, five six, seven, etc.) nucleotides internally within these regions.

TABLE 4

| Section 1 (CAAG) | | | | Section 2 (TTT) | | |
|---|---|---|---|---|---|---|
| aaaa | cccc | gggg | tttt | aaa | cca | ttc |
| aaac | ccca | ggga | ttta | aac | cac | ttg |
| aaag | ccct | gggc | tttc | aag | cgc | tat |
| aaat | cccg | gggt | tttg | aat | ctc | tct |
| aaca | ccac | ggag | ttat | aca | ggg | tgt |
| aaga | ccgc | ggtg | ttct | aga | gga | |
| aata | cctc | ggcg | ttgt | ata | ggc | |
| acaa | cacc | gagg | tatt | caa | ggt | |
| agaa | cgcc | gcgg | tctt | gaa | gag | |
| ataa | ctcc | gtgg | tgtt | taa | gcg | |
| caaa | accc | aggg | attt | ccc | gtg | |

TABLE 4-continued

| Section 1 (CAAG) | | | | Section 2 (TTT) | | |
|---|---|---|---|---|---|---|
| gaaa | gccc | CGG | cttt | ccg | ttt | |
| taaa | tccc | tggg | gttt | cct | tta | |

In most instances where one seeks to prevent recombination events with respect to a particular nucleic acid segment, the altered sequence will be located proximally to the nucleic acid segment. Using the following schematic for illustration: =5' Nucleic Acid Segment 3'=caac ttt [Seven Base Pair Overlap Region] AAA GTTG, the lower case nucleotide sequence which represent a seven base pair inverted repeat region (i.e., caac ttt) will generally have a sequence altered by insertion, deletion, and/or substitution to form a single use recombination site when one seeks to prevent recombination at the 3' end (i.e., proximal end with respect to the nucleic acid segment) of the nucleic acid segment shown. Thus, a single recombination reaction can be used, for example, to integrate the nucleic acid segments into another nucleic acid molecule, then the recombination site becomes effectively non-functional, preventing the site from engaging in further recombination reactions. Similarly, single use recombination sites can be position at both ends of a nucleic acid segment so that the nucleic acid segment can be integrated into another nucleic acid molecule, or circularized, and will remain integrated, or circularized even in the presence of recombinases.

A number of methods may be used to screen potential single use recombination sites for functional activity (e.g., undergo one recombination event followed by the failure to undergo subsequent recombination events). For example, with respect to the screening of recombination sites to identify those which become non-functional after a single recombination event, a first recombination reaction may be performed to generate a plasmid in which a negative selection marker is linked to one or more potentially defective recombination sites. The plasmid may then be reacted with another nucleic acid molecule which comprises a positive selection marker similarly linked to recombination sites. Thus, this selection system is designed such that molecules which recombine are susceptible to negative selection and molecules which do not recombine may be selected fro by positive selection. Using such a system, one may then directly select for desired single use core site mutants.

As one skilled in the art would recognize, any number of screening assays may be designed which achieve the same results as those described above. In many instances, these assays will be designed so that an initial recombination event takes place and then recombination sites which are unable to engage in subsequent recombination events are identified or molecules which contain such recombination sites are selected for. A related screening assay would result in selection against nucleic acid molecule which have undergone a second recombination event. Further, as noted above, screening assays can be designed where there is selection against molecules which have engaged in subsequent recombination events and selection for those which have not engaged in subsequent recombination events.

Single use recombination sites are especially useful for either decreasing the frequency of or preventing recombination when either large number of nucleic acid segments are attached to each other or multiple recombination reactions are performed. Thus, the invention further includes nucleic acid molecules which contain single use recombination sites, as well as methods for performing recombination using these sites.

Construction and Uses Nucleic Acid Molecules of the Invention

As discussed below in more detail, in one aspect, the invention provides a modular system for constructing nucleic acid molecules having particular functions or activities. The invention further provides methods for combining populations of nucleic acid molecules with one or more known or unknown target sequences of interest (e.g., two, three, four, five seven, ten, twelve, fifteen, twenty, thirty, fifty, etc.) or with other populations of nucleic acid molecules (known or unknown), thereby creating populations of combinatorial molecules (e.g., combinatorial libraries) from which unique and/or novel molecules (e.g., hybrid molecules) and proteins or peptides encoded by these molecules may be obtained and further analyzed.

Figure 16:
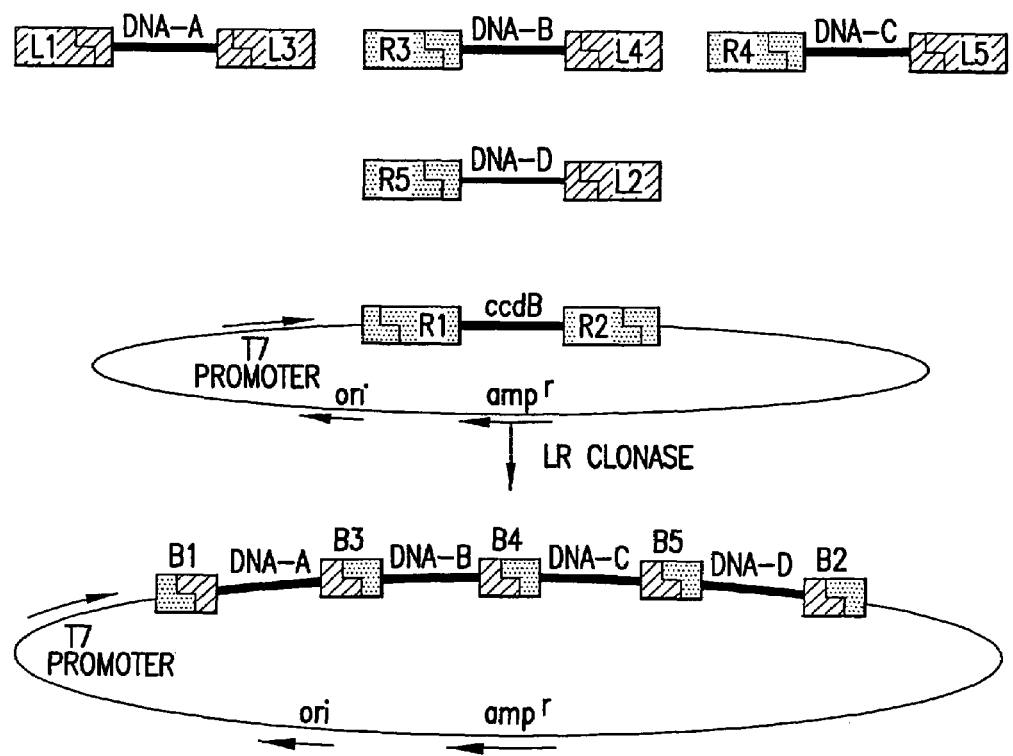
FIG. 16 is a schematic representation of the single step insertion of four separate DNA segments into a Destination Vector using LR reactions. In particular, a first DNA segment having an attL1 site at the 5' end and an attL3 site at the 3' end is linked to a second DNA segment having an attR3 site at the 5' end and an attL4 site at the 3' end. The second DNA segment is then linked to a third DNA segment having an attR4 site at the 5' end and an attL5 site at the 3' end. The third DNA segment is then linked to a fourth DNA segment having an attR5 site at the 5' end and an attL2 site at the 3' end. Thus, upon reaction with LR CLONASE™, the first, second, third, and fourth DNA segments are inserted into a Destination Vector which contains a ccdB gene flanked by attR1 and attR2 sites. The inserted DNA segments are separated from each other and vector sequences by attB1, attB3, attB4, attB5, and attB2 sites.

The present invention also includes methods for preparing vectors containing more than one nucleic acid insert (e.g. two, three, four, five, six, eight, ten, twelve, fifteen, twenty, thirty, forty, fifty, etc. inserts). In one general embodiment of the invention, vectors of the invention are prepared as follows. Nucleic acid molecules which are to ultimately be inserted into the Destination Vector are obtained (e.g., purchased, prepared by PCR or by the preparation of cDNA using reverse transcriptase). Suitable recombination sites are either incorporated into the 5' and 3' ends of the nucleic acid molecules during synthesis or added later. When one seeks to prepare a vector containing multiple nucleic acid inserts, these inserts can be inserted into a vector in either one reaction mixture or a series of reaction mixtures. For example, as shown in FIG. 16, multiple nucleic acid segments can be linked end to end and inserted into a vector using reactions performed, for example, in a single reaction mixture. The nucleic acid segments in this reaction mixture can be designed so that recombination sites on their 5' and 3' ends result in their insertion into a Destination Vector in a specific order and a specific 5' to 3' orientation. Alternatively, nucleic acid segments can be designed so that they are inserted into a Destination Vector without regard to order, orientation (i.e., 5' to 3' orientation), the number of inserts, and/or the number of duplicate inserts.

Further, in some instances, one or more of the nucleic acid segments will have a recombination site on only one end. Also, if desired, this end, or these ends, may be linked to other nucleic acid segments by the use of, for example, ligases or topoisomerases. As an example, a linear nucleic acid molecule with an attR1 site on its 5' terminus can be recombined with a Destination Vector containing a ccdb gene flanked by an attL1 site and an attL2 site. Before, during, or after an LR reaction, the Destination Vector can be cut, for example, by a restriction enzyme on the side of the attR2 site which is opposite to the ccdB gene. Thus, the Destination Vector will be linear after being cut and undergoing recombination. Further, the attR1 site of the nucleic acid molecule will undergo recombination with the attL1 site of the Destination Vector to produce a linear vector which contains the nucleic acid molecule. The resulting linear product can then be circularized using an enzyme such as a ligase or topoisomerases.

Figure 17A:
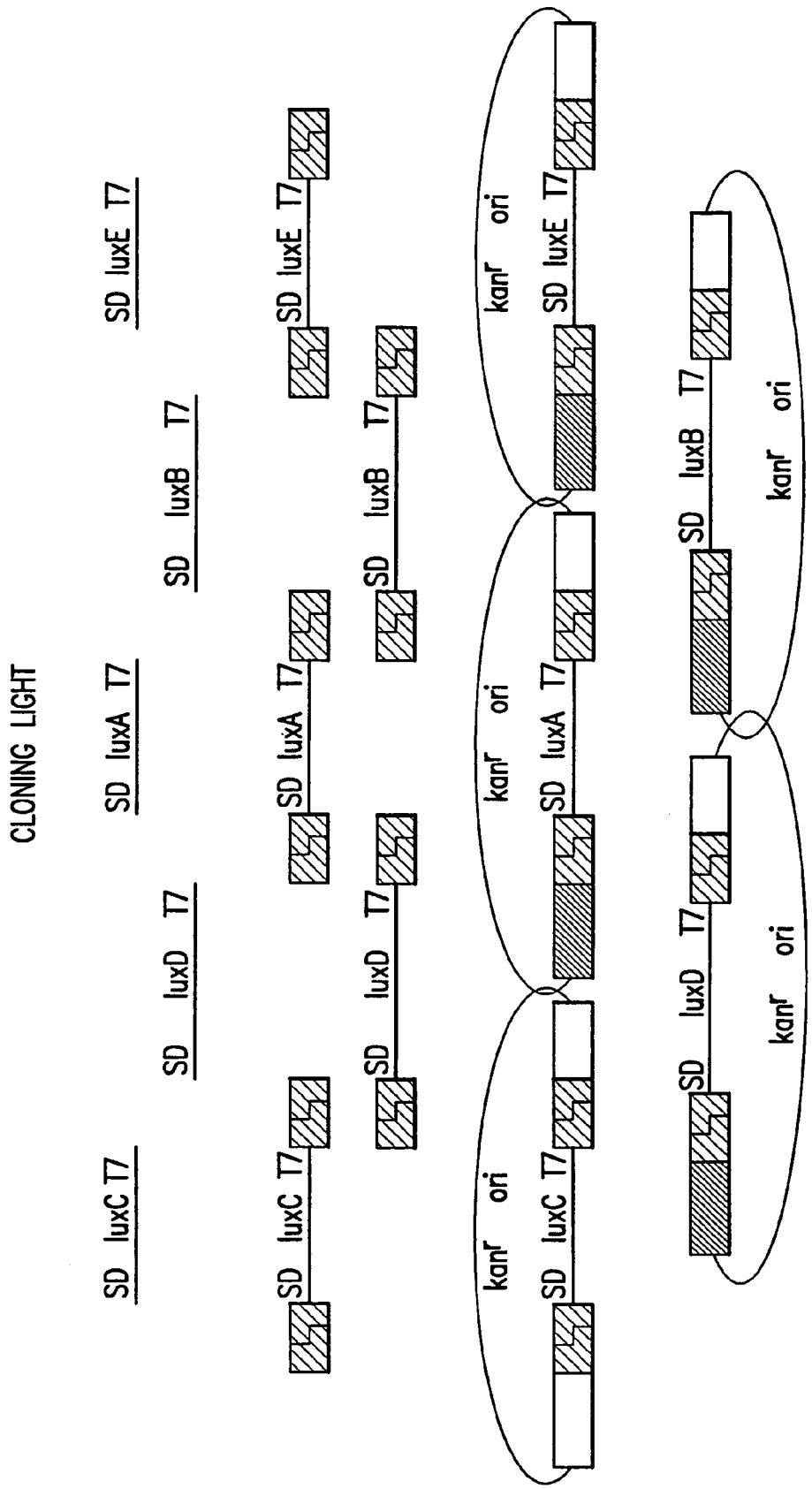
FIGS. 17A and 17B show schematic representations of the construction of a lux operon prepared according to the methods set out below in Example 18. In accordance with the invention, one or more genes of the operon can be replaced or deleted through recombination to construct one or more modified operons and then tested for activity and/or effect on host cells. Alternatively, other genes (including variants and mutants) can be used in the initial construction of the operon to replace one or more genes of interest, thereby producing one or more modified operons.
Figure 17B:
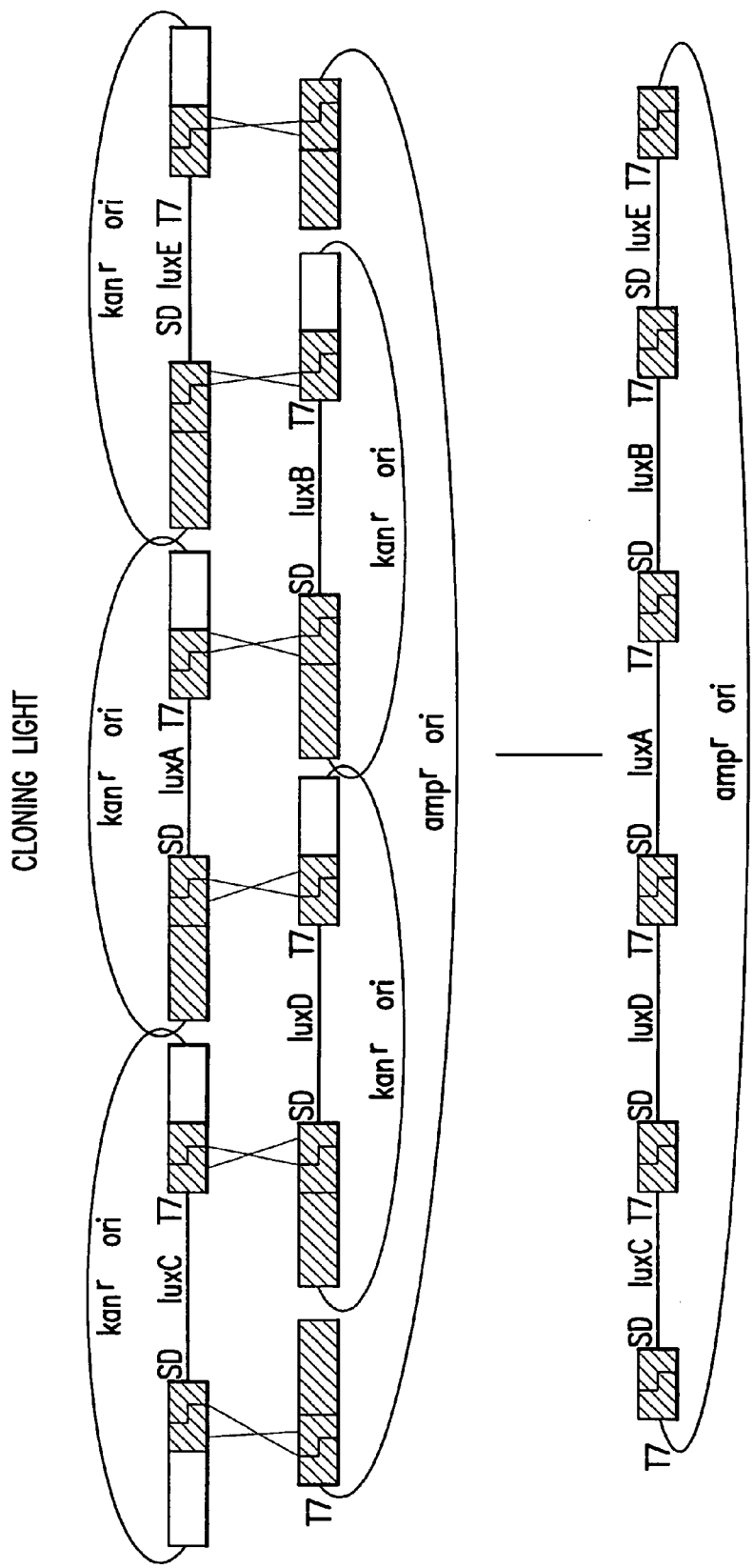

Using the embodiment shown in FIG. 16 to exemplify another aspect of the invention, a first DNA segment having an attL1 site at the 5' end and an attL3 site at the 3' end is attached by recombination to a second DNA segment having an attR3 site at the 5' end and an attL4 site at the 3' end. A third DNA segment having an attR4 site at the 5' end and an attL5 site at the 3' end is attached by recombination with the attL4 site on the 3' end of the second DNA segment. A fourth DNA segment having an attR5 site at the 5' end and an attL2 site at the 3' end is attached by recombination with the attL5 site on the 3' end of the third DNA segment. The Destination Vector contains an attR1 site and an attR2 site which flanks a ccdb gene. Thus, upon reaction with LR CLONASE™, the first, second, third, and fourth DNA segments are inserted into the insertion vector but are flanked or separated by attB1, attB3, attB4, attB5, and attB2 sites. A similar process involving assembly of the lux operon is shown in FIGS. 17A-17B and described below in Example 18.

As one skilled in the art would recognize, multiple variations of the process shown in FIG. 16 are possible. For example, various combinations of attB, attP, attL, and attR sites, as well as other recombination sites, can be used. Similarly, various selection markers, origins of replication, promoters, and other genetic elements can be used. Further, regions which allow for integration into eukaryotic chromosomes (e.g., transposable elements) can be added to these vectors.

Figure 18:
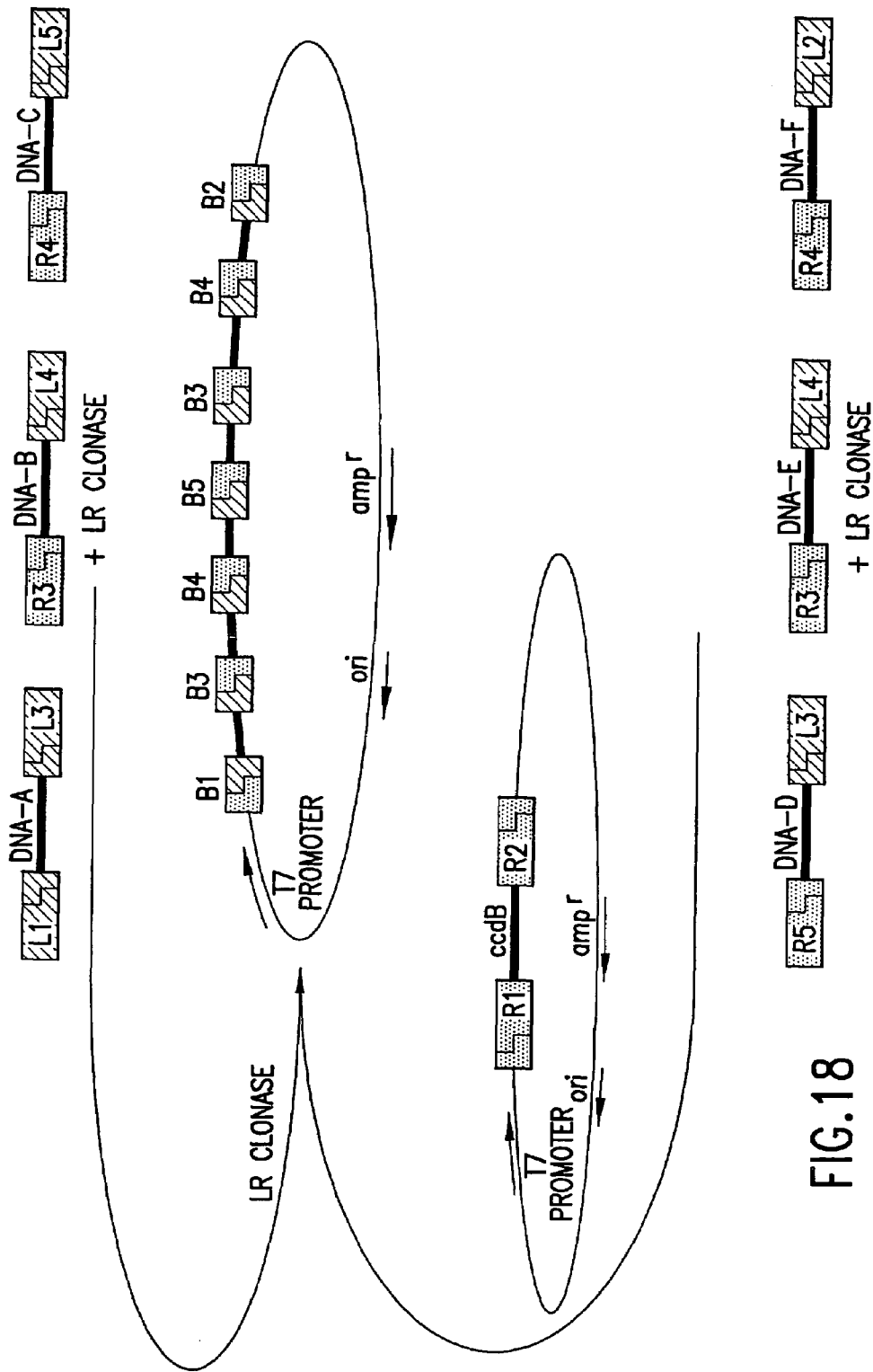
FIG. 18 is a schematic representation of the insertion of six separate DNA segments into a vector using a two step, one vector process. In particular, a first DNA segment (DNA-A) having an attL1 site at the 5' end and an attL3 site at the 3' end is linked to a second DNA segment (DNA-B) having an attR3 site at the 5' end and an attL4 site at the 3' end. The second DNA segment is then linked to a third DNA segment (DNA-C) having an attR4 site at the 5' end and an attL5 site at the 3' end. A fourth DNA segment (DNA-D) having an attR1 site at the 5' end and an attL3 site at the 3' end is linked to a fifth DNA segment (DNA-E) having an attR3 site at the 5' end and an attL4 site at the 3' end. The fifth DNA segment is then linked to a sixth DNA segment (DNA-F) having an attR4 site at the 5' end and an attL2 site at the 3' end. The two resulting molecules (i.e., DNA-A-DNA-B-DNA-C and DNA-D-DNA-E-DNA-F) are then inserted into the insertion vector. Each of the above reactions is catalyzed by LR CLONASE™. An LR reaction is also used to insert the joined DNA segments into a Destination Vector which contains a ccdb gene flanked by attR1 and attR2 sites. The inserted DNA segments are separated from each other and the vector by attB1, attB3, attB4, attB5, and attB2 sites. As described in FIG. 6, for example, the assembled segments may be inserted into contiguous or non-contiguous sites.

One example of a multi-reaction process for inserting multiple DNA segments into a vector is shown in FIG. 18. In this exemplary embodiment, three DNA segments recombine with each other in two separate reaction mixtures. The products generated in these mixtures are then mixed together under conditions which facilitate both recombination between the products of the two reaction mixtures and insertion of the linked product into a vector (e.g., a Destination Vector). This embodiment has the advantages that the (1) DNA segments can be inserted directly into a Destination Vector without prior insertion into another vector, and (2) the same att sites, as well as other recombination sites, can be used to prepare each of the linked DNA segments for insertion into the vector.

As one skilled in the art would recognize, multiple variations of the processes described herein are possible. For example, single use recombination sites can be used to connect individual nucleic acid segments. Thus, eliminating or reducing potential problems associated with arrays of nucleic acid segments engaging in undesired recombination reactions. Further, the processes described above can be used to connect large numbers of individual nucleic acid molecules together in a varying ways. For example, nucleic acid segments can be connected randomly, or in a specified order, both with or without regard to 5' to 3' orientation of the segments.

Further, identical copies of one or more nucleic acid segments can be incorporated into another nucleic acid molecule. Thus, the invention also provides nucleic acid molecules which contain multiple copies of a single nucleic acid segment. Further, the selection of recombination sites positioned at the 5' and 3' ends of these segments can be used to determine the exact number of identical nucleic acid segments which are connected and then inserted, for example, into a vector. Such vectors may then be inserted into a host cell where they can, for example, replicate autonomously or integrate into one or more nucleic acid molecules which normally reside in the host cell (e.g., integrate by site-specific recombination or homologous recombination).

Nucleic acid molecules which contain multiple copies of a nucleic acid segment may be used, for example, to amplify the copy number of a particular gene. Thus, the invention also provides methods for gene amplification, nucleic acid molecules which contain multiple copies of a nucleic acid segment, and host cells which contain nucleic acid molecules of the invention.

As another example, two different nucleic acid segments can be connected using processes of the invention. Recombination sites can be positioned on these segments, for example, such that the segments alternate upon attachment (e.g., Segment A+Segment B+Segment A+Segment B, etc.). A nucleic acid molecule having such a structure will be especially useful for when one seeks to use increased copy number of a nucleic acid to increase the amount of expression product produced. In such an instance, "Segment A" can be, for example, a nucleic acid molecule comprising an inducible promoter and "Segment B " can be, for example, a nucleic acid molecule comprising an ORF. Thus, cells can be prepared which contain the above construct and do not express substantial quantities of the product of Segment B in the absence of the inducing signal but produce high levels of this product upon induction. Such a system will be especially useful when the Segment B expression product is toxic to cells. Thus, the methods set out above can be used for the construction and maintenance of cells which contain Segment B in the absence of deleterious effects resulting from the Segment B expression product. Further, induction of expression of the ORF residing in Segment B can then be used, for example, to transiently produce high levels of the Segment B expression product.

Figure 19:
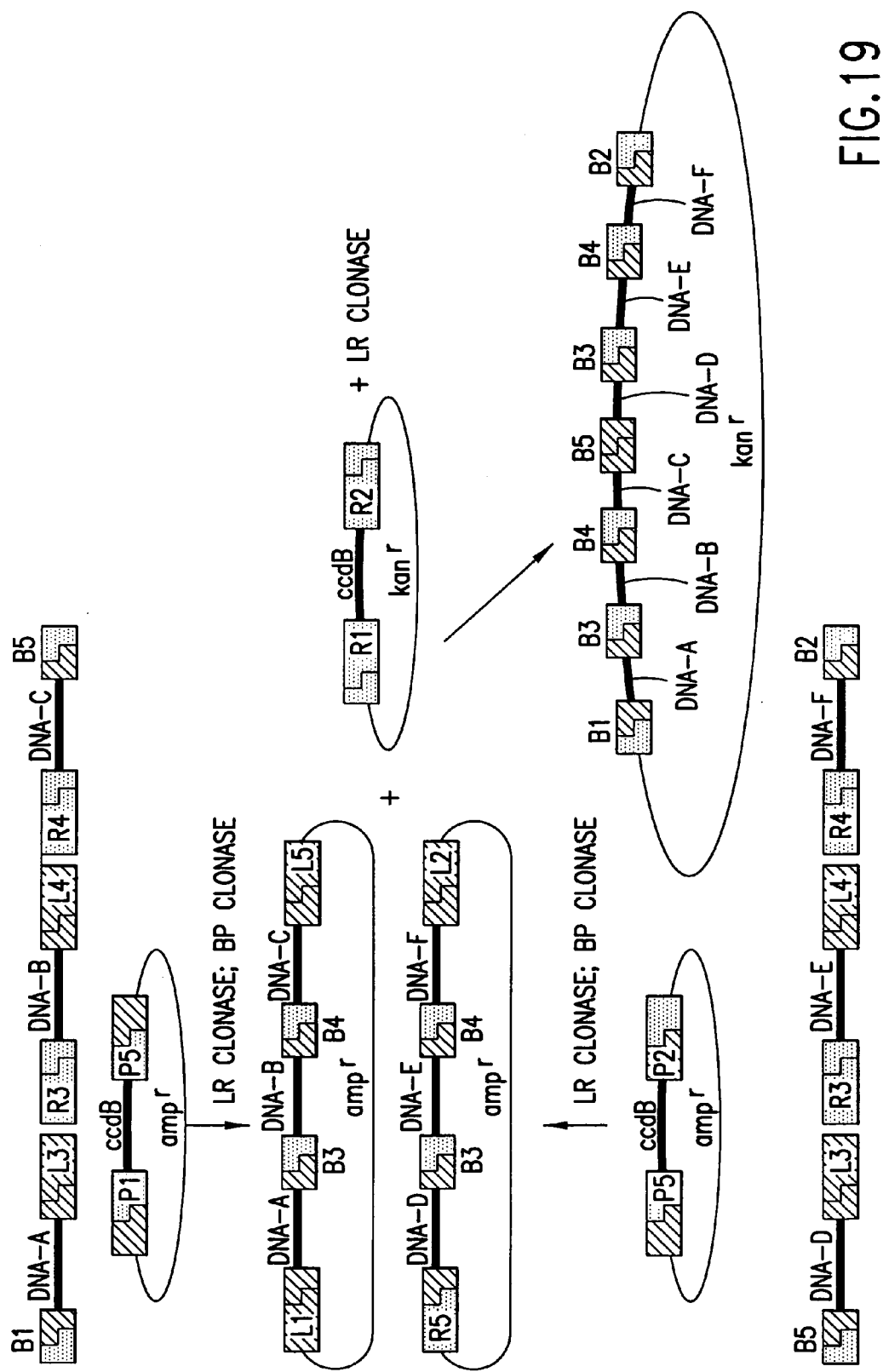
FIG. 19 is a schematic representation of the insertion of six separate DNA segments into a vector using a two step, two vector process. In particular, a first DNA segment (DNA-A) having an attB1 site at the 5' end and an attL3 site at the 3' end is linked to a second DNA segment (DNA-B) having an attR3 site at the 5' end and an attL4 site at the 3' end. The second DNA segment is then linked to a third DNA segment (DNA-C) having an attR4 site at the 5' end and an attB5 site at the 3' end. The linked DNA segments are then inserted into a vector which contains attP1 and attP5 sites. Further, a fourth DNA segment (DNA-D) having an attB5 site at the 5' end and an attL3 site at the 3' end is linked to a fifth DNA segment (DNA-E) having an attR3 site at the 5' end and an attL4 site at the 3' end. The fifth DNA segment is then linked to a sixth DNA segment (DNA-F) having an attR4 site at the 5' end and an attB2 site at the 3' end. The linked DNA segments are then inserted into a vector which contains attP1 and attP2 sites.

Another example of a multi-step process for inserting multiple DNA segments into a vector is shown in FIG. 19. In this embodiment, three DNA segments are linked to each other in separate recombination reactions and then inserted into separate vectors using LR and BP CLONASE™ reactions. After construction of these two vectors, the inserted DNA segments are transferred to another vector using an LR reaction. This results in all six DNA segments being inserted into a single Destination Vector. As one skilled in the art would recognize, numerous variations of the process shown in FIG. 19 are possible and are included within the scope of the invention.

The number of genes which may be connected using methods of the invention in a single step will in general be limited by the number of recombination sites with different specificities which can be used. Further, as described above and represented schematically in FIGS. 18 and 19, recombination sites can be chosen so as to link nucleic acid segments in one reaction and not engage recombination in later reactions. For example, again using the process set out in FIG. 18 for reference, a series of concatamers of ordered nucleic acid segments can be prepared using attL and attR sites and LR Clonase™. These concatamers can then be connected to each other and, optionally, other nucleic acid molecules using another LR reaction. Numerous variations of this process are possible.

Similarly, single use recombination sites may be used to prevent nucleic acid segments, once incorporated into another nucleic acid molecule, from engaging in subsequent recombination reactions. The use of single use recombination sites allows for the production of nucleic acid molecules prepared from an essentially limitless number of individual nucleic acid segments.

In one aspect, the invention further provides method for combining nucleic acid molecules in a single population with each other or with other molecules or populations of molecules, thereby creating populations of combinatorial molecules from which unique and/or novel molecules (e.g., hybrid molecules) and proteins or peptides encoded by these molecules may also be obtained and further analyzed. The invention further provides methods for screening populations of nucleic acid molecules to identify those which have particular activities or which encode expression products (e.g., RNAs or polypeptides) which have particular activities. Thus, methods of the invention can be used to combine nucleic acid segments which encode functional domains (e.g., $SH_3$ domains, antibody binding sites, transmembrane domains, signal peptides, enzymatic active sites) in various combinations with each other and to identify products of these methods which have particular activities.

For example, nucleic acid segments which contain transcriptional regulatory sequences can be identified by the following methods. The nucleic acid molecules of a genomic DNA library are modified to contain recombination sites on their 5' and 3' termini. These nucleic acid molecules are then inserted into a Destination Vector such that they are located 5' to a selectable marker. Thus, expression of the selectable marker will occur in vectors where the marker is in operable linkage with a nucleic acid molecule which activates its transcription. The invention thus further provides isolated nucleic acid molecules which are capable of activating transcription. In many instances, these nucleic acid molecules which activate transcription will be identified using methods and/or compositions of the invention.

Further, because some transcriptional regulatory sequences activate gene expression in a tissue-specific manner, methods of the invention can be used to identify tissue-specific transcriptional regulatory sequences. For example, when one seeks to identify transcriptional regulatory sequences which activate transcription in a specific cell or tissue type, the above screening process can be performed in cells of that cell or tissue type. Similarly, when one seeks to identify regulatory sequences which activate transcription in cells at a particular time, at a particular stage of development, or incubated under particular conditions (e.g., at a particular temperature), the above screening process can be performed in cells at an appropriate time, at the particular stage of development or incubated under the particular conditions. Once a sequence which activates transcription has been identified using such methods, the transcriptional regulatory sequences can then be tested to determine if it is capable of activating transcription in other cells types or under conditions other than those which resulted in its identification and/or selection. Thus, in one general aspect, the invention provides methods for constructing and/or identifying transcriptional regulatory sequences, as well as nucleic acid molecules which contain transcriptional regulatory sequences identified by methods of the invention in operable linkage with nucleic acid segments which encode expression products and methods for preparing such molecules.

Methods similar to those described above can also be used to identify origins of replication. Thus, the invention further includes methods for identifying nucleic acid molecules which contain origins of replication, as well as nucleic acid molecules which contain origins of replication identified by methods of the invention and methods for preparing such molecules.

As discussed below in Example 1, the invention is thus particularly suited for the construction of combinatorial libraries. For example, methods of the invention can also be used to "shuffle" nucleic acid molecules which encode domains and regions of proteins to generate new nucleic acid molecules which can be used to express proteins having specific properties or activities. In such embodiments, nucleic acid segments which encode portions of proteins are joined and then screened for one or more properties or activities.

The nucleic acid segments in these combinatorial libraries may be prepared by any number of methods, including reverse transcription of mRNA. Altered forms of the nucleic acid segments in these libraries may be generated using methods such as error prone PCR. In many applications, it will be desirable for the nucleic acid segments in these libraries to encode subportions of protein. When this is the case, the methods can be adjusted to generate populations of nucleic acid segments the majority of which do not contain full length ORFs. This can be done, for example, by shearing the cDNA library and then separating the sheared molecules (e.g., using polyacrylamide or agarose gel electrophoresis). Fragments between, for example, 300 and 600 nucleotides in length (fragments which potentially encode 100 to 200 amino acid residues) may then be recombined and inserted into a vector in operable linkage with a transcriptional regulatory sequence. Polypeptide expression products of the individual members of such a combinatorial library may then be screened to identify those with particular properties or activities.

The invention further provides methods for producing combinatorial libraries generated using exon nucleic acid derived from genomic DNA. Intron/exon splice boundaries are known in the art; thus the locations of exons in genomic DNA can be identified using routine, art-known methods without undue experimentation. Further, primers corresponding to intron/exon splice boundaries can be used to generate nucleic acid molecules which correspond to exon sequences. Further, these nucleic acid molecules may then be connected to each other to generate combinatorial libraries comprising nucleic acid molecules which correspond to exon sequences. For example, primers corresponding to intron/exon splice boundaries can be used to generate nucleic acid molecules which correspond to exon sequences using PCR. Recombination sites may then be added to the termini of the resulting PCR products using ligases or amplifying the sequences using primers containing recombination sites. The PCR products may then be connected to each other using recombination reactions and inserted into an expression vector. The resulting combinatorial library may then be screened to identify nucleic acid molecules which, for example, encode polypeptides having particular functions or activities. Further, recombination sites in expression products (e.g., RNA or protein) of nucleic acid molecules of the combinatorial library can be removed by splicing as described elsewhere herein.

Further, nucleic acid molecules used to produce combinatorial libraries, as well as the combinatorial libraries themselves, may be mutated to produce nucleic acid molecules which are, on average, at least 50%, at least 55%, at least 60%, at least 65%, at least 70%, at least 75%, at least 80%, at least 85%, at least 90%, at least 95%, at least 96%, at least 97%, at least 98%, or at least 99% identical to the corresponding original nucleic acid molecules. Similarly, nucleic acid molecules used to produce combinatorial libraries may be mutated to produce nucleic acid molecules which, encode polypeptides that are, on average, are at least 50%, at least 55%, at least 60%, at least 65%, at least 70%, at least 75%, at least 80%, at least 85%, at least 90%, at least 95%, at least 96%, at least 97%, at least 98%, or at least 99% identical to polypeptides encoded by the corresponding original nucleic acid molecules.

In one aspect the invention provides methods for generating and identifying dominant/negative suppressors of biological processes or biological pathways. For example, combinatorial libraries described above can be screened for dominant/negative activity. In general, dominant/negative activity results in the suppression of a biological process or biological pathway. In most instances, dominant/negative suppressors exhibit their affects through interaction with cellular components. For example, many dominant/negative suppressors contain domains having binding activities associated with one or more cellular proteins but do not have other activities associated with the cellular proteins. While not intending to be bound by theory, upon expression in a cell, dominant/negative suppressors generally interact with one or more cellular ligands and block activation by cellular proteins. Thus, one mechanism by which dominant/negative suppressors are believed to interfere with normal cellular processes is by ligand sequestration.

Dominant/negative activity can be conferred by mutations in a wild-type protein such as an alteration of a single amino acid residue or a deletion of an entire region of the protein. Oury et al., *J Biol. Chem.* 275:22611–22614(2000), for example, describe a dominant/negative receptor where dominant/negative activity results from the deletion of a single amino acid residue.

Protein fragments can also have dominant/negative activity. For example, McNellis et al., *Plant Cell* 8:1491–1503 (1996), describe an N-terminal fragment of constitutive photomorphogenic 1 protein (COP1) which has dominant/negative activity when expressed in *Arabidopsis* seedlings.

Any number of assays can be used to screen for dominant/negative activities. Maemura et al., *J Biol. Chem.* 274:31565–31570 (1999), for example, describe a deletion mutant of a transcription factor referred to as endothelial PAS domain protein 1 (EPAS1) which has dominant/negative activity. In particular, Maemura et al. demonstrated that expression of the EPAS1 mutant in cells inhibits induction of VEGF mRNA production, an activity associated with wild-type EPAS1.

The invention also provides methods for identifying nucleic acid molecules which encode polypeptides having particular functions or activities, as well as nucleic acid molecules produced by these methods, expression products of these nucleic acid molecules, and host cells which contain these nucleic acid molecules. Such functions or activities include secretion from cells, enzymatic activities, ligand binding activities (e.g., binding affinity for metal ions, cell surface receptors, nucleic acids, soluble proteins), and the ability to target the expression product to a sub-cellular localization (e.g., localization to mitochondria, chloroplasts, endoplasmic reticulum, etc.). Assays for identifying these nucleic acid molecules will generally be designed to identify the function of activity associated with the polypeptide.

The invention also provides methods for identifying nucleic acid molecules which encode polypeptides having regions which interact with other polypeptides. One example of such a method involves the use of two hybrid assays. (See, e.g., Fields et al., U.S. Pat. No. 5,667,973, the entire disclosure of which is incorporated herein by reference.) More specifically, nucleic acid molecules can be prepared using methods of the invention which encode a fusion protein between a polypeptide (e.g., a Gal4N-terminal domain) that exhibits a particular function when in close proximity with another polypeptide (e.g., a Gal4C-terminal domain) and protein or region of a protein for which a ligand is sought. Other nucleic acid molecules are then prepared which encode fusions between the other polypeptide referred to in the previous sentence and protein segments encoded by a combinatorial library. Thus, nucleic acid segments in the combinatorial library which encode desired ligands can be identified by screening for activities associated conferred by bringing the two polypeptides into close proximity with each other.

Phage and bacterial surface display libraries may also be generated by methods of the invention to identify domains which have particular functional activities (e.g., binding activity for a particular ligand). For example, Kim et al., *Appl. Environ. Microbiol.* 66:788–793 (2000), describe a bacterial surface display method for the selectively screening for improved variants of carboxymethyl cellulase (CMCase).

According to this method, a library of mutated CMCase genes is generated by DNA shuffling and fused to the ice nucleation protein (Inp) gene, which results in the fusion proteins being displayed on the bacterial cell surface.

The invention thus provide methods for identifying nucleic acid segments which encode proteins or protein regions that interact with other proteins or have particular functional activities, as well as nucleic acid segments identified by such methods and polypeptide expression products of these nucleic acid segments. In one aspect, methods of the invention involve generating combinatorial libraries and screening these libraries to identify individual nucleic acid molecules which encode expression products that interact with a particular protein or have a particular activity. In many instances, the combinatorial libraries described above will encode fusion proteins.

Thus, methods of the invention can be used to prepare and identify nucleic acid molecules which encode proteins and protein variants having particular properties, functions or activities. One example of a protein property which is readily assayable is solubility. For example, fluorescence generated by GFP is quenched when an insoluble GFP fusion protein is produced. Further, alterations in a relatively small number of amino acid residues of a protein (e.g., one, two, three, four, etc.), when appropriately positioned, can alter the solubility of that protein. Thus, combinatorial libraries which express GFP fusion proteins can be used to isolate proteins and protein variants which have altered solubility. In one specific example, a combinatorial library designed to express GFP fused with variants of a single, insoluble polypeptide can be used to isolate nucleic acid molecules which encode soluble variants of the polypeptide.

Methods of the invention can be used to construct nucleic acid molecules which contain two or more nucleic acid segments, wherein expression one nucleic acid segment is facilitated by the expression product of one of the other nucleic ;acid segments. For example, one nucleic acid segment may be operably linked to a T7 polymerase promoter and another nucleic acid segments encodes a T7 polymerase. Thus, the nucleic acid segment operably linked to the T7 polymerase promoter will be expressed upon expression of the T7 polymerase. Numerous variations of such systems fall within the scope of the invention. For example, nucleic acid encoding components or having particular activities referred to above can reside in a vector into which one or more the nucleic acid segments are inserted.

Methods of the invention can also be used to construct nucleic acid molecules which encode more than one subunit of a multi-subunit enzyme. Further, expression of each of the subunits of this enzyme may be regulated by the same promoter or different promoter. When the same promoter is used to drive expression of nucleic acid which encode two or more proteins, the mRNA may contain, for example one or more internal ribosome entry sites (IRES) which allow for translation of protein encoded by RNA which is 3' to the 540 most coding sequence.

Methods of the invention can be used to construct nucleic acid molecules and cells which contain a wide variety of specific inserts. Thus, in one aspect, methods of the invention can be used to prepare nucleic acid molecules and cells which contain multiple genes encode specific products. These methods allow for the generation of nucleic acid molecules and organisms which have specific characteristics. For example, as discussed below in Example 18, nucleic acids which contain all of the genes involved in a particular biological pathway can be prepared. Such genes may each be linked to different transcriptional regulatory sequences or one or more copies of the same transcriptional regulatory sequence. In addition, genes involved in the same or different biological pathways or biological processes may be operably linked to transcriptional regulatory sequences which facilitate transcription in the presence of the same or different inducing agents, under the same or different environmental conditions (e.g., temperature), or in the same or different cell types. Further, when genes encode polypeptide expression products involved in a pathway or process, one or more of these expression products may be expressed as fusion proteins. Additionally, cells can be constructed using methods of the invention which contain inserted nucleic acid segments that encode gene products involved in more than one different biological pathway or biological process.

One may also use methods of the invention, for example, to modify one or more particular nucleic acid segments in a multi-nucleic acid segment array constructed with a multisite recombination system. Using the lux operon construct shown in FIG. 17B for illustration, where each gene is flanked by attB sites having different recombination specificities, one or more specific nucleic acid segments in the molecule may be substituted with another nucleic acid segment. For example, the second coding region in the lux operon construct shown in FIG. 17B, luxD, can be replaced by reacting the vector containing the operon with an appropriate plasmid (e.g., a pDONR plasmid), such that luxD is substituted with an element comprising attRx-ccdB-cat-attRy to create a vector (i.e., an output construct) wherein the locus previously occupied by luxD becomes an acceptor site for Entry clones with an attLx-gene-attLy configuration. The product vector may then be reacted with an attLx-gene-attLy Entry clone, which will result in the replacement of the attRx-ccdB-cat-attRy cassette with the new gene flanked by attBx and attBy. In related embodiments, populations of Entry clones with the general configuration of attLx-gene-attLy may be reacted with the product vector, prepared as described above, such that a population of output constructs is generated and for any given construct in the population the segment comprising attRx-ccdB-cat-attRy will have been replaced by another nucleic acid segment flanked by attBx and attBy. In any given output construct within the population, the attRx-ccdB-cat-attRy cassette will have been replaced by a new gene flanked by attBx and attBy. Thus, the composition of a given nucleic acid segment array can be permuted in a parallel manner, while other genes in the operon construct remain substantially unaffected by these manipulations.

Further, nucleic acids segments which encode expression products involved in one or more specific biological processes or pathways may be recombined on supports. For example, a first nucleic acid molecule which has a free end on which there is a recombination site and encodes one of three enzymes involved in a biological pathway or process can be attached to a support. Nucleic acid molecules of a library having recombination sites on at least one end which are capable of recombining with the nucleic acid molecule attached to the support can then be contacted with the support under conditions which facilitate recombination, leading to the attachment of a second nucleic acid molecule to the first nucleic acid molecule. A similar process can be used to attached a third nucleic acid molecule to the free end of the second nucleic acid molecule. These resulting nucleic acid products may then be either released from the support prior to assaying for biological activity or such assaying may be performed while the nucleic acid products remain attached the support. Examples of assays which can be performed are hybridization assays to detect whether specific nucleic acid molecules are present, assays for polypeptide expression products of the connected nucleic acid molecules, or assays for end products produced by the polypeptide expression products (e.g., taxol, amino acids, carbohydrates, etc.) of the connected nucleic acid molecules.

In embodiments related to the above, nucleic acid segments may be cycled on and off the supports described above. Thus, after a second nucleic acid molecule has recombined with the first nucleic acid molecule, a second recombination reaction, for example, could be used to release the second nucleic acid molecule.

Thus, in one aspect, the invention provides methods for performing recombination between nucleic acid molecules wherein at least one of the nucleic acid molecules is bound to a support. The invention further provides methods for identifying nucleic acid molecules involved in the same biological process or pathway by recombining these nucleic acid molecules on supports (e.g., solid and semi-solid supports). The invention thus provides methods for screening nucleic acid libraries to identify nucleic acid molecules which encode expression products involved in particular biological processes or pathways, as well as nucleic acid molecules identified by these methods, expressions products produced from the nucleic acid molecules, and products produced by these biological processes or pathways.

The phrases "biochemical pathway" and "biological pathway" refer to any series of related biochemical reactions that are carried out by an organism or cell. Such pathways may include but are not limited to biosynthetic or biodegradation pathways, or pathways of energy generation or conversion.

Nucleic acid molecules of the invention can be used for a wide variety of applications. For example, methods of the invention can be used to prepare Destination Vectors which contain all of the structural genes of an operon. As discussed below in Example 18 the lux operon has been reconstructed using nucleic acids encoding the luxCDABE genes obtained from the bioluminescent bacterium *Vibrio fischeri*.

Further, as noted above, expression products of nucleic acid molecules of the invention, including multiple proteins which are part of the same or different biological pathway or process, can be produced as fusion proteins. These fusion proteins may contain amino acids which facilitate purification (e.g., 6 His tag), "target" the fusion protein to a particular cellular compartment (e.g., a signal peptide), facilitate solubility (e.g., maltose binding protein), and/or alter the characteristics of the expression product of the cloned gene (e.g., the Fc portion of an antibody molecule, a green flourescent protein (GFP), a yellow fluorescent protein (YFP), or a cyan flourescent protein (CFP)).

Methods of the invention can also be used to prepare nucleic acid molecule which, upon expression, produce fusion proteins having more than one property, function, or activity. One example of such a nucleic acid molecule is a molecule which encodes a three component fusion protein comprising a polypeptide of interest, Domain II of *Pseudomonas* exotoxin, and a polypeptide which promotes binding of the fusion protein to a cell type of interest. Domain II of *Pseudomonas* exotoxin often confers upon fusion proteins the ability to translocate across cell membranes. Thus, the expression product could be designed so that it both localizes to a particular cell-type and crosses the cell membrane. An expression product of this type would be especially useful when, for example, the polypeptide of interest is cytotoxic (e.g., induced apoptosis). Nucleic acid molecules which encode proteins similar to those described above are described in Pastan et al., U.S. Pat. No. 5,328,984.

Further, the expression product can be produced in such a manner as to facilitate its export from the cell. For example, these expression products can be fusion proteins which contain a signal peptide which results in export of the protein from the cell. One application where cell export may be desirable is where the proteins that are to be exported are enzymes which interact with extracellular substrates.

In one aspect, the invention provides methods for preparing nucleic acid molecules which encode one or more expression products involved in the same or different biological pathway or process, as well as cells which contain these nucleic acid molecules and the resulting products of such biological pathways or processes. For example, methods of the invention can be used to construct cells which export multiple proteins involved in the same or different biological processes. Thus, in one aspect, the invention provides a system for cloning multiple nucleic acid segments in a cell, which export one or more gene products of the expression products of these nucleic acid segments (e.g., two, three, four, five, seven, ten, twelve, fifteen, twenty, thirty, fifty, etc.). Further, these expression products may perform functions (e.g., catalyze chemical reactions) in extracellular media (e.g., culture media, soils, salt water marshes, etc.).

When nucleic acid molecules are prepared and/or expressed using methods of the invention, these nucleic acid molecules may encode expression products which are involved in the same or different processes (e.g., biosynthetic pathways, degradation pathway). As explained below, when one seeks to provide a wide range of functional characteristics to an organism, the nucleic acid molecules may encode expression products which confer relatively unrelated properties upon the organism.

Further, nucleic acid molecules can be prepared using methods of the invention which encode all of parts of biosynthetic pathways that lead to desired end products. Further, methods of the invention can be used to generate nucleic acid molecules which encode expression products having unique properties. Thus, the invention also provides methods generating novel end products of biological pathways or processes. In this regard, methods of the invention are useful for generating an identifying novel compounds, including therapeutic agents. Thus, in one aspect, the invention further provides drug discovery methods and therapeutic agents identified by these methods.

Examples of end products which can be produced by biological pathways or processes reconstituted and/or altered by methods of the invention include chemotherapeutic agents (e.g., antibiotics, antivirals, taxol), carbohydrates, nucleotides, amino acids, lipids, ribosomes, and membrane-bound organelles, as well as novel forms of each. Thus, the methods of the invention can be used to prepare nucleic acids which confer upon cells the ability to produce a wide variety of natural compounds, as well as modified forms of these compounds. Examples of such compounds include those which fall into the following broad classes: anti-bacterial therapeutics, anti-viral therapeutics, anti-parasitic therapeutics, anti-fungal therapeutics, anti-malarial therapeutics, amebicide therapeutics, and anti-neoplastic therapeutics.

Due to the rapid rate at which microorganisms are developing resistance to antibiotics, there is a great need for the development of new antibiotics. Further, it has been postulated that microorganisms will develop resistance more slowly to novel antibiotics for which there is no naturally occurring equivalent. Thus, in one aspect, the invention provides methods for producing novel antibiotics, as well as antibiotics produced by methods of the invention.

One example of an organism which can be produced using methods of the invention is an organism which produces novel antibiotic agents. Stassi et al., *Proc. Natl. Acad. Sci.*

USA 95:7305–7309 (1998) describe the production of novel ethyl-substituted erythromycin derivatives produced by genetically engineered cells of *Saccharopolyspora erythracea*. Thus, methods of the invention can be used to insert into the cell genetic elements which encode proteins that generate novel antibiotics. The invention further includes cells produced by these methods and methods for using such cells to produce antibiotics, as well as antibiotics produced by the methods of the invention.

Nucleic acid molecules encoding products involved in biosynthetic pathways for numerous therapeutic agents are known in the art. For example, genes and enzymes involved in the biosynthesis of β-lactam antibiotics are described, for example, in Martin, *Appl. Microbiol. Biotechnol.* 50(1):1–15 (1998). Thus, in specific aspects, the invention includes methods for producing these antibiotics and altered forms of these antibiotics, as well as the antibiotics themselves.

The invention further provides methods for producing antibacterial therapeutics, anti-viral therapeutics, anti-parasitic therapeutics, anti-fungal therapeutics, anti-malarial therapeutics, amebicide therapeutics, and anti-neoplastic therapeutics and altered forms of such agents, as well as the agents themselves. Examples of anti-bacterial therapeutics include compounds such as penicillins, ampicillin, amoxicillin, cyclacillin, epicillin, methicillin, nafcillin, oxacillin, cloxacillin, dicloxacillin, flucloxacillin, carbenicillin, cephalexin, cepharadine, cefadoxil, cefaclor, cefoxitin, cefotaxime, ceftizoxime, cefinenoxine, ceftriaxone, moxalactam, imipenem, clavulanate, timentin, sulbactam, erythromycin, neomycin, gentamycin, streptomycin, metronidazole, chloramphenicol, clindamycin, lincomycin, quinolones, rifampin, sulfonamides, bacitracin, polymyxin B, vancomycin, doxycycline, methacycline, minocycline, tetracycline, amphotericin B, cycloserine, ciprofloxacin, norfloxacin, isoniazid, ethambutol, and nalidixic acid, as well as derivatives and altered forms of each of these compounds.

Examples of anti-viral therapeutics include acyclovir, idoxuridine, ribavirin, trifluridine, vidirabine, dideoxycytidine, dideoxyinosine, zidovudine and gancyclovir, as well as derivatives and altered forms of each of these compounds.

Examples of anti-parasitic therapeutics include bithionol, diethylcarbamazine citrate, mebendazole, metrifonate, niclosamine, niridazole, oxamniquine (and other quinine derivatives), piperazine citrate, praziquantel, pyrantel pamoate and thiabendazole, as well as derivatives and altered forms of each of these compounds.

Examples of anti-fungal therapeutics include amphotericin B, clotrimazole, econazole nitrate, flucytosine, griseofulvin, ketoconazole and miconazole, as well as derivatives and altered forms of each of these compounds. Anti-fungal compounds also include aculeacin A and papulocandin B. (See, e.g., Komiyama et al, *Biol. Pharm. Bull.* (1998) 21(10):1013–1019).)

Examples of anti-malarial therapeutics include chloroquine HCl, primaquine phosphate, pyrimethamine, quinine sulfate, and quinacrine HCl, as well as derivatives and altered forms of each of these compounds.

Examples of amebicide therapeutics include dehydroemetine dihydrochloride, iodoquinol, and paramomycin sulfate, as well as derivatives and altered forms of each of these compounds.

Examples of anti-neoplastic therapeutics include aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate, as well as derivatives and altered forms of each of these compounds.

Additional anti-microbial agents include peptides. Examples of anti-microbial peptides are disclosed in Hancock et al., U.S. Pat. No. 6,040,435 and Hancock et al., *Proc. Natl. Acad. Sci. USA* 97:8856–8861 (2000).

Nucleic acid molecules can also be prepared using the methods of the invention which encode more than one subunit of a multi-protein complex. Examples of such multi-protein complexes include splicesomes, ribosomes, the human 26S proteasome, and yeast RNA polymerase III. (See, e.g., Saito et al., *Gene* 203(2):241–250 (1997); Flores et al., *Proc. Natl. Acad. Sci. USA* 96(14):7815–7820 (1999).)

Methods of the invention can also be used for the partial synthesis of non-naturally occurring products, as well as variants of these products (e.g., novel variants). For example, microorganisms which express enzymes which catalyze particular reactions can be supplied with precursors which these organisms do not normally produce. In cases where these precursors act as substrates for enzymes expressed by the microorganisms, novel compounds may be produced. "Feeding" processes of this type have been used in the past to produce novel antibiotics. In one aspect, feeding of this type is used in combination with microorganisms which express enzymes encoded by combinatorial libraries described above.

Methods of the invention can be used to either (1) introduce a new pathway into a cells or (2) alter an existing cellular pathway so that, for example, one or more additional catalytic steps (e.g., two, three, four, five, seven, ten, etc.) occur during product synthesis. One example of such an application of methods of the invention involves the modification of a protein which is naturally produced by a cell. In this example, genes encoding one or more catalytic steps which alter the protein (e.g., encode enzymes involved in post-translation modification reactions) are introduced into the cell. For example, nucleic acids which encode enzymes involved in ADP-ribosylation, glycosylation, sialylation, acetylation, ubiquination, serine to D-alanine conversion, biotinylation, acylation, amidation, formylation, carboxylation, GPI anchor formation, hydroxylation, methylation, myristoylation, oxidation, proteolytic processing, phosphorylation, prenylation, racemization, selenoylation, sulfation, arginylation can be inserted into the cell. Post-translational modifications of proteins are discussed in PROTEINS-STRUCTURE AND MOLECULAR PROPERTIES, 2nd Ed., T. E. Creighton, W. H. Freeman and Company, New York, 1993; Wold, F., POST-TRANSLATIONAL PROTEIN MODIFICATIONS: PERSPECTIVES AND PROSPECTS, pgs. 1–12 in Post-translational Covalent Modification of Proteins, B. C. Johnson, Ed., Academic Press, New York, 1983; Seifter et al., "Analysis for Protein Modifications and Nonprotein Cofactors", *Meth. Enzymol.* (1990) 182:626–646 and Rattan et al., "Protein Synthesis: Post-translational Modifications and Aging", *Ann. NY Acad. Sci.* (1992) 663:48–62.

Methods of the invention can be used, for example, to produce cells which contain nucleic acid molecules which encode proteins involved in signaling pathways. Further, these cells may be used to screen agents which modulate cell signaling. For example, cells may be produced using methods of the invention which express all of the components necessary for responding to tumor necrosis factors (TNFs). These cells can then be used to screen agents which either induce TNF mediated responses (TNF agonists) or block TNF mediated responses (TNF antagonists). Thus, included within the scope of the invention are methods for producing cells which can be used to screen for agonists and antagonists of cellular ligands, as well as cells produced by such methods. Further included within the scope of the invention are methods for using cells of the invention to identify agonists and antagonists of cellular ligands and agonists and antagonists identified by methods of the invention.

As noted above, methods of the invention can also be used to generate nucleic acids and cells which produce nutrients such as carbohydrates and amino acids. Carbohydrates and amino acids, as well as other carbon sources, can be used for a number of purposes. For example, carbohydrates and amino acids to prepare culture medium components for growing microorganisms, mammalian cells, and plant cells. Further, these compounds can be added to food products for both humans and livestock. One specific example of a use of carbohydrates and amino acids is in the preparation of nutritional formula for infants. (See, e.g., Highman et al., U.S. Pat. No. 6,120,814.) Thus, the invention further provides food products (e.g., infant formula) made using carbon sources produced using methods of the invention.

Carbon sources which can be produced using cells prepared using methods of the invention include carbohydrates (e.g., glucose, fructose, lactose, molasses, cellulose hydrolyzates, crude sugar hydrolyzates, and starch hydrolyzates), organic acids (e.g., pyruvic acid, acetic acid, fumaric acid, malic acid, and lactic acid), alcohols (glycerol, 1,3,-propanediol, and ethanol), lipids, fatty acids, nucleotides, nucleosides, and amino acids. (See, e.g., Skraly et al., *Appl. Environ Microbiol* 64:98–105 (1998).)

One example of an organism which can be produced using methods of the invention is an organism which has acquired the ability to produce ethanol. Deng et al., *Appl. Environ. Microbiol.* 65:523–528 (1999), for example, describe Cyanobacteria which have been engineered to produce ethanol. Thus, methods of the invention can be used to insert into cell genetic elements which encode proteins involved in the production of ethanol. The invention further includes cells produced by these methods and methods for using such cells to produce ethanol.

Another example of an organism which can be produced using methods of the invention is an organism which has acquired the ability to produce either poly(3-hydroxyalkanoates) or increased amounts of poly(3-hydroxyalkanoates). Poly(3-hydroxyalkanoates) are compounds which, on extraction from cells, have plastic like properties. (See, e.g., Madison et al., *Microbiol. Molec. Biol. Rev.* 63:21–53 (1999).) Thus, methods of the invention can be used to insert into cell genetic elements which encode proteins involved in the production of poly(3-hydroxyalkanoates). The invention further includes cells produced by these methods and methods for using such cells to produce poly(3-hydroxyalkanoates), poly(3-hydroxyalkanoates) derivatives, and compounds formed from poly(3-hydroxyalkanoates).

Amino acids which can be produced using cells prepared using methods of the invention include phenylalanine, tryptophan, tyrosine, leucine, isoleucine, valine, glutamine, asparagine, arginine, lysine, histidine, aspartic acid, glutamic acid, alanine, proline, serine, threonine, methionine, cysteine, and glycine. Genes and enzymes involved in the biosynthesis of amino acids and amino acid precursors in a considerable number of organism are known in the art. (See, e.g., G. N. Cohen, "The Common Pathway to Lysine, Methionine and Threonine," pp. 147–171 in *Amino Acids. Biosynthesis and Genetic Regulation*, K. M. Herrmann and R. L. Somerville, eds., Addison-Welesley Publishing Co., Inc., Reading, Mass. (1983).)

In addition to altering cells to produce new compounds, methods of the invention can also be used to engineer cells so that they either overproduce or underproduce products of the cells normal metabolism. For example, Donnelly et al., U.S. Pat. No. 5,770,435 described a mutant strain of *E. coli* which produce increased amounts of succinic acid. Methods of the invention can be used, for example, to construct nucleic acid molecules which encode enzymes in the succinic acid biosynthetic pathway. Further, the expression of one or more of these enzymes can be regulated at the transcriptional level. Thus, the introduction of these nucleic acid molecules into the above described *E. coli* cells will effectively result in an amplification of one or more genes in the succinic acid biosynthetic pathway. Further, one or more of these genes can be operably linked to an inducible promoter (e.g. the lacI promoter) so that increased succinic acid occurs only in the presence of the inducing signal (e.g., IPTG).

Methods of the invention can also be used to generate nucleic acids and cells which produce components and precursors that can be used in manufacturing processes. Examples of such components include plastics, plastic-like compounds (e.g., polyketides), soaps, fertilizers, papers, synthetic rubber, dyes, inks, etc. The invention further includes components and precursors produced by methods and cells of the invention.

Similarly, nucleic acid molecules prepared by the methods of the invention can also be used to down regulate expression of, for example, one or more endogenous genes. One example of this is when nucleic acid inserts prepared by methods of the invention are transcribed to produce antisense RNA. Again, nucleic acid molecules which encode antisense RNAs may be operably linked to a regulatable promoter.

Thus, the invention further includes methods for producing cells which either overproduce or underproduce products of the cells normal metabolism, as well as cells produced by these methods.

As noted above, nucleic acid molecules prepared by methods of the invention can be used to alter the physical characteristics of an organism so that the organism has particular characteristics. For example, a cell which lacks specific enzymes required to produce either recombinant or native proteins having particular glycosylation patterns can be introduced into the cell using the vectors of the invention. Glycosylation patterns of proteins has been found to be, to some extent, cell-type and species specific. (See, e.g., Jarvis et al., *Curr. Opin. Biotechnol.* 9:528–533 (1998).) Thus, in one aspect, the invention provides methods for producing cells which exhibit altered glycosylation pathways, as well as cells produced by these methods and glycosylated compounds produced by these cells. This process is generally termed "glycosylation engineering." Stanley, *Glycobiology* 2:99–107 (1992).

For example, bacterial cells which do not glycosylate proteins may be modified using methods of the invention to produce enzymes which glycosylate proteins. Examples of such enzymes include N-acetylglucosaminlytransferases III and V, $\beta$1,4-galactosyltransferase, $\alpha$2,6-sialyltransferase, $\alpha$2,3-sialyltransferase, $\alpha$1,3-fucosyltransferase III and VI, and $\alpha$1,2-mannosyltransferase.

In another aspect, the invention provides methods for producing cells which exhibit altered metabolic properties leading to increased production of compounds synthesized by these cells, as well as cells produced by these methods and products produced by these cells. One example of such methods result in the production of cells which produce increased quantities of precursors for biological pathways. This process is referred to herein as metabolic channeling or funneling. For example, when one seeks to produce a cell which produces increased amounts of serine, nucleic acid molecules which encode enzymes of pathways which lead to the production of 3-phosphoglycerate can be inserted into the cell. Optionally, nucleic acid molecules which encode enzymes involved in the conversion of 3-phosphoglycerate to serine can also be inserted into the cell. Parameters useful for consideration when engineering cells which contain increased intracellular concentrations of precursor pools an compounds include the rate limiting set in the particular pathway and pathway fluxes. (See, e.g., Kholodenko et al., *Biotechnol. Bioeng.* 59:239–247 (1997).)

Polyketides represent a large family of diverse compounds synthesized from 2-carbon units through a series of condensations and subsequent modifications. Polyketides are produced in many types of organisms, including fungi and numerous bacteria, in particular, the actinomycetes. There are a wide variety of polyketide structures and polyketides encompasses numerous compounds with diverse activities. (See, e.g., PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; and 5,712,146; and Fu et al., 1994, *Biochemistry* 33:9321–9326; McDaniel et al., 1993, *Science* 262:1546–1550; and Rohr, 1995, *Angew. Chem. Int. Ed. Engl.* 34:881–888, each of which is incorporated herein by reference.)

Polyketide synthases (PKSs) assemble structurally diverse natural products using a common mechanistic strategy that relies on a cysteine residue to anchor the polyketide during a series of decarboxylative condensation reactions that build the final reaction product. PKSs generally catalyze the assembly of complex natural products from simple precursors such as propionyl-CoA and methylmalonyl-CoA in a biosynthetic process that closely parallels fatty acid biosynthesis. Examples of polyketides include callystatin A, ansatrienin A, actinorhodin, rapamycin, methymycin, and pikromycin.

In one aspect, the invention provides methods for preparing nucleic acid molecules which encode one or more PKSs, as well as cells which contain these nucleic acid molecules and the resulting polyketide products. The invention further provides methods for generating novel PKSs using combinatorial libraries and products produced by these novel PKSs (e.g., novel macrolide antibiotics), as well methods for producing these novel PKS products.

Methods of the invention can also be used to construct strains of microorganisms which are useful for decreasing the toxicity of various agents. Such agents include petroleum-based pollutants (e.g., chlorinated and non-chlorinated aliphatic compounds (e.g., $C_5$–$C_{36}$), chlorinated and non-chlorinated aromatic compounds (e.g., $C_9$–$C_{22}$), crude oil, refined oil, fuel oils (e.g., Nos. 2, 4 and 6 fuel oils), diesel oils, gasoline, hydraulic oils, kerosene, benzene, toluene, ethylbenzene and xylenes, trimethylbenzenes, naphthalene, anthracene, acenaphthene, acenaphthylene, benzo(a)anthracene, benzo(a)pyrene, benzo(b)fluoranthene, benzo(g,h,i)perylene, benzo(k)fluoranthene, pyrene, methylene chloride, 1,1-dichloroethane, chloroform, 1,2-dichloropropane, dibromochloromethane, 1,1,2-trichloroethane, 2-chloroethylvinyl ether, tetrachloroethene (PCE), chlorobenzene, 1,2-dichloroethane, 1,1,1-trichloroethane, bromodichloromethane, trans-1,3-dichloropropene, cis-1,3-dichloropropene, bromoform, chloromethane, bromomethane, vinyl chloride, chloroethane, 1,1-dichloroethene, trans-1,2-dichloroethene, trichloroethene (TCE), dichlorobenzenes, cis-1,2-dichloroethene, dibromomethane, 1,4-dichlorobutane, 1,2,3-trichloropropane, bromochloromethane, 2,2-dichloropropane, 1,2-dibromoethane, 1,3-dichloropropane, bromobenzene, chlorotoluenes, trichlorobenzenes, trans-1,4-dichloro-2-butene and butylbenzenes).

One example of an organism which can be produced using methods of the invention is an organism which degrades toluene. Panke et al., *Appl. Environ. Microbiol.* 64:748–751 (1998) describe strains of *Pseudomonas putida* which converts toluene, as well as several toluene derivatives, to benzoates. Thus, methods of the invention can be used to insert into cell genetic elements which encode proteins that convert toluene, as well as derivatives thereof, to less toxic compounds. The invention further includes cells produced by these methods and methods for using such cells to convert toluene, as well as several toluene derivatives, to less toxic compounds.

Methods of the invention can also be used to prepare organism suitable for the detoxifying non-petroleum agents such as heavy metal ions (e.g., mercury, copper, cadmium, silver, gold, tellurite, selenite, and uranium). Methods by which mercury, for example, can be detoxified include reduction of mercury ions to generate metallic mercury and through volatilization. Genes involved in the detoxification by bacterial are described in Miller, "*Bacterial Detoxification of Hg(II) and Organomercurials*", Essays Biochem. 34:17–30 (1999).

Another example of a heavy metal ion detoxification system has been identified in a strain of *Rhodobacter sphaeroide* (see O'Gara et al., *Appl. Environ. Microbiol.* 63(12):4713–4720 (1997)). Tellurite-resistance in this strain appears to be conferred by two loci. The first genetic locus contains four genes; two of these genes (i.e., trgA and trgB) confer increased tellurite-resistance when inserted into another bacterium. Disruption of another gene at this locus, cysK (cysteine synthase), results in decreased tellurite resistance. The second genetic locus contains the telA gene. Inactivation of telA results in a significant decreased tellurite resistance compared to the wild-type strain.

Microorganisms which are capable of detoxifying agents are described, for example, in Perriello, U.S. Pat. No. 6,110,372. Microorganisms suitable for bioremediation applications include those of the Pseudomonadaceae family, the Actinomycetes family, the Micrococcaceae family, the Vibrionaceae family, the Rhizobiaceae family, the Cytophagaceae family, and the Corynebacterium family. Specific examples of organisms suitable for use after modification using the methods of the invention for bioremediation applications include *Pseudomonas rubrisubalbicans, Pseudomonas aeruginosa, Variovorax paradoxus, Nocardia asteroides, Deinococcus radiodurans, Nocardia restricta, Chryseobacterium indologenes, Comamonas acidovorans, Acidovorax delafieldii, Rhodococcus rhodochrous, Rhodococcus erytlropolis, Aureobacterium esteroaromaticum, Aureobacterium saperdae, Micrococcus varians, Micrococcus kristinae, Aeromonas caviae, Stenotrophomonas maltophilia, Sphingobacterium thalpophilum, Clavibacter michiganense, Alcaligenes xylosoxydans, Corynebacterium aquaticum B* and *Cytophaga johnsonae*.

Organisms suitable for bioremediation further include plants. Meagher et al., U.S. Pat. No. 5,965,796, for example, describes transgenic plants which express a metal ion resistance protein and reduce metal ions such as those of copper, mercury, gold, cadmium, lead and silver. Further, genes encoding phytochelatins can be introduced into plants to increase phytochelatin synthesis. Phytochelatins are glutathione derivatives which detoxify metal ions through sequestration. Genes from a number of plant species involved in phytochelatin synthesis are discussed in Corbett, "*Phytochelatin Biosynthesis and Function in Heavy-Metal Detoxification*" Curr. Opin. Plant Biol. 3(3):211–216 (2000).

Specific plants suitable for bioremediation applications after modification by methods of the invention include *Lepi-*

*dium sativum, Brassica juncea, Brassica oleracea, Brassica rapa, Acena sativa, Triticum aestivum, Helianthus annuus,* Colonial bentgrass, Kentucky bluegrass, perennial ryegrass, creeping bentgrass, Bermudagrass, Buffalograss, centipedegrass, switch grass, Japanese lawngrass, coastal panicgrass, spinach, sorghum, tobacco and corn. Methods for generating transgenic plants are known in the art and, as noted above, are described, for example, in Meagher et al., U.S. Pat. No. 5,965, 796.

Methods of the invention can also be used to prepare organisms which have diverse characteristics and contain a considerable number of inserted genes. As noted above, methods of the invention can be used to insert an almost unlimited number of nucleic acid segments into cells. For example, in one specific embodiment, the invention provides methods for producing cells which express pesticidal proteins (e.g., pesticidal proteins of *Bacillus thurginiensis*). (See, e.g., Schnepf et al., *Microbiol. Molec. Biol. Rev.* 62:775–806 (1998).) Thus, methods of the invention can be used to insert into cell genetic elements which encode pesticidal proteins. The invention further includes cells produced by these methods and methods for using such cells to produce pesticidal proteins. The invention further includes methods for using cells (e.g., bacterial or plant cells) and pesticidal proteins produced by methods of the invention to control insect populations. In certain embodiments, cells produced by methods of the invention and used in methods of the invention will be plant cells.

Thus, in one aspect, methods of the invention may be used to prepare nucleic acid molecules which contain one or more ORFs and/or nucleic acid segments which encode one or more non-protein expression products (e.g., functional RNAs such as tRNAs or ribozymes). In most embodiments of the invention, the number of ORFs and/or nucleic acid segments which encode one or more non-protein expression products will generally range between about 1 and about 300 (e.g., 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, etc.). Nucleic acid molecules which contain one or more ORFs and/or nucleic acid segments which encode one or more non-protein expression products will be especially useful for altering organisms to have specified characteristics such as those described above.

Depending on a number of factors, including the number of functional segments present, the size of nucleic acid molecules of the invention will vary considerably in size but, in general, will range between from about 0.5 kb to about 300 kb (e.g., about 0.5 kb, about 1 kb, about 2 kb, about 3 kb, about 4 kb, about 5 kb, about 7 kb, about 10 kb, about 12 kb, about 15 kb, about 20 kb, about 40 kb, about 60 kb, about 80 kb, about 100 kb, about 200 kb, about 300 kb, etc.).

In a specific embodiment, the invention further provides methods for introducing nucleic acid molecules of the invention into animals (e.g., humans) and animal cells (e.g., human cells), as part of a gene therapy protocol. Gene therapy refers to therapy performed by the administration to a subject of an expressed or expressible nucleic acid molecule. In many embodiment of the invention, nucleic acid molecules of the invention will encoded one or more proteins which mediates at least one therapeutic effect. Thus, the invention provide nucleic acid molecules and methods for use in gene therapy.

Nucleic acid molecules of the invention can be used to prepare gene therapy vectors designed to replace genes which reside in the genome of a cell, to delete such genes, or to insert a heterologous gene or groups of genes. When nucleic acid molecules of the invention function to delete or replace a gene or genes, the gene or genes being deleted or replaced may lead to the expression of either a "normal" phenotype or an aberrant phenotype. One example of an aberrant phenotype is the disease cystic fibrosis. Further, the gene therapy vectors may be either stably maintained (e.g., integrate into cellular nucleic acid by homologous recombination) or non-stably maintained in cells.

Further, nucleic acid molecules of the invention may be used to suppress "abnormal" phenotypes or complement or supplement "normal" phenotypes which result from the expression of endogenous genes. One example of a nucleic acid molecule of the invention designed to suppress an abnormal phenotype would be where an expression product of the nucleic acid molecule has dominant/negative activity. An example of a nucleic acid molecule of the invention designed to supplement a normal phenotype would be where introduction of the nucleic acid molecule effectively results in the amplification of a gene resident in the cell.

Further, nucleic acid molecules of the invention may be used to insert into cells nucleic acid segments which encode expression products involved in each step of particular biological pathways (e.g., biosynthesis of amino acids such as lysine, threonine, etc.) or expression products involved in one or a few steps of such pathways. These nucleic acid molecules can be designed to, in effect, amplify genes encoding expression products in such pathways, insert genes into cells which encode expression products involved in pathways not normally found in the cells, or to replace one or more genes involved one or more steps of particular biological pathways in cells. Thus, gene therapy vectors of the invention may contain nucleic acid which results in the production one or more products (e.g., one, two, three, four, five, eight, ten, fifteen, etc.). Such vectors, especially those which lead to the production of more than one product, will be particularly useful for the treatment of diseases and/or conditions which result from the expression and/or lack of expression of more than one gene or for the treatment of more than one diseases and/or conditions.

Thus, in related aspects, the invention provides gene therapy vectors which express one or more expression products (e.g., one or more fusion proteins), methods for producing such vectors, methods for performing gene therapy using vectors of the invention, expression products of such vector (e.g., encoded RNA and/or proteins), and host cells which contain vectors of the invention.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11 (5): 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

Delivery of the nucleic acid molecules of the invention into a patient may be either direct, in which case the patient is directly exposed to the nucleic acid or nucleic acid carrying vectors, or indirect, in which case, cells are first transformed with the nucleic acid in vitro, then transplanted into the patient. These two approaches are known, respectively, as in vivo or ex vivo gene therapy.

In a specific embodiment, nucleic acid molecules of the invention are directly administered in vivo, where they are expressed to produce one or more expression products. This can be accomplished by any of numerous methods known in the art, such as by constructing an expression vector and administering it so that they become intracellular (e.g., by infection using defective or attenuated retroviral vectors or other viral vectors (see U.S. Pat. No. 4,980,286), by direct injection of naked DNA, by use of microparticle bombardment (e.g., a gene gun; Biolistic, Dupont), by coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J Biol. Chem.* 262:4429–4432) (which can be used to target cell types specifically expressing the receptors), etc.). In another embodiment, nucleic acid molecules of the invention can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26,1992 (Findeis et al.); WO93/14188 dated Jul. 22, 1993 (Clarke et al.), WO 93/20221 dated Oct. 14, 1993 (Young)). Alternatively, nucleic acid molecules of the invention can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342: 435–438). Example of such nucleic acid construct suitable for such an application are shown in FIGS. 21C and 22B.

In another specific embodiment, viral vectors that contains nucleic acid sequences encoding an antibody or other antigen-binding protein of the invention are used. For example, a retroviral vector can be used (see Miller et al., 1993, Meth. Enzymol. 217:581–599). These retroviral vectors have been used to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia and the use of such vectors are included within the scope of the invention. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication Nos. WO94/12649 and WO 96/17053; U.S. Pat. No. 5,998,205; and Wang et al., 1995, Gene Therapy 2:775–783, the disclosures of all of which are incorporated herein by reference in their entireties. In a one embodiment, adenovirus vectors are used.

Adeno-associated virus (AAV) and Herpes viruses, as well as vectors prepared from these viruses have also been proposed for use in gene therapy (Walsh et al., 1993, *Proc. Soc. Exp. Biol. Med.* 204:289–300; U.S. Pat. No. 5,436,146; Wagstaff et al., *Gene Ther.* 5:1566–70 (1998)). Herpes viral vectors are particularly useful for applications where gene expression is desired in nerve cells.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and, optionally, heritable and expressible by its cell progeny.

The resulting recombinant cells can be delivered to a patient by various methods known in the art. Recombinant blood cells (e.g., hematopoietic stem or progenitor cells) will generally be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells (e.g., as obtained from bone marrow, umbilical cord blood, peripheral blood, fetal liver, etc.).

In a certain embodiment, the cell used for gene therapy is autologous to the patient.

In an embodiment in which recombinant cells are used in gene therapy, nucleic acid sequences encoding an antibody or other antigen-binding protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, nucleic acid molecules to be introduced for purposes of gene therapy comprises an inducible promoter operably linked to the coding region, such that expression of the nucleic acid molecules are controllable by controlling the presence or absence of the appropriate inducer of transcription.

The nucleic acid molecules of the invention can also be used to produce transgenic organisms (e.g., animals and plants). Animals of any species, including, but not limited to, mice, rats, rabbits, hamsters, guinea pigs, pigs, micro-pigs, goats, sheep, cows and non-human primates (e.g., baboons, monkeys, and chimpanzees) may be used to generate transgenic animals. Further, plants of any species, including but not limited to *Lepidium sativum, Brassica juncea, Brassica oleracea, Brassica rapa, Acena sativa, Triticum aestivum, Helianthus annuus*, Colonial bentgrass, Kentucky bluegrass, perennial ryegrass, creeping bentgrass, Bermudagrass, Buffalograss, centipedegrass, switch grass, Japanese lawngrass, coastal panicgrass, spinach, sorghum, tobacco and corn, may be used to generate transgenic plants.

Any technique known in the art may be used to introduce nucleic acid molecules of the invention into organisms to produce the founder lines of transgenic organisms. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol. Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pluripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115: 171–229 (1989), which is incorporated by reference herein in its entirety. Further, the contents of each of the documents recited in this paragraph is herein incorporated by reference in its entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing nucleic acid molecules of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic organisms that carry nucleic acid molecules of the invention in all their cells, as well as organisms which carry these nucleic acid molecules, but not all their cells, i.e., mosaic organisms or chimeric. The nucleic acid molecules of the invention may be integrated as a single copy or as multiple copies such as in concatamers, e.g., head-to-head tandems or head-to-tail tandems. The nucleic acid molecules of the invention may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that nucleic acid molecules of the invention be integrated into the chromosomal site of the endogenous gene, this will normally be done by gene targeting. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. Nucleic acid molecules of the invention may also be selectively introduced into a particular cell type, thus inactivating the endogenous gene in only that cell type, by following, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic organisms have been generated, the expression of the recombinant gene may be assayed utilizing standard techniques. Initial screening may be accomplished by Southern blot analysis or PCR techniques to analyze organism tissues to verify that integration of nucleic acid molecules of the invention has taken place. The level of mRNA expression of nucleic acid molecules of the invention in the tissues of the transgenic organisms may also be assessed using techniques which include, but are not limited to, Northern blot analysis of tissue samples obtained from the organism, in situ hybridization analysis, and reverse transcriptase-PCR (rt-PCR). Samples of tissue may which express nucleic acid molecules of the invention also be evaluated immunocytochemically or immunohistochemically using antibodies specific for the expression product of these nucleic acid molecules.

Once the founder organisms are produced, they may be bred, inbred, outbred, or crossbred to produce colonies of the particular organism. Examples of such breeding strategies include, but are not limited to: outbreeding of founder organisms with more than one integration site in order to establish separate lines; inbreeding of separate lines in order to produce compound transgenic organisms that express nucleic acid molecules of the invention at higher levels because of the effects of additive expression of each copy of nucleic acid molecules of the invention; crossing of heterozygous transgenic organisms to produce organisms homozygous for a given integration site in order to both augment expression and eliminate the need for screening of organisms by DNA analysis; crossing of separate homozygous lines to produce compound heterozygous or homozygous lines; and breeding to place the nucleic acid molecules of the invention on a distinct background that is appropriate for an experimental model of interest.

Transgenic and "knock-out" organisms of the invention have uses which include, but are not limited to, model systems (e.g., animal model systems) useful in elaborating the biological function of expression products of nucleic acid molecules of the invention, studying conditions and/or disorders associated with aberrant expression of expression products of nucleic acid molecules of the invention, and in screening for compounds effective in ameliorating such conditions and/or disorders.

As one skilled in the art would recognize, in many instances when nucleic acid molecules of the invention are introduced into metazoan organisms, it will be desirable to operably link sequences which encode expression products to tissue-specific transcriptional regulatory sequences (e.g., tissue-specific promoters) where production of the expression product is desired. Such promoters can be used to facilitate production of these expression products in desired tissues. A considerable number of tissue-specific promoters are known in the art. Further, methods for identifying tissue-specific transcriptional regulatory sequences are described elsewhere herein.

Host Cells

The invention also relates to host cells comprising one or more of the nucleic acid molecules or vectors of the invention (e.g., two, three, four, five, seven, ten, twelve, fifteen, twenty, thirty, fifty, etc.), particularly those nucleic acid molecules and vectors described in detail herein. Representative host cells that may be used according to this aspect of the invention include, but are not limited to, bacterial cells, yeast cells, plant cells and animal cells. Preferred bacterial host cells include *Escherichia* spp. cells (particularly *E. coli* cells and most particularly *E. coli* strains DH10B, Stbl2, DH5α, DB3, DB3.1 (preferably *E. coli* LIBRARY EFFICIENCY® DB3.1 ™ Competent Cells; Invitrogen Corp., Life Technologies Division, Rockville, Md.), DB4 and DB5 (see U.S. application Ser. No. 09/518,188, filed on Mar. 2, 2000, and U.S. Provisional Application Ser. No. 60/122,392, filed on Mar. 2, 1999, the disclosures of which are incorporated by reference herein in their entireties), *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Preferred animal host cells include insect cells (most particularly *Drosophila melanogaster* cells, *Spodoptera frugiperda* Sf9 and Sf21 cells and Trichoplusa High-Five cells), nematode cells (particularly *C. elegans* cells), avian cells, amphibian cells (particularly *Xenopus laevis* cells), reptilian cells, and mammalian cells (most particularly NIH3T3, CHO, COS, VERO, BHK and human cells). Preferred yeast host cells include *Saccharomyces cerevisiae* cells and *Pichia pastoris* cells. These and other suitable host cells are available commercially, for example, from Invitrogen Corp., Life Technologies Division (Rockville, Md.), American Type Culture Collection (Manassas, Va.), and Agricultural Research Culture Collection (NRRL; Peoria, Ill.).

Methods for introducing the nucleic acid molecules and/or vectors of the invention into the host cells described herein, to produce host cells comprising one or more of the nucleic acid molecules and/or vectors of the invention, will be familiar to those of ordinary skill in the art. For instance, the nucleic acid molecules and/or vectors of the invention may be introduced into host cells using well known techniques of infection, transduction, electroporation, transfection, and transformation. The nucleic acid molecules and/or vectors of the invention may be introduced alone or in conjunction with other the nucleic acid molecules and/or vectors and/or proteins, peptides or RNAs. Alternatively, the nucleic acid molecules and/or vectors of the invention may be introduced into host cells as a precipitate, such as a calcium phosphate precipitate, or in a complex with a lipid. Electroporation also may be used to introduce the nucleic acid molecules and/or vectors of the invention into a host. Likewise, such molecules may be introduced into chemically competent cells such as *E. coli*. If the vector is a virus, it may be packaged in vitro or introduced into a packaging cell and the packaged virus may be transduced into cells. Thus nucleic acid molecules of the invention may contain and/or encode one or more packaging signal (e.g., viral packaging signals which direct the packaging of viral nucleic acid molecules). Hence, a wide variety of techniques suitable for introducing the nucleic acid molecules and/or vectors of the invention into cells in accordance with this aspect of the invention are well known and routine to those of skill in the art. Such techniques are reviewed at length, for example, in Sambrook, J., et al., *Molecular Cloning, a Laboratory Manual*, 2nd Ed., Cold Spring Harbor, N.Y.: Cold Spring Harbor Laboratory Press, pp. 16.30–16.55 (1989), Watson, J. D., et al., *Recombinant DNA*, 2nd Ed., New York: W. H. Freeman and Co., pp. 213–234 (1992), and Winnacker, E.-L., *From Genes to Clones*, New York: VCH Publishers (1987), which are illustrative of the many laboratory manuals that detail these techniques and which are incorporated by reference herein in their entireties for their relevant disclosures.

Polymerases

Polymerases for use in the invention include but are not limited to polymerases (DNA and RNA polymerases), and reverse transcriptases. DNA polymerases include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Pyrococcus* sp KOD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), *E. coli* pol I DNA polymerase, T5 DNA polymerase, T7 DNA polymerase, and generally pol I type DNA polymerases and mutants, variants and derivatives thereof. RNA polymerases such as T3, T5, T7 and SP6 and mutants, variants and derivatives thereof may also be used in accordance with the invention.

The nucleic acid polymerases used in the present invention may be mesophilic or thermophilic, and are preferably thermophilic. Preferred mesophilic DNA polymerases include Pol I family of DNA polymerases (and their respective Klenow fragments) any of which may be isolated from organism such as *E. coli, H. influenzae, D. radiodurans, H. pylori, C. aurantiacus, R. prowazekii, T pallidum, Synechocystis* sp., *B. subtilis, L. lactis, S. pneumoniae, M. tuberculosis, M. leprae, M. smegmatis*, Bacteriophage L5, phi-C31, T7, T3, T5, SP01, SP02, mitochondrial from *S. cerevisiae* MIP-1, and eukaryotic *C. elegans*, and *D. melanogaster* (Astatke, M. et al., 1998, *J Mol. Biol.* 278, 147–165), pol III type DNA polymerase isolated from any sources, and mutants, derivatives or variants thereof, and the like. Preferred thermostable DNA polymerases that may be used in the methods and compositions of the invention include Taq, Tne, Tma, Pfu, KOD, Tfl, Tth, Stoffel fragment, VENT™ and DEEPVENT™ DNA polymerases, and mutants, variants and derivatives thereof (U.S.

Pat. Nos. 5,436,149; 4,889,818; 4,965,188; 5,079,352; 5,614,365; 5,374,553; 5,270,179; 5,047,342; 5,512,462; WO 92/06188; WO 92/06200; WO 96/10640; WO 97/09451; Barnes, W. M., Gene 112:29–35 (1992); Lawyer, F. C., et al., PCR Meth. Appl. 2:275–287 (1993); Flaman, J.-M., et al., Nucl. Acids Res. 22(15):3259–3260 (1994)).

Reverse transcriptases for use in this invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., Science 239:487–491 (1988); U.S. Pat. Nos. 4,889,818 and 4,965,188), Tne DNA polymerase (WO 96/10640 and WO 97/09451), Tma DNA polymerase (U.S. Pat. No. 5,374,553) and mutants, variants or derivatives thereof (see, e.g., WO 97/09451 and WO 98/47912). Preferred enzymes for use in the invention include those that have reduced, substantially reduced or eliminated RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wild-type or RNase H$^+$ enzyme such as wild-type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., Nucl. Acids Res. 16:265 (1988) and in Gerard, G. F., et al., FOCUS 14(5):91 (1992), the disclosures of all of which are fully incorporated herein by reference. Particularly preferred polypeptides for use in the invention include, but are not limited to, M-MLV H$^-$ reverse transcriptase, RSV H- reverse transcriptase, AMV H$^-$ reverse transcriptase, RAV (rous-associated virus) H$^-$ reverse transcriptase, MAV (myeloblastosis-associated virus) H$^-$ reverse transcriptase and HIV H$^-$ reverse transcriptase. (See U.S. Pat. No. 5,244,797 and WO 98/47912). It will be understood by one of ordinary skill, however, that any enzyme capable of producing a DNA molecule from a ribonucleic acid molecule (i.e., having reverse transcriptase activity) may be equivalently used in the compositions, methods and kits of the invention.

The enzymes having polymerase activity for use in the invention may be obtained commercially, for example from Invitrogen Corp., Life Technologies Division (Rockville, Md.), Perkin-Elmer (Branchburg, N.J.), New England BioLabs (Beverly, Mass.) or Boehringer Mannheim Biochemicals (Indianapolis, Ind.). Enzymes having reverse transcriptase activity for use in the invention may be obtained commercially, for example, from Invitrogen Corp., Life Technologies Division (Rockville, Md.), Pharmacia (Piscataway, N.J.), Sigma (Saint Louis, Mo.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., J. Virol. 29:517 (1979)). In addition, such polymerases/reverse transcriptases may be prepared by recombinant DNA techniques that are familiar to one of ordinary skill in the art (see, e.g., Kotewicz, M. L., et al., Nucl. Acids Res. 16:265 (1988); U.S. Pat. No. 5,244,797; WO 98/47912; Soltis, D. A., and Skalka, A. M., Proc. Natl. Acad. Sci. USA 85:3372–3376 (1988)). Examples of enzymes having polymerase activity and reverse transcriptase activity may include any of those described in the present application.

Supports and Arrays

Supports for use in accordance with the invention may be any support or matrix suitable for attaching nucleic acid molecules comprising one or more recombination sites or portions thereof. Such molecules may be added or bound (covalently or non-covalently) to the supports of the invention by any technique or any combination of techniques well known in the art. Supports of the invention may comprise nitrocellulose, diazocellulose, glass, polystyrene (including microtitre plates), polyvinylchloride, polypropylene, polyethylene, polyvinylidenedifluoride (PVDF), dextran, Sepharose, agar, starch and nylon. Supports of the invention may be in any form or configuration including beads, filters, membranes, sheets, frits, plugs, columns and the like. Solid supports may also include multi-well tubes (such as microtitre plates) such as 12-well plates, 24-well plates, 48-well plates, 96-well plates, and 384-well plates. Preferred beads are made of glass, latex or a magnetic material (magnetic, paramagnetic or superparamagnetic beads).

In a preferred aspect, methods of the invention may be used to prepare arrays of proteins or nucleic acid molecules (RNA or DNA) or arrays of other molecules, compounds, and/or substances. Such arrays may be formed on microplates, glass slides or standard blotting membranes and may be referred to as microarrays or gene-chips depending on the format and design of the array. Uses for such arrays include gene discovery, gene expression profiling, genotyping (SNP analysis, pharmacogenomics, toxicogenetics), and the preparation of nanotechnology devices.

Synthesis and use of nucleic acid arrays and generally attachment of nucleic acids to supports have been described (see, e.g., U.S. Pat. Nos. 5,436,327, 5,800,992, 5,445,934, 5,763,170, 5,599,695 5,837,832). An automated process for attaching various reagents to positionally defined sites on a substrate is provided in Pirrung, et al. U.S. Pat. No. 5,143,854 and Barrett, et al. U.S. Pat. No. 5,252,743. For example, disulfide-modified oligonucleotides can be covalently attached to solid supports using disulfide bonds. (See Rogers et al., Anal. Biochem. 266:23–30 (1999).) Further, disulfide-modified oligonucleotides can be peptide nucleic acid (PNA) using solid-phase synthesis. (See Aldrian-Herrada et al., J Pept. Sci. 4:266–281 (1998).) Thus, nucleic acid molecules comprising one or more recombination sites or portions thereof can be added to one or more supports (or can be added in arrays on such supports) and nucleic acids, proteins or other molecules and/or compounds can be added to such supports through recombination methods of the invention. Conjugation of nucleic acids to a molecule of interest are known in the art and thus one of ordinary skill can produce molecules and/or compounds comprising recombination sites (or portions thereof) for attachment to supports (in array format or otherwise) according to the invention.

Essentially, any conceivable support may be employed in the invention. The support may be biological, non-biological, organic, inorganic, or a combination of any of these, existing as particles, strands, precipitates, gels, sheets, tubing, spheres, containers, capillaries, pads, slices, films, plates, slides, etc. The support may have any convenient shape, such as a disc, square, sphere, circle, etc. The support is preferably flat but may take on a variety of alternative surface configurations. For example, the support may contain raised or depressed regions which may be used for synthesis or other reactions. The support and its surface preferably form a rigid support on which to carry out the reactions described herein.

The support and its surface are also chosen to provide appropriate light-absorbing characteristics. For instance, the support may be a polymerized Langmuir Blodgett film, functionalized glass, Si, Ge, GaAs, GaP, SiO$_2$, SIN$_4$, modified silicon, or any one of a wide variety of gels or polymers such as (poly)tetrafluoroethylene, (poly)vinylidenedifluoride, polystyrene, polycarbonate, or combinations thereof. Other support materials will be readily apparent to those of skill in the art upon review of this disclosure. In a preferred embodiment the support is flat glass or single-crystal silicon.

Thus, the invention provides methods for preparing arrays of nucleic acid molecules attached to supports. In some embodiments, these nucleic acid molecules will have recombination sites at one or more (e.g., one, two, three or four) of their termini. In some additional embodiments, one nucleic acid molecule will be attached directly to the support, or to a specific section of the support, and one or more additional nucleic acid molecules will be indirectly attached to the support via attachment to the nucleic acid molecule which is attached directly to the support. In such cases, the nucleic acid molecule which is attached directly to the support provides a site of nucleation around which a nucleic acid array may be constructed.

Figure 11:
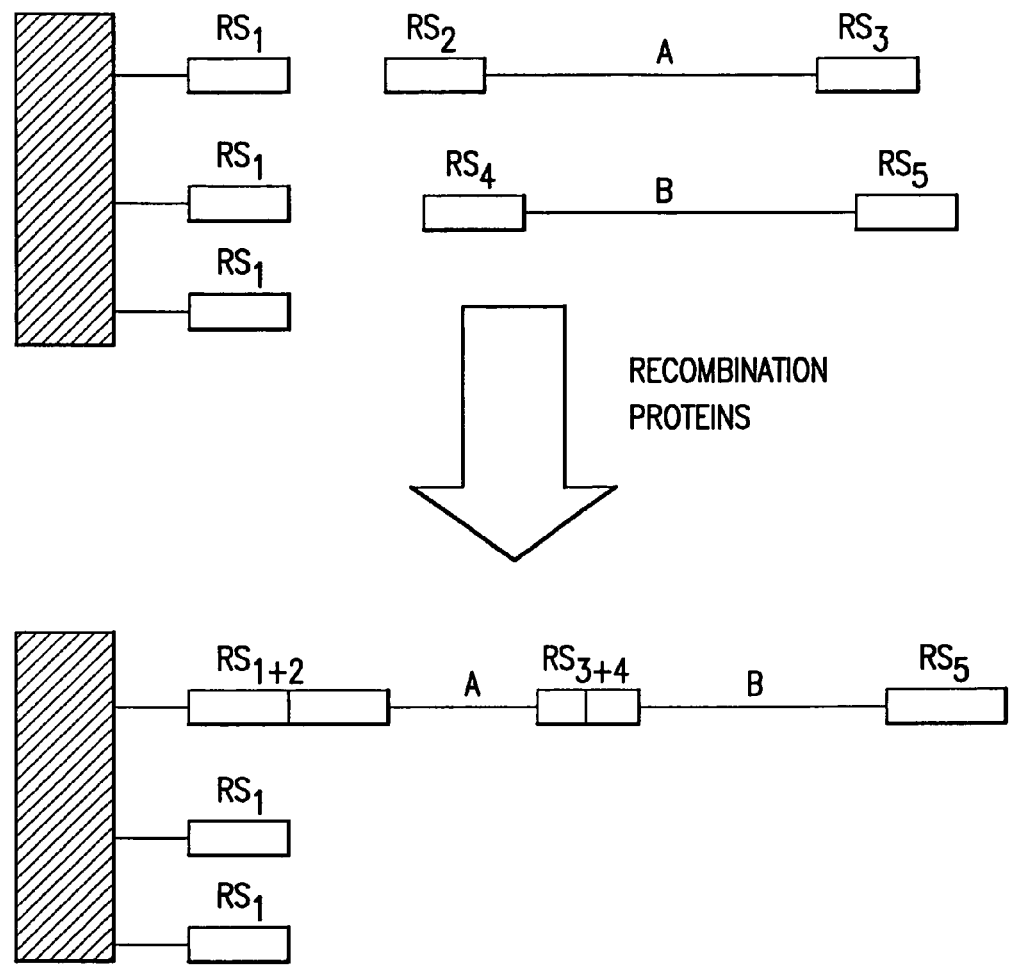
FIG. 11 is a schematic representation of joining multiple molecules and/or compounds (A and B). Labels used in this figure correspond to those in FIG. 10. The addition of A and B can be simultaneous or sequential.
Figure 12:
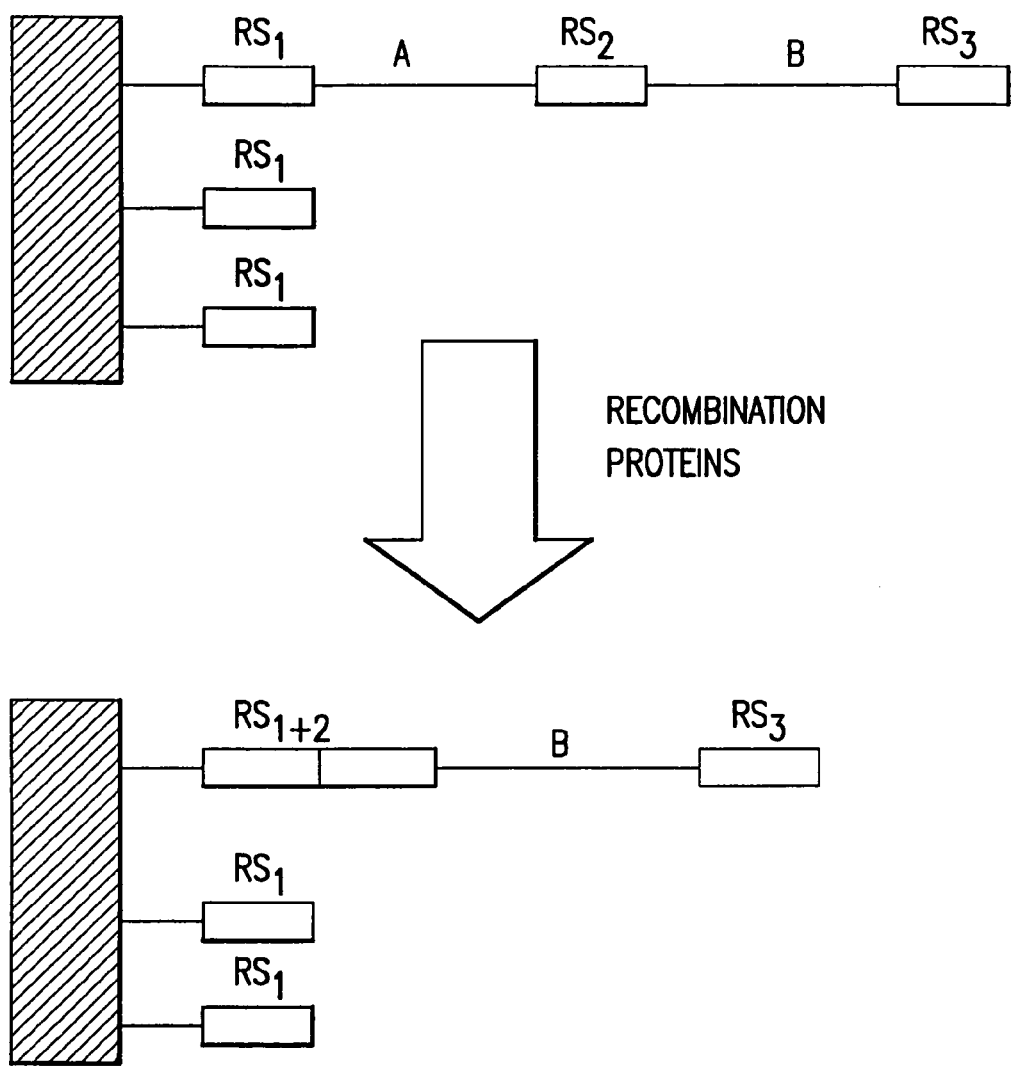
FIG. 12 is a schematic representation of deleting a portion of a molecule or compound (A) from a support. Labels used in this figure correspond to those in FIG. 10.
Figure 13:
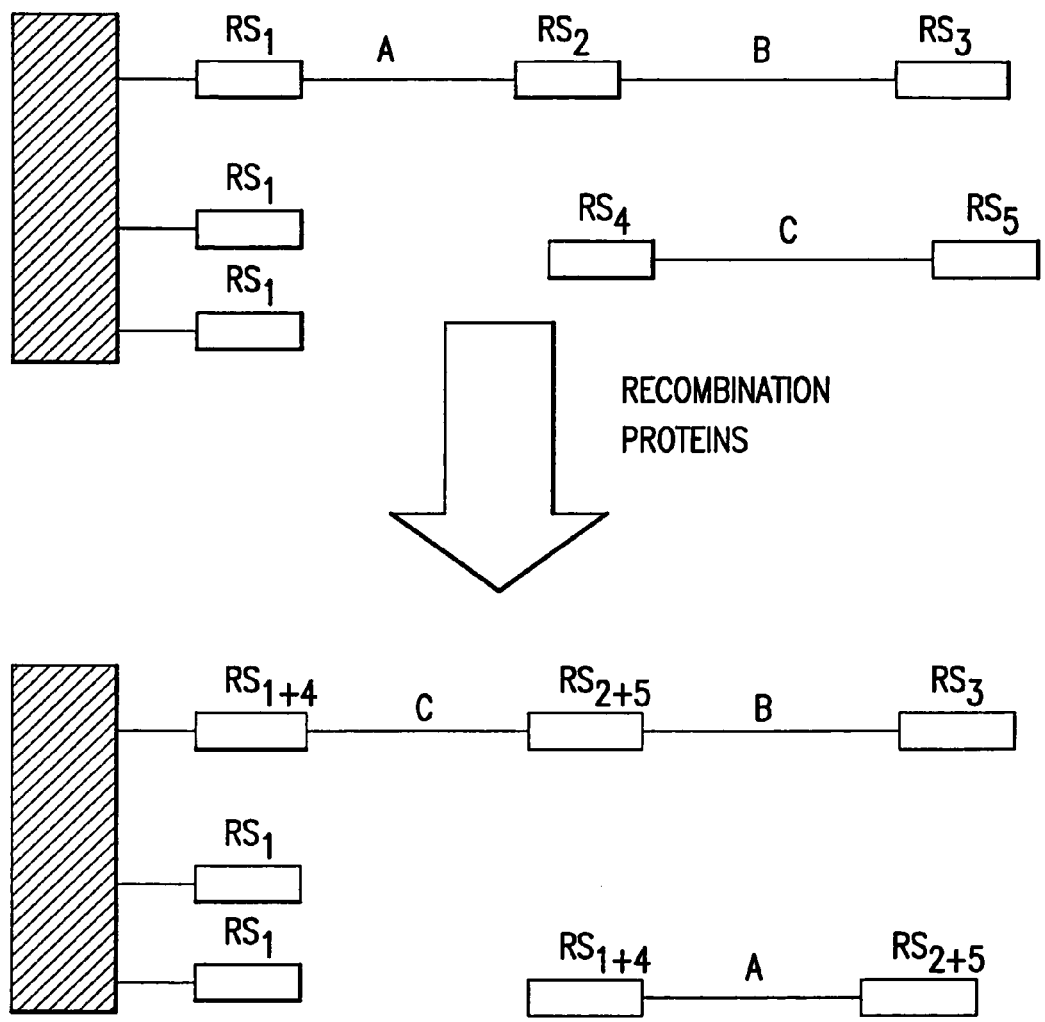
FIG. 13 is a schematic representation of replacing a portion of a molecule or compound (A) with a second molecule or compound (C). Labels used in this figure correspond to those in FIG. 10.

The invention further provides methods for linking supports to each other and for linking molecules bound to the same support together. Using FIG. 11 for non-limiting illustration of one embodiment of such a process, a recombination site designated RS$_6$ can be positioned at the end of the RS$_5$ site on the A/B composition shown attached to the support in the lower portion of the figure. Further, an identical composition may also be attached to another part of the same or different support. Recombination between the RS$_6$ sites can then be used to connect the two compositions, thereby forming either a linkage between two compositions attached to the same support or two compositions attached to the different support. The invention thus provides methods for cross-linking compounds attached to the same support by linking one or more compositions bound to the support using recombination sites. The invention also provides methods for cross-linking separate supports by linking one or more compositions bound to these supports suing recombination sites.

In one aspect, the invention provides supports containing nucleic acid molecules which are produced by methods of the invention. In many embodiments, the nucleic acid molecules of these supports will contain at least one recombination site. In some embodiments, this recombination site will have undergone recombination prior to attachment of the nucleic acid molecule to the support. These bound nucleic acid molecules are useful, for example, for identifying other nucleic acid molecules (e.g., nucleic acid molecules which hybridize to the bound nucleic acid molecules under stringent hybridization conditions) and proteins which have binding affinity for the bound nucleic acid molecules. Expression products may also be produced from these bound nucleic acid molecules while the nucleic acid molecules remain bound to the support. Thus, compositions and methods of the invention can be used to identify expression products and products produced by these expression products.

In other embodiments, nucleic acid molecules bound to supports will undergo recombination after attachment of the nucleic acid molecule to the support. As already discussed, these bound nucleic acid molecules may thus be used to identify nucleic acid molecules which encode expression products involved in one or a specified number of biological processes or pathways.

Further, nucleic acid molecules attached to supports may be released from these supports. Methods for releasing nucleic acid molecules include restriction digestion, recombination, and altering conditions (e.g., temperature, salt concentrations, etc.) to induce the dissociation of nucleic acid molecules which have hybridized to bound nucleic acid molecules. Thus, methods of the invention include the use of supports to which nucleic acid molecules have been bound for the isolation of nucleic acid molecules.

As noted above, in one aspect, the invention provides methods for screening nucleic acid libraries to identifying nucleic acid molecules which encode expression products involved in the same biological processes or pathways. In specific embodiments, such methods involve (1) attaching a nucleic acid molecule comprising at least one recombination site to a support, (2) contact the bound nucleic acid molecule with a library of nucleic acid molecules, wherein individual nucleic acid molecules of the library comprise at least one recombination site, under conditions which facilitate recombination between the bound nucleic acid molecule and nucleic acid molecules of the library, and (3) screening for either expression products of the nucleic acid molecule formed by recombination or products produced by the expression products of these nucleic acid molecules.

Examples of compositions which can be formed by binding nucleic acid molecules to supports are "gene chips," often referred to in the art as "DNA microarrays" or "genome chips" (see U.S. Pat. Nos. 5,412,087 and 5,889,165, and PCT Publication Nos. WO 97/02357, WO 97/43450, WO 98/20967, WO 99/05574, WO 99/05591, and WO 99/40105, the disclosures of which are incorporated by reference herein in their entireties). In various embodiments of the invention, these gene chips may contain two- and three-dimensional nucleic acid arrays described herein.

The adressability of nucleic acid arrays of the invention means that molecules or compounds which bind to particular nucleotide sequences can be attached to the arrays. Thus, components such as proteins and other nucleic acids can be attached to specific locations/positions in nucleic acid arrays of the invention.

Thus, in one aspect, the invention provides affinity purification methods comprising (1) providing a support to which nucleic acid molecules comprising at least one recombination site are bound, (2) attaching one or more additional nucleic acid molecules to the support using recombination reactions, (3) contacting the support with a composition containing molecules or compounds which have binding affinity for nucleic acid molecules bound to the support, under conditions which facilitate binding of the molecules or compounds to the nucleic acid molecules bound to the support, (4) altering the conditions to facilitate the release of the bound molecules or compounds, and (5) collecting the released molecules or compounds.

Methods of Nucleic Acid Synthesis, Amplification and Sequencing

The present invention may be used in combination with any method involving the synthesis of nucleic acid molecules, such as DNA (including cDNA) and RNA molecules. Such methods include, but are not limited to, nucleic acid synthesis methods, nucleic acid amplification methods and nucleic acid sequencing methods. Such methods may be used to prepare molecules (e.g., starting molecules) used in the invention or to further manipulate molecules or vectors produced by the invention.

Nucleic acid synthesis methods according to this aspect of the invention may comprise one or more steps (e.g., two, three, four, five, seven, ten, twelve, fifteen, etc.). For example, the invention provides a method for synthesizing a nucleic acid molecule comprising (a) mixing a nucleic acid template (e.g., a nucleic acid molecules or vectors of the invention) with one or more primers (e.g., two, three, four, five, seven, ten, twelve, fifteen, twenty, thirty, fifty, etc.) and one or more enzymes (e.g., two, three, four, five, seven, etc.) having polymerase or reverse transcriptase activity to form a mixture; and (b) incubating the mixture under conditions sufficient to make a first nucleic acid molecule complementary to all or a portion of the template. According to this aspect of the invention, the nucleic acid template may be a DNA molecule such as a cDNA molecule or library, or an RNA molecule such as a mRNA molecule. Conditions sufficient to allow synthesis such as pH, temperature, ionic strength, and incubation times may be optimized by those skilled in the art. If desired, recombination sites may be added to such synthesized molecules during or after the synthesis process (see, e.g., U.S. patent application Ser. No. 09/177,387 filed Oct. 23, 1998 based on U.S. provisional patent application No. 60/065,930 filed Oct. 24, 1997).

In accordance with the invention, the target or template nucleic acid molecules or libraries may be prepared from nucleic acid molecules obtained from natural sources, such as a variety of cells, tissues, organs or organisms. Cells that may be used as sources of nucleic acid molecules may be prokaryotic (bacterial cells, including those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces*) or eukaryotic (including fungi (especially yeast's), plants, protozoans and other parasites, and animals including insects (particularly *Drosophila* spp. cells), nematodes (particularly *Caenorhabditis elegans* cells), and mammals (particularly human cells)).

Of course, other techniques of nucleic acid synthesis which may be advantageously used will be readily apparent to one of ordinary skill in the art.

In other aspects of the invention, the invention may be used in combination with methods for amplifying or sequencing nucleic acid molecules. Nucleic acid amplification methods according to this aspect of the invention may include the use of one or more polypeptides having reverse transcriptase activity, in methods generally known in the art as one-step (e.g., one-step RT-PCR) or two-step (e.g., two-step RT-PCR) reverse transcriptase-amplification reactions. For amplification of long nucleic acid molecules (i.e., greater than about 3–5 Kb in length), a combination of DNA polymerases may be used, as described in WO 98/06736 and WO 95/16028.

Amplification methods according to the invention may comprise one or more steps (e.g., two, three, four, five, seven, ten, etc.). For example, the invention provides a method for amplifying a nucleic acid molecule comprising (a) mixing one or more enzymes with polymerase activity (e.g., two, three, four, five, seven, ten, etc.) with one or more nucleic acid templates (e.g., two, three, four, five, seven, ten, twelve, fifteen, twenty, thirty, fifty, one hundred, etc.); and (b) incubating the mixture under conditions sufficient to allow the enzyme with polymerase activity to amplify one or more nucleic acid molecules complementary to all or a portion of the templates. The invention also provides nucleic acid molecules amplified by such methods. If desired, recombination sites may be added to such amplified molecules during or after the amplification process (see, e.g., U.S. patent application Ser. No. 09/177,387 filed Oct. 23, 1998 based on U.S. provisional patent application No. 60/065,930 filed Oct. 24, 1997).

General methods for amplification and analysis of nucleic acid molecules or fragments are well known to one of ordinary skill in the art (see, e.g., U.S. Pat. Nos. 4,683,195; 4,683,202; and 4,800,159; Innis, M. A., et al., eds., PCR Protocols: A Guide to Methods and Applications, San Diego, Calif.: Academic Press, Inc. (1990); Griffin, H. G., and Griffin, A. M., eds., PCR Technology: Current Innovations, Boca Raton, Fla.: CRC Press (1994)). For example, amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822).

Typically, these amplification methods comprise: (a) mixing one or more enzymes with polymerase activity with the nucleic acid sample in the presence of one or more primers, and (b) amplifying the nucleic acid sample to generate a collection of amplified nucleic acid fragments, preferably by PCR or equivalent automated amplification technique.

Following amplification or synthesis by the methods of the present invention, the amplified or synthesized nucleic acid fragments may be isolated for further use or characterization. This step is usually accomplished by separation of the amplified or synthesized nucleic acid fragments by size or by any physical or biochemical means including gel electrophoresis, capillary electrophoresis, chromatography (including sizing, affinity and immunochromatography), density gradient centrifugation and immunoadsorption. Separation of nucleic acid fragments by gel electrophoresis is particularly preferred, as it provides a rapid and highly reproducible means of sensitive separation of a multitude of nucleic acid fragments, and permits direct, simultaneous comparison of the fragments in several samples of nucleic acids. One can extend this approach, in another preferred embodiment, to isolate and characterize these fragments or any nucleic acid fragment amplified or synthesized by the methods of the invention. Thus, the invention is also directed to isolated nucleic acid molecules produced by the amplification or synthesis methods of the invention.

In this embodiment, one or more of the amplified or synthesized nucleic acid fragments are removed from the gel which was used for identification (see above), according to standard techniques such as electroelution or physical excision. The isolated unique nucleic acid fragments may then be inserted into standard vectors, including expression vectors, suitable for transfection or transformation of a variety of prokaryotic (bacterial) or eukaryotic (yeast, plant or animal including human and other mammalian) cells. Alternatively, nucleic acid molecules produced by the methods of the invention may be further characterized, for example by sequencing (i.e., determining the nucleotide sequence of the nucleic acid fragments), by methods described below and others that are standard in the art (see, e.g., U.S. Pat. Nos. 4,962,022 and 5,498,523, which are directed to methods of DNA sequencing).

Nucleic acid sequencing methods according to the invention may comprise one or more steps. For example, the invention may be combined with a method for sequencing a nucleic acid molecule comprising (a) mixing an enzyme with polymerase activity with a nucleic acid molecule to be sequenced, one or more primers, one or more nucleotides, and one or more terminating agents (such as a dideoxynucleotides) to form a mixture; (b) incubating the mixture under conditions sufficient to synthesize a population of molecules complementary to all or a portion of the molecule to be sequenced;

and (c) separating the population to determine the nucleotide sequence of all or a portion of the molecule to be sequenced.

Nucleic acid sequencing techniques which may be employed include dideoxy sequencing methods such as those disclosed in U.S. Pat. Nos. 4,962,022 and 5,498,523.

Kits

In another aspect, the invention provides kits which may be used in conjunction with the invention. Kits according to this aspect of the invention may comprise one or more containers, which may contain one or more components selected from the group consisting of one or more nucleic acid molecules or vectors of the invention, one or more primers, the molecules and/or compounds of the invention, supports of the invention, one or more polymerases, one or more reverse transcriptases, one or more recombination proteins (or other enzymes for carrying out the methods of the invention), one or more buffers, one or more detergents, one or more restriction endonucleases, one or more nucleotides, one or more terminating agents (e.g., ddNTPs), one or more transfection reagents, pyrophosphatase, and the like.

A wide variety of nucleic acid molecules or vectors of the invention can be used with the invention. Further, due to the modularity of the invention, these nucleic acid molecules and vectors can be combined in wide range of ways. Examples of nucleic acid molecules which can be supplied in kits of the invention include those that contain promoters, signal peptides, enhancers, repressors, selection markers, transcription signals, translation signals, primer hybridization sites (e.g., for sequencing or PCR), recombination sites, restriction sites and polylinkers, sites which suppress the termination of translation in the presence of a suppressor tRNA, suppressor tRNA coding sequences, sequences which encode domains and/or regions (e.g., 6 His tag) for the preparation of fusion proteins, origins of replication, telomeres, centromeres, and the like. Similarly, libraries can be supplied in kits of the invention. These libraries may be in the form of replicable nucleic acid molecules or they may comprise nucleic acid molecules which are not associated with an origin of replication. As one skilled in the art would recognize, the nucleic acid molecules of libraries, as well as other nucleic acid molecules, which are not associated with an origin of replication either could be inserted into other nucleic acid molecules which have an origin of replication or would be an expendable kit components.

Further, in some embodiments, libraries supplied in kits of the invention may comprise two components: (1) the nucleic acid molecules of these libraries and (2) 5' and/or 3' recombination sites. In some embodiments, when the nucleic acid molecules of a library are supplied with 5' and/or 3' recombination sites, it will be possible to insert these molecules into vectors, which also may be supplied as a kit component, using recombination reactions. In other embodiments, recombination sites can be attached to the nucleic acid molecules of the libraries before use (e.g., by the use of a ligase, which may also be supplied with the kit). In such cases, nucleic acid molecule which contain recombination sites or primers which can be used to generate recombination sites may be supplied with the kits.

Vector supplied in kits of the invention can vary greatly. In most instances, these vectors will contain an origin of replication, at least one selectable marker, and at least one recombination site. For example, vectors supplied in kits of the invention can have four separate recombination sites which allow for insertion of nucleic acid molecules at two different locations. A vector of this type is shown schematically in FIG. 6. Other attributes of vectors supplied in kits of the invention are described elsewhere herein.

Kits of the invention can also be supplied with primers. These primers will generally be designed to anneal to molecules having specific nucleotide sequences. For example, these primers can be designed for use in PCR to amplify a particular nucleic acid molecule. Further, primers supplied with kits of the invention can be sequencing primers designed to hybridize to vector sequences. Thus, such primers will generally be supplied as part of a kit for sequencing nucleic acid molecules which have been inserted into a vector.

One or more buffers (e.g., one, two, three, four, five, eight, ten, fifteen) may be supplied in kits of the invention. These buffers may be supplied at a working concentrations or may be supplied in concentrated form and then diluted to the working concentrations. These buffers will often contain salt, metal ions, co-factors, metal ion chelating agents, etc. for the enhancement of activities of the stabilization of either the buffer itself or molecules in the buffer. Further, these buffers may be supplied in dried or aqueous forms. When buffers are supplied in a dried form, they will generally be dissolved in water prior to use. Examples of buffers suitable for use in kits of the invention are set out in the following examples.

Supports suitable for use with the invention (e.g., solid supports, semi-solid supports, beads, multi-well tubes, etc., described above in more detail) may also be supplied with kits of the invention. Exemplary uses of supports in processes of the invention are shown in FIGS. 10–13.

Kits of the invention may contain virtually any combination of the components set out above or described elsewhere herein. As one skilled in the art would recognize, the components supplied with kits of the invention will vary with the intended use for the kits. Thus, kits may be designed to perform various functions set out in this application and the components of such kits will vary accordingly.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

The entire disclosures of U.S. application Ser. No. 08/486,139 (now abandoned), filed Jun. 7, 1995, U.S. application Ser. No. 08/663,002, filed Jun. 7, 1996 (now U.S. Pat. No. 5,888,732), U.S. application Ser. No. 09/233,492, filed Jan. 20, 1999, U.S. Pat. No. 6,143,557, issued Nov. 7, 2000, U.S. Appl. No. 60/065,930, filed Oct. 24,1997, U.S. application Ser. No. 09/177,387 filed Oct. 23,1998, U.S. application Ser. No. 09/296,280, filed Apr. 22, 1999, U.S. application Ser. No. 09/296,281, filed Apr. 22, 1999, U.S. Appl. No. 60/108,324, filed Nov. 13, 1998,U.S. application Ser. No. 09/438,358, filed Nov. 12, 1999, U.S. application Ser. No. 09/695,065, filed Oct. 25, 2000, U.S. application Ser. No. 09/432,085 filed Nov. 2, 1999, U.S. Appl. No. 60/122,389, filed Mar. 2, 1999, U.S. application Ser. No. 60/126,049, filed Mar. 23, 1999, U.S. Appl. No. 60/136,744, filed May 28, 1999, U.S. application Ser. No. 60/122,392, filed Mar. 2, 1999, and U.S. Appl. No. 60/161,403, filed Oct. 25, 1999, are herein incorporated by reference.

EXAMPLES

EXAMPLE 1

Simultaneous Cloning of Two Nucleic Acid Segments Using an LR Reaction

Two nucleic acid segments may be cloned in a single reaction using methods of the present invention. Methods of the present invention may comprise the steps of providing a first nucleic acid segment flanked by a first and a second recombination site, providing a second nucleic acid segment flanked by a third and a fourth recombination site, wherein either the first or the second recombination site is capable of recombining with either the third or the fourth recombination site, conducting a recombination reaction such that the two nucleic acid segments are recombined into a single nucleic acid molecule and cloning the single nucleic acid molecule.

With reference to FIG. 2, two nucleic acid segments flanked by recombination sites may be provided. Those skilled in the art will appreciate that the nucleic acid segments may be provided either as discrete fragments or as part of a larger nucleic acid molecule and may be circular and optionally supercoiled or linear. The sites can be selected such that one member of a reactive pair of sites flanks each of the two segments.

By "reactive pair of sites," what is meant is two recombination sites that can, in the presence of the appropriate enzymes and cofactors, recombine. For example, in some preferred embodiments, one nucleic acid molecule may comprise an attR site while the other comprises an attL site that reacts with the attR site. As the products of an LR reaction are two molecules, one of which comprises an attB site and one of which comprises an attP site, it is possible to arrange the orientation of the starting attL and attR sites such that, after joining, the two starting nucleic acid segments are separated by a nucleic acid sequence that comprises either an attB site or an attP site.

In some preferred embodiments, the sites may be arranged such that the two starting nucleic acid segments are separated by an attB site after the recombination reaction. In other preferred embodiments, recombination sites from other recombination systems may be used. For example, in some embodiments one or more of the recombination sites may be a lox site or derivative. In some preferred embodiments, recombination sites from more than one recombination system may be used in the same construct. For example, one or more of the recombination sites may be an att site while others may be lox sites. Various combinations of sites from different recombination systems may occur to those skilled in the art and such combinations are deemed to be within the scope of the present invention.

As shown in FIG. 2, nucleic acid segment A (DNA-A) may be flanked by recombination sites having unique specificity, for example attL1 and attL3 sites and nucleic acid segment B (DNA-B) may be flanked by recombination sites attR3 and attL2. For illustrative purposes, the segments are indicated as DNA. This should not be construed as limiting the nucleic acids used in the practice of the present invention to DNA to the exclusion of other nucleic acids. In addition, in this and the subsequent examples, the designation of the recombination sites (i.e., L1, L3, R1, R3, etc.) is merely intend to convey that the recombination sites used have different specificities and should not be construed as limiting the invention to the use of the specifically recited sites. One skilled in the art could readily substitute other pairs of sites for those specifically exemplified.

The attR3 and attL3 sites comprise a reactive pair of sites. Other pairs of unique recombination sites may be used to flank the nucleic acid segments. For example, lox sites could be used as one reactive pair while another reactive pair may be att sites and suitable recombination proteins included in the reaction. Likewise, the recombination sites discussed above can be used in various combinations. In this embodiment, the only critical feature is that, of the recombination sites flanking each segment, one member of a reactive pair of sites, in this example an LR pair L3 and R3, is present on one nucleic acid segment and the other member of the reactive pair is present on the other nucleic acid segment. The two segments may be contacted with the appropriate enzymes and a Destination Vector.

The Destination Vector comprises a suitable selectable marker flanked by two recombination sites. In some embodiments, the selectable marker may be a negative selectable marker (such as a toxic gene, e.g., ccdb). One site in the Destination Vector will be compatible with one site present on one of the nucleic acid segments while the other compatible site present in the Destination Vector will be present on the other nucleic acid segment.

Absent a recombination between the two starting nucleic acid segments, neither starting nucleic acid segment has recombination sites compatible with both the sites in the Destination Vector. Thus, neither starting nucleic acid segment can replace the selectable marker present in the Destination Vector.

The reaction mixture may be incubated at about 25° C. for from about 60 minutes to about 16 hours. All or a portion of the reaction mixture will be used to transform competent microorganisms and the microorganisms screened for the presence of the desired construct.

In some embodiments, the Destination Vector comprises a negative selectable marker and the microorganisms transformed are susceptible to the negative selectable marker present on the Destination Vector. The transformed microorganisms will be grown under conditions permitting the negative selection against microorganisms not containing the desired recombination product.

In FIG. 2, the resulting desired product consists of DNA-A and DNA-B separated by an attB3 site and cloned into the Destination Vector backbone. In this embodiment, the same type of reaction (i.e., an LR reaction) may be used to combine the two fragments and insert the combined fragments into a Destination Vector.

In some embodiments, it may not be necessary to control the orientation of one or more of the nucleic acid segments and recombination sites of the same specificity can be used on both ends of the segment.

With reference to FIG. 2, if the orientation of segment A with respect to segment B were not critical, segment A could be flanked by L1 sites on both ends oriented as inverted repeats and the end of segment B to be joined to segment A could be equipped with an RI site. This might be useful in generating additional complexity in the formation of combinatorial libraries between segments A and B. That is, the joining of the segments can occur in various orientations and given that one or both segments joined may be derived from one or more libraries, a new population or library comprising hybrid molecules in random orientations may be constructed according to the invention.

Although, in the present examples, the recombination between the two starting nucleic acid segments is shown as occurring before the recombination reactions with the Destination Vector, the order of the recombination reactions is not important. Thus, in some embodiments, it may be desirable to conduct the recombination reaction between the segments and isolate the combined segments. The combined segments can be used directly, for example, may be amplified, sequenced or used as linear expression elements as taught by Sykes, et al. (*Nature Biotechnology* 17:355–359, 1999). In some embodiments, the joined segments may be encapsulated as taught by Tawfik, et al. (*Nature Biotechnology* 16:652–656, 1998) and subsequently assayed for one or more desirable properties. In some embodiments, the combined segments may be used for in vitro expression of RNA by, for example, including a promoter such as the T7 promoter or SP6 promoter on one of the segments. Such in vitro expressed RNA may optionally be translated in an in vitro translation system such as rabbit reticulocyte lysate.

Optionally, the joined segments may be further reacted with a Destination Vector resulting in the insertion of the combined segments into the vector. In some instances, it may be desirable to isolate an intermediate comprising one of the segments and the vector. For insertion of the segments into a vector, it is not critical to the practice of the present invention whether the recombination reaction joining the two segments occurs before or after the recombination reaction between the segments and the Destination Vector.

According to the invention, all three recombination reactions preferably occur (i.e., the reaction between segment A and the Destination Vector, the reaction between segment B and the Destination Vector, and the reaction between segment A and segment B) in order to produce a nucleic acid molecule in which both of the two starting nucleic acid segments are now joined in a single molecule. In some embodiments, recombination sites may be selected such that, after insertion into the vector, the recombination sites flanking the joined segments form a reactive pair of sites and the joined segments may be excised from the vector by reaction of the flanking sites with suitable recombination proteins.

With reference to FIG. 2, if the L2 site on segment B were replaced by an L1 site in the opposite orientation with respect to segment B (i.e., the long portion of the box indicating the recombination site was not adjacent to the segment) and the R2 site in the vector were replaced by an R1 site in opposite orientation, the recombination reaction would produce an attP1 site in the vector. The attP I site would then be capable of reaction with the attB1 site on the other end of the joined segments. Thus, the joined segments could be excised using the recombination proteins appropriate for a BP reaction.

This embodiment of the invention is particularly suited for the construction of combinatorial libraries. In some preferred embodiments, each of the nucleic acid segments in FIG. 2 may represent libraries, each of which may have a known or unknown nucleic acid sequence to be screened. In some embodiments, one or more of the segments may have a sequence encoding one or more permutations of the amino acid sequence of a given peptide, polypeptide or protein. In some embodiments, each segment may have a sequence that encodes a protein domain or a library representing various permutations of the sequence of protein domain. For example, one segment may represent a library of mutated forms of the variable domain of an antibody light chain while the other segment represents a library of mutated forms of an antibody heavy chain. Thus, recombination would generate a population of molecules (e.g., antibodies, single-chain antigen-binding proteins, etc.) each potentially containing a unique combination of sequences and, therefore, a unique binding specificity.

In other preferred embodiments, one of the segments may represent a single nucleic acid sequence while the other represents a library. The result of recombination will be a population of sequences all of which have one portion in common and are varied in the other portion. Embodiments of this type will be useful for the generation of a library of fusion constructs. For example, DNA-A may comprise a regulatory sequence for directing expression (i.e., a promoter) and a sequence encoding a purification tag. Suitable purification tags include, but are not limited to, glutathione S-transferase (GST), the maltose binding protein (MBP), epitopes, defined amino acid sequences such as epitopes, haptens, six histidines (HIS6), and the like. DNA-B may comprise a library of mutated forms of a protein of interest. The resultant constructs could be assayed for a desired characteristic such as enzymatic activity or ligand binding.

Alternatively, DNA-B might comprise the common portion of the resulting fusion molecule. In some embodiments, the above described methods may be used to facilitate the fusion of promoter regions or transcription termination signals to the 5'-end or 3'-end of structural genes, respectively, to create expression cassettes designed for expression in different cellular contexts, for example, by adding a tissue-specific promoter to a structural gene.

In some embodiments, one or more of the segments may represent a sequence encoding members of a random peptide library. This approach might be used, for example, to generate a population of molecules with a certain desirable characteristic. For example, one segment might contain a sequence coding for a DNA binding domain while the other segment represents a random protein library. The resulting population might be screened for the ability to modulate the expression of a target gene of interest. In other embodiments, both segments may represent sequences encoding members of a random protein library and the resultant synthetic proteins (e.g., fusion proteins) could be assayed for any desirable characteristic such as, for example, binding a specific ligand or receptor or possessing some enzymatic activity.

It is not necessary that the nucleic acid segments encode an amino acid sequence. For example, both of the segments may direct the transcription of an RNA molecule that is not translated into protein. This will be useful for the construction of tRNA molecules, ribozymes and anti-sense molecules. Alternatively, one segment may direct the transcription of an untranslated RNA molecule while the other codes for a protein. For example, DNA-A may direct the transcription of an untranslated leader sequence that enhances protein expression such as the encephalomyocarditis virus leader sequence (EMC leader) while DNA-B encodes a peptide, polypeptide or protein of interest. In some embodiments, a segment comprising a leader sequence might further comprise a sequence encoding an amino acid sequence. For example, DNA-A might have a nucleic acid sequence corresponding to an EMC leader sequence and a purification tag while DNA-B has a nucleic acid sequence encoding a peptide, polypeptide or protein of interest.

The above process is especially useful for the preparation of combinatorial libraries of single-chain antigen-binding proteins. Methods for preparing single-chain antigen-binding proteins are known in the art. (See, e.g., PCT Publication No. WO 94/07921, the entire disclosure of which is incorporated herein by reference.) Using the constructs shown in FIG. 6 for illustration, DNA-A could encode, for example, mutated forms of the variable domain of an antibody light chain and DNA-B could encode, for example, mutated forms of the variable domain of an antibody light chain. Further, the intervening nucleic acid between DNA-A and DNA-B could encode a peptide linker for connecting the light and heavy chains. Cells which express the single-chain antigen-binding proteins can then be screened to identify those which produce molecules that bind to a particular antigen.

Numerous variation of the above are possible. For example, instead of using a construct illustrated in FIG. 6, a constructs such as that illustrated in FIG. 2 could be used with the linker peptide coding region being embedded in the recombination site. This is one an example of recombination site embedded functionality discussed above.

As another example, single-chain antigen-binding proteins composed of two antibody light chains and two antibody heavy chains can also be produced. These single-chain antigen-binding proteins can be designed to associate and form multivalent antigen binding complexes. Using the constructs shown in FIG. 2 again for illustration, DNA-A and DNA-B could each encode, for example, mutated forms of the variable domain of an antibody light chain. At the same site in a similar vector or at another site in a vector which is designed for the insertion of four nucleic acid inserts, DNA-A and DNA-B could each encode, for example, mutated forms of the variable domain of an antibody heavy chain. Cells which express both single-chain antigen-binding proteins could then be screened to identify, for example, those which produce multivalent antigen-binding complexes having specificity for a particular antigen.

Thus, the methods of the invention can be used, for example, to prepare and screen combinatorial libraries to identify cells which produce antigen-binding proteins (e.g., antibodies and/or antibody fragments or antibody fragment complexes comprising variable heavy or variable light domains) having specificities for particular epitopes. The methods of the invention also methods for preparing antigen-binding proteins and antigen-binding proteins prepared by the methods of the invention.

EXAMPLE 2

Figure 3:
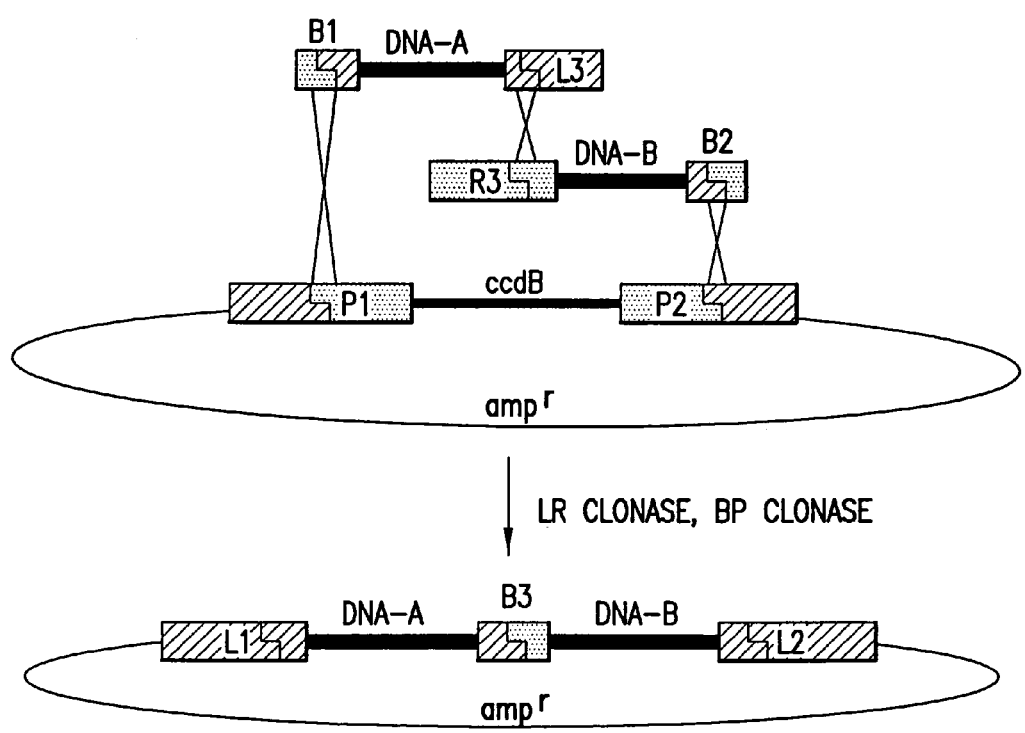
FIG. 3 is a schematic representation of the use of the present invention to clone two nucleic acid segments by joining the segments using an LR reaction and then inserting the joined fragments into a Destination Vector using a BP recombination reaction.

Simultaneous Cloning of Two Nucleic Acid Fragments Using an LR Reaction to Join the Segments and a BP Reaction to Insert the Segments into a Vector As shown in FIG. 3, a first nucleic acid segment flanked by an attB recombination site and an attL recombination site may be joined to a second nucleic acid segment flanked by an attR recombination site that is compatible with the attL site present on the first nucleic acid segment and flanked by an attB site that may be the same or different as the attB site present on the first segment. FIG. 3 shows an embodiment wherein the two attB sites are different. The two segments may be contacted with a vector containing attP sites in a BP reaction.

A subsequent LR reaction would generate a product consisting of DNA-A and DNA-B separated by either an attP site or an attB site (the product of the LR reaction) and cloned into the vector backbone. In the embodiment shown in FIG. 3, the attL and attR sites are arranged so as to generate an attB site between the segments upon recombination. In other embodiments, the attL and the attR may be oriented differently so as to produce an attP site between the segments upon recombination. In preferred embodiments, after recombination, the two segments may be separated by an attB site.

Those skilled in the art can readily optimize the conditions for conducting the reactions described above without the use of undue experimentation. In a typical reaction from about 50 ng to about 1000 ng of vector may be contacted with the fragments to be cloned under suitable reaction conditions. Each fragment may be present in a molar ratio of from about 25:1 to about 1:25 vector:fragment. In some embodiments, one or more of the fragments may be present at a molar ratio of from about 10:1 to 1:10 vector:fragment. In a preferred embodiment, each fragment may be present at a molar ratio of about 1:1 vector:fragment.

Typically, the nucleic acid may be dissolved in an aqueous buffer and added to the reaction mixture. One suitable set of conditions is 4 μl CLONASE™ enzyme mixture (e.g., Invitrogen Corp., Life Technologies Division, Cat. Nos. 11791-019 and 11789-013), 4 μl 5× reaction buffer and nucleic acid and water to a final volume of 20 μl. This will typically result in the inclusion of about 200 ng of Int and about 80 ng of IHF in a 20 μl BP reaction and about 150 ng Int, about 25 ng IHF and about 30 ng Xis in a 20 μl LR reaction.

In some preferred embodiments, particularly those in which attL sites are to be recombined with attR sites, the final reaction mixture may include about 50 mM Tris HCl, pH 7.5, about 1 mM EDTA, about 1 mg/ml BSA, about 75 mM NaCl and about 7.5 mM spermidine in addition to recombination enzymes and the nucleic acids to be combined. In other preferred embodiments, particularly those in which an attB site is to be recombined with an attP site, the final reaction mixture may include about 25 mM Tris HCl, pH 7.5, about 5 mM EDTA, about 1 mg/ml bovine serum albumin (BSA), about 22 mM NaCl, and about 5 mM spermidine.

When it is desired to conduct both a BP and an LR reaction without purifying the nucleic acids in between, the BP reaction can be conducted first and then the reaction conditions adjusted to about 50 mM NaCl, about 3.8 mM spermidine, about 3.4 mM EDTA and about 0.7 mg/ml by the addition of the LR CLONASE™ enzymes and concentrated NaCl. The reaction solution may be incubated at suitable temperature such as, for example, 25° C. for from about 60 minutes to 16 hours. After the recombination reaction, the solution may be used to transform competent host cells and the host cells screened as described above.

One example of a "one-tube" reaction protocol, which facilitates the transfer of PCR products directly to Expression Clones in a two-step reaction performed in a single tube follows. This process can also be used to transfer a gene from one Expression Clone plasmid backbone to another. The Expression Clone is first be linearized within the plasmid backbone to achieve the optimal topology for the BP reaction and to eliminate false-positive colonies due to co-transformation.

Twenty-five μl BP reaction mixture is prepared in a 1.5 ml tube with the following components:

| | |
|---|---|
| attB DNA (100–200 ng) | 1–12.5 μl |
| attP DNA (pDONR201) 150 ng/μl | 2.5 μl |
| BP Reaction Buffer | 5.0 μl |
| TE | to 20 μl |
| BP Clonase | 5.0 μl |
| Total vol. | 25 μl |

The contents of the tube is mixed and incubated for 4 hours, or longer, at 25° C. If the PCR product is amplified from a plasmid template containing selectable markers present on the GATEWAY™ pDONR or pDEST vectors (i.e., kan$^r$ or amp$^r$), the PCR product may be treated with the restriction endonuclease DpnI to degrade the plasmid. Such plasmids are a potential source of false-positive colonies in the transformation of GATEWAY™ reactions. Further, when the template for PCR or starting Expression Clone has the same selectable marker as the final Destination Vector (e.g., amp$^r$), plating on LB plates containing 100 μg/ml ampicillin can be used to determine the amount of false positive colonies carried over to the LR reaction step.

Five µl of the reaction mixture is transferred to a separate tube to which is added 0.5 µl Proteinase K Solution. This tube is then incubate for 10 minutes at 37° C. One hundred ill of competent cells are then transformed with 1–2 µl of the mixture and plated on LB plates containing 50 µg/ml kanamycin. This yields colonies for isolation of individual Entry Clones and for assessment of the BP Reaction efficiency.

The following components are added to the remaining 20 µl BP reaction described above:

| NaCl | 0.75 M | 1 µl |
|---|---|---|
| Destination Vector | 150 ng/µl | 3 µl |
| LR Clonase | | 6 µl |
| Total vol. | | 30 µl |

The mixture is then incubate at 25° C. for 2 hours, after which 3 µl of proteinase K solution, followed by a further incubation of 10 minutes at 37° C. 1–2 µl of this mixtures is then used to transform 100 µl competent cells, which are then plated on LB plates containing 100 µg/ml ampicillin.

EXAMPLE 3

Cloning of PCR Products Using Fragments by Converting attB Sites into a Reactive Pair of attL and attR Sites in a BP Reaction and Subsequent LR Reaction A similar strategy to that described in Example 2 can be used to recombine two PCR products and clone them simultaneously into a vector backbone. Since attL and attR sites are 100 and 125 base pairs long, respectively, it may be desirable to incorporate attB sites into the PCR primers since an attB site is 25 base pairs in length. Depending on the orientation of the attB site with respect to the nucleic acid segment being transferred, attB sites can be converted to either an attL or attR site by the BP reaction. Thus, the orientation of the attB site in the attB PCR primer determines whether the attB site is converted to attL or attR. This affords the GATEWAY™ system and methods of the invention great flexibility in the utilization of multiple att sites with unique specificity.

Figure 4:
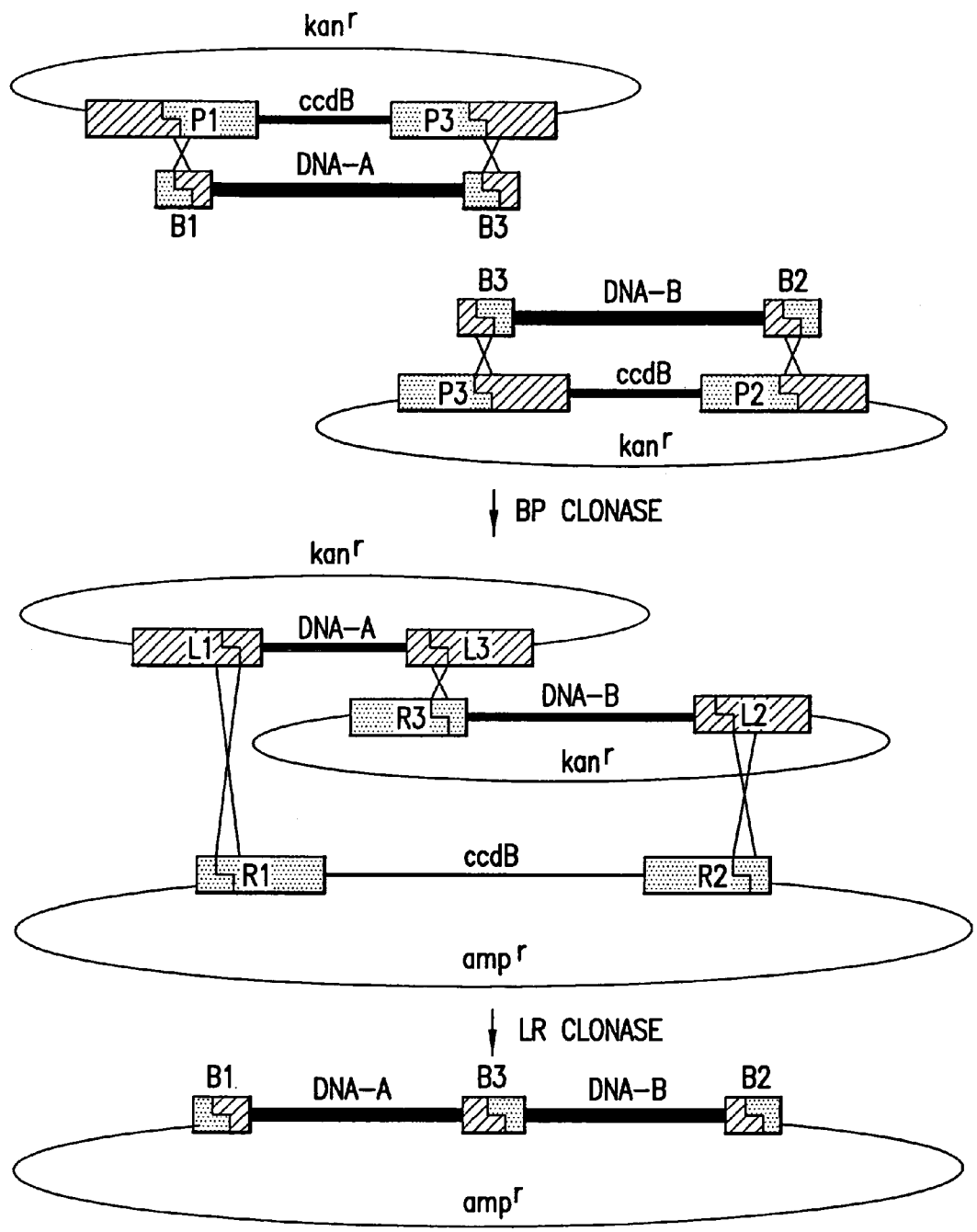
FIG. 4 is a schematic representation of the use of the present invention to clone two nucleic acid segments by performing a BP reaction followed by an LR reaction.

As shown in FIG. 4, two segments (e.g., PCR products) consisting of segment A flanked by mutated attB sites each having a different specificity (e.g., by attB1 and attB3) and segment B flanked by mutated attB sites of different specificity, wherein one of the attB sites present on segment A is the same as one of the attB sites present on segment B (e.g., segment B may contain attB3 and attB2 sites) may be joined and inserted into a vector. The segments may be reacted either individually or together with two attP site containing vectors in a BP reaction. Alternatively, the attP sites might be present on linear segments. One vector contains attP sites compatible with the attB sites present on segment A (e.g., attP1 and attP3 sites). The other vector contains attP sites compatible with the attB sites present on segment B (e.g., attP3 and attP2 sites). When linear segments are used to provide the attP sites, each attP site may be provided on a segment. The orientations of the attB3 and attP3 sites are such that an attR3 site would be generated at the 5'-end of the DNA-B segment and an attL3 site generated at the 3'-end of segment A. The resulting entry clones are mixed with a Destination Vector in a subsequent LR reaction to generate a product consisting of DNA-A and DNA-B separated by an attB3 site and cloned into the Destination Vector backbone.

This basic scheme has been used to link two segments, an attL1-fragment A-attL3 entry clone that is reacted with an attR3-fragment B-attL2 entry clone, and to insert the linked fragments into the destination vector. To generate the appropriate entry clones, two attP Donor vectors were constructed consisting of attP1-ccdB-attP3 and attP3R-ccdB-attP2 such that they could be reacted with appropriate attB PCR products in order to convert the attB sites to attL and attR sites. The designation attP3R is used to indicated that the orientation of the attP3 site is such that reaction with a DNA segment having a cognate attB site will result in the production of an attR site on the segment. This is represented schematically in FIG. 4 by the reversed orientation of the stippled and lined sections of the attB3 on segment B as compared to segment A. On segment B the stippled portion is adjacent to the segment while on segment A the lined portion is adjacent to the segment.

This methodology was exemplified by constructing a DNA segment in which the tetracycline resistance gene (tet) was recombined with the β-galactosidase gene such that the two genes were separated by an attB site in the product. The tet gene was PCR amplified with 5'-attB1 and 3'-attB3 ends. The lacZ gene was PCR amplified with 5'-attB3R and 3'-attB2 ends. The two PCR products were precipitated with polyethylene glycol (PEG). The B1-tet-B3 PCR product was mixed with an attP1-ccdB-attP3 donor vector and reacted with BP CLONASE™ using a standard protocol to generate an attL1-tet-attL3 entry clone. A correct tet entry clone was isolated and plasmid DNA prepared using standard techniques. In a similar fashion, the attB3R-lacZ-attB2 PCR product was mixed with an attP3R-ccdB-attP2 donor vector and reacted with BP CLONASE™ to generate an attR3-lacZ-attL2 entry clone.

In order to join the two segments in a single vector, an LR CLONASE™ reaction was prepared in a reaction volume of 20 µl containing the following components: 60 ng (25 fmoles) of the supercoiled tet entry clone; 75 ng (20 fmoles) of the supercoiled lacZ entry clone; 150 ng (35 fmoles) of pDEST6 (described in PCT Publication WO 00/52027, the entire disclosure of which is incorporated herein by reference) linearized with NcoI; 4 µl reaction buffer and 4 µl of LR CLONASE™. The final reaction mixture contained 51 mM Tris-HCl, 1 mM EDTA, 1 mg/ml BSA, 76 mM NaCl, 7.5 mM spermidine, 160 ng of Int, 35 ng of IHF and 35 ng of Xis. The reaction was incubated at 25° C. overnight and stopped with 2 µl of proteinase K solution (2 mg/ml). A 2 µl aliquot was used to transform 100 µl of E. coli DH5α LE cells and plated on LB plates containing ampicillin and XGal. Approximately 35,000 colonies were generated in the transformation mixture with cells at an efficiency of $1.6 \times 10^8$ cfu/µg of pUC DNA. All the colonies appeared blue indicating the presence of the lacZ gene. 24 colonies were streaked onto plates containing tetracycline and XGal. All of the colonies tested, 24/24, were resistant to tetracycline. 12 colonies were used to inoculate 2 ml of LB broth containing ampicillin for mini preps. 12/12 minipreps contained a supercoiled plasmid of the correct size (7 kb).

Figure 5:
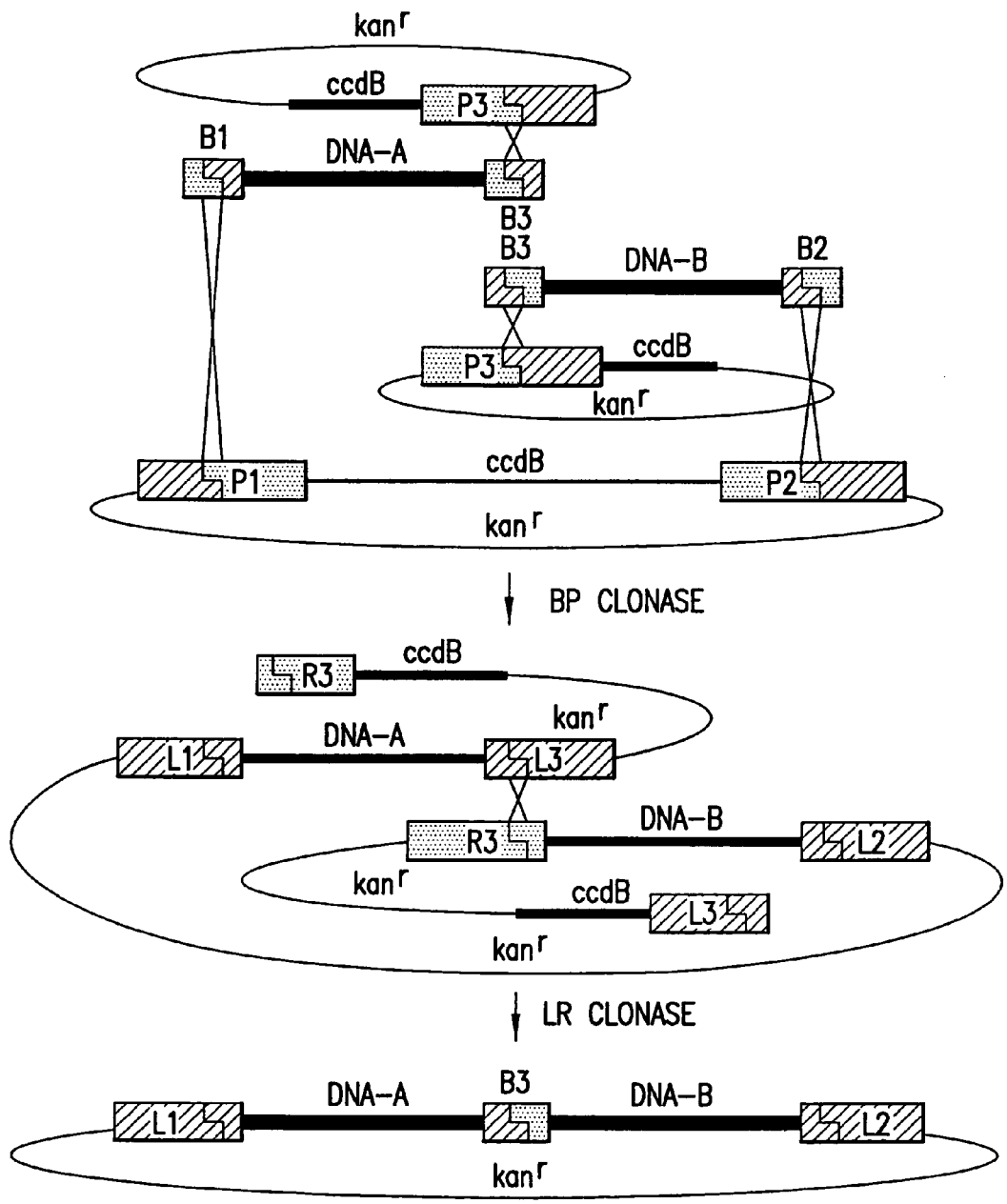
FIG. 5 is a schematic representation of two nucleic acid segments having attB sites being cloned by performing a first BP reaction to generate an attL site on one segment and an attR on the other followed by an LR reaction to combine the segments. In variations of this process, P1, P2, and/or P3 can be oligonucleotides or linear stretches of nucleotides.

In some embodiments, such as that shown in FIG. 5, two segments can be reacted with a vector containing a single recombination site in order to convert one of the recombination sites on the segments into a different recombination site. In some embodiments, segments containing attB sites may be reacted with a target vector having attP sites. For example, segments A and B are reacted either together or separately with a vector having an attP3 site in order to convert the attB3 sites on the segments into an attL3 and an attR3, respectively. This is done so that the subsequent LR reaction between the two segments results in their being joined by an attB site. The segments may be joined with the attP site containing vector before, simultaneously with or after the recombination reaction to convert the sites to generate a co-integrate molecule consisting of DNA-A flanked by attL1 and attL3 and DNA-B flanked by attR3 and attL2. A subsequent LR reaction will generate a product clone consisting of DNA-A and DNA-B separated by attB3 cloned into a vector backbone.

In some embodiments, an attP site designed to convert the attB used to link the segments to a reactive pair of attL and attR sites may be provided as shorter segments such as restriction fragments, duplexes of synthetic oligonucleotides or PCR fragments. Reactions involving a linear fragment in a BP reaction may require longer incubation times, such a overnight incubation.

The conversion of attB sites to attL or attR sites can also be accomplished solely by PCR. PCR primers containing attL or attR sites can be used to amplify a segment having an attB site on the end. Since the sequence of attL and attR sites contains a portion of the sequence of an attB site, the attB site in this case serves as an overlap region to which the attL or attR PCR primer can anneal. Extension of the annealed attL or attR primer through to the end of the PCR product will generate a fusion template for PCR amplification of the full length PCR product using flanking primers that anneal to the ends of the attL or attR sites. The primers for the PCR reaction may be provided as single stranded oligonucleotides. In some preferred embodiments, the primers may be provided as a duplex, for example, as the product of a PCR reaction to amplify either an attL or attR site.

EXAMPLE 4

Cloning of Two or More Nucleic Acid Fragments into Different Places in the Same Vector Two or more nucleic acid fragments can be cloned simultaneously into different regions of a vector having multiple sets of recombination sites each flanking a selectable marker. In some embodiments, one or more of the selectable markers may be a negative selectable marker.

Figure 6:
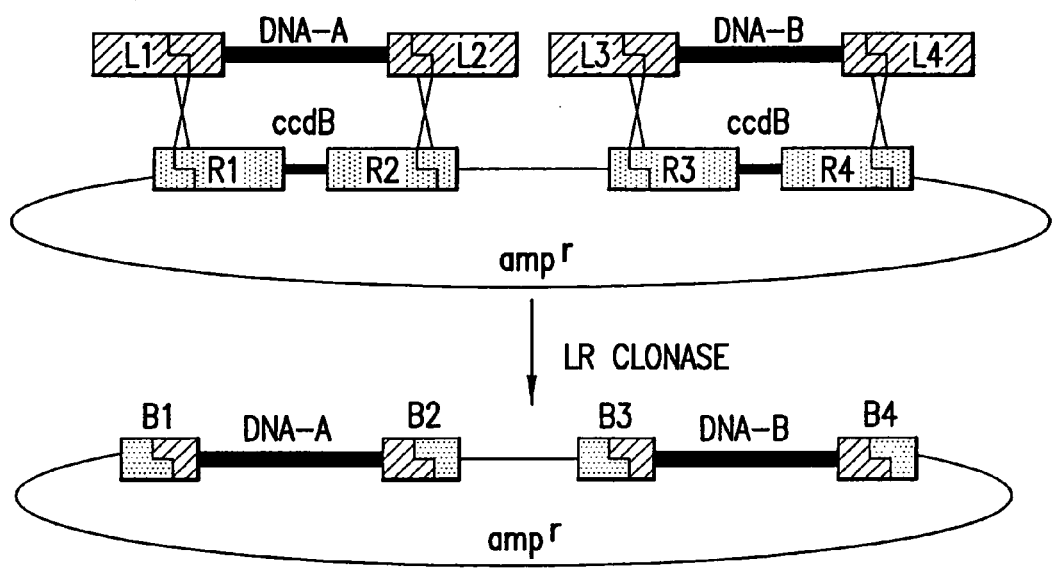
FIG. 6 is a schematic representation of the cloning of two nucleic acid segments into two separate sites in a Destination Vector using an LR reaction.

As shown in FIG. 6, two nucleic acid segments A and B which may be present as discrete fragments or as part of a larger nucleic acid molecule such as a plasmid, can be simultaneously cloned into the same destination vector. Nucleic acid segment A (DNA-A) flanked by recombination sites that do not recombine with each other (e.g., attL1 and attL2) and nucleic acid segment B (DNA-B) flanked by recombination sites that do not recombine with each other and do not recombine with the sites flanking segment A (e.g., attL3 and attL4) may be combined with a Destination Vector in an LR reaction. The Destination Vector will contain two pairs of recombination sites, each pair selected to recombine with the sites flanking one of the segments. As an example, FIG. 6 shows two pairs of attR sites (attR1/attR2 and attR3/attR4) each flanking a ccdb negative selectable marker. The three nucleic acids can be combined in a single LR reaction. The resulting product will consist of DNA-A and DNA-B flanked by pairs of attB sites and cloned into distinct regions of the Destination Vector.

Figure 7:
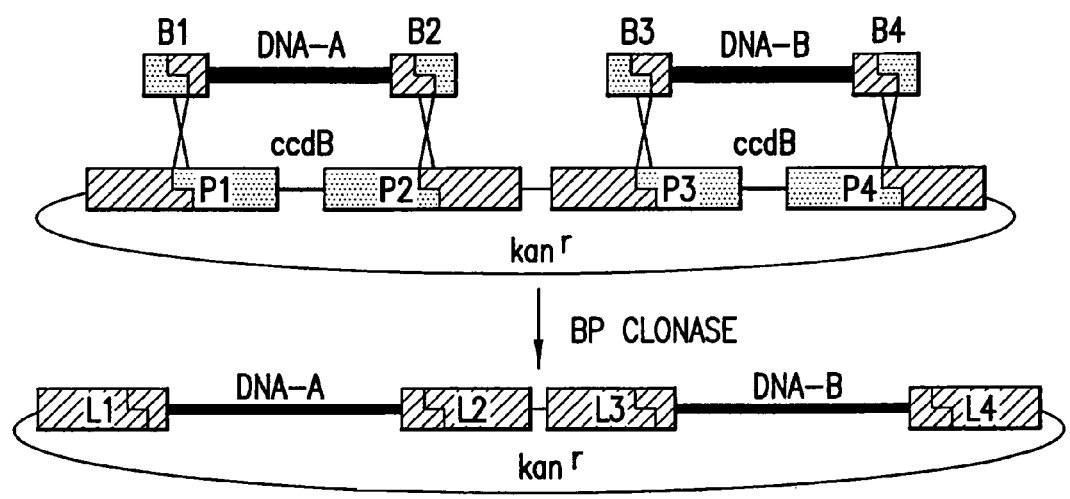
FIG. 7 is a schematic representation of the cloning of two nucleic acid segments into two separate sites in a vector using a BP reaction.

As shown in FIG. 7, an analogous method for inserting nucleic acid segments into a vector can be accomplished using a BP reaction. For example, DNA-A flanked by recombination sites attB1 and attB2 can be combined with DNA-B flanked by recombination sites attB3 and attB4 and a vector containing attP sites in a BP reaction. The resulting product would consist of DNA-A and DNA-B cloned between pairs of attL sites into distinct regions of the vector. In some embodiments, it may be desirable to insert the segments into the target vector sequentially and isolate an intermediate molecule comprising only one of the segments.

It is not necessary that all of the sites be derived form the same recombination system. For example, one segment may be flanked by lox sites while the other segment is flanked by att sites. A segment may have a lox site on one end and an att site on the other end or an fit site on one end. Various combinations of sites may be envisioned by those skilled in the art and such combinations are within the scope of the present invention.

In some embodiments, it may be desirable to isolate intermediates in the reaction shown in FIGS. 6 and 7. For example, it may be desirable to isolate a vector having only one of the segments inserted. The intermediate might be used as is or might serve as the substrate in a subsequent recombination reaction to insert the second segment.

In some embodiments, the present invention is a method of cloning n nucleic acid segments, wherein n is an integer greater than 1, comprising the steps of providing n nucleic acid segments, each segment flanked by two unique recombination sites, providing a vector comprising 2n recombination sites wherein each of the 2n recombination sites is capable of recombining with one of the recombination sites flanking one of the nucleic acid segments and conducting a recombination reaction such that the n nucleic acid segments are recombined into the vector thereby cloning the n nucleic acid segments. In further embodiments, the vector comprises n copies of a selectable marker each copy flanked by two recombination sites. In other embodiments, the vector comprises two or more different selectable markers each flanked by two recombination sites. In some embodiments, one or more of the selectable markers may be a negative selectable marker.

In some embodiments, the present invention provides a method of cloning, comprising the steps of providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and none of the first, fourth, fifth or sixth recombination sites is capable of recombining with any of the first through sixth recombination sites, providing a vector comprising a seventh and an eighth recombination site flanking a first selectable marker and comprising a ninth and a tenth recombination site flanking a second selectable marker wherein none of the seventh through tenth recombination sites can recombine with any of the seventh through tenth recombination sites, conducting a first recombination reaction such that the second and the third recombination sites recombine and conducting a second recombination reaction such that the first and the fourth recombination sites recombine with the seventh and the eighth recombination sites respectively and the fifth and the sixth recombination sites recombine with the ninth and the tenth recombination sites thereby cloning the first, second and third nucleic acid segments.

In some embodiments, a nucleic acid segment may comprise a sequence that functions as a promoter. In some embodiments, the first and the second nucleic acid segments may comprise a sequence encoding a polypeptide and the recombination places both polypeptides in the same reading frame. In some embodiments, a nucleic acid segment may comprise a sequence that functions as a transcription termination sequence.

The present invention provides an extremely versatile method for the modular construction of nucleic acids and proteins. Both the inserted nucleic acid segments and the vector can contain sequences selected so as to confer desired characteristics on the product molecules. In those embodiments exemplified in FIGS. 6 and 7, in addition to the inserted segments, one or more of the portions of the vector adjacent to the inserted segments as well as the portion of the vector separating the inserted segments can contain one or more selected sequences.

In some embodiments, the selected sequences might encode ribozymes, epitope tags, structural domains, selectable markers, internal ribosome entry sequences, promoters, enhancers, recombination sites and the like. In some preferred embodiments, the portion of the vector separating the inserted segments may comprise one or more selectable markers flanked by a reactive pair of recombination sites in addition to the recombination sites used to insert the nucleic acid segments.

This methodology will be particularly well suited for the construction of gene targeting vectors. For example, the segment of the vector between the pairs of recombination sites may encode one or more a selectable markers such as the neomycin resistance gene. Segments A and B may contain nucleic acid sequences selected so as to be identical or substantially identical to a portion of a gene target that is to be disrupted. After the recombination reaction, the Destination Vector will contain two portions of a gene of interest flanking a positive selectable marker. The vector can then be inserted into a cell using any conventional technology, such as transfection, whereupon the portions of the gene of interest present on the vector can recombine with the homologous portions of the genomic copy of the gene. Cells containing the inserted vector can be selected based upon one or more characteristics conferred by the selectable marker, for example, in the case when the selectable marker is the neomycin resistance gene, their resistance to G-418.

In some embodiments, one or more a negative selectable markers may be included in the portion of the Destination Vector that does not contain the target gene segments and the positive selectable marker. The presence of one or more negative selectable markers permits the selection against cells in which the entire Destination Vector was inserted into the genome or against cells in which the Destination Vector is maintained extrachromosomally.

In some preferred embodiments, additional recombination sites may be positioned adjacent to the recombination sites used to insert the nucleic acid segments. Molecules of this type will be useful in gene targeting application where it is desirable to remove the selectable marker from the targeted gene after targeting, the so called "hit and run" methodology. Those skilled in the art will appreciate that the segments containing homologous sequence need not necessarily correspond to the sequence of a gene. In some instances, the sequences may be selected to be homologous to a chromosomal location other than a gene.

This methodology is also well suited for the construction of bi-cistronic expression vectors. In some embodiments, expression vectors containing bi-cistronic expression elements where two structural genes are expressed from a single promoter and are separated by an internal ribosome entry sequence (IRES, see Encarnación, *Current Opinion in Biotechnology* 10:458–464 (1999), specifically incorporated herein by reference). Such vectors can be used to express two proteins from a single construct.

In some embodiments, it may not be necessary to control the orientation of one or more of the nucleic acid segments and recombination sites of the same specificity can be used on both ends of the segment. With reference to FIG. 6, if the orientation of segment A with respect to segment B were not critical, segment A could be flanked by L1 sites on both ends and the vector equipped with two R1 sites. This might be useful in generating additional complexity in the formation of combinatorial libraries between segments A and B.

EXAMPLE 5

Combining Multiple Fragments into a Single Site in a Vector

In some embodiments, the present invention provides a method of cloning n nucleic acid segments, wherein n is an integer greater than 1, comprising the steps of providing a $1^{st}$ through an $n^{th}$ nucleic acid segment, each segment flanked by two unique recombination sites, wherein the recombination sites are selected such that one of the two recombination sites flanking the $i^{th}$ segment, $n_i$, reacts with one of the recombination sites flanking the $n_{i-1}$th segment and the other recombination site flanking the $i^{th}$ segment reacts with one of the recombination sites flanking the $n_{i+1}$th segment, providing a vector comprising at least two recombination sites wherein one of the two recombination sites on the vector reacts with one of the sites on the $1^{st}$ nucleic acid segment and another site on the vector reacts with a recombination site on the $n^{th}$ nucleic acid segment. It is a further object of the present invention to provide a method of cloning, comprising the steps of providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and the fourth recombination site is capable of recombining with the fifth recombination site, providing a vector having at least a seventh and an eighth recombination site such that the seventh recombination site is capable of reacting with the first recombination site and the eighth recombination site is capable of reacting with the sixth recombination site and conducting at least one recombination reaction such that the second and the third recombination sites recombine, the fourth and the fifth recombination sites recombine, the first and the seventh recombination sites recombine and the sixth and the eighth recombination sites recombine thereby cloning the first, second and third nucleic acid segments. In some embodiments, at least one nucleic acid segment comprises a sequence that functions as a promoter.

In some embodiments, at least two nucleic acid segments comprise sequences encoding a polypeptide and the recombination places both polypeptides in the same reading frame. In some embodiments, at least one nucleic acid segment comprises a sequence that functions as a transcription termination sequence. In some embodiments, at least one fragment comprises an origin of replication. In some embodiments, at least one fragment comprises a sequence coding for a selectable marker.

Figure 8:
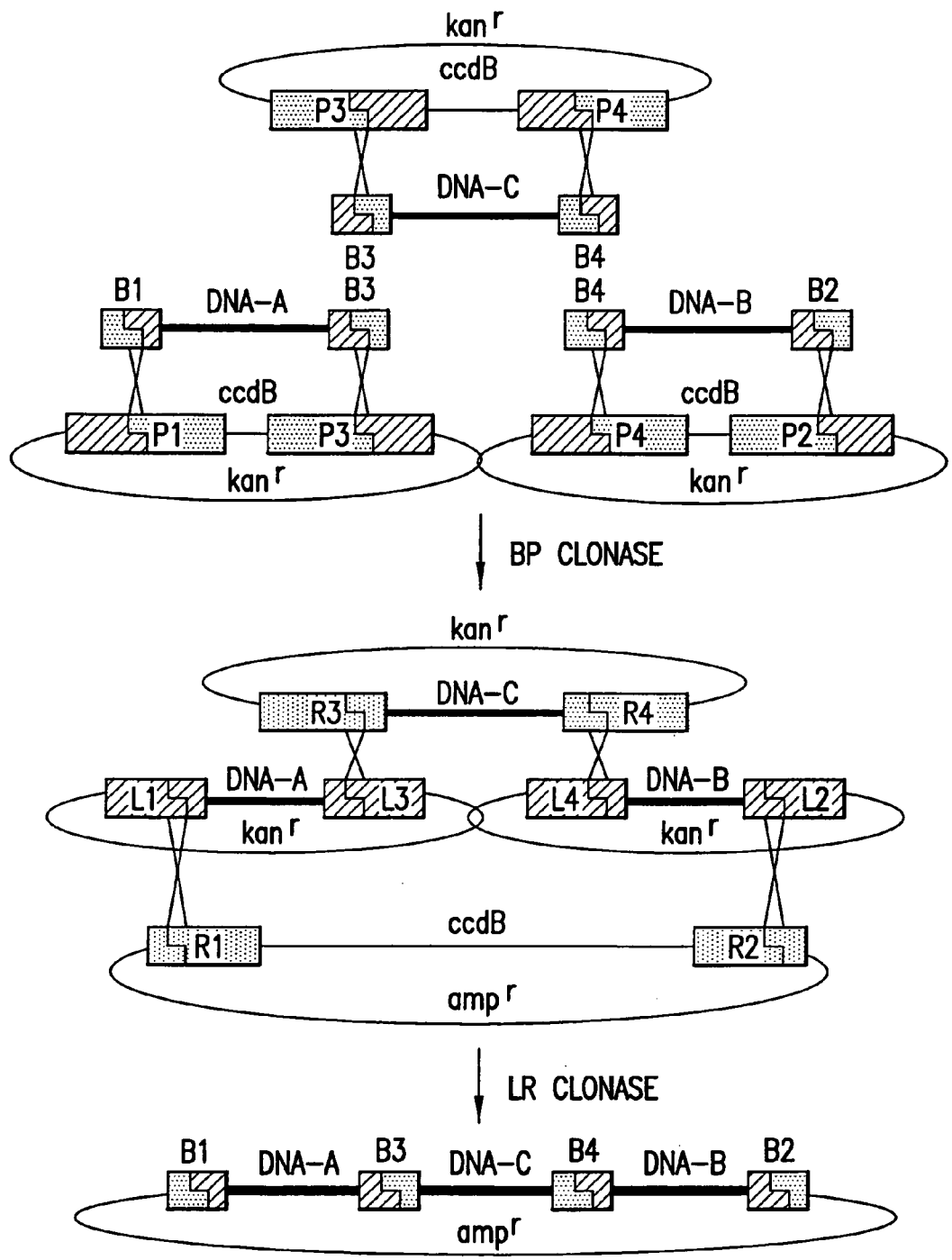
FIG. 8 is a schematic representation of the cloning of three nucleic acid segments into three vectors using BP reactions, cloning the three segments into a single vector using an LR reaction, and generating segments separated by attB sites.
Figure 9:
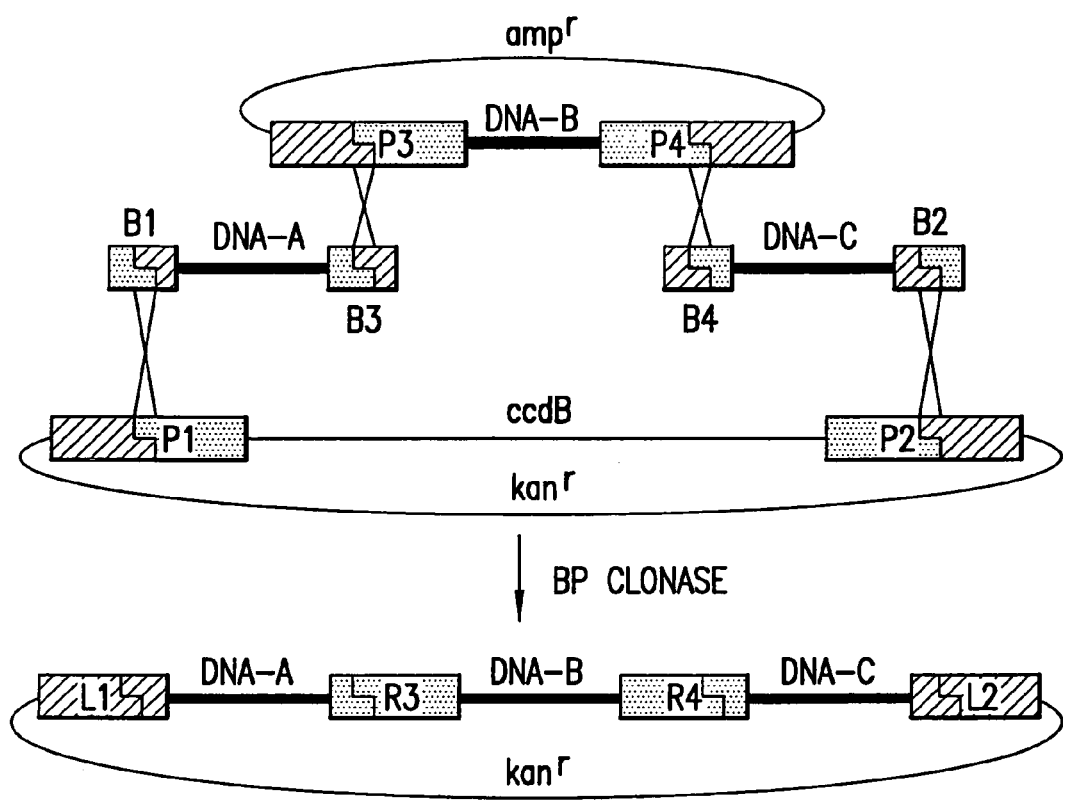
FIG. 9 is a schematic representation of the cloning of three nucleic acid segments into a single vector using a BP reaction and generating segments separated by attR sites.
Figure 10:
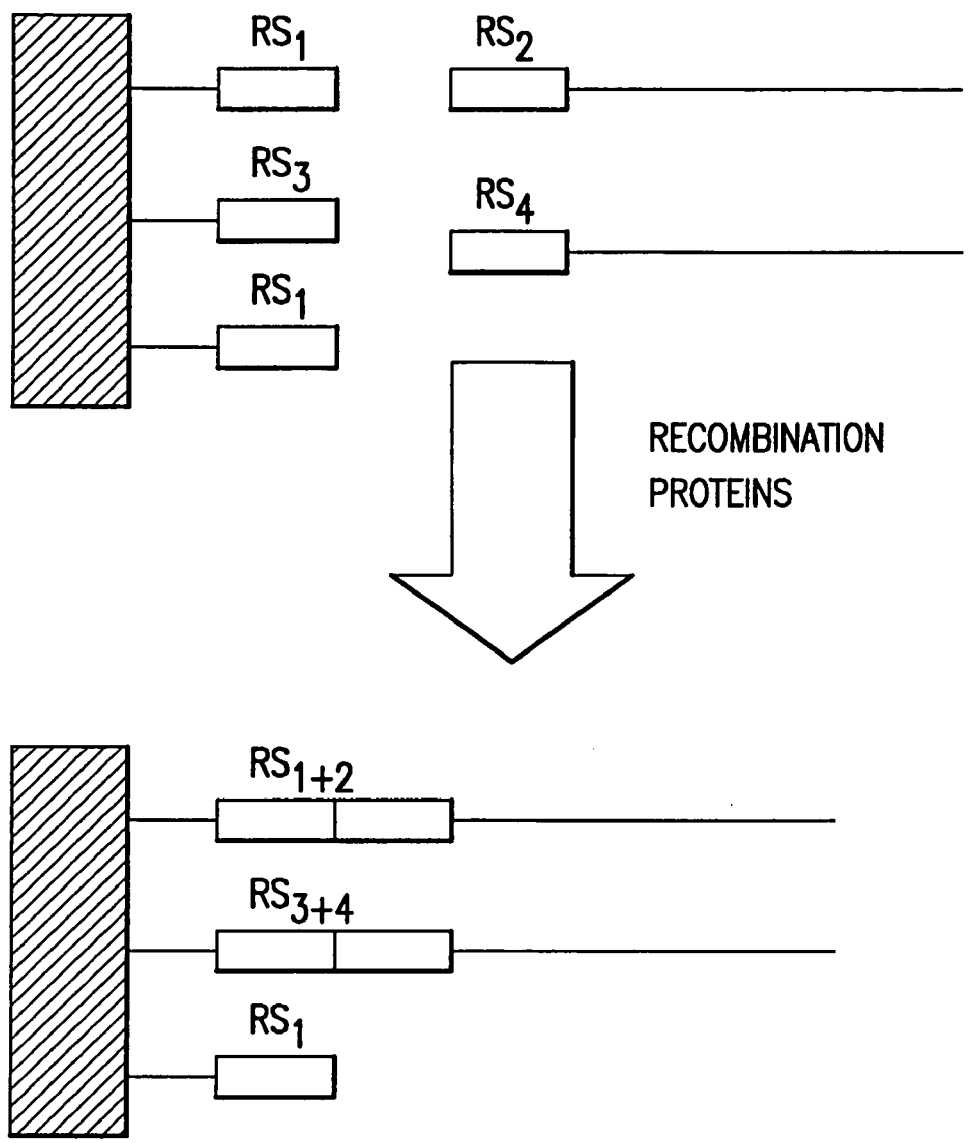
FIG. 10 is a schematic representation of adding one or more of the same or different molecules (nucleic acid, protein/peptide, carbohydrate, and/or other compounds) to a support (shaded box) by recombination. The open boxes represent recombination sites.

This embodiment is exemplified in FIGS. 8 and 9 for the case when n=3. In this embodiment, the present invention provides a method of cloning, comprising the steps of providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and the fourth recombination site is capable of recombining with the fifth recombination site, providing a vector comprising a seventh and an eighth recombination site and conducting at least one recombination reaction such that the second and the third recombination sites recombine and the fourth and the fifth recombination sites recombine and the first and the sixth recombination sites recombine with the seventh and the eighth recombination sites respectively, thereby cloning the first, second and third nucleic acid segments.

As discussed above, when the orientation of a given segment is not critical, the invention may be modified by placing recombination sites having the same specificity on both ends of the given segment and adjusting the recombination sites of the adjacent segments and/or the recombination sites in the vector accordingly.

In addition to the utilities discussed above for the combination of two fragments in a single vector, embodiments of this type will be useful for the construction of vectors from individual fragments containing various functions. Thus, the invention provides a modular method for the construction of vectors.

In some embodiments, at least one nucleic acid segment comprises a sequence that functions as a promoter. In some embodiments, at least two nucleic acid segments comprise a sequence encoding a polypeptide and the recombination places both polypeptides in the same reading frame. In some embodiments, at least one nucleic acid segment comprises a sequence that functions as a transcription termination sequence. In some embodiments, at least one fragment comprises an origin of replication. In some embodiments, at least one fragment comprises a sequence coding for a selectable marker. In some embodiments, a fragment may comprise sequence coding for more than one function. In some embodiments, a fragment may comprise sequence coding for an origin of replication and sequence encoding a selectable marker.

When multiple nucleic acid segments are inserted into vectors using methods of the invention, expression of these segments may be driven by the same regulatory sequence or different regulatory sequences. FIG. 20A shows one example of a vector which contains two inserted DNA segments, the expression of which is driven by different promoters (i.e., two different T7 promoters).

The methods of the invention may also be used to produce constructs which allow for silencing of genes in vivo. One method of silencing genes involves the production of involves the production of double-stranded RNA, termed RNA interference (RNAi). (See, e.g., Mette et al., *EMBO J*, 19:5194–5201 (2000)). Methods of the invention can be used in a number of ways to produce molecules such as RNAi. Thus, expression products of nucleic acid molecules of the invention can be used to silence gene expression.

One example of a construct designed to produce RNAi is shown in FIG. 20B. In this construct, a DNA segment is inserted into a vector such that RNA corresponding to both strands are produced as two separate transcripts. Another example of a construct designed to produce RNAi is shown in FIG. 20C. In this construct, two copies of a DNA segment are inserted into a vector such that RNA corresponding to both strands are again produced. Yet another example of a construct designed to produce RNAi is shown in FIG. 20D. In this construct, two copies of a DNA segment are inserted into a vector such that RNA corresponding to both strands are produced as a single transcript. The exemplary vector system shown in shown in FIG. 20E comprises two vectors, each of which contain copies of the same DNA segment. Expression of one of these DNA segments results in the production of sense RNA while expression of the other results in the production of an anti-sense RNA. RNA strands produced from vectors represented in FIGS. 20B–20E will thus have complementary nucleotide sequences and will generally hybridize either to each or intramolecularly under physiological conditions.

Nucleic acid segments designed to produce RNAi, such as the vectors represented in FIGS. 20B–20E, need not correspond to the full-length gene or open reading frame. For example, when the nucleic acid segment corresponds to an ORF, the segment may only correspond to part of the ORF (e.g., 50 nucleotides at the 5' or 3' end of the ORF). Further, while FIGS. 20B–20E show vectors designed to produce RNAi, nucleic acid segments may also perform the same function in other forms (e.g., when inserted into the chromosome of a host cell).

Gene silencing methods involving the use of compounds such as RNAi and antisense RNA, for examples, are particularly useful for identifying gene functions. More specifically, gene silencing methods can be used to reduce or prevent the expression of one or more genes in a cell or organism. Phenotypic manifestations associated with the selective inhibition of gene functions can then be used to assign role to the "silenced" gene or genes. As an example, Chuang et al., *Proc. Natl. Acad. Sci.* (*USA*) 97:4985–4990(2000), have demonstrated that in vivo production of RNAi can alter gene activity in *Arabidopsis thaliana*. Thus, the invention provides methods for regulating expression of nucleic acid molecules in cells and tissues comprising the expression of RNAi and antisense RNA. The invention further provides methods for preparing nucleic acid molecules which can be used to produce RNA corresponding to one or both strands of a DNA molecule.

Similarly, the invention relates to compounds and methods for gene silencing involving ribozymes. In particular, the invention provides antisense RNA/ribozymes fusions which comprise (1) antisense RNA corresponding to a target gene and (2) one or more ribozymes which cleave RNA (e.g., hammerhead ribozyme, hairpin ribozyme, delta ribozyme, *Tetrahymena* L-21 ribozyme, etc.). Further, provided by the invention are vectors which express these fusions, methods for producing these vectors, and methods for using these vector to suppress gene expression.

In one embodiment, a Destination Vector is constructed which encodes a ribozyme located next to a ccdB gene, wherein the a ccdB gene is flanked by attR sites. An LR reaction is used to replace the ccdB gene with a nucleic acid molecule which upon expression produces an antisense RNA molecule. Thus, the expression product will result in the production of an antisense sequence fused to the ribozyme by an intervening sequence encoded by an attB site. As discussed below in Example 13, this attB site can be removed from the transcript (e.g., using intron and exon slice sequences), if desired, or, in certain cases, nucleic acid which encodes the ribozyme can be embedded in the attB site.

Expression of antisense molecules fused to ribozymes can be used, for example, to cleave specific RNA molecules in a cell. This is so because the antisense RNA portion of the transcript can be designed to hybridize to particular mRNA molecules. Further, the ribozyme portion of the transcript can be designed to cleave the RNA molecule to which it has hybridized. For example, the ribozyme can be one which cleaves double-stranded RNA (e.g., *Tetrahymena* L-21 ribozyme).

EXAMPLE 6

Use of Suppressor tRNAs to Generate Fusion Proteins

The recently developed recombinational cloning techniques described above permit the rapid movement of a target nucleic acid from one vector background to one or more other vector backgrounds. Because the recombination event is site specific, the orientation and reading frame of the target nucleic acid can be controlled with respect to the vector. This control makes the construction of fusions between sequences present on the target nucleic acid and sequences present on the vector a simple matter.

In general terms, a gene may be expressed in four forms: native at both amino and carboxy termini, modified at either end, or modified at both ends. A construct containing the target gene of interest may include the N-terminal methionine ATG codon, and a stop codon at the carboxy end, of the open reading frame, or ORF, thus ATG-ORF-stop. Frequently, the gene construct will include translation initiation sequences, tis, that may be located upstream of the ATG that allow expression of the gene, thus tis-ATG-ORF-stop. Constructs of this sort allow expression of a gene as a protein that contains the same amino and carboxy amino acids as in the native, uncloned, protein. When such a construct is fused in-frame with an amino-terminal protein tag, e.g., GST, the tag will have its own tis, thus tis-ATG-tag-tis-ATG-ORF-stop, and the bases comprising the tis of the ORF will be translated into amino acids between the tag and the ORF. In addition, some level of translation initiation may be expected in the interior of the mRNA (i.e., at the ORF's ATG and not the tag's ATG) resulting in a certain amount of native protein expression contaminating the desired protein.

DNA (lower case): tis1-atg-tag-tis2-atg-orf-stop
RNA (lower case, italics): tis1-atg-tag-tis2-atg-orf-stop
Protein (upper case): ATG-TAG-TIS2-ATG-ORF (tis1 and stop are not translated)+contaminating ATG-ORF (translation of ORF beginning at tis2).

Using recombinational cloning, it is a simple matter for those skilled in the art to construct a vector containing a tag adjacent to a recombination site permitting the in frame fusion of a tag to the C- and/or N-terminus of the ORF of interest.

Given the ability to rapidly create a number of clones in a variety of vectors, there is a need in the art to maximize the number of ways a single cloned gene can be expressed without the need to manipulate the gene construct itself. The present invention meets this need by providing materials and methods for the controlled expression of a C- and/or N-terminal fusion to a target gene using one or more suppressor tRNAs to suppress the termination of translation at a stop codon. Thus, the present invention provides materials and methods in which a gene construct is prepared flanked with recombination sites.

The construct is prepared with a sequence coding for a stop codon preferably at the C-terminus of the gene encoding the protein of interest. In some embodiments, a stop codon can be located adjacent to the gene, for example, within the recombination site flanking the gene. The target gene construct can be transferred through recombination to various vectors which can provide various C-terminal or N-terminal tags (e.g., GFP, GST, His Tag, GUS, etc.) to the gene of interest. When the stop codon is located at the carboxy terminus of the gene, expression of the gene with a "native" carboxy end amino acid sequence occurs under non-suppressing conditions (i.e., when the suppressor tRNA is not expressed) while expression of the gene as a carboxy fusion protein occurs under suppressing conditions. The present invention is exemplified using an amber suppressor supF, which is a particular tyrosine tRNA gene (tyrT) mutated to recognize the UAG stop codon. Those skilled in the art will recognize that other suppressors and other stop codons could be used in the practice of the present invention.

In the present example, the gene coding for the suppressing tRNA has been incorporated into the vector from which the target gene is to be expressed. In other embodiments, the gene for the suppressor tRNA may be in the genome of the host cell. In still other embodiments, the gene for the suppressor may be located on a separate vector and provided in trans. In embodiments of this type, the vector containing the suppressor gene may have an origin of replication selected so as to be compatible with the vector containing the gene construct. The selection and preparation of such compatible vectors is within ordinary skill in the art. Those skilled in the art will appreciate that the selection of an appropriate vector for providing the suppressor tRNA in trans may include the selection of an appropriate antibiotic resistance marker. For example, if the vector expressing the target gene contains an antibiotic resistance marker for one antibiotic, a vector used to provide a suppressor tRNA may encode resistance to a second antibiotic. This permits the selection for host cells containing both vectors.

In some preferred embodiments, more than one copy of a suppressor tRNA may be provided in all of the embodiments described above. For example, a host cell may be provided that contains multiple copies of a gene encoding the suppressor tRNA. Alternatively, multiple gene copies of the suppressor tRNA under the same or different promoters may be provided in the same vector background as the target gene of interest. In some embodiments, multiple copies of a suppressor tRNA may be provided in a different vector than the one use to contain the target gene of interest. In other embodiments, one or more copies of the suppressor tRNA gene may be provided on the vector containing the gene for the protein of interest and/or on another vector and/or in the genome of the host cell or in combinations of the above. When more than one copy of a suppressor tRNA gene is provided, the genes may be expressed from the same or different promoters which may be the same or different as the promoter used to express the gene encoding the protein of interest.

In some embodiments, two or more different suppressor tRNA genes may be provided. In embodiments of this type one or more of the individual suppressors may be provided in multiple copies and the number of copies of a particular suppressor tRNA gene may be the same or different as the number of copies of another suppressor tRNA gene. Each suppressor tRNA gene, independently of any other suppressor tRNA gene, may be provided on the vector used to express the gene of interest and/or on a different vector and/or in the genome of the host cell. A given tRNA gene may be provided in more than one place in some embodiments. For example, a copy of the suppressor tRNA may be provided on the vector containing the gene of interest while one or more additional copies may be provided on an additional vector and/or in the genome of the host cell. When more than one copy of a suppressor tRNA gene is provided, the genes may be expressed from the same or different promoters which may be the same or different as the promoter used to express the gene encoding the protein of interest and may be the same or different as a promoter used to express a different tRNA gene.

Figure 14A:
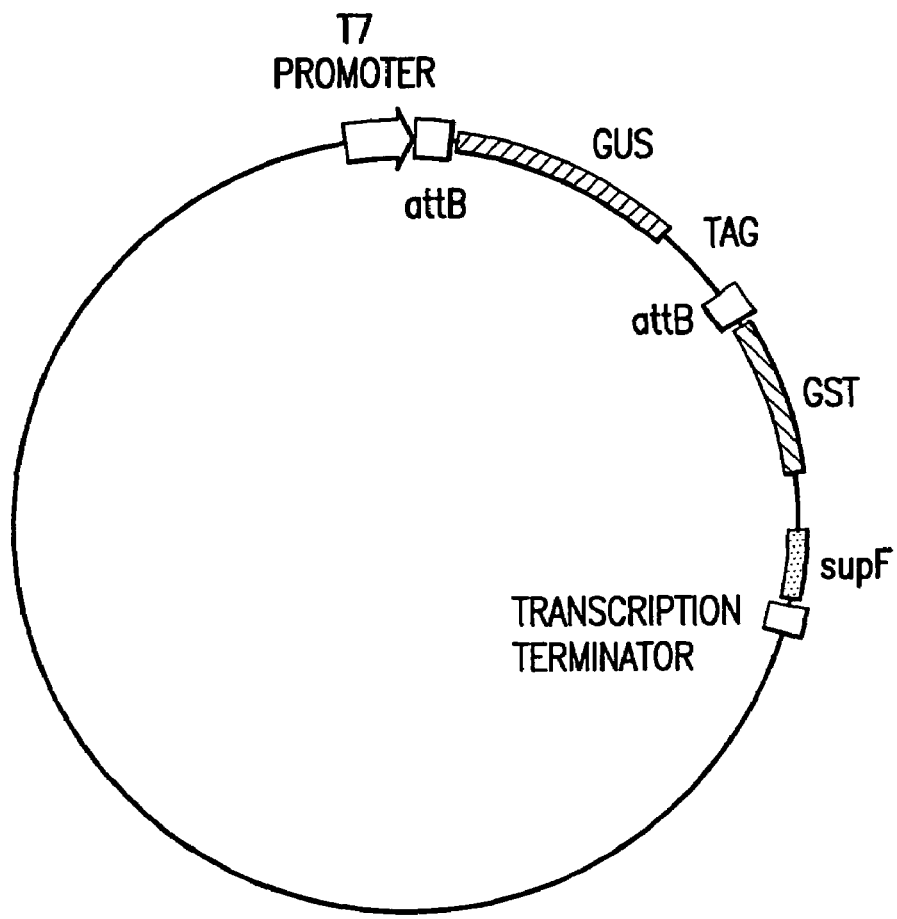
FIG. 14A is a plasmid map showing a construct for providing a C-terminal fusion to a gene of interest. SupF encodes a suppressor function. Thus, when supF is expressed, a GUS-GST fusion protein is produced. In variations of this molecules, GUS can be any gene.
Figure 14B:
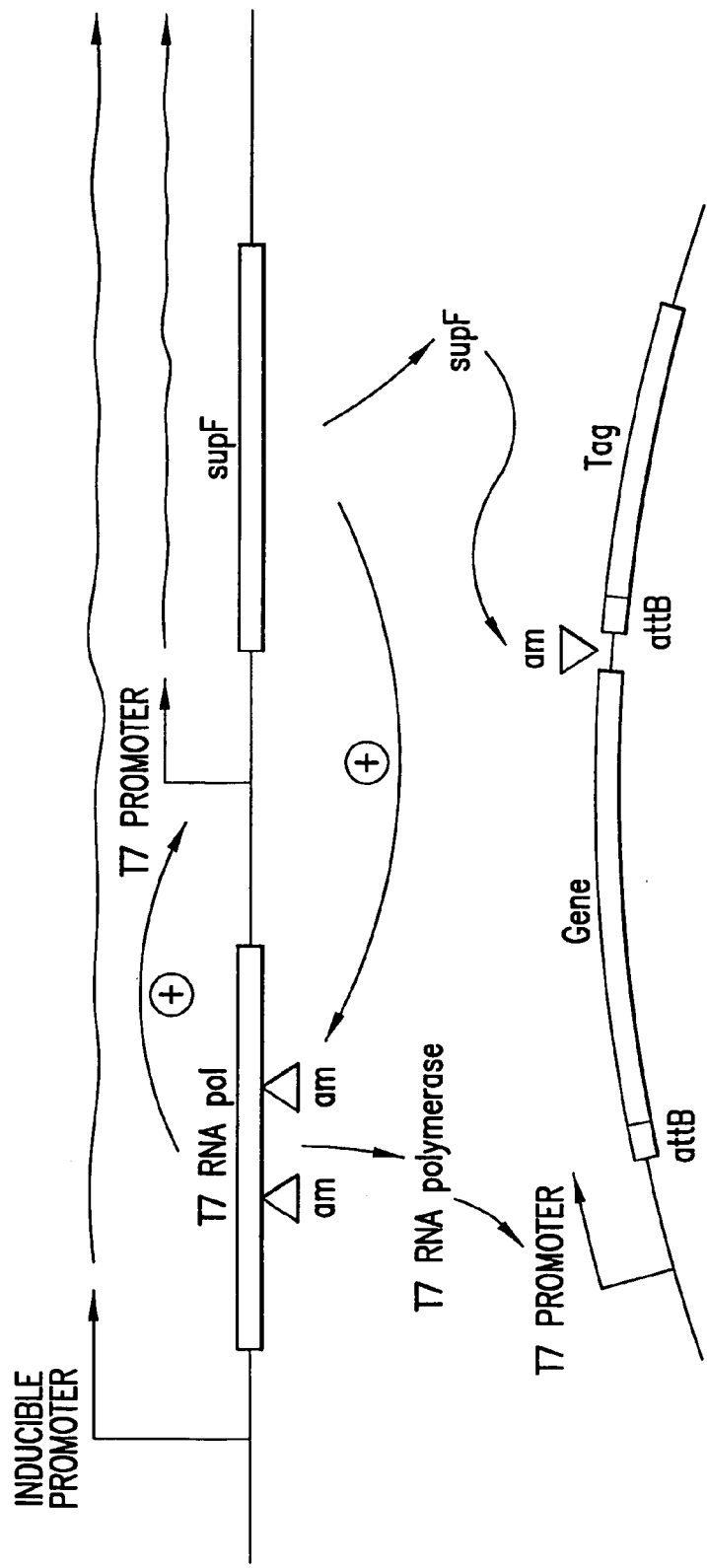
FIG. 14B is a schematic representation of method for controlling both gene suppression and expression. The T7 RNA polymerase gene contains one or more (two are shown) amber stop codons (labeled "am") in place of tyrosine codons. Leaky (uninduced) transcription from the inducible promoter makes insufficient supF to result in the production of active T7 RNA polymerase. Upon induction, sufficient supF is produced to make active T7 RNA polymerase, which results in increased expression of supF, which results in further increased expression of T7 RNA polymerase. The T7 RNA polymerase further induces expression of Gene. Further, expression of supF results in the addition of a C-terminal tag to the Gene expression product by suppression of the intervening amber stop codon.

With reference to FIG. 14, the GUS gene was cloned in frame with a GST gene separated by the TAG codon. The plasmid also contained a supF gene expressing a suppressor tRNA. The plasmid was introduced into a host cell where approximately 60 percent of the GUS gene was expressed as a fusion protein containing the GST tag. In control experiments, a plasmid containing the same GUS-stop codon-GST construct did not express a detectable amount of a fusion protein when expressed from a vector lacking the supF gene. In this example, the supF gene was expressed as part of the mRNA containing the GUS-GST fusion. Since tRNAs are generally processed from larger RNA molecules, constructs of this sort can be used to express the suppressor tRNAs of the present invention. In other embodiments, the RNA containing the tRNA sequence may be expressed separately from the mRNA containing the gene of interest.

In some embodiments of the present invention, the target gene of interest and the gene expressing the suppressor tRNA may be controlled by the same promoter. In other embodiments, the target gene of interest may be expressed from a different promoter than the suppressor tRNA. Those skilled in the art will appreciate that, under certain circumstances, it may be desirable to control the expression of the suppressor tRNA and/or the target gene of interest using a regulatable promoter. For example, either the target gene of interest and/or the gene expressing the suppressor tRNA may be controlled by a promoter such as the lac promoter or derivatives thereof such as the tac promoter. In the embodiment shown, both the target gene of interest and the suppressor tRNA gene are expressed from the T7 RNA polymerase promoter. Induction of the T7 RNA polymerase turns on expression of both the gene of interest (GUS in this case) and the supF gene expressing the suppressor tRNA as part of one RNA molecule.

In some preferred embodiments, the expression of the suppressor tRNA gene may be under the control of a different promoter from that of the gene of interest. In some embodiments, it may be possible to express the suppressor gene before the expression of the target gene. This would allow levels of suppressor to build up to a high level, before they are needed to allow expression of a fusion protein by suppression of a the stop codon. For example, in embodiments of the invention where the suppressor gene is controlled by a promoter inducible with IPTG, the target gene is controlled by the T7 RNA polymerase promoter and the expression of the T7 RNA polymerase is controlled by a promoter inducible with an inducing signal other than IPTG, e.g., NaCl, one could turn on expression of the suppressor tRNA gene with IPTG prior to the induction of the T7 RNA polymerase gene and subsequent expression of the gene of interest. In some preferred embodiments, the expression of the suppressor tRNA might be induced about 15 minutes to about one hour before the induction of the T7 RNA polymerase gene. In a preferred embodiment, the expression of the suppressor tRNA may be induced from about 15 minutes to about 30 minutes before induction of the T7 RNA polymerase gene. In the specific example shown, the expression of the T7 RNA polymerase gene is under the control of a salt inducible promoter. A cell line having an inducible copy of the T7 RNA polymerase gene under the control of a salt inducible promoter is commercially available from Invitrogen Corp., Life Technologies Division under the designation of the BL21 SI strain.

In some preferred embodiments, the expression of the target gene of interest and the suppressor tRNA can be arranged in the form of a feedback loop. For example, the target gene of interest may be placed under the control of the T7 RNA polymerase promoter while the suppressor gene is under the control of both the T7 promoter and the lac promoter, and the T7 RNA polymerase gene itself is transcribed by both the T7 promoter and the lac promoter, and the T7 RNA polymerase gene has an amber stop mutation replacing a normal tyrosine stop codon, e.g., the $28^{th}$ codon (out of 883). No active T7 RNA polymerase can be made before levels of suppressor are high enough to give significant suppression. Then expression of the polymerase rapidly rises, because the T7 polymerase expresses the suppressor gene as well as itself. In other preferred embodiments, only the suppressor gene is expressed from the T7 RNA polymerase promoter. Embodiments of this type would give a high level of suppressor without producing an excess amount of T7 RNA polymerase. In other preferred embodiments, the T7 RNA polymerase gene has more than one amber stop mutation (see, e.g., FIG. 14B). This will require higher levels of suppressor before active T7 RNA polymerase is produced.

Figure 15:
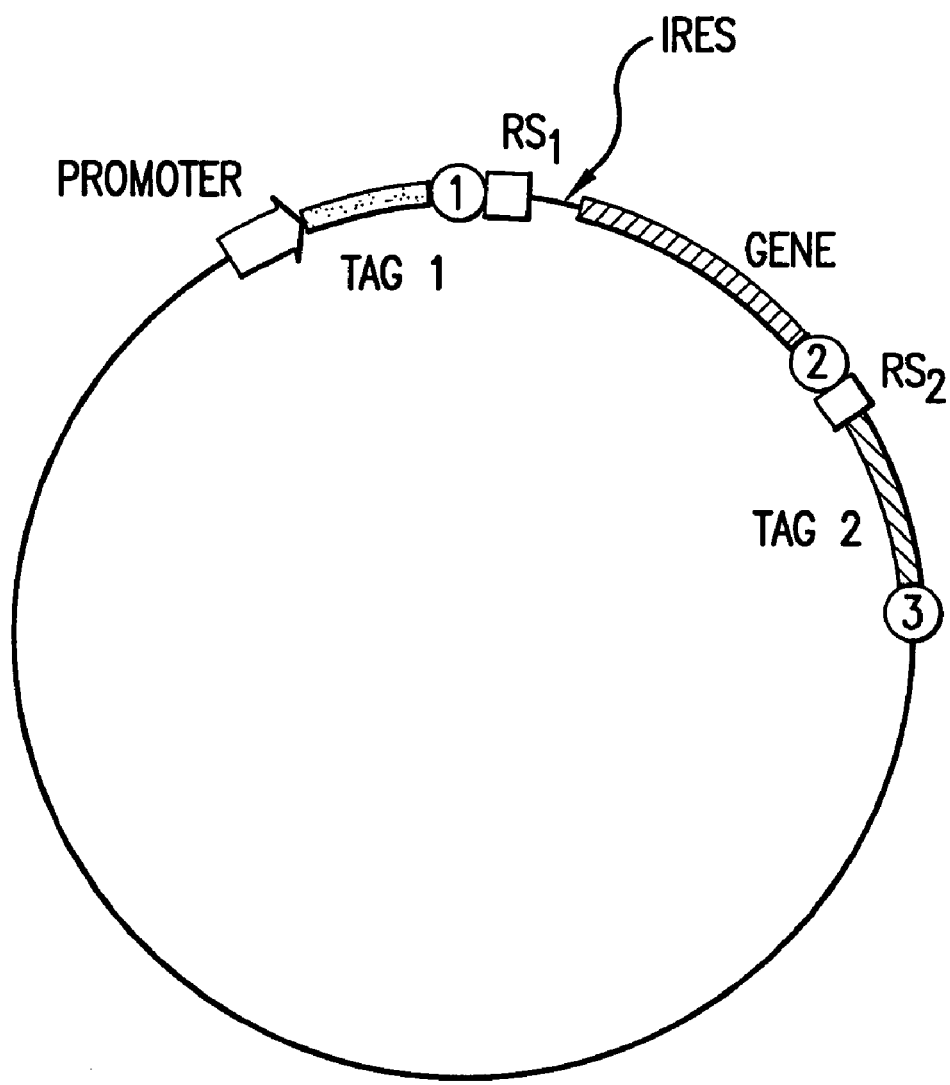
FIG. 15 is a plasmid map showing a construct for the production of N-and/or C-terminal fusions of a gene of interest. Circled numbers represent amber, ochre, or opal stop codons. Suppression of these stop codons result in expression of fusion tags on the N-terminus, the C-terminus, or both termini. In the absence of suppression, native protein is produced.

In some embodiments of the present invention it may be desirable to have more than one stop codon suppressible by more than one suppressor tRNA. With reference to FIG. 15, a vector may be constructed so as to permit the regulatable expression of N- and/or C-terminal fusions of a protein of interest from the same construct. A first tag sequence, TAG1 in FIG. 15, is expressed from a promoter represented by an arrow in the figure. The tag sequence includes a stop codon in the same reading frame as the tag. The stop codon 1, may be located anywhere in the tag sequence and is preferably located at or near the C-terminal of the tag sequence. The stop codon may also be located in the recombination site $RS_1$ or in the internal ribosome entry sequence (IRES). The construct also includes a gene of interest (GENE) which includes a stop codon 2. The first tag and the gene of interest are preferably in the same reading frame although inclusion of a sequence that causes frame shifting to bring the first tag into the same reading frame as the gene of interest is within the scope of the present invention. Stop codon 2 is in the same reading frame as the gene of interest and is preferably located at or near the end of the coding sequence for the gene. Stop codon 2 may optionally be located within the recombination site $RS_2$. The construct also includes a second tag sequence in the same reading frame as the gene of interest indicated by TAG2 in FIG. 15 and the second tag sequence may optionally include a stop codon 3 in the same reading frame as the second tag. A transcription terminator may be included in the construct after the coding sequence of the second tag (not shown in FIG. 15). Stop codons 1, 2 and 3 may be the same or different. In some embodiments, stop codons 1, 2 and 3 are different. In embodiments where 1 and 2 are different, the same construct may be used to express an N-terminal fusion, a C-terminal fusion and the native protein by varying the expression of the appropriate suppressor tRNA. For example, to express the native protein, no suppressor tRNAs are expressed and protein translation is controlled by the IRES. When an N-terminal fusion is desired, a suppressor tRNA that suppresses stop codon 1 is expressed while a suppressor tRNA that suppresses stop codon 2 is expressed in order to produce a C-terminal fusion. In some instances it may be desirable to express a doubly tagged protein of interest in which case suppressor tRNAs that suppress both stop codon 1 and stop codon 2 may be expressed.

The present invention has been described in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

Example 7

Testing Functionality of Entry and Destination Vectors

As part of assessment of the functionality of particular vectors of the invention, it is important to functionally test the ability of the vectors to recombine. This assessment can be carried out by performing a recombinational cloning reaction by transforming *E. coli* and scoring colony forming units. However, an alternative assay may also be performed to allow faster, more simple assessment of the functionality of a given Entry or Destination Vector by agarose gel electrophoresis. The following is a description of such an in vitro assay.

Materials and Methods

Plasmid templates pEZC1301 and pEZC1313 (described in PCT Publication WO 00/52027, the entire disclosure of which is incorporated herein by reference), each containing a single wild-type att site, were used for the generation of PCR products containing attL or attR sites, respectively. Plasmid templates were linearized with AlwNI, phenol extracted, ethanol precipitated and dissolved in TE to a concentration of 1 ng/µl.

```
    PCR primers (capital letters represent base changes from wild-type):

attL1       gggg agcct gctttttGtacAaa gttggcatta taaaaaagca ttgc    (SEQ ID NO:41)

attL2       gggg agcct gctttCttGtacAaa gttggcatta taaaaaagca ttgc    (SEQ ID NO:42)

attL right  tgttgccggg aagctagagt aa                                 (SEQ ID NO:43)

attR1       gggg Acaag ttTgtaCaaaaaagc tgaacgaga aacgtaaaat          (SEQ ID NO:44)

attR2       gggg Acaag ttTgtaCaaGaaagc tgaacgaga aacgtaaaat          (SEQ ID NO:45)

attR right  ca gacggcatga tgaacctgaa                                 (SEQ ID NO:46)
```

PCR primers were dissolved in TE to a concentration of 500 pmol/µl. Primer mixes were prepared, consisting of attL1+attLright primers, attL2+attLright primers, attR1+attRright primers, and attR2+attRright primers, each mix containing 20 pmol/µl of each primer.

PCR Reactions

1 µl plasmid template (1 ng)
1 µl primer pairs (20 pmoles of each)
3 µl of H$_2$0
45 µl of Platinum PCR SuperMix® (Invitrogen Corp., Life Technologies Division)
Cycling Conditions (Performed in MJ Thermocycler):
95° C./2 minutes
94° C./30 seconds
25 cycles of 58° C./30 seconds and 72° C./1.5 minutes
72° C./5 minutes
5° C./hold The resulting attL PCR product was 1.5 kb, and the resulting attR PCR product was 1.0 kb.

PCR reactions were PEG/MgCl$_2$ precipitated by adding 150 µl H$_2$O and 100 µl of 3×PEG/MgCl$_2$ solution followed by centrifugation. The PCR products were dissolved in 50 µl of TE. Quantification of the PCR product was performed by gel electrophoresis of 1 µl and was estimated to be 50–100 ng/µl.

Recombination reactions of PCR products containing attL or attR sites with GATEWAY™ plasmids was performed as follows:

8 µl of H$_2$0
2 µl of attL or attR PCR product (100–200 ng)
2 µl of GATEWAY® plasmid (100 ng)
4 µl of 5× Destination buffer
4 µl of GATEWAY® LR Clonase™ Enzyme Mix
20 µl total volume (the reactions can be scaled down to a 5 µl total volume by adjusting the volumes of the components to about ¼ of those shown above, while keeping the stoichiometries the same).

Clonase reactions were incubated at 25° C. for 2 hours. Two µl of proteinase K (2 mg/ml) was added to stop the reaction. Ten µl was then run on a 1% agarose gel. Positive control reactions were performed by reacting attL1 PCR product (1.0 kb) with attR1 PCR product (1.5 kb) and by similarly reacting attL2 PCR product with attR2 PCR product to observe the formation of a larger (2.5 kb) recombination product. Negative controls were similarly performed by reacting attL1 PCR product with attR2 PCR product and vice versa or reactions of attL PCR product with an attL plasmid, etc.

In alternative assays, to test attB Entry vectors, plasmids containing single attP sites were used. Plasmids containing single att sites could also be used as recombination substrates in general to test all Entry and Destination vectors (i.e., those containing attL, attR, attB and attP sites). This would eliminate the need to do PCR reactions.

Results

Destination and Entry plasmids when reacted with appropriate att-containing PCR products formed linear recombinant molecules that could be easily visualized on an agarose gel when compared to control reactions containing no attL or attR PCR product. Thus, the functionality of Destination and Entry vectors constructed according to the invention may be determined, for example, by carrying out the linearization assay described above.

EXAMPLE 8

PCR Cloning Using Universal Adapter-Primers

As described herein, the cloning of PCR products using the GATEWAY™ PCR Cloning System (Invitrogen Corp., Life Technologies Division; Rockville, Md.) requires the addition of attB sites (attB1 and attB2) to the ends of gene-specific primers used in the PCR reaction. Available data suggested that the user add 29 bp (25 bp containing the attB site plus four G residues) to the gene-specific primer. It would be advantageous to high volume users of the GATEWAY™ PCR Cloning System to generate attB-containing PCR product using universal attB adapter-primers in combination with shorter gene-specific primers containing a specified overlap to the adapters. The following experiments demonstrate the utility of this strategy using universal attB adapter-primers and gene-specific primers containing overlaps of various lengths from 6 bp to 18 bp. The results demonstrate that gene-specific primers with overlaps of 10 bp to 18 bp can be used successfully in PCR amplifications with universal attB adapter-primers to generate full-length PCR products. These PCR products can then be successfully cloned with high fidelity in a specified orientation using the GATEWAY™ PCR Cloning System.

Methods and Results

To demonstrate that universal attB adapter-primers can be used with gene-specific primers containing partial attB sites in PCR reactions to generate full-length PCR product, a small 256 bp region of the human hemoglobin cDNA was chosen as a target so that intermediate sized products could be distinguished from full-length products by agarose gel electrophoresis.

The following oligonucleotides were used:

The aim of these experiments was to develop a simple and efficient universal adapter PCR method to generate attB containing PCR products suitable for use in the GATEWAY™ PCR Cloning System. The reaction mixtures and thermocycling conditions should be simple and efficient so that the universal adapter PCR method could be routinely applicable to any PCR product cloning application.

PCR reaction conditions were initially found that could successfully amplify predominately full-length PCR product using gene-specific primers containing 18 bp and 15 bp overlap with universal attB primers. These conditions are outlined below:

10 pmoles of gene-specific primers
    10 pmoles of universal attB adapter-primers
    1 ng of plasmid containing the human hemoglobin cDNA.
    100 ng of human leukocyte cDNA library DNA.
    5 µl of 10× PLATINUM Taq HiFi® reaction buffer (Invitrogen Corp., Life Technologies Division)
    2 µl of 50 mM $MgSO_4$
    1 µl of 10 mM dNTPs

```
B1-Hgb:         GGGG ACA AGT TTG TAC AAA AAA GCA GGC T-5'-Hgb*  (SEQ ID NO:47)

B2-Hgb:         GGGG ACC ACT TTG TAC AAG AAA GCT GGG T-3'-Hgb** (SEQ ID NO:48)

18B1-Hgb:                    TG TAC AAA AAA GCA GGC T-5'-Hgb    (SEQ ID NO:49)

18B2-Hgb:                    TG TAC AAG AAA GCT GGG T-3'-Hgb    (SEQ ID NO:50)

15B1-Hgb:                       AC AAA AAA GCA GGC T-5'-Hgb     (SEQ ID NO:51)

15B2-Hgb:                       AC AAG AAA GCT GGG T-3'-Hgb     (SEQ ID NO:52)

12B1-Hgb:                          AA AAA GCA GGC T-5'-Hgb      (SEQ ID NO:53)

12B2-Hgb:                          AG AAA GCT GGG T-3'-Hgb      (SEQ ID NO:54)

11B1-Hgb:                           A AAA GCA GGC T-5'-Hgb      (SEQ ID NO:55)

11B2-Hgb:                           G AAA GCT GGG T-3'-Hgb      (SEQ ID NO:56)

10B1-Hgb:                             AAA GCA GGC T-5'-Hgb      (SEQ ID NO:57)

10B2-Hgb:                             AAA GCT GGG T-3'-Hgb      (SEQ ID NO:58)

9B1-Hgb:                               AA GCA GGC T-5'-Hgb

9B2-Hgb:                               AA GCT GGG T-3'-Hgb

8B1-Hgb:                                A GCA GGC T-5'-Hgb

8B2-Hgb:                                A GCT GGG T-3'-Hgb

7B1-Hgb:                                  GCA GGC T-5'-Hgb

7B2-Hgb:                                  GCT GGG T-3'-Hgb

6B1-Hgb:                                   CA GGC T-5'-Hgb

6B2-Hgb:                                   CT GGG T-3'-Hgb attB1 adapter:  GGGG ACA AGT TTG TAC AAA AAA GCA GGC T         (SEQ ID NO:47)

aatB2 adapter:  GGGG ACC ACT TTG TAC AAG AAA GCT GGG T         (SEQ ID NO:48)
```

*5'-Hgb = GTC ACT AGC CTG TGG AGC AAG A (SEQ ID NO:59)
**3'-Hgb = AGG ATG GCA GAG GGA GAC GAC A (SEQ ID NO:60)

0.2 μl of PLATINUM Taq HiFi® (1.0 unit)
H₂O to 50 μl total reaction volume

Cycling conditions:

25× {
95° C./5 min
94° C./15 sec
50° C./30 sec
68° C./1 min
68° C./5 min
5° C./hold
}

To assess the efficiency of the method, 2 μl (1/25) of the 50 μl PCR reaction was electrophoresed in a 3% Agarose-1000 gel. With overlaps of 12 bp or less, smaller intermediate products containing one or no universal attB adapter predominated the reactions. Further optimization of PCR reaction conditions was obtained by titrating the amounts of gene-specific primers and universal attB adapter-primers. The PCR reactions were set up as outlined above except that the amounts of primers added were:
0, 1, 3 or 10 pmoles of gene-specific primers
0, 10, 30 or 100 pmoles of adapter-primers Cycling Conditions 25× {
95° C./3 min
94° C./15 sec
50° C./45 sec
68° C./1 min
68° C./5 min
5° C./hold
}

The use of limiting amounts of gene-specific primers (3 pmoles) and excess adapter-primers (30 pmoles) reduced the amounts of smaller intermediate products. Using these reaction conditions the overlap necessary to obtain predominately full-length PCR product was reduced to 12 bp. The amounts of gene-specific and adapter-primers was further optimized in the following PCR reactions:
0, 1, 2 or 3 pmoles of gene-specific primers
0, 30, 40 or 50 pmoles of adapter-primers Cycling Conditions 25× {
95° C./3 min
94° C./15 sec
48° C./1 min
68° C./1 min
68° C./5 min
5° C./hold
}

The use of 2 pmoles of gene-specific primers and 40 pmoles of adapter-primers further reduced the amounts of intermediate products and generated predominately full-length PCR products with gene-specific primers containing an 11 bp overlap. The success of the PCR reactions can be assessed in any PCR application by performing a no adapter control. The use of limiting amounts of gene-specific primers should give faint or barely visible bands when 1/25 to 1/10 of the PCR reaction is electrophoresed on a standard agarose gel.

Addition of the universal attB adapter-primers should generate a robust PCR reaction with a much higher overall yield of product.

PCR products from reactions using the 18 bp, 15 bp, 12 bp, 11 bp and 10 bp overlap gene-specific primers were purified using the CONCERT®; Rapid PCR Purification System (PCR products greater than 500 bp can be PEG precipitated). The purified PCR products were subsequently cloned into an attP containing plasmid vector using the GATEWAY™ PCR Cloning System (Invitrogen Corp., Life Technologies Division; Rockville, Md.) and transformed into $E.\ coli$. Colonies were selected and counted on the appropriate antibiotic media and screened by PCR for correct inserts and orientation.

Raw PCR products (unpurified) from the attB adapter PCR of a plasmid clone of part of the human beta-globin (Hgb) gene were also used in GATEWAY™ PCR Cloning System reactions. PCR products generated with the full attB B1/B2-Hgb, the 12B1/B2, 11B1/B2 and 10B1/B2 attB overlap Hgb primers were successfully cloned into the GATEWAY™ pENTR21 attP vector (described in PCT Publication WO 00/52027, the entire disclosure of which is incorporated herein by reference). 24 colonies from each (24×4=96 total) were tested and each was verified by PCR to contain correct inserts. The cloning efficiency expressed as cfu/ml is shown below:

| Primer Used | cfu/ml |
| --- | --- |
| Hgb full attB | 8,700 |
| Hgb 12 bp overlap | 21,000 |
| Hgb 11 bp overlap | 20,500 |
| Hgb 10 bp overlap | 13,500 |
| GFP control | 1,300 |

Interestingly, the overlap PCR products cloned with higher efficiency than did the full attB PCR product. Presumably, and as verified by visualization on agarose gel, the adapter PCR products were slightly cleaner than was the full attB PCR product. The differences in colony output may also reflect the proportion of PCR product molecules with intact attB sites.

Using the attB adapter PCR method, PCR primers with 12 bp attB overlaps were used to amplify cDNAs of different sizes (ranging from 1 to 4 kb) from a leukocyte cDNA library and from first strand cDNA prepared from HeLa total RNA. While three of the four cDNAs were able to be amplified by this method, a non-specific amplification product was also observed that under some conditions would interfere with the gene-specific amplification. This non-specific product was amplified in reactions containing the attB adapter-primers alone without any gene-specific overlap primers present. The non-specific amplification product was reduced by increasing the stringency of the PCR reaction and lowering the attB adapter PCR primer concentration.

These results indicate that the adapter-primer PCR approach described in this Example will work well for cloned genes. These results also demonstrate the development of a simple and efficient method to amplify PCR products that are compatible with the GATEWAY™ PCR Cloning System that allows the use of shorter gene-specific primers that partially overlap universal attB adapter-primers. In routine PCR cloning applications, the use of 12 bp overlaps is recommended. The methods described in this Example can thus reduce the length of gene-specific primers by up to 17 residues or more, resulting in a significant savings in oligonucleotide costs for high volume users of the GATEWAY™ PCR Cloning System. In addition, using the methods and assays described in this Example, one of ordinary skill can, using only routine experimentation, design and use analogous primer-adapters based on or containing other recombination sites or fragments thereof, such as attL, attR, attP, lox, FRT, etc.

As an alternative to adding 29 bases to the ends of PCR primers, attB PCR products can be generated with primers containing as few as 12 bases of attB added to template-specific primers using a two-step PCR protocol. In the first step template-specific primers containing 12 bases of attB are used in 10 cycles of PCR to amplify the target gene. A portion of this PCR reaction is transferred to a second PCR reaction containing universal attB adapter primers to amplify the full-attB PCR product.

Template-specific primers with 12 bases of attB1 and attB2 at their 5'-ends are designed as shown below:

```
12 attB1:   AA AAA GCA GGC TNN (SEQ ID NO:139) -
            forward template-specific primer 12 attB2:   A GAA AGC TGG GTN (SEQ ID NO:140) -
            reverse template-specific primer
```

The template-specific part of the primers is generally be designed to have a Tm of greater than 50° C. The optimal annealing temperature is determined by the Tm of the template-specific part of the primer.

```
attB1 adapter primer: GGGGACAAGTTTGTACAAAAAAGCAGGCT
                      (SEQ ID NO:47)

attB2 adapter primer: GGGGACCACTTTGTACAAGAAAGCTGGGT
                      (SEQ ID NO:48)
```

A 50 µl PCR reaction containing 10 pmoles of each template-specific primer and the appropriate amount of template DNA is prepared. Tubes containing this PCR reaction mixture are placed in a thermal cycler at 95° C. and incubated for 2 minutes.

Ten cycles of PCR are performed as follows:
Denature 94° C. for 15 seconds
Anneal 50–60° C. for 30 seconds
Extend 68° C. for 1 minute/kb of target amplicon Ten µl of the PCR reaction product is transferred to a 40 µl PCR reaction mixture containing 40 pmoles each of the attB1 and attB2 adapter primers. Tubes containing this mixtures are then placed in a thermal cycler at 95° C. and incubated for 1 minute.

Five cycles of PCR are performed as follows:
Denature 94° C. for 15 seconds
Anneal 45° C. for 30 seconds
Extend 68° C. for 1 minute/kb of target amplicon Fifteen to twenty cycles of PCR are then performed as follows:
Denature 94° C. for 15 seconds
Anneal 55° C. for 30 seconds
Extend 68° C. for 1 minute/kb of target amplicon The amplification products are then analyzed by agarose gel electrophoresis.

EXAMPLE 9

Mutational Analysis of the Bacteriophage Lambda attL and attR Sites: Determinants of att Site Specificity in Site-specific Recombination To investigate the determinants of att site specificity, the bacteriophage lambda attL and attR sites were systematically mutagenized and examined to define precisely which mutations produce unique changes in att site specificity. As noted herein, the determinants of specificity have previously been localized to the 7 bp overlap region (TTTATAC, which is defined by the cut sites for the integrase protein and is the region where strand exchange takes place) within the 15 bp core region (GCTTTTTTATACTAA (SEQ ID NO:37)) that is identical in all four lambda att sites, attB, attP, attL and attR.

Therefore, to examine the effect of att sequence on site specificity, mutant attL and attR sites were generated by PCR and tested in an in vitro site-specific recombination assay. In this way all possible single base pair changes within the 7 bp overlap region of the core att site were generated as well as five additional changes outside the 7 bp overlap but within the 15 bp core att site. Each attL PCR substrate was tested in the in vitro recombination assay with each of the attR PCR substrates.

Methods

To examine both the efficiency and specificity of recombination of mutant attL and attR sites, a simple in vitro site-specific recombination assay was developed. Since the core regions of attL and attR lie near the ends of these sites, it was possible to incorporate the desired nucleotide base changes within PCR primers and generate a series of PCR products containing mutant attL and attR sites. PCR products containing attL and attR sites were used as substrates in an in vitro reaction with GATEWAY™ LR CLONASE™ Enzyme Mix (Invitrogen Corp., Life Technologies Division, Rockville, Md.). Recombination between a 1.5 kb attL PCR product and a 1.0 kb attR PCR product resulted in a 2.5 kb recombinant molecule that was monitored using agarose gel electrophoresis and ethidium bromide staining.

Plasmid templates pEZC1301 and pEZC1313 (described in PCT Publication WO 00/52027, the entire disclosure of which is incorporated herein by reference), each containing a single wild-type attL or attR site, respectively, were used for the generation of recombination substrates. The following list shows primers used in PCR reactions to generate the attL PCR products that were used as substrates in LR CLONASE™ reactions (capital letters represent changes from the wild-type sequence, and the underline represents the 7 bp overlap region within the 15 bp core att site; a similar set of PCR primers was used to prepare the attR PCR products containing matching mutations):

GATEWAY™ sites (note: attL2 sequence in GATEWAY™ plasmids begins "accca" while the attL2 site in this example begins "agcct" to reflect wild-type attL outside the core region.):

```
attL1:   gggg agcct gcttttttGtacAaa gttggcatta taaaaaagca ttgc  (SEQ ID NO:41)

attL2:   gggg agcct gctttCttGtacAaa gttggcatta taaaaaagca ttgc  (SEQ ID NO:42)
```

```
Wild-type:
attL0:   gggg agcct gcttttttatactaa gttggcatta taaaaaagca ttgc   (SEQ ID NO:61)

Single base changes from wild-type:
attLT1A: gggg agcct gctttAttatactaa gttggcatta taaaaaagca ttgc   (SEQ ID NO:62)

attLT1C: gggg agcct gctttCttatactaa gttggcatta taaaaaagca ttgc   (SEQ ID NO:63)

attLT1G: gggg agcct gctttGttatactaa gttggcatta taaaaaagca ttgc   (SEQ ID NO:64)

attLT2A: gggg agcct gcttttAtatactaa gttggcatta taaaaaagca ttgc   (SEQ ID NO:65)

attLT2C: gggg agcct gcttttCtatactaa gttggcatta taaaaaagca ttgc   (SEQ ID NO:66)

attLT2G: gggg agcct gcttttGtatactaa gttggcatta taaaaaagca ttgc   (SEQ ID NO:67)

attLT3A: gggg agcct gcttttAatactaa gttggcatta taaaaaagca ttgc   (SEQ ID NO:68)

attLT3C: gggg agcct gcttttCatactaa gttggcatta taaaaaagca ttgc   (SEQ ID NO:69)

attLT3G: gggg agcct gcttttGatactaa gttggcatta taaaaaagca ttgc   (SEQ ID NO:70)

attLA4C: gggg agcct gcttttttCtactaa gttggcatta taaaaaagca ttgc   (SEQ ID NO:71)

attLA4G: gggg agcct gcttttttGtactaa gttggcatta taaaaaagca ttgc   (SEQ ID NO:72)

attLA4T: gggg agcct gcttttttTtactaa gttggcatta taaaaaagca ttgc   (SEQ ID NO:73)

attLT5A: gggg agcct gctttttaAactaa gttggcatta taaaaaagca ttgc   (SEQ ID NO:74)

attLT5C: gggg agcct gctttttaCactaa gttggcatta taaaaaagca ttgc   (SEQ ID NO:75)

attLT5G: gggg agcct gctttttaGactaa gttggcatta taaaaaagca ttgc   (SEQ ID NO:76)

attLA6C: gggg agcct gctttttatCctaa gttggcatta taaaaaagca ttgc   (SEQ ID NO:77)

attLA6G: gggg agcct gctttttatGctaa gttggcatta taaaaaagca ttgc   (SEQ ID NO:78)

attLA6T: gggg agcct gctttttatTctaa gttggcatta taaaaaagca ttgc   (SEQ ID NO:79)

attLC7A: gggg agcct gctttttataAtaa gttggcatta taaaaaagca ttgc   (SEQ ID NO:80)

attLC7G: gggg agcct gctttttataGtaa gttggcatta taaaaaagca ttgc   (SEQ ID NO:81)

attLC7T: gggg agcct gctttttataTtaa gttggcatta taaaaaagca ttgc   (SEQ ID NO:82)

Single base changes outside of the 7 bp overlap:
attL8:   gggg agcct Acttttttatactaa gttggcatta taaaaaagca ttgc   (SEQ ID NO:83)

attL9:   gggg agcct gcCtttttatactaa gttggcatta taaaaaagca ttgc   (SEQ ID NO:84)

attL10:  gggg agcct gcttCtttatactaa gttggcatta taaaaaagca ttgc   (SEQ ID NO:85)

attL14:  gggg agcct gctttttatacCaa gttggcatta taaaaaagca ttgc   (SEQ ID NO:86)

attL15:  gggg agcct gctttttatactaG gttggcatta taaaaaagca ttgc   (SEQ ID NO:87)
```

Note: Additional vectors wherein the first nine bases are gggg agcca (i.e., substituting an adenine for the thymine in the position immediately preceding the 15-bp core region), which may or may not contain the single base pair substitutions (or deletions) outlined above, can also be used in these experiments.

Recombination reactions of attL- and attR-containing PCR products was performed as follows:

8 µl of $H_2O$
2 µl of attL PCR product (100 ng)
2 µl of attR PCR product (100 ng)
4 µl of 5× buffer
4 µl of GATEWAY™ LR CLONASE™ Enzyme Mix
20 µl total volume CLONASE™ reactions were incubated at 25° C. for 2 hours.

2 µl of 10× CLONASE™ stop solution (proteinase K, 2 mg/ml) were added to stop the reaction.

10 µl of the reaction mixtures were run on a 1% agarose gel.

Results

Each attL PCR substrate was tested in the in vitro recombination assay with each of the attR PCR substrates. The results indicate that changes within the first three positions of the 7 bp overlap (TTTATAC) strongly altered the specificity of recombination. These mutant att sites each recombined as well as the wild-type, but only with their cognate partner mutant; they did not recombine detectably with any other att site mutant. In contrast, changes in the last four positions (TTTATAC) only partially altered specificity; these mutants recombined with their cognate mutant as well as wild-type att sites and recombined partially with all other mutant att sites except for those having mutations in the first three positions of the 7 bp overlap. Changes outside of the 7 bp overlap were found not to affect specificity of recombination, but some did influence the efficiency of recombination.

Based on these results, the following rules for att site specificity were determined:

Only changes within the 7 bp overlap affect specificity.
Changes within the first 3 positions strongly affect specificity.
Changes within the last 4 positions weakly affect specificity.

Mutations that affected the overall efficiency of the recombination reaction were also assessed by this method. In these experiments, a slightly increased (less than 2-fold) recombination efficiency with attLT1A and attLC7T substrates was observed when these substrates were reacted with their cognate attR partners. Also observed were mutations that decreased recombination efficiency (approximately 2-3 fold), including attLA6G, attL14 and attL15. These mutations presumably reflect changes that affect Int protein binding at the core att site.

The results of these experiments demonstrate that changes within the first three positions of the 7 bp overlap (TTTATAC) strongly altered the specificity of recombination (i.e., att sequences with one or more mutations in the first three thymidines would only recombine with their cognate partners and would not cross-react with any other att site mutation). In contrast, mutations in the last four positions (TTTATAC) only partially altered specificity (i.e., att sequences with one or more mutations in the last four base positions would cross-react partially with the wild-type att site and all other mutant att sites, except for those having mutations in one or more of the first three positions of the 7 bp overlap). Mutations outside of the 7 bp overlap were not found to affect specificity of recombination, but some were found to influence (i.e., to cause a decrease in) the efficiency of recombination.

EXAMPLE 10

Discovery of Att Site Mutations That Increase the Cloning Efficiency of GATEWAY™ Cloning Reactions In experiments designed to understand the determinants of att site specificity, point mutations in the core region of attL were made. Nucleic acid molecules containing these mutated attL sequences were then reacted in an LR reaction with nucleic acid molecules containing the cognate attR site (i.e., an attR site containing a mutation corresponding to that in the attL site), and recombinational efficiency was determined as described above. Several mutations located in the core region of the att site were noted that either slightly increased (less than 2-fold) or decreased (between 2–4-fold) the efficiency of the recombination reaction (Table 5).

TABLE 5

Effects of attL mutations on Recombination Reactions.

| Site | Sequence | SEQ ID | Effect on Recombination |
|---|---|---|---|
| attL0 | agcctgcttttttatactaagttggcatta | 88 | N/A |
| attL5 | agcctgctttAttatactaagttggcatta | 89 | slightly increased |
| attL6 | agcctgcttttttataTtaagttggcatta | 90 | slightly increased |
| attL13 | agcctgcttttttatGctaagttggcatta | 91 | decreased |
| attL14 | agcctgcttttttatacCaagttggcatta | 92 | decreased |
| attL15 | agcctgcttttttatactaGgttggcatta | 93 | decreased |
| consensus | CAACTTnnTnnnAnnAAGTTG | 94 | N/A |

It was also noted that these mutations presumably reflected changes that either increased or decreased, respectively, the relative affinity of the integrase protein for binding the core att site. A consensus sequence for an integrase core-binding site (CAACTTNNT) has been inferred in the literature but not directly tested (see, e.g., Ross and Landy, *Cell* 33:261–272 (1983)). This consensus core integrase-binding sequence was established by comparing the sequences of each of the four core att sites found in attP and attB as well as the sequences of five non-att sites that resemble the core sequence and to which integrase has been shown to bind in vitro. These experiments suggest that many more att site mutations might be identified which increase the binding of integrase to the core att site and thus increase the efficiency of GATEWAY™ cloning reactions.

EXAMPLE 11

Effects of Core Region Mutations on Recombination Efficiency

To directly compare the cloning efficiency of mutations in the att site core region, single base changes were made in the attB2 site of an attB1-tet-attB2 PCR product. Nucleic acid molecules containing these mutated attB2 sequences were then reacted in a BP reaction with nucleic acid molecules containing non-cognate attP sites (i.e., wild-type attP2), and recombinational efficiency was determined as described above. The cloning efficiency of these mutant attB2 containing PCR products compared to standard attB1-tet-attB2 PCR product are shown in Table 6.

TABLE 6

Efficiency of Recombination With Mutated attB2 Sites.

| Site | Sequence | SEQ ID NO. | Mutation | Cloning Efficiency |
|---|---|---|---|---|
| attB0 | tcaagttagtataaaaaagcaggct | 95 | | |
| attB1 | ggggacaagtttgtacaaaaaagcaggct | 47 | | |
| attB2 | ggggaccactttgtacaagaaagctgggt | 48 | | 100% |
| attB2.1 | ggggaAcactttgtacaagaaagctgggt | 96 | C → A | 40% |
| attB2.2 | ggggacAacttgtacaagaaagctgggt | 97 | C → A | 131% |
| attB2.3 | ggggaccCctttgtacaagaaagctgggt | 98 | A → C | 4% |
| attB2.4 | ggggaccaAtttgtacaagaaagctgggt | 99 | C → A | 11% |
| attB2.5 | ggggaccacGttgtacaagaaagctgggt | 100 | T → G | 4% |
| attB2.6 | ggggaccactGtgtacaagaaagctgggt | 101 | T → G | 6% |
| attB2.7 | ggggaccacttGgtacaagaaagctgggt | 102 | T → G | 1% |
| attB2.8 | ggggaccactttTtacaagaaagctgggt | 103 | G → T | 0.5% |

As noted above, a single base change in the attB2.2 site increased the cloning efficiency of the attB1-tet-attB2.2 PCR product to 131% compared to the attB1-tet-attB2 PCR product. Interestingly, this mutation changes the integrase core binding site of attB2 to a sequence that matches more closely the proposed consensus sequence.

Additional experiments were performed to directly compare the cloning efficiency of an attB1-tet-attB2 PCR product with a PCR product that contained attB sites containing the proposed consensus sequence of an integrase core binding site. The following attB sites were used to amplify attB-tet PCR products:

| attB1 | ggggacaagtttgtacaaaaaagcaggct (SEQ ID NO:47) |
|---|---|
| attB1.6 | ggggacaaCtttgtacaaaaaagTTggct (SEQ ID NO:104) |
| attB2 | ggggaccactttgtacaagaaagctgggt (SEQ ID NO:48) |
| attB2.10 | ggggacAactttgtacaagaaagTtgggt (SEQ ID NO:105) |

BP reactions were carried out between 300 ng (100 fmoles) of pDONR201 (Invitrogen Corp., Life Technologies Division, Cat. No. 11798-014) with 80 ng (80 fmoles) of attB-tet PCR product in a 20 μl volume with incubation for 1.5 hours at 25° C., creating pENTR201-tet Entry clones. A comparison of the cloning efficiencies of the above-noted attB sites in BP reactions is shown in Table 7.

TABLE 7

Cloning efficiency of BP Reactions.

| PCR product | CFU/ml | Fold Increase |
|---|---|---|
| B1-tet-B2 | 7,500 | |
| B1.6-tet-B2 | 12,000 | 1.6 x |
| B1-tet-B2.10 | 20,900 | 2.8 x |
| B1.6-tet-B2.10 | 30,100 | 4.0 x |

These results demonstrate that attB PCR products containing sequences that perfectly match the proposed consensus sequence for integrase core binding sites can produce Entry clones with four-fold higher efficiency than standard GATEWAY™ attB1 and attB2 PCR products.

The entry clones produced above were then transferred to pDEST20 (Invitrogen Corp., Life Technologies Division, Cat. No. 11807-013) via LR reactions (300 ng (64 fmoles) pDEST20 mixed with 50 ng (77 fmoles) of the respective pENTR201-tet Entry clone in 20 μl volume; incubated for a 1 hour incubation at 25° C.). The efficiencies of cloning for these reactions are compared in Table 8.

TABLE 8

Cloning Efficiency of LR Reactions.

| pENTR201-tet × pDEST20 | CFU/ml | Fold Increase |
|---|---|---|
| L1-tet-L2 | 5,800 | |
| L1.6-tet-L2 | 8,000 | 1.4 |
| L1-tet-L2.10 | 10,000 | 1.7 |
| L1.6-tet-L2.10 | 9,300 | 1.6 |

These results demonstrate that the mutations introduced into attB1.6 and attB2.10 that transfer with the gene into entry clones slightly increase the efficiency of LR reactions. Thus, the present invention encompasses not only mutations in attB sites that increase recombination efficiency, but also to the corresponding mutations that result in the attL sites created by the BP reaction.

To examine the increased cloning efficiency of the attB1.6-tet-attB2.10 PCR product over a range of PCR product amounts, experiments analogous to those described above were performed in which the amount of attB PCR product was titrated into the reaction mixture. The results are shown in Table 9.

TABLE 9

Titration of attB PCR products.

| Amount of attB PCR product (ng) | PCR product | CFU/ml | Fold Increase |
|---|---|---|---|
| 20 | attB1-tet-attB2 | 3,500 | 6.1 |
| | attB1.6-tet-attB2.10 | 21,500 | |
| 50 | attB1-tet-attB2 | 9,800 | 5.0 |
| | attB1.6-tet-attB2.10 | 49,000 | |
| 100 | attB1-tet-attB2 | 18,800 | 2.8 |
| | attB1.6-tet-attB2.10 | 53,000 | |
| 200 | attB1-tet-attB2 | 19,000 | 2.5 |
| | attB1.6-tet-attB2.10 | 48,000 | |

These results demonstrate that as much as a six-fold increase in cloning efficiency is achieved with the attB1.6- tet-attB2.10 PCR product as compared to the standard attB1-tet-attB2 PCR product at the 20 ng amount.

EXAMPLE 12

Determination of attB Sequence Requirements for Optimum Recombination Efficiency To examine the sequence requirements for attB and to determine which attB sites would clone with the highest efficiency from populations of degenerate attB sites, a series of experiments was performed. Degenerate PCR primers were designed which contained five bases of degeneracy in the B-arm of the attB site. These degenerate sequences would thus transfer with the gene into Entry clone in BP reactions and subsequently be transferred with the gene into expression clones in LR reactions. The populations of degenerate attB and attL sites could thus be cycled from attB to attL back and forth for any number of cycles. By altering the reaction conditions at each transfer step (for example, by decreasing the reaction time and/or decreasing the concentration of DNA) the reaction can be made increasingly more stringent at each cycle and thus enrich for populations of attB and attL sites that react more efficiently.

The following degenerate PCR primers were used to amplify a 500 bp fragment from pUC18 which contained the lacZ alpha fragment (only the attB portion of each primer is shown):

```
attB1:         GGGG ACAAGTTTGTACAAA AAAGC AGGCT
               (SEQ ID NO:47)

attB1n16-20:   GGGG ACAAGTTTGTACAAA nnnnn AGGCT
               (SEQ ID NO:106)

attB1n21-25:   GGGG ACAAGTTTGTACAAA AAAGC nnnnn
               (SEQ ID NO:107)

attB2:         GGGG ACCACTTTGTACAAG AAAGC TGGGT
               (SEQ ID NO:48)

attB2n16-20:   GGGG ACCACTTTGTACAAG nnnnn TGGGT
               (SEQ ID NO:108)

attB2n21-25:   GGGG ACCACTTTGTACAAG AAAGC nnnnn
               (SEQ ID NO:109)
```

The starting population size of degenerate att sites is $4^5$ or 1024 molecules. Four different populations were transferred through two BP reactions and two LR reactions. Following transformation of each reaction, the population of transformants was amplified by growth in liquid media containing the appropriate selection antibiotic. DNA was prepared from the population of clones by alkaline lysis miniprep and used in the next reaction. The results of the BP and LR cloning reactions are shown below.

BP-1, overnight reactions:

|  | cfu/ml | percent of control |
|---|---|---|
| attB1-lacZa-attB2 | 78,500 | 100% |
| attB1n16–20-lacZa-attB2 | 1,140 | 1.5% |
| attB1n21–25-lacZa-attB2 | 11,100 | 14% |
| attB1-lacZa-attB2n16–20 | 710 | 0.9% |
| attB1-lacZa-attB2n21–25 | 16,600 | 21% |

LR-1, pENTR201-lacZa x pDEST20/EcoRI, 1 hour reactions

|  | cfu/ml | percent of control |
|---|---|---|
| attL1-lacZa-attL2 | 20,000 | 100% |
| attL1n16–20-lacZa-attL2 | 2,125 | 11% |
| attL1n21–25-lacZa-attL2 | 2,920 | 15% |
| attL1-lacZa-attL2n16–20 | 3,190 | 16% |
| attL1-lacZa-attL2n21–25 | 1,405 | 7% |

BP-2, pEXP20-lacZa/ScaI x pDONR201, 1 hour reactions

|  | cfu/ml | percent of control |
|---|---|---|
| attB1-lacZa-attB2 | 48,600 | 100% |
| attB1n16–20-lacZa-attB2 | 22,800 | 47% |
| attB1n21–25-lacZa-attB2 | 31,500 | 65% |
| attB1-lacZa-attB2n16–20 | 42,400 | 87% |
| attB1-lacZa-attB2n21–25 | 34,500 | 71% |

LR-2, pENTR201-lacZa x pDEST6/NcoI, 1 hour reactions

|  | cfu/ml | percent of control |
|---|---|---|
| attL1-lacZa-attL2 | 23,000 | 100% |
| attL1n16–20-lacZa-attL2 | 49,000 | 213% |
| attL1n21–25-lacZa-attL2 | 18,000 | 80% |
| attL1-lacZa-attL2n16–20 | 37,000 | 160% |
| attL1-lacZa-attL2n21–25 | 57,000 | 250% |

These results demonstrate that at each successive transfer, the cloning efficiency of the entire population of att sites increases, and that there is a great deal of flexibility in the definition of an attB site. Specific clones may be isolated from the above reactions, tested individually for recombination efficiency, and sequenced. Such new specificities may then be compared to known examples to guide the design of new sequences with new recombination specificities. In addition, based on the enrichment and screening protocols described herein, one of ordinary skill can easily identify and use sequences in other recombination sites (e.g., other att sites, lox, FRT, etc.), that result in increased specificity in the recombination reactions using nucleic acid molecules containing such sequences.

EXAMPLE 13

Embedding of Functional Components in Recombination Sites

Recombination sites used with the invention may also have embedded functions or properties. An embedded functionality is a function or property conferred by a nucleotide sequence in a recombination site which is not directly associated with recombination efficiency or specificity. For example, recombination sites may contain protein coding sequences (e.g., intein coding sequences), intron/exon splice sites, origins of replication, and/or stop codons. In generally, the longer the stretch of nucleic acid which makes up a recombination site the more amendable the site will be to the incorporation of embedded functions or properties. On the contrary, longer recombination sites will be more likely to have features (e.g., stop codons) which interfere with desired functions or properties. Further, recombination sites which have more than one (e.g., two, three, four, five, etc.) embedded functions or properties may also be prepared.

As explained below, in one aspect, the invention provides methods for removing nucleotide sequences encoded by recombination sites from RNA molecules. One example of such a method employs the use of intron/exon splice sites to remove RNA encoded by recombination sites from RNA transcripts. Again, as explained below, nucleotide sequences which encode these intron/exon splice sites may be fully or partially embedded in the recombination sites which encode sequences excised from RNA molecules or these intron/exon splice sites may be encoded by adjacent nucleic acid sequence. Similarly, one intron/exon splice sites may be encoded by recombination site and another intron/exon splice sites may be encoded by other nucleotide sequences (e.g., nucleic acid sequences of the vector or a nucleic acid of interest). Nucleic acid splicing is discussed in the following publications: R. Reed, *Curr. Opin. Genet. Devel* 6:215–220 (1996); S. Mount, *Nucl. Acids. Res.* 10:459–472, (1982); P. Sharp, *Cell* 77:805–815, (1994); K. Nelson and M. Green, *Genes and Devel.* 23:319–329 (1988); and T. Cooper and W. Mattox, *Am. J Hum. Genet.* 61:259–266 (1997).

In some instances it will be advantageous to remove either RNA corresponding to recombination sites from RNA transcripts or amino acid residues encoded by recombination sites. Removal of such sequences can be performed in several ways and can occur at either the RNA or protein level. One instance where it will generally be advantageous to remove RNA transcribed from a recombination site will be where a nucleic acid molecule which an ORF is inserted into a vector in an orientation which is intended to result in the expression of a fusion protein (e.g., GFP) between amino acid residues encoded by the ORF and amino acid residues encoded by the vector (e.g., GFP). In such an instance, the presence of an intervening recombination site between the ORF and the vector coding sequences may result in the recombination site (1) contributing codons to the mRNA which results in the inclusion of additional amino acid residues in the expression product, (2) contributing a stop codon to the mRNA which prevents the production of the desired fusion protein, and/or (3) shifting the reading frame of the mRNA such that the two protein are not fused "in-frame."

One method for removing recombination sites from mRNA molecules involves the use intron/exon splice sites (i.e., splice donor and splice acceptor sites). Splice sites can be suitably positioned in a number of locations. Using a Destination Vector designed to express an inserted ORF with an N-terminal GFP fusion, as an example, the first splice site could be encoded for by vector sequences located 3' to the GFP coding sequences and the second splice site could be partially embedded in the recombination site which separates the GFP coding sequences from the coding sequences of the ORF. Further, the second splice site either could abut the 3' end of the recombination site or could be positioned a short distance (e.g., 2, 4, 8, 10, 20 nucleotides) 3' to the recombination site. In addition, depending on the length of the recombination site, the second splice site could be fully embedded in the recombination site.

A modification of the method described above involves the connection of multiple nucleic acid segments which, upon expression, results in the production of a fusion protein. In one specific example, one nucleic acid segment encodes GFP and another nucleic acid segment which contains an ORF of interest. Each of these segments is flanked by recombination sites. In addition, the nucleic acid segments which encodes GFP contains an intron/exon splice site near its 3' terminus and the nucleic acid segments which contains the ORF of interest also contains an intron/exon splice site near its 5' terminus. Upon recombination, the nucleic acid segment which encodes GFP is positioned 5' to the nucleic acid segment which encodes the ORF of interest. Further, these two nucleic acid segments are separated by a recombination site which is flanked by intron/exon splice sites. Excision of the intervening recombination site thus occurs after transcription of the fusion mRNA. Thus, in one aspect, the invention is directed to methods for removing RNA transcribed from recombination sites from transcripts generated from nucleic acids described herein.

One method which could be used to introduce intron/exon splice sites into nucleic acid segments is by the use of PCR. For example, primers could be used to generate nucleic acid segments corresponding to an ORF of interest and containing both a recombination site and an intron/exon splice site.

The above methods can also be used to remove RNA corresponding to recombination sites when the nucleic acid segment which is recombined with another nucleic acid segment encodes RNA which is not produced in a translatable format. One example of such an instance is where a nucleic acid segment is inserted into a vector in a manner which results in the production of antisense RNA. As discussed below, this antisense RNA may be fused, for example, with RNA which encodes a ribozyme. Thus, the invention also provides methods for removing RNA corresponding to recombination sites from such molecules.

The invention further provides methods for removing amino acid sequences encoded by recombination sites from protein expression products by protein splicing. Nucleotide sequences which encode protein splice sites may be fully or partially embedded in the recombination sites which encode amino acid sequences excised from proteins or protein splice sites may be encoded by adjacent nucleotide sequences. Similarly, one protein splice site may be encoded by a recombination site and another protein splice sites may be encoded by other nucleotide sequences (e.g., nucleic acid sequences of the vector or a nucleic acid of interest).

It has been shown that protein splicing can occur by excision of an intein from a protein molecule and ligation of flanking segments. (See, e.g., Derbyshire et al., *Proc. Natl. Acad. Sci.* (*USA*) 95:1356–1357 (1998).) In brief, inteins are amino acid segments which are post-translationally excised from proteins by a self-catalytic splicing process. A considerable number of intein consensus sequences have been identified. (See, e.g., Perler, *Nucleic Acids Res.* 27:346–347 (1999).)

Similar to intron/exon splicing, N- and C-terminal intein motifs have been shown to be involved in protein splicing. Thus, the invention further provides compositions and methods for removing amino acid residues encoded by recombination sites from protein expression products by protein splicing. In particular, this aspect of the invention is related to the positioning of nucleic acid sequences which encode intein splice sites on both the 5' and 3' end of recombination sites positioned between two coding regions. Thus, when the protein expression product is incubated under suitable conditions, amino acid residues encoded these recombination sites will be excised.

Protein splicing may be used to remove all or part of the amino acid sequences encoded by recombination sites. Nucleic acid sequence which encode inteins may be fully or partially embedded in recombination sites or may be adjacent to such sites. In certain circumstances, it may be desirable to remove considerable numbers of amino acid residues beyond the N- and/or C-terminal ends of amino acid sequences encoded by recombination sites. In such instances, intein coding sequence may be located a distance (e.g., 30, 50, 75, 100, etc. nucleotides) 5' and/or 3' to the recombination site.

While conditions suitable for intein excision will vary with the particular intein, as well as the protein which contains this intein, Chong et al., *Gene* 192:271–281 (1997), have demonstrated that a modified *Saccharomyces cerevisiae* intein, referred to as Sce VMA intein, can be induced to undergo self-cleavage by a number of agents including 1,4-dithiothreitol (DTT), β-mercaptoethanol, and cysteine. For example, intein excision/splicing can be induced by incubation in the presence of 30 mM DTT, at 4° C. for 16 hours.

EXAMPLE 14

Removal of att Sites from RNA Transcripts by Pre-mRNA Splicing in Eukaryotic Cells Consensus RNA sequences in metazoan cells needed for removal of introns by splicing of pre-mRNA transcripts normally contain the following three elements:

1). At the 5' end of the intron: exon-AG|GTRAGT-intron; where | denotes the border between the intron and exon, and R=purine nucleotide. This element is referred to herein as (GT);
2). At the 3' end of the intron: intron-Yn-N-CAG|G-exon; where Yn=a pyrimidine-rich sequence of 10–12 nucleotides. This element is referred to herein as (Yn-AG);
3). At the branch point within the intron, ~20–40 bases 5' to (Yn-AG): YNRA*Y; where Y is a pyrimidine nucleotide and A* is the branch point adenosine that participates in the initial transesterification reaction to form an RNA lariat. This element is referred to herein as (BP-A*).

Underlined sequences shown above are those highly conserved and are generally believed to be required for splicing activity; other nucleotides in the consensus sequences are less highly conserved.

1. attB Splicing

These splicing elements can be combined with GATEWAY™ att-site-containing vectors in at least the following three ways to remove attB1 sites by RNA splicing.

Method 1: (GT) - - - (BP-A*)[attB1](Yn-AG) - - - ORF

In this method, the (BP-A*) element is located just 5' to the end of attB1, and the (Yn-AG) consensus is merged with the 3'-end of the attB1 sequence, exploiting the flexibility of the 5 nucleotides flanking the core of the attB sequence. The (GT) consensus can be positioned conveniently ten or more nucleotides upstream from (BP-A*) element.

This arrangement has the advantage that it requires a minimum sequence addition between the 3' end of the attB1 site and the sequence encoding the ORF. A potential difficulty with the use of this approach is that the pyrimidine-rich sequence in (Yn-AG) overlaps with the attB1 sequence, which is relatively purine rich. Thus, in certain instances, sufficient nucleotide changes (to C or T) in the attB1 site to permit efficient splicing may not be compatible with efficient B×P recombination.

Sequences positioned 5' to the recombination cleavage site within attB1 are contributed in Expression Clones by the Destination Vector, while sequences 3' to this site are derived (in most cases) from an attB-PCR product. If the splicing reaction is intended to fuse RNA encoding an N-terminal protein (contributed by a Destination Vector) to RNA encoding another ORF (contributed by an Entry Clone), the positioning of (GT) and (Yn-AG) will generally be positioned so that the spliced product maintains the desired translational reading frame.

Method 2: (GT) - - - (BP-A*)[attB1](Yn-AG) - - - ORF

In this method, the (Yn-AG) consensus is immediately next to the attB1 site; consequently the branch point A* in (BP-A*) element will generally need to be close to the attB1 site. Thus, the distance from AG in (Yn-AG) will generally be no more than about 40 nucleotides.

The (Yn-AG) sequence can be added as part of a primer adapter, assuming the Entry Clone is constructed using attB-PCR. Further, this primer can be designed using a consensus (Yn-AG) sequence which favors efficient splicing. In some instances, the presence of the attB1 sequence between (BP-A*) and (Yn-AG) may interfere with splicing. If such cases, the attB1 sequence can be mutated to accommodate a more optimal splicing sequence.

Method 3: (GT) - - - [attB1]-(BP-A*) - - - (Yn-AG) - - - ORF

This method employs an arrangement which allows one to choose an optimal splicing sequence and spacing for the combined elements comprising (BP-A*) - - - (Yn-AG). The minimum size for this combination is expected to be about 20 nucleotides. Therefore this sequence will normally be added to PCR products as an attB1-primer adapter of about 45–50 nucleotides.

Similar considerations apply to designing sequences that allow splicing to remove the attB2 site from mRNA. But since in this case (BP-A*) and (Yn-AG) can be contributed by the Destination Vector, the most attractive option is:

ORF-(GT)[attB2]- - - (BP-A*) - - - (Yn-AG), where the sequence between (GT) and attB2 is minimized, to reduce the size of the attB2-PCR adapter primer. Minimized sequences suitable for use in particular cases can be determined experimentally using methods described herein.

Another way to produce a vector that splices attB sites is to construct a vector directly that contains splicing signals flanking the attB1 and attB2 sites. The main difference from the approaches described above is that any sequences added there using attB primer adapters (as in B and C) could be pre-installed into the vector itself next to a multiple cloning site positioned between the attB sites.

2. attL Splicing

The sequences encoding attL1 and attL2 sites may be removed from transcripts by RNA splicing. However, the 100 nucleotide length of attL imposes a constraint on the options for arranging the splicing sequence elements. This distance is generally too great for the placement of attL1 between (BP-A*) and (Yn-AG). One alternative which can be employed is that either or both of these elements can be embedded in a mutated version of attL1. Another approach is that these elements (i.e., (BP-A*) and (Yn-AG)) can be contributed by an attB-adapter primer and (GT) can be provided by the attP Donor plasmid. By recombining these elements in a B×P reaction an entry clone with splice sites for splicing attB1 is created.

Similarly, for splicing of attL2, there is no practical limit to the length of sequence allowed between (GT) and (BP-A*). So (GT) could be provided on the attB2 adapter primer, while (BP-A*) and (Yn-AG) would be contributed by the attP Donor Vector. For such uses, the attP Donor Vector will generally need to contain a eukaryotic promoter and the rrnB transcription termination sequences will generally need to be removed. The potential for an adverse effect of the attL2 sequence between (GT) and (BP-A*) seems low, but may need to be determined on a case by case basis.

A potential advantage of splicing attL sequences from Entry Clone transcripts is that users could clone and express PCR products directly as Entry Clones, without need for further subcloning into a Destination Vector. Further, the presence of a termination codon in our attL1 sequence, which appears difficult to remove without diminishing L×R recombination, would be of no consequence to translation of ORFs fused with N-terminal peptides.

The above describes some applications of RNA splicing with the GATEWAY™ system, which is to remove attB1 between ORF and N-terminal sequences and to remove attB2 sequences between ORF sequences and C-terminal sequences of protein fusions. Other applications would be apparent to one skilled in the art. Further, one such application is the use of the RNA splicing process to remove att sequences interposed (as a result of performing a GATEWAY™ recombination-based subcloning reaction) between the sequences encoding multiple protein domains in a eukaryotic expression vector, where the ORFs encoding the various domains are separated by an att site sequence. Such vectors can be constructed readily by GATEWAY™ recombination with att sites of multiple specificities, such as att1, att2, att3, att4, etc. Although this approach permits rapid construction of protein fusions, as well as shuffling of DNA sequences encoding protein domains, the recombination products typically will contain 25 bp attB sites (or 100 bp attL sites) intervening between these domains, whose removal often will be desirable. The RNA splicing mechanism described is one way to remove these intervening sequences. The use of splicing to remove att sites between multiple protein domains also makes it practical to make these constructs using GATEWAY™ recombination reactions between attB and attP sites, which yield attL and attR sites. This is because either type of att sequence (attB or attL) could be removed by an RNA splicing reaction in a properly designed vector. In other situations, it will be useful to remove by splicing attR and/or attP sites as well.

A second application addresses the common problem of obtaining copies of large or rare mRNAs. Some mRNAs are difficult to reverse transcribe (into cDNA) in their entirety due to their large size and/or low abundance. Often, one or both ends of the cDNA can be obtained, but the entire sequence as one molecule is unobtainable. When two or more different portions of the cDNA are available which together constitute the entire mRNA sequence, the sequence of these cDNA sequences can be determined and PCR primers synthesized. Then using attB-primers each non-overlapping portion of the entire transcript can be amplified by PCR. These amplified sequences then can be combined in the proper order using GATEWAY™ recombination. Such a recombination product will comprise the various sequences in their proper order, but separated by att sites. Given the appropriate transcription promoter and termination signals, such constructs can be used to prepare RNA either in vitro for use in an in vitro splicing reaction, or to transfect metazoan cells with an appropriate construct allowing transcription followed by RNA splicing within the cell. In this manner, transcripts of the authentic mRNA can then be produced. Such mRNA transcripts can be used directly for studies of biological function of the protein encoded by the spliced transcript. Alternatively, because the transcripts can be produced in abundance with this approach, it becomes more feasible to produce a cDNA copy of the spliced RNA. This cDNA, which lacks the intervening att sequences, is useful for producing the encoded protein in cells lacking the proper splicing machinery, such as E. coli.

A third application of this technology makes it possible to produce replicas of mRNAs that are difficult to obtain due to their low abundance or lack of suitable tissue sources. Most metazoan genes encoding proteins consist of exons sequences separated by intron sequences. Whenever exon-intron borders of a gene can be predicted accurately from genomic DNA sequences by bioinformatic algorithms, PCR products flanked by att site sequences can be synthesized that contain the exon sequences. With proper design of the att sequences flanking these products, they can be linked each together in the proper order, while preserving the correct translational reading frame, using GATEWAY™ recombination. By including the appropriate transcription signals, these constructs can serve as templates to synthesize an RNA transcript containing the ordered exon sequences, each separated by an att sequence. Given that the appropriate splicing signals are included in these constructs, the transcripts produced will be processed by the splicing reactions of metazoan cells to yield nucleic acids which correspond to naturally produced mRNA sequences. In this manner one can eliminate the need first to isolate mRNA from cells. Further, cells producing such mRNA from splicing of transcripts made as described above can be used directly for studies of biological function or as a source of a desired mRNA to produce its cDNA. Alternatively, these constructs could be spliced in vitro using properly constituted splicing extracts.

EXAMPLE 15

Determination of Gene Expression Profiles of Cells

The invention further provides compositions and methods for cloning and sequencing multiple cDNA molecules. In general, these methods involve generating concatamers of cDNA molecules and performing sequencing reactions on these molecule to determine the nucleotide sequences of the individual inserts. Such methods are particularly useful for determining the gene expression profile of particular cells and/or tissues. One example of such a method, as well as a vector produced by the described method, are shown in FIG. 23.

The vector shown in FIG. 23 contains a series of relatively short cDNA inserts (e.g., 10, 15, 20, 25, 30, 45, or 50 nucleotides in length) connected to each other by attB sites. The vector shown in FIG. 23 also contains sequencing primer sites adjacent to each side of the cDNA insertion site.

Nucleic acid molecules which represent genes expressed in a cell or tissue may be broken into relatively small fragments in a number of ways, including mechanical shearing, digestion with one or a combination of restriction enzymes (e.g., NlaIII, Sau3A, etc.), or digestion with an endonuclease having little or no sequence specificity (e.g., Micrococcal nuclease, DNAseI, etc.). The conditions will generally be adjusted so that nucleic acid fragments of a specific average size are produced. Further, if desired, nucleic acid fragments of a particular size can be isolated before insertion into a vector. Methods of separating nucleic acid molecules based on size are known in the art and include the column chromatography and gel electrophoresis (e.g., agarose and polyacrylamide gel electrophoresis).

Nucleotide sequence data may be obtained by sequencing nucleic acids connected by methods of the invention and inserted in a sequencing vector using standard methods known in the art. In most instances, neither the 5' to 3' orientation of the nucleic acid inserts in the sequencing vector nor the strand which is sequenced will not be relevant for determining the gene expression profile of a cell or tissue. This is so because it will generally be possible to identity of the mRNA from which the sequenced nucleic acid was derived regardless of the orientation of the sequenced nucleic acid segment or strand which is sequenced.

Thus, the invention provides methods for determining the gene expression profile of cells and/or tissues. In one aspect, the invention provides methods for determining the gene expression profile of cells and/or tissues, comprising (a) generating one or more populations of cDNA molecules from RNA obtained from the cells and/or tissues, wherein the individual cDNA molecules of these populations comprise at least two recombination sites capable of recombining with at least one recombination site present on the individual members of the same or a different population of cDNA molecules, (b) contacting the nucleic acid molecules of (a) with one or more recombination proteins under conditions which cause the nucleic acid molecules to join, and (c) determining the sequence of the joined nucleic acid molecules.

EXAMPLE 16

Use of GATEWAY™ System to Clone the Tet and LacZ Genes

The following attB sites was added to PCR primers which were synthesized by standard methods. The attB1 and attB2 sites were shown as the standard GATEWAY™ reading frame (see GATEWAY™ GATEWAY™ Cloning Technology Instruction Manual (Invitrogen Corp., Life Technologies Division)) and is indicated below. The reading frame of attB5 may be altered as appropriate. The selection of a reading frame can be used to generate fusion proteins.

overnight at 25° C. Miniprep DNA was prepared from individual DH5α colonies and quantitated by agarose gel electrophoresis.

An LR CLONASE™ reaction was prepared in a reaction volume of 20 μl containing the following components:
  60 ng (25 fmoles) of the supercoiled tet entry clone
  75 ng (20 fmoles) of the supercoiled lacZ entry clone
  150 ng (35 fmoles) of pDEST6 (described in PCT Publication WO 00/52027, the entire disclosure of which is incorporated herein by reference) linearized with NcoI
  4 μl of LR4 reaction buffer
  4 μl of LR CLONASE™

The reaction was incubated at 25° C. overnight and stopped with 2 μl of proteinase K solution (2 mg/ml). 2 μl was used to transform 100 μl of LE DH5α cells and plated on LBamp plates containing XGal. Approximately 35,000 colonies were generated in the transformation mixture with cells at an efficiency of $1.6 \times 10^8$ cfu/μg of pUC DNA. All the colonies appeared blue indicating the presence of the lacZ gene. 24 colonies were streaked onto plates containing tetracycline and XGal. 24 out of 24 colonies were tetracycline resistant. 15 colonies were used to inoculate 2 ml of LB amp broth for mini preps. 15/15 minipreps contained a supercoiled plasmid of the correct size (8.8 kb). Three miniprep DNAs were digested with EcoRV. A banding pattern was observed that was consistent with the two fragments cloned in the correct orientation.

The resulting nucleic acid product consists of the two fragments linked together and cloned into the destination vector.

```
attB1  (5'-end of fragment A):   GGGG ACA ACT TTG TAC AAA AAA GTT GNN  (SEQ ID NO:110)

attb5  (3'-end of fragment A):   GGGG A CAA CTT TGT ATA ATA AAG TTG   (SEQ ID NO:111)

attB5R (5'-end of fragment B):   GGGG A CAA CTT TAT TAT ACA AAG TTG   (SEQ ID NO:112)

attb2  (3'-end of fragment B):   GGG AC AAC TTT GTA TAATAA AGT TGN    (SEQ ID NO:113)
```

Nucleic acid fragments encoding the tet gene (primed with 5'-attB1 and 3'-attB5) and the lacZ gene (primed with 5'-attB5R and 3'-attB2) were amplified by PCR and precipitated using polyethylene glycol as follows. 150 μl of TE is added to a 50 μl PCR reaction, followed by the addition of 100 μl of 30% PEG8000, 30 mM MgCl$_2$. The solution is then mixed an centrifuged at about 10,000×g at room temperature for 15 minutes. The PEG solution is then removed and the pellet id dissolved in TE.

The B1-tet-B5 PCR product was mixed with an attP1-ccdB-attP5 donor vector (pDONR-P1/P5) and reacted with BP CLONASE™ using a standard protocol (see Example 3 herein) to generate an attL1-tet-attL5 entry clone. The B5R-lacZ-B2 PCR product was mixed with an attP5R-ccdB-attP2 donor vector (pDONR-P5R/P2) and reacted with BP CLONASE™ to generate an attR5-lacZ-attL2 entry clone.

After incubation for 1–4 hours at 25° C., 2 Al of Proteinase K (2 mg/ml) was added stop the BP reactions. DH5α cells were then transformed with the LR vectors (i.e., entry clones) and plated on LB-Kan plates. The plates were incubated The structure of these two fragments, as the are inserted into the destination vector, is as follows (arrows indicate the orientation of attB sites with respect to the overlap sequence):
attB1→tet←attB5-lacZ←attB2

EXAMPLE 17

Use of GATEWAY™ System to Clone the Tet, LacZ and Neo Genes

The following attB sites are added to PCR primers which are synthesized by standard methods. The attB1 and attB2 sites are shown as the standard GATEWAY™ reading frame (see GATEWAY™ GATEWAY™ Cloning Technology Instruction Manual (Invitrogen Corp., Life Technologies Division) and is indicated below. The reading frame of attB5 and attB21 may be specified by the user.

| | |
|---|---|
| attB1 (5'-end of fragment A): | GGGG ACA ACT TTG TAC AAA AAA GTT GNN (SEQ ID NO:114) |
| attB5 (3'-end of fragment A) | GGGG A CAA CTT TGT ATA ATA AAG TTG (SEQ ID NO:111) |
| attB5 (3'-end of fragment A) | GGGG A CAA CTT TGT ATA ATA AAG TTG (SEQ ID NO:111) |
| attB5R (5'-end of fragment B): | GGGG A CAA CTT TAT TAT ACA AAG TTG (SEQ ID NO:112) |
| attB21R (3'-end of fragment B): | GGG A CAA CTT TTT AAT ACA AAG TTG (SEQ ID NO:115) |
| attB21 (5'-end of fragment C): | GGGG A CAA CTT TGT ATT AAA AAG TTG (SEQ ID NO:116) |
| attB2 (3'-end of fragment C): | GGGG AC AAC TTT GTA TAA TAA AGT TGN (SEQ ID NO:117) |

Nucleic acid fragments encoding the tet gene (primed with 5'-attB1 and 3'-attB5), the Neo gene (primed with 5'-attB5R and 3'-attB21R), and the lacZ gene (primed with 5'-attB21 and 3'-attB2) were amplified by PCR and precipitated using polyethylene glycol.

The B1-tet-B5PCR product was mixed with an attP1-ccdB-attP5 donor vector (pDONR-P1/P5) and reacted with BP CLONASE™ using a standard protocol to generate an attL1-tet-attL3 entry clone. The B5R-Neo-B21R PCR product was mixed with an attP5R-ccdB-attP21R donor vector (PDONR-P5R/P21R) and reacted with BP CLONASE™ to generate an attR5-Neo-attR21entry clone. The B21-lacZ-B2 PCR product was mixed with an attP21-ccdB-attP2 donor vector (pDONR-P21/P2) and reacted with BP CLONASE™ to generate an attL21-lacZ-attL2 entry clone.

An LR CLONASE™ reaction was prepared in a reaction volume of 20 µl containing the following components:
40 ng (17 fmoles) of the supercoiled tet entry clone
50 ng (19 fmoles) of the supercoiled or linear (VspI digested) Neo entry clone
75 ng (20 fmoles) of the supercoiled lacZ entry clone
150 ng (35 fmoles) of pDEST6 linearized with NcoI
4 µl of LR4 reaction buffer (200 mM Tris HCl (pH7.5), 4.75 mM EDTA, 4.8 mg/ml BSA, 445 mM NaCl, 47.5 mM spermidine)
4 µl of LR CLONASE™

The reaction was incubated at 25° C. overnight and stopped with 2 µl of proteinase K solution (2 mg/ml). Two µl was used to transform 100 µl of DH5α LE cells and plated on LBamp plates containing XGal. Approximately 3,200 colonies were generated in the transformation mixture with supercoiled entry clones. 5,300 colonies were generated in the transformation mixture with the reaction containing the VspI digested Neo entry clone. The efficiency of the competent cells was $1.2 \times 10^8$ cfu/µg of pUC DNA. All the colonies appeared blue indicating the presence of the lacZ gene. Nine colonies were streaked onto tet plates containing XGal. Nine out of 9 colonies were tetracycline resistant. Nine colonies were used to inoculate 2 ml of LBamp broth for mini preps. Nine out of 9 minipreps contained a supercoiled plasmid of the correct size (11 kb). Nine miniprep DNAs were digested with EcoRV. A banding pattern was observed that was consistent with the three fragments cloned in the correct orientation.

The resulting nucleic acid product consists of the three fragments linked together and cloned into the destination vector. The structure of these three fragments, as the are inserted into the destination vector, is as follows (arrows indicate the orientation of attB sites with respect to the overlap sequence): attB1→tet←attB5-Neo-attB21→lacZ←attB2

EXAMPLE 18

Use of the GATEWAY™ and Multiple att Sites with Different Specificities to Clone a Lux Operon The lux operon genes (luxA, luxB, luxC, luxD and luxE) of Vibrio fischeria genomic DNA were amplified using the primers listed immediately below that introduced an optimal Shine-Delgarno and Kozak sequence (ggaggtatataccatg (SEQ ID NO:118)) at the 5'-end and a T7 promoter and stop codon (gaagctatagtgagtcgtatta (SEQ ID NO:141)) at the 3'-end of each ORF.

TABLE 10

| SD 5' and T7 3' lux primers. | | | |
|---|---|---|---|
| SD 5' | luxA | ggaggtatataccatgAAGTTTGGAAATATTTGTTTTTC | (SEQ ID NO:119) |
| T7 3' | luxA | gaagctatagtgagtcgtattaTTTAGGTTCTTTTAAGAAAGGAGCGAC | (SEQ ID NO:120) |
| SD 5' | luxB | ggaggtatataccatgAAATTTGGATTATTTTTTCTAAAC | (SEQ ID NO:121) |
| T7 3' | luxB | gaagctatagtgagtcgtattaTGGTAAATTCATTTCGATTTTTGG | (SEQ ID NO:122) |
| SD 5' | luxC | ggaggtatataccatgAATAAATGTATTCCAATGATAATTAATGG | (SEQ ID NO:123) |
| T7 3' | luxC | gaagctatagtgagtcgtattaTGGGACAAAAACTAAAAACTTATCTTCC | (SEQ ID NO:124) |
| SD 5' | luxD | ggaggtatataccatgAAAGATGAAAGTGCTTTTTTACGATTG | (SEQ ID NO:125) |
| T7 3' | luxD | gaagctatagtgagtcgtattaAGCCAATTCTAATAATTCATTTTC | (SEQ ID NO:126) |

TABLE 10-continued

SD 5' and T7 3' lux primers.

| | | |
|---|---|---|
| SD 5' luxE | ggaggtatataccatgACTGTCCATACTGAATATAAAAGAAATC | (SEQ ID NO:127) |
| T7 3' luxE | gaagctatagtgagtcgtattaAATCCTTGATATTCTTTTGTATGACATTAGC | (SEQ ID NO:128) |

The PCR products were further amplified with attB-SD and attB-T7 adapter primers listed immediately below utilizing the Shine-Delgarno and T7 promoter sequences as primer sites to add attB sites to the ends of the PCR products.

TABLE 11 attB SD and T7 adapter primers.

| | | |
|---|---|---|
| B1.6 SD | GGGGACAACTTTGTACAAAAAAGTTGAAggaggtatataccatg | (SEQ ID NO:129) |
| B5 T7 | GGGGACAACTTTGTATAATAAAGTTGgaagctatagtgagtcgt | (SEQ ID NO:130) |
| B5R SD | GGGGACAACTTTATTATACAAAGTTGAAggaggtatataccatg | (SEQ ID NO:131) |
| B11 T7 | GGGGACAACTTTGTATAGAAAAGTTGgaagctatagtgagtcgt | (SEQ ID NO:132) |
| B11R SD | GGGGACAACTTTTCTATACAAAGTTGAAggaggtatataccatg | (SEQ ID NO:133) |
| B17 T7 | GGGGACAACTTTGTATACAAAAGTTGgaagctatagtgagtcgt | (SEQ ID NO:134) |
| B17R SD | GGGGACAACTTTTCTATACAAAGTTGAAggaggtatataccatg | (SEQ ID NO:135) |
| B21 T7 | GGGGACAACTTTGTATTAAAAGTTGgaagctatagtgagtcgt | (SEQ ID NO:136) |
| B21R SD | GGGGACAACTTTTTAATACAAAGTTGAAggaggtatataccatg | (SEQ ID NO:137) |
| B2.10 T7 | GGGGACAACTTTGTACAAGAAAGTTGgaagctatagtgagtcgt | (SEQ ID NO:138) |

In this way the following attB PCR products were generated:
attB1.6-SD-luxC-T7-attB5
attB5R-SD-luxD-T7-attB11
attB11R-SD-luxA-T7-attB17
attB17R-SD-luxB-T7-attB21
attB21 R-SD-luxE-T7-attB2.10

Each attB PCR product was precipitated with polyethylene glycol and reacted with the appropriate attP plasmid to generate Entry Clones of each lux ORF.

TABLE 12

| | BP Reaction Setup | | | | | | | | | |
|---|---|---|---|---|---|---|---|---|---|---|
| | 1 | 2 | 3 | 4 | 5 | 6 | 7 | 8 | 9 | 10 |
| TE | 7 μl | 7 μl | 7 μl | 7 μl | 7 μl | 7 μl | 7 μl | 7 μl | 7 μl | 7 μl |
| attB1-luxC-attB5 (10 ng/μl) | 2 μl | 2 μl | | | | | | | | |
| attP1-attP5 (150 ng/μl) | 2 μl | 2 μl | | | | | | | | |
| attB5R-luxD-attB11 (10 ng/μl) | | | 2 μl | 2 μl | | | | | | |
| attP5R-attP11 (150 ng/μl) | | | 2 μl | 2 μl | | | | | | |
| attB11R-luxA-attB17 (10 ng/μl) | | | | | 2 μl | 2 μl | | | | |
| attP17R-attP17 (150 ng/μl) | | | | | 2 μl | 2 μl | | | | |
| attB17R-luxB-attB21 (10 ng/μl) | | | | | | | 2 μl | 2 μl | | |
| attP17R-attP21 (150 ng/μl) | | | | | | | 2 μl | 2 μl | | |
| attB21R-luxE-attB2 (10 ng/μl) | | | | | | | | | 2 μl | 2 μl |
| attP21R-attP2 (150 ng/μl) | | | | | | | | | 2 μl | 2 μl |
| BP Buffer | 4 μl | 4 μl | 4 μl | 4 μl | 4 μl | 4 μl | 4 μl | 4 μl | 4 μl | 4 μl |
| BP Clonase Storage Buffer | 4 μl | — | 4 μl | — | 4 μl | — | 4 μl | — | 4 μl | — |
| BP Clonase | — | 4 μl | — | 4 μl | — | 4 μl | — | 4 μl | — | 4 μl |

The reactions were incubated at 25° C. overnight. Each reaction was stopped by the addition of 2 μl of Proteinase K (2 mg/ml) solution and incubated 10 minutes at 37° C. Two μl of each reaction was used to transform LEDH5a cells. One hundred μl (1/10) of each transformation was plated on LB agar containing 50 μg/ml kanamycin. The appropriate pENTR-lux clone was isolated from each reaction as determined by rapid miniprep analysis.

The luxA Entry Clone (pENTR-luxA) was digested with VspI to linearize the plasmid in the plasmid backbone. Equal amounts (40 ng) of each of the five lux Entry Clones were mixed with 150 ng of pDEST14 in a single LR reaction containing LR4 buffer and LR Clonase. Negative control reactions were prepared consisting of a no Clonase reaction and a no pENTRluxA reaction.

TABLE 13

LR Reaction Setup

|  | 1 | 2 | 3 |
|---|---|---|---|
| TE | — | 4 μl | — |
| pENTR/uxC (20 ng/μl) | 4 μl | 4 μl | 4 μl |
| pENTR/uxD (20 ng/μl) | 4 μl | 4 μl | 4 μl |
| pENTR/uxA/VspI cut (20 ng/μl) | 4 μl | — | 4 μl |
| pENTR/uxB (20 ng/μl) | 4 μl | 4 μl | 4 μl |
| pENTR/uxE (20 ng/μl) | 4 μl | 4 μl | 4 μl |
| pDEST14/NcoI (150 ng/μl) | 1 μl | 1 μl | 1 μl |
| LR4 Buffer | 8 μl | 8 μl | 8 μl |
| LR Clonase Storage Buffer | 8 μl | — | — |
| LR Clonase | — | 8 μl | 8 μl |

The reactions were incubated at 25° C. overnight. Each reaction was stopped by the addition of 4 μl Proteinase K (2 mg/ml) solution and incubated for 10 minutes at 37° C. Two μl of each reaction was used to transform LEDH5a cells. One hundred μl (1/10) of each transformation was plated on LB agar containing 100 μg/ml ampicillin.

The transformations generated no colonies for reaction 1 (no clonase), approximately 200 colonies for reaction 2 (no pENTRluxA DNA) and approximately 2500 colonies for reaction 3 (complete reaction). Ten colonies were picked from reaction 3 and examined by miniprep analysis. All 10 clones were determined to be correct based on size of the supercoiled plasmid DNA (10.3 kb) and by diagnostic restriction digests. The synthetic lux operon construct was transformed into BL21SI cells and luciferase activity was monitored by luminometry. Four independent isolates were demonstrated to generate titratable salt-inducible light in BL21SI cells. No light was detected in BL21SI cells containing pUC DNA. Since the light output was generated and detected in live *E. coli* cells the functional activity of all five lux genes was confirmed.

EXAMPLE 19

Generation of pDONR Vectors.

As in the example above (lux operon cloning), a collection of vector element Entry Clones was generated by attB PCR cloning. The Entry Clones were designed such that when a set of 4 vector element Entry Clones are reacted together, each vector element is linked together to assemble a new vector (FIG. 26A–26B). In this example two new attP DONOR vectors were constructed.

The following set of attB PCR products was generated:
attB21 R-attP1-ccdB-cat-attP2-attB5
attB5R-kan-attB11
attB5R-amp-attB11
attB11R-loxP-attB17
attB17R-pUC ori-attB21

Each attB PCR product was purified by PEG precipitation and reacted with the appropriate attP plasmid to generate Entry Clones of each vector element as follows:

TABLE 14

BP Reaction Setup

|  | 1 | 2 | 3 | 4 | 5 | 6 | 7 | 8 | 9 | 10 |
|---|---|---|---|---|---|---|---|---|---|---|
| TE | 7 μl | 7 μl | 7 μl | 7 μl | 7 μl | 7 μl | 7 μl | 7 μl | 7 μl | 7 μl |
| attB21R-attP1-ccdB-cat-attP2-attB5 (10 ng/μl) | 2 μl | 2 μl | | | | | | | | |
| attP21R-attP5 (150 ng/μl) | 2 μl | 2 μl | | | | | | | | |
| attB5R-kan-attB11 (10 ng/μl) | | | 2 μl | 2 μl | | | | | | |
| attB5R-attP11 (150 ng/μl) | | | 2 μl | 2 μl | | | | | | |
| attB5R-amp-attB11 (10 ng/μl) | | | | | 2 μl | 2 μl | | | | |
| attP5R-attP11 (150 ng/μl) | | | | | 2 μl | 2 μl | | | | |
| attB11R-loxP-attB17 (10 ng/μl) | | | | | | | 2 μl | 2 μl | | |
| attP11R-attP17 (150 ng/μl) | | | | | | | 2 μl | 2 μl | | |
| attB17R-pUC ori-attB21 (10 ng/μl) | | | | | | | | | 2 μl | 2 μl |
| attP17R-attP21 (150 ng/μl) | | | | | | | | | 2 μl | 2 μl |
| BP Buffer | 4 μl | 4 μl | 4 μl | 4 μl | 4 μl | 4 μl | 4 μl | 4 μl | 4 μl | 4 μl |
| BP Clonase Storage Buffer | 4 μl | — | 4 μl | — | 4 μl | — | 4 μl | — | 4 μl | — |
| BP Clonase | — | 4 μl | — | 4 μl | — | 4 μl | — | 4 μl | — | 4 μl |

The reactions were incubated at 25° C. overnight. Each reaction was stopped by the addition of 2 µl of Proteinase K (2 mg/ml) solution and incubated 10 minutes at 37° C. Two µl of each reaction was used to transform LEDH5a cells. 100 µl (1/10) of each transformation was plated on LB agar containing 50 µg/ml kanamycin. Colonies were picked and used to isolate the following pENTR clones by rapid miniprep analysis:
pENTR-attR21-attP1-ccdB-cat-attP2-attL5 (isolated from reaction 2)
pENTR-attR5-kan-attL11 (isolated from reaction 4)
pENTR-attR5-amp-attL11 (isolated from reaction 6)
pENTR-attR11-loxP-attL17 (isolated from reaction 8)
pENTR-attR17-ori-attL211 (from reaction 10)

The attR21-attP1-ccdB-cat-attP2-attL5 Entry Clone was digested with VspI to linearize the plasmid in the plasmid backbone. Equal amounts (40 ng) of each of four Entry Clones were mixed in a single LR reaction containing LR4 buffer and LR Clonase. Negative control reactions were prepared consisting of a no Clonase reaction and reactions containing no pENTR-attR21-attP1-ccdB-cat-attP2-attL5 DNA.

TABLE 15

LR Reaction Setup

|  | 1 | 2 | 3 | 4 |
|---|---|---|---|---|
| TE | — | 4 µl | — | — |
| pENTR-attR21-attP1-ccdB-cat-attP2-attL5 VspI cut (20 ng/µl) | 4 µl | — | 4 µl | 4 µl |
| pENTR-attR5-kan-attL11 (20 ng/µl) | 4 µl | 4 µl | 4 µl | — |
| pENTR-attR5-amp-attL11 (20 ng/µl) | — | — | — | 4 µl |
| pENTR-attR11-loxP-attL17 (20 ng/µl) | 4 µl | 4 µl | 4 µl | 4 µl |
| pENTR-attR17-ori-attL211 (20 ng/µl) | 4 µl | 4 µl | 4 µl | 4 µl |
| LR4 Buffer | 8 µl | 8 µl | 8 µl | 8 µl |
| LR Clonase Storage Buffer | 8 µl | — | — | — |
| LR Clonase | — | 8 µl | 8 µl | 8 µl |

The reactions were incubated at 25° C. overnight. Four µl of proteinase K (2 mg/ml) solution was added to each reaction and 2 µl used to transform DB3.1 cells. One hundred µl (1/10) of the transformation was plated on LB agar containing 20 µg/ml chloramphenicol and 50 µg/ml kanamycin (reactions 1, 2 and 3) or 20 µg/ml chloramphenicol and 100 µg/ml ampicillin (reaction 4).

The transformations generated approximately 5000 and 10,000 colonies for reactions 3 and 4, respectively compared to the negative controls of approximately 500 colonies for reaction 1 (no clonase) and 80 colonies for reaction 2 (no pENTR-attR21-attP1-ccdB-cat-attP2-attL5 DNA). Six colonies were picked from both reactions 3 and 4 and examined by miniprep analysis. All of the clones were determined to be correct based on size of the supercoiled plasmid DNA and by diagnostic restriction digests. The assembled vectors were shown to be functional by testing their ability to clone attB PCR products.

EXAMPLE 20

Construction of attP DONOR plasmids for Multisite Gateway

Four attP DONOR plasmids were constructed which contain the following arrangements of attP sites (FIG. 26A):
attPx→ccdB-cat←attPy
attPx←ccdB-cat→attPy
attPx→ccdB-cat←attPy
attPx←ccdB-cat→attPy The plasmids were constructed by PCR amplification of attP sites and attP DONOR vectors using primers containing compatible restriction endonuclease sites. Each PCR product was digested with the appropriate restriction enzyme. The digested attP DONOR vector PCR products were dephosphorylated and ligated to the digested attP sites. The products of the ligations consisted of plasmids containing of attP sites cloned into the pDONOR vector in both orientations.

The attP plasmids described above were subsequently used as templates for PCR reactions (FIG. 26B). PCR was performed using primers that would anneal specifically to the core of an attP site and thus create an attL or attR site of any desired specificity at the ends of the PCR products (see the primers used in the methods of Example 9). For each new attP DONOR vector two such PCR products were generated, one consisting of the plasmid backbone (ori-kan) and a second consisting of the ccdB and cat genes. The PCR products were generated and reacted together in LR Clonase reactions to generate new plasmids containing attP sites of any orientation and specificity.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of cloning a nucleic acid molecule comprising:

(a) providing a first nucleic acid segment flanked by a first and a second recombination site and a second nucleic acid segment flanked by a third and a fourth recombination site, wherein none of the recombination sites flanking the first and second nucleic acid segment is capable of recombining with any of the other sites flanking the first and second nucleic acid segment;

(b) providing a vector comprising a fifth, sixth, seventh and eighth recombination site, wherein each of the fifth, sixth, seventh and eighth recombination sites is capable of recombining with one of the first, second, third or fourth recombination site; and (c) conducting a recombination reaction such that the two nucleic acid segments are recombined into the vector thereby cloning the first and the second nucleic acid segments.

2. A method of cloning two or more nucleic acid segments, comprising:

(a) providing two or more nucleic acid segments, each segment flanked by two recombination sites which do not recombine with each other;

(b) providing a vector comprising a number of recombination sites equal to twice the number of nucleic acid segments, wherein each of the recombination sites is capable of recombining with one of the recombination sites flanking one of the nucleic acid segments; and (c) conducting a recombination reaction such that the nucleic acid segments are recombined into the vector thereby cloning the nucleic acid segments, wherein transcription of at least two of the nucleic acid segments results in the production of a single RNA.

3. The method of claim 2, wherein at least one of the nucleic acid segments produces a sense RNA strand upon transcription and at least one of the nucleic acid segments produces an antisense RNA strand upon transcription.

4. The method of claim 3, wherein the sense RNA and antisense RNA have at least one complementary region and are capable of hybridizing to each other.

5. The method of claim 2, wherein the nucleic acid segments comprise one or more libraries of nucleic acid molecules which encode variable domains of antibody molecules.

6. The method of claim 5, wherein the one or more libraries comprise nucleic acid molecules which encode variable domains of antibody light and heavy chains.

7. The method of claim 2, further comprising screening to identify nucleic acid molecules which encode proteins having binding specificity for one or more antigens.

8. A method of cloning at least one nucleic acid molecule comprising:

(a) providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and none of the first, fourth, fifth or sixth recombination sites is capable of recombining with any of the first through sixth recombination sites;

(b) providing a vector comprising a seventh and an eighth recombination site flanking a first negative selectable marker and comprising a ninth and a tenth recombination site flanking a second negative selectable marker, wherein none of the seventh through tenth recombination sites can recombine with any of the seventh through tenth recombination sites;

(c) conducting a first recombination reaction such that the second and the third recombination sites recombine; and (d) conducting a second recombination reaction such that the first and the fourth recombination sites recombine with the seventh and the eighth recombination sites and the fifth and the sixth recombination sites recombine with the ninth and the tenth recombination sites thereby cloning the first, second and third nucleic acid segments.

9. A method of cloning at least one nucleic acid molecule comprising:

(a) providing a first, a second and a third nucleic acid segment, wherein the first nucleic acid segment is flanked by a first and a second recombination site, the second nucleic acid segment is flanked by a third and a fourth recombination site and the third nucleic acid segment is flanked by a fifth and a sixth recombination site, wherein the second recombination site is capable of recombining with the third recombination site and the fourth recombination site is capable of recombining with the fifth recombination site;

(b) providing a vector comprising a seventh and an eighth recombination site; and (c) conducting at least one recombination reaction such that the second and the third recombination sites recombine and the fourth and the fifth recombination sites recombine and the first and the sixth recombination sites recombine with the seventh and the eighth recombination sites respectively, thereby cloning the first, second and third nucleic acid segments.

10. The method of claim 9, wherein the recombination reaction is conducted in the presence of one or more recombination proteins under conditions which favor the recombination.

11. A method of cloning n nucleic acid fragments, wherein n is an integer greater than 2, comprising:

(a) providing a $1^{st}$ through an $n^{th}$ nucleic acid segment, each segment flanked by two recombination sites, wherein the recombination sites are selected such that one of the two recombination sites flanking the $i^{th}$ segment, $n_i$, reacts with one of the recombination sites flanking the $n_{i-1}$th segment and the other recombination site flanking the $i^{th}$ segment reacts with one of the recombination sites flanking the $n_{i+1}$th segment;

(b) providing a vector comprising at least two recombination sites, wherein one of the two recombination sites on the vector reacts with one of the sites on the $1^{st}$ nucleic acid segment and another site on the vector reacts with a recombination site on the $n^{th}$ nucleic acid segment; and (c) conducting at least one recombination reaction such that all of the nucleic acid fragments are recombined into the vector.

12. The method of claim 11, wherein the recombination reaction is conducted in the presence of one or more recombination proteins under conditions which favor the recombination.

13. The method of claim 12, wherein the recombination proteins comprise one or more proteins selected from the group consisting of:

(a) Cre; (b) Int; (c) IHF; (d) Xis; (e) Fis; (f) Hin; (g) Gin; (h) Cin; (i) Tn3 resolvase; (j) TndX; (k) XerC; and (l) XerD.

14. The method of claim 11, wherein the recombination sites of the nucleic acid segments and the vector comprise one or more recombination sites selected from the group consisting of: (a) lox sites; (b) psi sites; (c) dif sites; (d) cer sites; (e) frt sites; (f) att sites; and (g) mutants, variants, and derivatives of the recombination sites of (a), (b), (c), (d), (e), or (f) which retain the ability to undergo recombination.

15. The method of claim 14, wherein the recombination sites which recombine with each other comprise att sites having identical seven base pair overlap regions.

16. A method of joining two or more segments of nucleic acid, comprising:

(a) providing two or more segments of nucleic acid, each segment comprising at least one recombination site capable of recombining with a recombination site present on the other segment; and (b) contacting the segments with one or more recombination proteins under conditions causing recombination between the recombination sites, thereby joining the segments, wherein the expression product is a ribozyme or an inhibitory RNA molecule.

17. A method of joining n nucleic acid segments, wherein n is an integer greater than 2, comprising:

(a) providing a $1^{st}$ through an $n^{th}$ nucleic acid segment, each segment flanked by two recombination sites, wherein the recombination sites are selected such that one of the two recombination sites flanking the $i^{th}$ segment, $n_i$, reacts with one of the recombination sites flanking the $n_{i-1}$th segment and the other recombination site flanking the $i^{th}$ segment reacts with one of the recombination sites flanking the $n_{i+1}$th segment; and (b) contacting the segments with one or more recombination proteins under conditions causing the segments to join.

18. The method of claim 17, wherein the recombination proteins comprise one or more proteins selected from the group consisting of: (a) Cre; (b) Int; (c) IHF; (d) Xis; (e) Fis; f) Hin; (g) Gin; (h) Cin; (i) Tn3 resolvase; (j) TndX; (k) XerC; and (l) XerD.

19. The method of claim 17, wherein the recombination sites which recombine with each other comprise att sites having identical seven base pair overlap regions.

20. The method of claim 19, wherein the first three nucleotides of the seven base pair overlap regions of the recombination sites which recombine with each other comprise nucleotide sequences selected from the group consisting of:

(a) AAA; (b) AAC; (c) AAG; (d) AAT; (e) ACA; (f) ACC; (g) ACG; (h) ACT; (i) AGA; (j) AGC; (k) AGG; (l) AGT; (m) ATA; (n) ATC; (o) ATG; and (p) ATT.

21. The method of claim 19, wherein the first three nucleotides of the seven base pair overlap regions of the recombination sites which recombine with each other comprise nucleotide sequences selected from the group consisting of:

(a) CAA; (b) CAC; (c) CAG; (d) CAT; (e) CCA; (f) CCC; (g) CCG; (h) CCT; (i) CGA; (j) CGC; (k) CGG; (l) CGT; (m) CTA; (n) CTC; (o) CTG; and (p) CTT.

22. The method of claim 19, wherein the first three nucleotides of the seven base pair overlap regions of the recombination sites which recombine with each other comprise nucleotide sequences selected from the group consisting of:

(a) GAA; (b) GAC; (c) GAG; (d) GAT; (e) GCA; (f) GCC; (g) GCG; (h) GCT; (i) GGA; (j) GGC; (k) GGG; (l) GGT; (m) GTA; (n) GTC; (o) GTG; and (p) GTT.

23. The method of claim 19, wherein the first three nucleotides of the seven base pair overlap regions of the recombination sites which recombine with each other comprise nucleotide sequences selected from the group consisting of:

(a) TAA; (b) TAC; (c) TAG; (d) TAT; (e) TCA; (f) TCC; (g) TCG; (h) TCT; (i) TGA; (j) TGC; (k) TGG; (l) TGT; (m) TTA; (n) TTC; (o) TTG; and (p) TTT.

24. The method of claim 17, further comprising inserting the nucleic acid segments joined in step (b) into a vector.

25. The method of claim 17, wherein the joined nucleic acid segments undergo intramolecular recombination to form a circular molecule.

26. The method of claim 25, wherein the recombination sites which undergo recombination to form the circular molecule are located at the 5' and 3' termini of the one or more of the nucleic acid segments.

27. The method of claim 17, wherein one or more of the nucleic acid segments encodes a selectable marker.

28. The method of claim 17, wherein one or more of the nucleic acid segments contains an origin of replication.

29. The method of claim 17, wherein some or all of the nucleic acid segments comprise nucleic acid molecules of one or more libraries.

30. The method of claim 17, wherein the one or more libraries comprise polynucleotides which encode variable domains of antibody molecules.

31. The method of claim 30, wherein at least one of the nucleic acid segments encodes a polypeptide linker for connecting variable domains of antibody molecules.

32. The method of claim 31, wherein the one or more libraries comprise polynucleotides which encode variable domains of antibody light and heavy chains.

33. The method of claim 17, further comprising screening to identify nucleic acid molecules which encode proteins having one or more identifiable activities.

34. The method of claim 33, wherein the one or more identifiable activities comprise binding specificity for one or more antigens.

35. The method of claim 33, wherein the one or more identifiable activities comprise an enzymatic activity.

36. The method of claim 33, wherein the one or more identifiable activities comprise an activity associated with a selectable marker.

37. The method of claim 17, wherein at least two of the nucleic acid segments encode expression products involved in the same biochemical pathway or biological process.

38. The method of claim 37, wherein the nucleic acid segments encode at least two different subunits of a multimeric enzyme complex.

39. The method of claim 17, wherein the nucleic acid segments encode at least two different enzymes which participate in reactions in the same biochemical pathway.

40. The method of claim 17, wherein the biochemical pathway leads to the production of an antibiotic or a carbohydrate.

41. A method of making a population of recombinant host cells comprising introducing nucleic acid segments joined by the method of claim 17 into a host cell.

42. A method of altering properties of a cell comprising introducing into the cell nucleic acid segments joined by the method of claim 17.

43. The method of claim 39, wherein the biochemical pathway leads to the post-translational modification of proteins.

44. The method of claim 43, wherein the post-translational modification is glycosylation or sialation.

45. The method of claim 44, wherein the cell is a bacterial cell.

46. A method of synthesizing a protein comprising:

(a) providing a nucleic acid molecule comprising at least one recombination site and comprising a coding sequence containing at least one suppressible stop codon;

(b) providing a vector comprising at least one recombination site and a coding sequence;

(c) causing recombination in vitro such that the nucleic acid molecule is inserted into the vector to produce a modified vector with the two coding sequences connected in frame and separated by said stop codon;

(d) transforming a host cell which expresses a suppressor tRNA with the modified vector; and (e) causing expression of the two coding sequences such that a fusion protein encoded by at least a portion of both of the coding sequences is produced.

47. The method according to claim 46, wherein the stop codon is selected from the group consisting of amber, opal and ochre codons.

48. The method according to claim 46, wherein the vector comprises a gene which encodes at least one suppressor tRNA molecule.

49. The method according to claim 46, wherein the chromosome of the host cell comprises a gene which encodes at least one suppressor tRNA molecule.

50. The method according to claim 46, further comprising the steps of transforming the host cell with a nucleic acid molecule comprising a gene which encodes at least one suppressor tRNA molecule.

51. The method according to claim 46, wherein the fusion protein comprises an N- or C-terminal tag encoded by at least a portion of the vector.

52. The method according to claim 51, wherein the tag is selected from the group consisting of:
(a) glutathione S-transferase; (b) β-glucuronidase; (c) green fluorescent protein; (d) yellow fluorescent protein; (e) red fluorescent protein; cyan fluorescent protein; (g) maltose binding protein; (h) a six histidine tag; and (i) an epitope tag.

53. A method for determining the gene expression profile in a cell or tissue comprising:
(a) generating at least one population of cDNA molecules from RNA obtained from the cell or tissue, wherein cDNA molecules of the population comprise at least one recombination site capable of recombining with at least one recombination site present on cDNA molecules of the same or a different population;
(b) contacting the nucleic acid molecules of (a) with one or more recombination proteins under conditions which cause the nucleic acid molecules to join;
(c) determining the sequence of the joined nucleic acid molecules; and
(d) comparing the sequence of said joined nucleic acid molecules to nucleic acid sequences cataloged in public databases to identify the gene expression profile.

54. The method of claim 53, wherein the joined cDNA molecules are inserted into a vector which contains sequencing primer binding sites flanking the insertion site.

55. The method of claim 53, wherein the joined cDNA molecules are separated by attB recombination sites.

56. The method of claim 55, wherein the attB recombination sites which recombine with each other have identical seven base pair overlap regions.

57. The method of claim 53, wherein the joined cDNA molecules contain between about 10 and about 30 nucleotides which corresponds to the RNA obtained from the cell or tissue.

58. A method of producing a population of hybrid nucleic acid molecules comprising:
(a) mixing at least a first population of nucleic acid and molecules, wherein: one or more nucleic acid molecules of said population comprises one or more recombination sites, with at least one target nucleic acid molecule comprising one or more recombination sites;
(b) causing some or all of the nucleic acid molecules of the at least first population to recombine in vitro with all or some of the target nucleic molecules, thereby forming the population of hybrid nucleic acid molecules; and
(c) selecting for the population of hybrid nucleic acid molecules and against the first population of nucleic acid molecules and against the target nucleic acid molecules.

59. A method of cloning at least one nucleic acid molecule comprising:
(a) providing a first population of nucleic acid molecules wherein all or a portion of such molecules are flanked by a first and a second recombination site;
(b) providing at least one nucleic acid segment encoding a polypeptide selected from the group consisting of: (i) the Fc portion of an immunoglobin; (ii) β-glucuronidase; (iii) a fluorescent protein; (iv) a purification tag; (v) an epitope tag; (vi) maltose binding protein; (vii) a six histidine tag; and (viii) glutathione S-transferase, flanked by a third and a fourth recombination site, wherein either the first or the second recombination site is capable of recombining with either the third or the fourth recombination site;
(c) conducting a recombination reaction in vitro such that all or a portion of the nucleic acid molecules in the population is recombined with the segment to form a second population of nucleic acid molecules; and
(d) cloning the second population of nucleic acid molecules.

60. A method of producing a nucleic acid molecule comprising:
(a) providing a first nucleic acid molecule comprising at least one recombination site and comprising a coding sequence containing at least one suppressible stop codon;
(b) providing a second nucleic acid molecule comprising at least one recombination site and a coding sequence; and
(c) causing recombination in vitro such that the first nucleic acid molecule is joined to the second nucleic acid molecule to produce a third nucleic acid molecule in which the two coding sequences are connected in frame and are separated by said stop codon.

61. The method of claim 60, wherein said first nucleic acid molecule and/or said second nucleic acid molecule and/or third nucleic acid molecule is a vector.

62. The method of claim 60, further comprising:
(d) transforming a host cell which expresses a suppressor tRNA with the third nucleic acid molecule.

63. The method of claim 60, wherein the stop codon is selected from the group consisting of amber, opal and ochre codons.

64. The method of claim 60, wherein said first and/or second nucleic acid molecule comprises a gene which encodes at least one suppressor tRNA molecule.

65. The method of claim 62 wherein the chromosome of the host cell comprises a gene which encodes at least one suppressor tRNA molecule.

* * * * *

SEQUENCE LISTING

<160> NUMBER OF SEQ ID NOS: 141

<210> SEQ ID NO 1
<211> LENGTH: 27
<212> TYPE: DNA
<213> ORGANISM: Artificial Sequence
<220> FEATURE:
<223> OTHER INFORMATION: recombination site

<400> SEQUENCE: 1
agcctgcttt tttatactaa cttgagc                                       27

<210> SEQ ID NO 2
<211> LENGTH: 27
<212> TYPE: DNA

```
<213> ORGANISM: Artificial Sequence
<220> FEATURE:
<223> OTHER INFORMATION: recombination site

<400> SEQUENCE: 2
gttcagcttt tttatactaa gttggca                                              27

<210> SEQ ID NO 3
<211> LENGTH: 27
<212> TYPE: DNA
<213> ORGANISM: Artificial Sequence
<220> FEATURE:
<223> OTHER INFORMATION: recombination site

<400> SEQUENCE: 3
agcctgcttt tttatactaa gttggca                                              27

<210> SEQ ID NO 4
<211> LENGTH: 27
<212> TYPE: DNA
<213> ORGANISM: Artificial Sequence
<220> FEATURE:
<223> OTHER INFORMATION: recombination site

<400> SEQUENCE: 4
gttcagcttt tttatactaa cttgagc                                              27

<210> SEQ ID NO 5
<211> LENGTH: 25
<212> TYPE: DNA
<213> ORGANISM: Artificial Sequence
<220> FEATURE:
<223> OTHER INFORMATION: recombination site

<400> SEQUENCE: 5
agcctgcttt tttgtacaaa cttgt                                                25

<210> SEQ ID NO 6
<211> LENGTH: 27
<212> TYPE: DNA
<213> ORGANISM: Artificial Sequence
<220> FEATURE:
<223> OTHER INFORMATION: recombination site

<400> SEQUENCE: 6
gttcagcttt tttgtacaaa gttggca                                              27

<210> SEQ ID NO 7
<211> LENGTH: 27
<212> TYPE: DNA
<213> ORGANISM: Artificial Sequence
<220> FEATURE:
<223> OTHER INFORMATION: recombination site

<400> SEQUENCE: 7
agcctgcttt tttgtacaaa gttggca                                              27

<210> SEQ ID NO 8
<211> LENGTH: 25
<212> TYPE: DNA
<213> ORGANISM: Artificial Sequence
<220> FEATURE:
<223> OTHER INFORMATION: recombination site

<400> SEQUENCE: 8
gttcagcttt tttgtacaaa cttgt                                                25
```

-continued

```
<210> SEQ ID NO 9
<211> LENGTH: 25
<212> TYPE: DNA
<213> ORGANISM: Artificial Sequence
<220> FEATURE:
<223> OTHER INFORMATION: recombination site

<400> SEQUENCE: 9
acccagcttt cttgtacaaa gtggt                                    25

<210> SEQ ID NO 10
<211> LENGTH: 27
<212> TYPE: DNA
<213> ORGANISM: Artificial Sequence
<220> FEATURE:
<223> OTHER INFORMATION: recombination site

<400> SEQUENCE: 10
gttcagcttt cttgtacaaa gttggca                                  27

<210> SEQ ID NO 11
<211> LENGTH: 27
<212> TYPE: DNA
<213> ORGANISM: Artificial Sequence
<220> FEATURE:
<223> OTHER INFORMATION: recombination site

<400> SEQUENCE: 11
acccagcttt cttgtacaaa gttggca                                  27

<210> SEQ ID NO 12
<211> LENGTH: 25
<212> TYPE: DNA
<213> ORGANISM: Artificial Sequence
<220> FEATURE:
<223> OTHER INFORMATION: recombination site

<400> SEQUENCE: 12
gttcagcttt cttgtacaaa gtggt                                    25

<210> SEQ ID NO 13
<211> LENGTH: 22
<212> TYPE: DNA
<213> ORGANISM: Artificial Sequence
<220> FEATURE:
<223> OTHER INFORMATION: recombination site

<400> SEQUENCE: 13
caactttatt atacaaagtt gt                                       22

<210> SEQ ID NO 14
<211> LENGTH: 27
<212> TYPE: DNA
<213> ORGANISM: Artificial Sequence
<220> FEATURE:
<223> OTHER INFORMATION: recombination site

<400> SEQUENCE: 14
gttcaacttt attatacaaa gttggca                                  27

<210> SEQ ID NO 15
<211> LENGTH: 24
<212> TYPE: DNA
<213> ORGANISM: Artificial Sequence
<220> FEATURE:
```

<223> OTHER INFORMATION: recombination site

<400> SEQUENCE: 15
caactttatt atacaaagtt ggca                                    24

<210> SEQ ID NO 16
<211> LENGTH: 25
<212> TYPE: DNA
<213> ORGANISM: Artificial Sequence
<220> FEATURE:
<223> OTHER INFORMATION: recombination site

<400> SEQUENCE: 16
gttcaacttt attatacaaa gttgt                                   25

<210> SEQ ID NO 17
<211> LENGTH: 22
<212> TYPE: DNA
<213> ORGANISM: Artificial Sequence
<220> FEATURE:
<223> OTHER INFORMATION: recombination site

<400> SEQUENCE: 17
caacttttct atacaaagtt gt                                      22

<210> SEQ ID NO 18
<211> LENGTH: 27
<212> TYPE: DNA
<213> ORGANISM: Artificial Sequence
<220> FEATURE:
<223> OTHER INFORMATION: recombination site

<400> SEQUENCE: 18
gttcaacttt tctatacaaa gttggca                                 27

<210> SEQ ID NO 19
<211> LENGTH: 24
<212> TYPE: DNA
<213> ORGANISM: Artificial Sequence
<220> FEATURE:
<223> OTHER INFORMATION: recombination site

<400> SEQUENCE: 19
caactttcct atacaaagtt ggca                                    24

<210> SEQ ID NO 20
<211> LENGTH: 25
<212> TYPE: DNA
<213> ORGANISM: Artificial Sequence
<220> FEATURE:
<223> OTHER INFORMATION: recombination site

<400> SEQUENCE: 20
gttcaacttt tctatacaaa gttgt                                   25

<210> SEQ ID NO 21
<211> LENGTH: 22
<212> TYPE: DNA
<213> ORGANISM: Artificial Sequence
<220> FEATURE:
<223> OTHER INFORMATION: recombination site

<400> SEQUENCE: 21 caactttttgt atacaaagtt gt                                     22

<210> SEQ ID NO 22
<211> LENGTH: 27
<212> TYPE: DNA
<213> ORGANISM: Artificial Sequence
<220> FEATURE:
<223> OTHER INFORMATION: recombination site

<400> SEQUENCE: 22
gttcaacttt tgtatacaaa gttggca                                    27

<210> SEQ ID NO 23
<211> LENGTH: 24
<212> TYPE: DNA
<213> ORGANISM: Artificial Sequence
<220> FEATURE:
<223> OTHER INFORMATION: recombination site

<400> SEQUENCE: 23 caactttttgt atacaaagtt ggca                                      24

<210> SEQ ID NO 24
<211> LENGTH: 25
<212> TYPE: DNA
<213> ORGANISM: Artificial Sequence
<220> FEATURE:
<223> OTHER INFORMATION: recombination site

<400> SEQUENCE: 24
gttcaacttt tgtatacaaa gttgt                                      25

<210> SEQ ID NO 25
<211> LENGTH: 22
<212> TYPE: DNA
<213> ORGANISM: Artificial Sequence
<220> FEATURE:
<223> OTHER INFORMATION: recombination site

<400> SEQUENCE: 25 caacttttc gtacaaagtt gt                                          22

<210> SEQ ID NO 26
<211> LENGTH: 27
<212> TYPE: DNA
<213> ORGANISM: Artificial Sequence
<220> FEATURE:
<223> OTHER INFORMATION: recombination site

<400> SEQUENCE: 26
gttcaacttt ttcgtacaaa gttggca                                    27

<210> SEQ ID NO 27
<211> LENGTH: 24
<212> TYPE: DNA
<213> ORGANISM: Artificial Sequence
<220> FEATURE:
<223> OTHER INFORMATION: recombination site

<400> SEQUENCE: 27 caacttttc gtacaaagtt ggca                                        24

<210> SEQ ID NO 28
<211> LENGTH: 25
<212> TYPE: DNA
<213> ORGANISM: Artificial Sequence
<220> FEATURE:
<223> OTHER INFORMATION: recombination site

```
<400> SEQUENCE: 28
gttcaacttt ttcgtacaaa gttgt                                          25

<210> SEQ ID NO 29
<211> LENGTH: 22
<212> TYPE: DNA
<213> ORGANISM: Artificial Sequence
<220> FEATURE:
<223> OTHER INFORMATION: recombination site

<400> SEQUENCE: 29
caactttttg gtacaaagtt gt                                             22

<210> SEQ ID NO 30
<211> LENGTH: 27
<212> TYPE: DNA
<213> ORGANISM: Artificial Sequence
<220> FEATURE:
<223> OTHER INFORMATION: recombination site

<400> SEQUENCE: 30
gttcaacttt ttggtacaaa gttggca                                        27

<210> SEQ ID NO 31
<211> LENGTH: 24
<212> TYPE: DNA
<213> ORGANISM: Artificial Sequence
<220> FEATURE:
<223> OTHER INFORMATION: recombination site

<400> SEQUENCE: 31
caactttttg gtacaaagtt ggca                                           24

<210> SEQ ID NO 32
<211> LENGTH: 25
<212> TYPE: DNA
<213> ORGANISM: Artificial Sequence
<220> FEATURE:
<223> OTHER INFORMATION: recombination site

<400> SEQUENCE: 32
gttcaacttt ttggtacaaa gttgt                                          25

<210> SEQ ID NO 33
<211> LENGTH: 22
<212> TYPE: DNA
<213> ORGANISM: Artificial Sequence
<220> FEATURE:
<223> OTHER INFORMATION: recombination site

<400> SEQUENCE: 33 caactttta atacaaagtt gt                                              22

<210> SEQ ID NO 34
<211> LENGTH: 27
<212> TYPE: DNA
<213> ORGANISM: Artificial Sequence
<220> FEATURE:
<223> OTHER INFORMATION: recombination site

<400> SEQUENCE: 34
gttcaacttt ttaatacaaa gttggca                                        27

<210> SEQ ID NO 35
<211> LENGTH: 24
```

```
<212> TYPE: DNA
<213> ORGANISM: Artificial Sequence
<220> FEATURE:
<223> OTHER INFORMATION: recombination site

<400> SEQUENCE: 35 caactttta atacaaagtt ggca                                              24

<210> SEQ ID NO 36
<211> LENGTH: 25
<212> TYPE: DNA
<213> ORGANISM: Artificial Sequence
<220> FEATURE:
<223> OTHER INFORMATION: recombination site

<400> SEQUENCE: 36
gttcaacttt ttaatacaaa gttgt                                            25

<210> SEQ ID NO 37
<211> LENGTH: 15
<212> TYPE: DNA
<213> ORGANISM: Artificial Sequence
<220> FEATURE:
<223> OTHER INFORMATION: 15 bp Core Region

<400> SEQUENCE: 37
gcttttttat actaa                                                       15

<210> SEQ ID NO 38
<211> LENGTH: 21
<212> TYPE: DNA
<213> ORGANISM: Artificial Sequence
<220> FEATURE:
<223> OTHER INFORMATION: Reference Sequence

<400> SEQUENCE: 38
caactttttt atacaaagtt g                                                21

<210> SEQ ID NO 39
<211> LENGTH: 21
<212> TYPE: DNA
<213> ORGANISM: Artificial Sequence
<220> FEATURE:
<223> OTHER INFORMATION: att system core integrase binding site
<220> FEATURE:
<221> NAME/KEY: misc_feature
<222> LOCATION: (8)..(14)
<223> OTHER INFORMATION: n is any nucleotide

<400> SEQUENCE: 39
caactttnnn nnnnaaagtt g                                                21

<210> SEQ ID NO 40
<211> LENGTH: 17
<212> TYPE: DNA
<213> ORGANISM: Artificial Sequence
<220> FEATURE:
<223> OTHER INFORMATION: attB altered site
<220> FEATURE:
<221> NAME/KEY: misc_feature
<222> LOCATION: (8)..(14)
<223> OTHER INFORMATION: n is any nucleotide

<400> SEQUENCE: 40
caactttnnn nnnnaaa                                                     17

<210> SEQ ID NO 41
```

```
<211> LENGTH: 48
<212> TYPE: DNA
<213> ORGANISM: Artificial Sequence
<220> FEATURE:
<223> OTHER INFORMATION: attL1 PCR Primer

<400> SEQUENCE: 41
ggggagcctg cttttttgta caaagttggc attataaaaa agcattgc                48

<210> SEQ ID NO 42
<211> LENGTH: 48
<212> TYPE: DNA
<213> ORGANISM: Artificial Sequence
<220> FEATURE:
<223> OTHER INFORMATION: attL2 PCR Primer

<400> SEQUENCE: 42
ggggagcctg ctttcttgta caaagttggc attataaaaa agcattgc                48

<210> SEQ ID NO 43
<211> LENGTH: 22
<212> TYPE: DNA
<213> ORGANISM: Artificial Sequence
<220> FEATURE:
<223> OTHER INFORMATION: attL right PCR Primer

<400> SEQUENCE: 43
tgttgccggg aagctagagt aa                                            22

<210> SEQ ID NO 44
<211> LENGTH: 43
<212> TYPE: DNA
<213> ORGANISM: Artificial Sequence
<220> FEATURE:
<223> OTHER INFORMATION: attR1 PCR Primer

<400> SEQUENCE: 44
ggggacaagt ttgtacaaaa aagctgaacg agaaacgtaa aat                     43

<210> SEQ ID NO 45
<211> LENGTH: 43
<212> TYPE: DNA
<213> ORGANISM: Artificial Sequence
<220> FEATURE:
<223> OTHER INFORMATION: attR2 PCR Primer

<400> SEQUENCE: 45
ggggacaagt ttgtacaaga aagctgaacg agaaacgtaa aat                     43

<210> SEQ ID NO 46
<211> LENGTH: 22
<212> TYPE: DNA
<213> ORGANISM: Artificial Sequence
<220> FEATURE:
<223> OTHER INFORMATION: attR right PCR Primer

<400> SEQUENCE: 46
cagacggcat gatgaacctg aa                                            22

<210> SEQ ID NO 47
<211> LENGTH: 29
<212> TYPE: DNA
<213> ORGANISM: Artificial Sequence
<220> FEATURE:
<223> OTHER INFORMATION: PCR Primer

<400> SEQUENCE: 47
```

```
gggggacaagt ttgtacaaaa aagcaggct                                    29

<210> SEQ ID NO 48
<211> LENGTH: 29
<212> TYPE: DNA
<213> ORGANISM: Artificial Sequence
<220> FEATURE:
<223> OTHER INFORMATION: PCR Primer

<400> SEQUENCE: 48 gggggaccact ttgtacaaga aagctgggt                                    29

<210> SEQ ID NO 49
<211> LENGTH: 18
<212> TYPE: DNA
<213> ORGANISM: Artificial Sequence
<220> FEATURE:
<223> OTHER INFORMATION: PCR Primer

<400> SEQUENCE: 49
tgtacaaaaa agcaggct                                                 18

<210> SEQ ID NO 50
<211> LENGTH: 18
<212> TYPE: DNA
<213> ORGANISM: Artificial Sequence
<220> FEATURE:
<223> OTHER INFORMATION: PCR Primer

<400> SEQUENCE: 50
tgtacaagaa agctgggt                                                 18

<210> SEQ ID NO 51
<211> LENGTH: 15
<212> TYPE: DNA
<213> ORGANISM: Artificial Sequence
<220> FEATURE:
<223> OTHER INFORMATION: PCR Primer

<400> SEQUENCE: 51
acaaaaaagc aggct                                                    15

<210> SEQ ID NO 52
<211> LENGTH: 15
<212> TYPE: DNA
<213> ORGANISM: Artificial Sequence
<220> FEATURE:
<223> OTHER INFORMATION: PCR Primer

<400> SEQUENCE: 52
acaagaaagc tgggt                                                    15

<210> SEQ ID NO 53
<211> LENGTH: 12
<212> TYPE: DNA
<213> ORGANISM: Artificial Sequence
<220> FEATURE:
<223> OTHER INFORMATION: PCR Primer

<400> SEQUENCE: 53
aaaaagcagg ct                                                       12

<210> SEQ ID NO 54
<211> LENGTH: 12
<212> TYPE: DNA
```

```
<213> ORGANISM: Artificial Sequence
<220> FEATURE:
<223> OTHER INFORMATION: PCR Primer

<400> SEQUENCE: 54
agaaagctgg gt                                                          12

<210> SEQ ID NO 55
<211> LENGTH: 11
<212> TYPE: DNA
<213> ORGANISM: Artificial Sequence
<220> FEATURE:
<223> OTHER INFORMATION: PCR Primer

<400> SEQUENCE: 55
aaaagcaggc t                                                           11

<210> SEQ ID NO 56
<211> LENGTH: 11
<212> TYPE: DNA
<213> ORGANISM: Artificial Sequence
<220> FEATURE:
<223> OTHER INFORMATION: PCR Primer

<400> SEQUENCE: 56
gaaagctggg t                                                           11

<210> SEQ ID NO 57
<211> LENGTH: 10
<212> TYPE: DNA
<213> ORGANISM: Artificial Sequence
<220> FEATURE:
<223> OTHER INFORMATION: PCR Primer

<400> SEQUENCE: 57
aaagcaggct                                                             10

<210> SEQ ID NO 58
<211> LENGTH: 10
<212> TYPE: DNA
<213> ORGANISM: Artificial Sequence
<220> FEATURE:
<223> OTHER INFORMATION: PCR Primer

<400> SEQUENCE: 58
aaagctgggt                                                             10

<210> SEQ ID NO 59
<211> LENGTH: 22
<212> TYPE: DNA
<213> ORGANISM: Artificial Sequence
<220> FEATURE:
<223> OTHER INFORMATION: PCR Primer

<400> SEQUENCE: 59
gtcactagcc tgtggagcaa ga                                               22

<210> SEQ ID NO 60
<211> LENGTH: 22
<212> TYPE: DNA
<213> ORGANISM: Artificial Sequence
<220> FEATURE:
<223> OTHER INFORMATION: PCR Primer

<400> SEQUENCE: 60
aggatggcag agggagacga ca                                               22
```

<210> SEQ ID NO 61
<211> LENGTH: 48
<212> TYPE: DNA
<213> ORGANISM: Artificial Sequence
<220> FEATURE:
<223> OTHER INFORMATION: PCR Primer attL0

<400> SEQUENCE: 61
ggggagcctg cttttttata ctaagttggc attataaaaa agcattgc       48

<210> SEQ ID NO 62
<211> LENGTH: 48
<212> TYPE: DNA
<213> ORGANISM: Artificial Sequence
<220> FEATURE:
<223> OTHER INFORMATION: PCR Primer attLT1A

<400> SEQUENCE: 62
ggggagcctg ctttattata ctaagttggc attataaaaa agcattgc       48

<210> SEQ ID NO 63
<211> LENGTH: 48
<212> TYPE: DNA
<213> ORGANISM: Artificial Sequence
<220> FEATURE:
<223> OTHER INFORMATION: PCR Primer attLT1C

<400> SEQUENCE: 63
ggggagcctg ctttcttata ctaagttggc attataaaaa agcattgc       48

<210> SEQ ID NO 64
<211> LENGTH: 48
<212> TYPE: DNA
<213> ORGANISM: Artificial Sequence
<220> FEATURE:
<223> OTHER INFORMATION: PCR Primer attLT1G

<400> SEQUENCE: 64
ggggagcctg ctttgttata ctaagttggc attataaaaa agcattgc       48

<210> SEQ ID NO 65
<211> LENGTH: 48
<212> TYPE: DNA
<213> ORGANISM: Artificial Sequence
<220> FEATURE:
<223> OTHER INFORMATION: PCR Primer attLT2A

<400> SEQUENCE: 65
ggggagcctg cttttatata ctaagttggc attataaaaa agcattgc       48

<210> SEQ ID NO 66
<211> LENGTH: 48
<212> TYPE: DNA
<213> ORGANISM: Artificial Sequence
<220> FEATURE:
<223> OTHER INFORMATION: PCR Primer attLT2C

<400> SEQUENCE: 66
ggggagcctg cttttctata ctaagttggc attataaaaa agcattgc       48

<210> SEQ ID NO 67
<211> LENGTH: 48
<212> TYPE: DNA
<213> ORGANISM: Artificial Sequence
<220> FEATURE:

```
<223> OTHER INFORMATION: PCR Primer attLT2G

<400> SEQUENCE: 67
ggggagcctg cttttgtata ctaagttggc attataaaaa agcattgc                48

<210> SEQ ID NO 68
<211> LENGTH: 48
<212> TYPE: DNA
<213> ORGANISM: Artificial Sequence
<220> FEATURE:
<223> OTHER INFORMATION: PCR Primer attLT3A

<400> SEQUENCE: 68
ggggagcctg ctttttaata ctaagttggc attataaaaa agcattgc                48

<210> SEQ ID NO 69
<211> LENGTH: 48
<212> TYPE: DNA
<213> ORGANISM: Artificial Sequence
<220> FEATURE:
<223> OTHER INFORMATION: PCR Primer attL3C

<400> SEQUENCE: 69
ggggagcctg ctttttcata ctaagttggc attataaaaa agcattgc                48

<210> SEQ ID NO 70
<211> LENGTH: 48
<212> TYPE: DNA
<213> ORGANISM: Artificial Sequence
<220> FEATURE:
<223> OTHER INFORMATION: PCR Primer attLT3G

<400> SEQUENCE: 70
ggggagcctg ctttttgata ctaagttggc attataaaaa agcattgc                48

<210> SEQ ID NO 71
<211> LENGTH: 48
<212> TYPE: DNA
<213> ORGANISM: Artificial Sequence
<220> FEATURE:
<223> OTHER INFORMATION: PCR Primer attLA4C

<400> SEQUENCE: 71
ggggagcctg cttttttcta ctaagttggc attataaaaa agcattgc                48

<210> SEQ ID NO 72
<211> LENGTH: 48
<212> TYPE: DNA
<213> ORGANISM: Artificial Sequence
<220> FEATURE:
<223> OTHER INFORMATION: PCR Primer attLA4G

<400> SEQUENCE: 72
ggggagcctg cttttttgta ctaagttggc attataaaaa agcattgc                48

<210> SEQ ID NO 73
<211> LENGTH: 48
<212> TYPE: DNA
<213> ORGANISM: Artificial Sequence
<220> FEATURE:
<223> OTHER INFORMATION: PCR Primer attLA4T

<400> SEQUENCE: 73
ggggagcctg cttttttta ctaagttggc attataaaaa agcattgc                 48
```

<210> SEQ ID NO 74
<211> LENGTH: 48
<212> TYPE: DNA
<213> ORGANISM: Artificial Sequence
<220> FEATURE:
<223> OTHER INFORMATION: PCR Primer attLT5A

<400> SEQUENCE: 74
ggggagcctg cttttttaaa ctaagttggc attataaaaa agcattgc         48

<210> SEQ ID NO 75
<211> LENGTH: 48
<212> TYPE: DNA
<213> ORGANISM: Artificial Sequence
<220> FEATURE:
<223> OTHER INFORMATION: PCR Primer attLT5C

<400> SEQUENCE: 75
ggggagcctg cttttttaca ctaagttggc attataaaaa agcattgc         48

<210> SEQ ID NO 76
<211> LENGTH: 48
<212> TYPE: DNA
<213> ORGANISM: Artificial Sequence
<220> FEATURE:
<223> OTHER INFORMATION: PCR Primer attLT5G

<400> SEQUENCE: 76
ggggagcctg cttttttaga ctaagttggc attataaaaa agcattgc         48

<210> SEQ ID NO 77
<211> LENGTH: 48
<212> TYPE: DNA
<213> ORGANISM: Artificial Sequence
<220> FEATURE:
<223> OTHER INFORMATION: PCR Primer attLA6C

<400> SEQUENCE: 77
ggggagcctg cttttttatc ctaagttggc attataaaaa agcattgc         48

<210> SEQ ID NO 78
<211> LENGTH: 48
<212> TYPE: DNA
<213> ORGANISM: Artificial Sequence
<220> FEATURE:
<223> OTHER INFORMATION: PCR Primer attLA6G

<400> SEQUENCE: 78
ggggagcctg cttttttatg ctaagttggc attataaaaa agcattgc         48

<210> SEQ ID NO 79
<211> LENGTH: 48
<212> TYPE: DNA
<213> ORGANISM: Artificial Sequence
<220> FEATURE:
<223> OTHER INFORMATION: PCR Primer attLA6T

<400> SEQUENCE: 79
ggggagcctg cttttttatt ctaagttggc attataaaaa agcattgc         48

<210> SEQ ID NO 80
<211> LENGTH: 48
<212> TYPE: DNA
<213> ORGANISM: Artificial Sequence
<220> FEATURE:
<223> OTHER INFORMATION: PCR Primer attLC7A -continued

<400> SEQUENCE: 80
ggggagcctg cttttttata ataagttggc attataaaaa agcattgc         48

<210> SEQ ID NO 81
<211> LENGTH: 48
<212> TYPE: DNA
<213> ORGANISM: Artificial Sequence
<220> FEATURE:
<223> OTHER INFORMATION: PCR Primer attLC7G

<400> SEQUENCE: 81
ggggagcctg cttttttata gtaagttggc attataaaaa agcattgc         48

<210> SEQ ID NO 82
<211> LENGTH: 48
<212> TYPE: DNA
<213> ORGANISM: Artificial Sequence
<220> FEATURE:
<223> OTHER INFORMATION: PCR Primer attLC7T

<400> SEQUENCE: 82
ggggagcctg cttttttata ttaagttggc attataaaaa agcattgc         48

<210> SEQ ID NO 83
<211> LENGTH: 48
<212> TYPE: DNA
<213> ORGANISM: Artificial Sequence
<220> FEATURE:
<223> OTHER INFORMATION: PCR Primer attL8

<400> SEQUENCE: 83
ggggagccta cttttttata ctaagttggc attataaaaa agcattgc         48

<210> SEQ ID NO 84
<211> LENGTH: 48
<212> TYPE: DNA
<213> ORGANISM: Artificial Sequence
<220> FEATURE:
<223> OTHER INFORMATION: PCR Primer attL9

<400> SEQUENCE: 84
ggggagcctg ccttttata ctaagttggc attataaaaa agcattgc         48

<210> SEQ ID NO 85
<211> LENGTH: 48
<212> TYPE: DNA
<213> ORGANISM: Artificial Sequence
<220> FEATURE:
<223> OTHER INFORMATION: PCR Primer attL10

<400> SEQUENCE: 85
ggggagcctg cttctttata ctaagttggc attataaaaa agcattgc         48

<210> SEQ ID NO 86
<211> LENGTH: 48
<212> TYPE: DNA
<213> ORGANISM: Artificial Sequence
<220> FEATURE:
<223> OTHER INFORMATION: PCR Primer attL14

<400> SEQUENCE: 86
ggggagcctg cttttttata ccaagttggc attataaaaa agcattgc         48

<210> SEQ ID NO 87
<211> LENGTH: 48

-continued

<212> TYPE: DNA
<213> ORGANISM: Artificial Sequence
<220> FEATURE:
<223> OTHER INFORMATION: PCR Primer attL15

<400> SEQUENCE: 87
ggggagcctg cttttttata ctaggttggc attataaaaa agcattgc          48

<210> SEQ ID NO 88
<211> LENGTH: 30
<212> TYPE: DNA
<213> ORGANISM: Artificial Sequence
<220> FEATURE:
<223> OTHER INFORMATION: recombination site

<400> SEQUENCE: 88
agcctgcttt tttatactaa gttggcatta                              30

<210> SEQ ID NO 89
<211> LENGTH: 30
<212> TYPE: DNA
<213> ORGANISM: Artificial Sequence
<220> FEATURE:
<223> OTHER INFORMATION: recombination site

<400> SEQUENCE: 89
agcctgcttt attatactaa gttggcatta                              30

<210> SEQ ID NO 90
<211> LENGTH: 30
<212> TYPE: DNA
<213> ORGANISM: Artificial Sequence
<220> FEATURE:
<223> OTHER INFORMATION: recombination site

<400> SEQUENCE: 90
agcctgcttt tttatattaa gttggcatta                              30

<210> SEQ ID NO 91
<211> LENGTH: 30
<212> TYPE: DNA
<213> ORGANISM: Artificial Sequence
<220> FEATURE:
<223> OTHER INFORMATION: recombination site

<400> SEQUENCE: 91
agcctgcttt tttatgctaa gttggcatta                              30

<210> SEQ ID NO 92
<211> LENGTH: 30
<212> TYPE: DNA
<213> ORGANISM: Artificial Sequence
<220> FEATURE:
<223> OTHER INFORMATION: recombination site

<400> SEQUENCE: 92
agcctgcttt tttataccaa gttggcatta                              30

<210> SEQ ID NO 93
<211> LENGTH: 30
<212> TYPE: DNA
<213> ORGANISM: Artificial Sequence
<220> FEATURE:
<223> OTHER INFORMATION: recombination site

<400> SEQUENCE: 93

```
agcctgcttt tttatactag gttggcatta                                          30

<210> SEQ ID NO 94
<211> LENGTH: 21
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(15)
<223> OTHER INFORMATION: n is any nucelotide

<400> SEQUENCE: 94
caacttnntn nnannaagtt g                                                   21

<210> SEQ ID NO 95
<211> LENGTH: 25
<212> TYPE: DNA
<213> ORGANISM: Artificial Sequence
<220> FEATURE:
<223> OTHER INFORMATION: recombination site

<400> SEQUENCE: 95
tcaagttagt ataaaaaagc aggct                                               25

<210> SEQ ID NO 96
<211> LENGTH: 29
<212> TYPE: DNA
<213> ORGANISM: Artificial Sequence
<220> FEATURE:
<223> OTHER INFORMATION: recombination site

<400> SEQUENCE: 96
ggggaacact ttgtacaaga aagctgggt                                           29

<210> SEQ ID NO 97
<211> LENGTH: 29
<212> TYPE: DNA
<213> ORGANISM: Artificial Sequence
<220> FEATURE:
<223> OTHER INFORMATION: recombination site

<400> SEQUENCE: 97
ggggacaact ttgtacaaga aagctgggt                                           29

<210> SEQ ID NO 98
<211> LENGTH: 29
<212> TYPE: DNA
<213> ORGANISM: Artificial Sequence
<220> FEATURE:
<223> OTHER INFORMATION: recombination site

<400> SEQUENCE: 98
ggggacccct ttgtacaaga aagctgggt                                           29

<210> SEQ ID NO 99
<211> LENGTH: 29
<212> TYPE: DNA
<213> ORGANISM: Artificial Sequence
<220> FEATURE:
<223> OTHER INFORMATION: recombination site

<400> SEQUENCE: 99
ggggaccaat ttgtacaaga aagctgggt                                           29
```

```
<210> SEQ ID NO 100
<211> LENGTH: 29
<212> TYPE: DNA
<213> ORGANISM: Artificial Sequence
<220> FEATURE:
<223> OTHER INFORMATION: recombination site

<400> SEQUENCE: 100
ggggaccacg ttgtacaaga aagctgggt                                    29

<210> SEQ ID NO 101
<211> LENGTH: 29
<212> TYPE: DNA
<213> ORGANISM: Artificial Sequence
<220> FEATURE:
<223> OTHER INFORMATION: recombination site

<400> SEQUENCE: 101
ggggaccact gtgtacaaga aagctgggt                                    29

<210> SEQ ID NO 102
<211> LENGTH: 29
<212> TYPE: DNA
<213> ORGANISM: Artificial Sequence
<220> FEATURE:
<223> OTHER INFORMATION: recombination site

<400> SEQUENCE: 102
ggggaccact tggtacaaga aagctgggt                                    29

<210> SEQ ID NO 103
<211> LENGTH: 29
<212> TYPE: DNA
<213> ORGANISM: Artificial Sequence
<220> FEATURE:
<223> OTHER INFORMATION: recombination site

<400> SEQUENCE: 103
ggggaccact ttgtacaaga aagctgggt                                    29

<210> SEQ ID NO 104
<211> LENGTH: 29
<212> TYPE: DNA
<213> ORGANISM: Artificial Sequence
<220> FEATURE:
<223> OTHER INFORMATION: recombination site

<400> SEQUENCE: 104
ggggacaact ttgtacaaaa aagttggct                                    29

<210> SEQ ID NO 105
<211> LENGTH: 29
<212> TYPE: DNA
<213> ORGANISM: Artificial Sequence
<220> FEATURE:
<223> OTHER INFORMATION: recombination site

<400> SEQUENCE: 105
ggggacaact ttgtacaaga aagttgggt                                    29

<210> SEQ ID NO 106
<211> LENGTH: 29
<212> TYPE: DNA
<213> ORGANISM: Artificial Sequence
<220> FEATURE:
<223> OTHER INFORMATION: recombination site
<220> FEATURE:
```

```
<221> NAME/KEY: misc_feature
<222> LOCATION: (20)..(24)
<223> OTHER INFORMATION: n is any nucleotide

<400> SEQUENCE: 106
ggggacaagt ttgtacaaan nnnnaggct                                    29

<210> SEQ ID NO 107
<211> LENGTH: 29
<212> TYPE: DNA
<213> ORGANISM: Artificial Sequence
<220> FEATURE:
<223> OTHER INFORMATION: recombination site
<220> FEATURE:
<221> NAME/KEY: misc_feature
<222> LOCATION: (25)..(29)
<223> OTHER INFORMATION: n is any nucleotide

<400> SEQUENCE: 107
ggggacaagt ttgtacaaaa aagcnnnnn                                    29

<210> SEQ ID NO 108
<211> LENGTH: 29
<212> TYPE: DNA
<213> ORGANISM: Artificial Sequence
<220> FEATURE:
<223> OTHER INFORMATION: recombination site
<220> FEATURE:
<221> NAME/KEY: misc_feature
<222> LOCATION: (20)..(24)
<223> OTHER INFORMATION: n is any nucleotide

<400> SEQUENCE: 108
ggggaccact ttgtacaagn nnnntgggt                                    29

<210> SEQ ID NO 109
<211> LENGTH: 29
<212> TYPE: DNA
<213> ORGANISM: Artificial Sequence
<220> FEATURE:
<223> OTHER INFORMATION: recombination site
<220> FEATURE:
<221> NAME/KEY: misc_feature
<222> LOCATION: (25)..(29)
<223> OTHER INFORMATION: n is any nucleotide

<400> SEQUENCE: 109
ggggaccact ttgtacaaga aagcnnnnn                                    29

<210> SEQ ID NO 110
<211> LENGTH: 28
<212> TYPE: DNA
<213> ORGANISM: Artificial Sequence
<220> FEATURE:
<223> OTHER INFORMATION: recombination site
<220> FEATURE:
<221> NAME/KEY: misc_feature
<222> LOCATION: (27)..(28)
<223> OTHER INFORMATION: n is any nucleotide

<400> SEQUENCE: 110
ggggacaact ttgtacaaaa aagttgnn                                     28

<210> SEQ ID NO 111
<211> LENGTH: 26
<212> TYPE: DNA
<213> ORGANISM: Artificial Sequence
<220> FEATURE:
<223> OTHER INFORMATION: recombination site
```

```
<400> SEQUENCE: 111
ggggacaact tgtataata aagttg                                                26

<210> SEQ ID NO 112
<211> LENGTH: 26
<212> TYPE: DNA
<213> ORGANISM: Artificial Sequence
<220> FEATURE:
<223> OTHER INFORMATION: recombination site

<400> SEQUENCE: 112
ggggacaact ttattataca aagttg                                               26

<210> SEQ ID NO 113
<211> LENGTH: 26
<212> TYPE: DNA
<213> ORGANISM: Artificial Sequence
<220> FEATURE:
<223> OTHER INFORMATION: recombination site
<220> FEATURE:
<221> NAME/KEY: misc_feature
<223> OTHER INFORMATION: n is any nucleotide
<220> FEATURE:
<221> NAME/KEY: misc_feature
<222> LOCATION: (26)..(26)
<223> OTHER INFORMATION: n is a, c, g, or t

<400> SEQUENCE: 113
gggacaactt tgtataataa agttgn                                               26

<210> SEQ ID NO 114
<211> LENGTH: 28
<212> TYPE: DNA
<213> ORGANISM: Artificial Sequence
<220> FEATURE:
<223> OTHER INFORMATION: PCR adaptor primer
<220> FEATURE:
<221> NAME/KEY: misc_feature
<222> LOCATION: (27)..(28)
<223> OTHER INFORMATION: n is any nucleotide

<400> SEQUENCE: 114
ggggacaact tgtacaaaaa aagttgnn                                             28

<210> SEQ ID NO 115
<211> LENGTH: 25
<212> TYPE: DNA
<213> ORGANISM: Artificial Sequence
<220> FEATURE:
<223> OTHER INFORMATION: PCR adaptor primer

<400> SEQUENCE: 115
gggacaactt tttaatacaa agttg                                                25

<210> SEQ ID NO 116
<211> LENGTH: 26
<212> TYPE: DNA
<213> ORGANISM: Artificial Sequence
<220> FEATURE:
<223> OTHER INFORMATION: PCR adaptor primer

<400> SEQUENCE: 116
ggggacaact tgtattaaa aagttg                                                26

<210> SEQ ID NO 117
<211> LENGTH: 27
```

<212> TYPE: DNA
<213> ORGANISM: Artificial Sequence
<220> FEATURE:
<223> OTHER INFORMATION: PCR adaptor primer
<220> FEATURE:
<221> NAME/KEY: misc_feature
<222> LOCATION: (27)..(27)
<223> OTHER INFORMATION: n is a, c, g, or t

<400> SEQUENCE: 117
ggggacaact ttgtataata aagttgn                                              27

<210> SEQ ID NO 118
<211> LENGTH: 16
<212> TYPE: DNA
<213> ORGANISM: Artificial Sequence
<220> FEATURE:
<223> OTHER INFORMATION: optimal Shine-Delgarno and Kozak sequence

<400> SEQUENCE: 118
ggaggtatat accatg                                                          16

<210> SEQ ID NO 119
<211> LENGTH: 39
<212> TYPE: DNA
<213> ORGANISM: Artificial Sequence
<220> FEATURE:
<223> OTHER INFORMATION: PCR adaptor primer

<400> SEQUENCE: 119
ggaggtatat accatgaagt tggaaatat ttgtttttc                                  39

<210> SEQ ID NO 120
<211> LENGTH: 49
<212> TYPE: DNA
<213> ORGANISM: Artificial Sequence
<220> FEATURE:
<223> OTHER INFORMATION: PCR adaptor primer

<400> SEQUENCE: 120
gaagctatag tgagtcgtat tatttaggtt cttttaagaa aggagcgac                      49

<210> SEQ ID NO 121
<211> LENGTH: 40
<212> TYPE: DNA
<213> ORGANISM: Artificial Sequence
<220> FEATURE:
<223> OTHER INFORMATION: PCR adaptor primer

<400> SEQUENCE: 121
ggaggtatat accatgaaat ttggattatt ttttctaaac                                40

<210> SEQ ID NO 122
<211> LENGTH: 47
<212> TYPE: DNA
<213> ORGANISM: Artificial Sequence
<220> FEATURE:
<223> OTHER INFORMATION: PCR adaptor primer

<400> SEQUENCE: 122
gaagctatag tgagtcgtat tatggtaaat tcatttcgat tttttgg                        47

<210> SEQ ID NO 123
<211> LENGTH: 45
<212> TYPE: DNA
<213> ORGANISM: Artificial Sequence
<220> FEATURE:

```
<223> OTHER INFORMATION: PCR adaptor primer

<400> SEQUENCE: 123
ggaggtatat accatgaata aatgtattcc aatgataatt aatgg              45

<210> SEQ ID NO 124
<211> LENGTH: 50
<212> TYPE: DNA
<213> ORGANISM: Artificial Sequence
<220> FEATURE:
<223> OTHER INFORMATION: PCR adaptor primer

<400> SEQUENCE: 124
gaagctatag tgagtcgtat tatgggacaa aaactaaaaa cttatcttcc         50

<210> SEQ ID NO 125
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 125
ggaggtatat accatgaaag atgaaagtgc ttttttacg attg               44

<210> SEQ ID NO 126
<211> LENGTH: 46
<212> TYPE: DNA
<213> ORGANISM: Artificial Sequence
<220> FEATURE:
<223> OTHER INFORMATION: PCR adaptor primer

<400> SEQUENCE: 126
gaagctatag tgagtcgtat taagccaatt ctaataattc attttc            46

<210> SEQ ID NO 127
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 127
ggaggtatat accatgactg tccatactga atataaaaga aatc              44

<210> SEQ ID NO 128
<211> LENGTH: 53
<212> TYPE: DNA
<213> ORGANISM: Artificial Sequence
<220> FEATURE:
<223> OTHER INFORMATION: PCR adaptor primer

<400> SEQUENCE: 128
gaagctatag tgagtcgtat taaatccttg atattctttt gtatgacatt agc    53

<210> SEQ ID NO 129
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 129
ggggacaact ttgtacaaaa aagttgaagg aggtatatac catg              44
```

<210> SEQ ID NO 130
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 130
ggggacaact ttgtataata aagttggaag ctatagtgag tcgt             44

<210> SEQ ID NO 131
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 131
ggggacaact ttattataca aagttgaagg aggtatatac catg             44

<210> SEQ ID NO 132
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 132
ggggacaact ttgtatagaa aagttggaag ctatagtgag tcgt             44

<210> SEQ ID NO 133
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 133
ggggacaact tttctataca aagttgaagg aggtatatac catg             44

<210> SEQ ID NO 134
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 134
ggggacaact ttgtatacaa aagttggaag ctatagtgag tcgt             44

<210> SEQ ID NO 135
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 135
ggggacaact tttgtataca aagttgaagg aggtatatac catg             44

<210> SEQ ID NO 136
<211> LENGTH: 44
<212> TYPE: DNA
<213> ORGANISM: Artificial Sequence
<220> FEATURE:
<223> OTHER INFORMATION: PCR adaptor primer -continued

```
<400> SEQUENCE: 136
ggggacaact ttgtattaaa aagttggaag ctatagtgag tcgt            44

<210> SEQ ID NO 137
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 137
ggggacaact ttttaataca aagttgaagg aggtatatac catg            44

<210> SEQ ID NO 138
<211> LENGTH: 44
<212> TYPE: DNA
<213> ORGANISM: Artificial Sequence
<220> FEATURE:
<223> OTHER INFORMATION: PCR adaptor primer

<400> SEQUENCE: 138
ggggacaact ttgtacaaga aagttggaag ctatagtgag tcgt            44

<210> SEQ ID NO 139
<211> LENGTH: 14
<212> TYPE: DNA
<213> ORGANISM: Artificial Sequence
<220> FEATURE:
<223> OTHER INFORMATION: 12 attB1 Forward Template-Specific Primer
<220> FEATURE:
<221> NAME/KEY: misc_feature
<222> LOCATION: (13)..(14)
<223> OTHER INFORMATION: n is any nucleotide

<400> SEQUENCE: 139
aaaaagcagg ctnn                                             14

<210> SEQ ID NO 140
<211> LENGTH: 13
<212> TYPE: DNA
<213> ORGANISM: Artificial Sequence
<220> FEATURE:
<223> OTHER INFORMATION: 12 attB2 Reverse Template-Specific Primer
<220> FEATURE:
<221> NAME/KEY: misc_feature
<222> LOCATION: (13)..(13)
<223> OTHER INFORMATION: n is any nucleotide

<400> SEQUENCE: 140
agaaagctgg gtn                                              13

<210> SEQ ID NO 141
<211> LENGTH: 22
<212> TYPE: DNA
<213> ORGANISM: Artificial Sequence
<220> FEATURE:
<223> OTHER INFORMATION: T7 promotor and stop codon

<400> SEQUENCE: 141
gaagctatag tgagtcgtat ta                                    22
```